US012460228B2

(12) United States Patent
Wilson et al.

(10) Patent No.: US 12,460,228 B2
(45) Date of Patent: *Nov. 4, 2025

(54) GENE THERAPY FOR TREATING WILSON'S DISEASE

(71) Applicant: The Trustees of the University of Pennsylvania, Philadelphia, PA (US)

(72) Inventors: James M. Wilson, Philadelphia, PA (US); Jenny Agnes Sidrane, Phoenixville, PA (US); Lakshmanan Govindasamy, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 661 days.

This patent is subject to a terminal disclaimer.

(21) Appl. No.: 17/812,322

(22) Filed: Jul. 13, 2022

(65) Prior Publication Data

US 2022/0389455 A1 Dec. 8, 2022

Related U.S. Application Data

(63) Continuation of application No. 16/474,958, filed as application No. PCT/US2017/068919 on Dec. 29, 2017, now Pat. No. 11,473,106.

(60) Provisional application No. 62/440,659, filed on Dec. 30, 2016, provisional application No. 62/473,656, filed on Mar. 20, 2017.

(51) Int. Cl.

| | |
|---|---|
| ***C12N 15/86*** | (2006.01) |
| ***A61K 48/00*** | (2006.01) |
| ***C07K 14/755*** | (2006.01) |

(52) U.S. Cl.

CPC .............. *C12N 15/86* (2013.01); *A61K 48/00* (2013.01); *C07K 14/755* (2013.01)

(58) Field of Classification Search

None

See application file for complete search history.

(56) References Cited

U.S. PATENT DOCUMENTS

| | | | |
|---|---|---|---|
| 8,999,380 B2 | 4/2015 | Bancel et al. | |
| 11,147,887 B2 | 10/2021 | Murillo Sauca et al. | |
| 11,473,106 B2 * | 10/2022 | Wilson .................. | A61K 48/00 |
| 2003/0228282 A1 | 12/2003 | Gao et al. | |
| 2006/0136184 A1 | 6/2006 | Gustafsson et al. | |
| 2014/0032186 A1 | 1/2014 | Gustafsson et al. | |
| 2014/0196176 A1 | 7/2014 | Heintz et al. | |
| 2015/0111955 A1 | 4/2015 | High et al. | |
| 2015/0315612 A1 | 11/2015 | Wilson et al. | |
| 2017/0348435 A1 | 12/2017 | Murillo Sauca et al. | |

FOREIGN PATENT DOCUMENTS

| | | |
|---|---|---|
| DE | 10156121 A1 | 5/2003 |
| WO | WO 2011/126808 | 10/2011 |
| WO | WO 2013/049493 | 4/2013 |
| WO | WO 2015/012924 | 1/2015 |
| WO | WO 2016/097218 | 6/2016 |
| WO | WO 2016/097219 | 6/2016 |
| WO | WO 2016/181123 A1 | 11/2016 |
| WO | WO 2017/100676 | 6/2017 |
| WO | WO 2018/126116 | 7/2018 |
| WO | WO 2020/102723 A1 | 5/2020 |
| WO | WO 2020/142653 | 7/2020 |

OTHER PUBLICATIONS

Nguyen, et al. (2008) "Evaluation of Gene Promoters for Liver Expression by Hydrodynamic Gene Transfer", Journal of Surgical Research, 148(1): 60-66. (Year: 2008).*

Brewer (2009) "Zinc and tetrathiomolybdate for the treatment of Wilson's disease and the potential efficacy of anticopper therapy in a wide variety of diseases", Metallomics, 1: 199-206. (Year: 2009).*

Office Action issued in Chinese Patent Application No. 201780085376.9 on Sep. 28, 2022, with translation provided by local agent.

Bartee et al., The loop connecting metal-binding domains 3 and 4 of ATP7B is a target of a kinase-mediated phosphorylation, Biochemistry. Jun. 23, 2009;48(24):5573-81.

Bernard JM et al., Hepatic lesions in 90 captive nondomestic felids presented for autopsy, Vet Pathol. Mar. 2015;52(2):369-76. Epub May 1, 2014.

Braiterman et al. Communication between the N and C termini is required for copper-stimulated Ser/Thr phosphorylation of Cu(I)-ATPase (ATP7B). J Biol Chem. Apr. 3, 2015;290(14):8803-19.

Bronson RT et al., Acute cerebral neuronal necrosis in copper deficient offspring of female mice with the toxic milk mutation, Mouse Genome 1995;93:152-154.

Buiakova OI et al., Null mutation of the murine ATP7B (Wilson disease) gene results in intracellular copper accumulation and late-onset hepatic nodular transformation, Hum Mol Genet. Sep. 1999;8(9):1665-71.

Bull PC et al., The Wilson disease gene is a putative copper transporting P-type ATPase similar to the Menkes gene, Blood. Jul. 15, 2003;102(2):480-8. Epub Mar. 13, 2003.

Calcedo et al., Worldwide Epidemiology of Neutralizing Antibodies to Adeno-Associated Viruses. J Infect Dis. Feb. 1, 2009;199(3):381-90.

Cardone et al., Correction of Hunter syndrome in the MPSII mouse model by AAV2/8-mediated gene delivery. Hum Mol Genet. Apr. 1, 2006;15(7):1225-36.

Chuah et al., Liver-specific transcriptional modules identified by genome-wide in silico analysis enable efficient gene therapy in mice and non-human primates. Mol Ther. Sep. 2014;22(9):1605-13.

Coronado V et al., The Jackson toxic milk mouse as a model for copper loading, Mamm Genome. Oct. 2001;12(10):793-5.

(Continued)

*Primary Examiner* — Robert M Kelly

(74) *Attorney, Agent, or Firm* — Howson & Howson LLP

(57) ABSTRACT

Compositions and regimens useful in treating Wilson's Disease are provided. The compositions include recombinant adeno-associated virus (rAAV) with a transthyretin enhancer and promoter driving expression of a human ATP7B.

20 Claims, 27 Drawing Sheets

Figure 1:
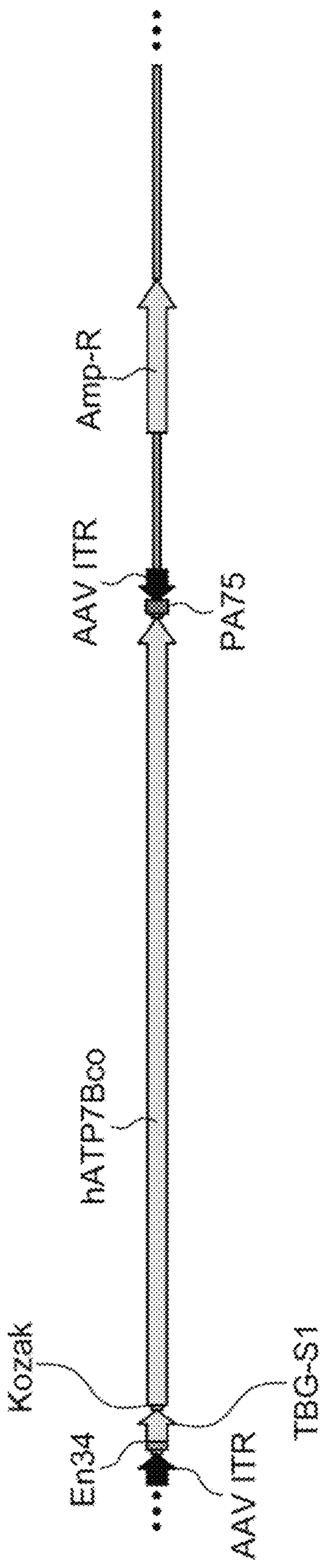

Specification includes a Sequence Listing.

(56) References Cited

OTHER PUBLICATIONS

Davidoff Am et al., Sex significantly influences transduction of murine liver by recombinant adeno-associated viral vectors through an androgen-dependent pathway, Blood 2003; 102:480-488.
Dong et al., Quantitative analysis of the packaging capacity of recombinant adeno-associated virus, Hum Gene Ther. Nov. 10, 1996;7(17):2101-12.
European Association for Study of Liver, EASL Clinical Practice Guidelines: Wilson's disease, J Hepatol. Mar. 2012;56(3):671-85. doi: 10.1016/j.jhep.2011.11.007.
Gao et al., Adeno-associated viruses undergo substantial evolution in primates during natural infections. Proc Natl Acad Sci U S A. May 13, 2003;100(10):6081-6. Epub Apr. 25, 2003.
Gao G et al., Biology of AAV serotype vectors in liver-directed gene transfer to nonhuman primates, Mol Ther. Jan. 2006;13(1):77-87. Epub Oct. 10, 2005.
Gourdon et al., Structural models of the human copper P-type ATPases ATP7A and ATP7B, Biol Chem. Apr. 2012;393(4):205-16. doi: 10.1515/hsz-2011-0249.
Gray LW et al., Urinary copper elevation in a mouse model of Wilson's disease is a regulated process to specifically decrease the hepatic copper load, PLoS One. 2012;7(6):e38327. doi: 10.1371/journal.pone.0038327. Epub Jun. 22, 2012.
Greig et al., A Gene Therapy Approach to Improve Copper Metabolism and Prevent Liver Damage in a Mouse Model of Wilson Disease, Hum Gene Ther Clin Dev. Mar. 2019;30(1):29-39.
Greig Ja et al., Characterization of Adeno-Associated Viral Vector-Mediated Human Factor VIII Gene Therapy in Hemophilia A Mice, May 2017;28(5):392-402. doi: 10.1089/hum.2016.128. Epub Jan. 5, 2017.
Grimm et al., Titration of AAV-2 particles via a novel capsid ELISA: packaging of genomes can limit production of recombinant AAV-2, Gene Ther. Jul. 1999;6(7):1322-30.
Hasan et al., Molecular events initiating exit of a copper-transporting ATPase ATP7B from the trans-Golgi network, J Biol Chem. Oct. 19, 2012;287(43):36041-50.
Huster D and Lutsenko S, The distinct roles of the N-terminal copper-binding sites in regulation of catalytic activity of the Wilson's disease protein, J Biol Chem. Aug. 22, 2003;278(34):32212-8. Epub Jun. 6, 2003.
Huster D et al., Consequences of copper accumulation in the livers of the Atp7b−/− (Wilson disease gene) knockout mice, Am J Pathol. Feb. 2006;168(2):423-34.
Irani An et al., Correction of liver disease following transplantation of normal rat hepatocytes into Long-Evans Cinnamon rats modeling Wilson's disease. Mol Ther. Mar. 2001;3(3):302-9.
Lock et al., Absolute determination of single-stranded and self-complementary adeno-associated viral vector genome titers by droplet digital PCR. Hum Gene Ther Methods. Apr. 2014;25(2):115-25. Epub Feb. 14, 2014.
Lock M et al., Rapid, simple, and versatile manufacturing of recombinant adeno-associated viral vectors at scale, Hum Gene Ther. Oct. 2010;21(10):1259-71. doi: 10.1089/hum.2010.055.
Loeb et al., Enhanced expression of transgenes from adeno-associated virus vectors with the woodchuck hepatitis virus post-transcriptional regulatory element: implications for gene therapy, Hum Gene Ther. Sep. 20, 1999;10(14):2295-305.
Lutsenko S et al., Function and regulation of human copper-transporting ATPases, Physiol Rev. Jul. 2007;87(3):1011-46.
McFarland et al., Evaluation of a novel short polyadenylation signal as an alternative to the SV40 polyadenylation signal, Plasmid. Jul. 2006;56(1):62-7.
McIntosh et al., Therapeutic levels of FVIII following a single peripheral vein administration of rAAV vector encoding a novel human factor VIII variant, Blood. Apr. 25, 2013;121(17):3335-44. doi: 10.1182/blood-2012-10-462200. Epub Feb. 20, 2013.
McMillin et al., Direct measurement of free copper in serum or plasma ultrafiltrate, Am J Clin Pathol. Feb. 2009;131(2):160-5.
Michalczyk A et al., ATP7B expression in human breast epithelial cells is mediated by lactational hormones, J Histochem Cytochem. Apr. 2008;56(4):389-99. doi: 10.1369/jhc.7A7300.2008. Epub Jan. 7, 2008.
Miyatake et al., Transcriptional targeting of herpes simplex virus for cell-specific replication. J Virol. Jul. 1997;71(7):5124-32.
Mizukami et al., A Protocol for AAV vector production and purification. Diss. Division of Genetic Therapeutics, Center for Molecular Medicine, 1998.
Murillo et al., Long-term metabolic correction of Wilson's disease in a murine model by gene therapy, J Hepatol. Feb. 2016;64(2):419-426. doi: 10.1016/j.jhep.2015.09.014. Epub Sep. 25, 2015.
NCBI Reference Sequence: NP_000044.2, copper-transporting ATPase 2 isoform a [*Homo sapiens*], Aug. 27, 2016.
NCBI Reference Sequence: NP_001005918.1, copper-transporting ATPase 2 isoform b [*Homo sapiens*], Aug. 27, 2016.
NCBI Reference Sequence: NP_001230111.1, copper-transporting ATPase 2 isoform c [*Homo sapiens*], Aug. 28, 2016.
NCBI Reference Sequence: NP_001317507.1, copper-transporting ATPase 2 isoform d [*Homo sapiens*], Sep. 11, 2016.
NCBI Reference Sequence: NP_001317508.1, copper-transporting ATPase 2 isoform e [*Homo sapiens*], Aug. 27, 2016.
NCBI Reference Sequence: XM_005266430.4, Predicted: *Homo sapiens* ATPase copper transporting beta (ATP7B), transcript variant X1, mRNA, Jun. 6, 2016.
Petrukhin K et al., Mapping, cloning and genetic characterization of the region containing the Wilson disease gene, Nat Genet. Dec. 1993;5(4):338-43.
Roberts EA and Schilsky ML, American Association for Study of Liver D. Diagnosis and treatment of Wilson disease: an update, Hepatology. Jun. 2008;47(6):2089-111. doi: 10.1002/hep.22261.
Roybal et al., Early gestational gene transfer with targeted ATP7B expression in the liver improves phenotype in a murine model of Wilson's disease, Gene Ther. Nov. 2012;19(11):1085-94. doi: 10.1038/gt.2011.186. Epub Dec. 8, 2011.
Safaei R et al., The role of metal binding and phosphorylation domains in the regulation of cisplatin-induced trafficking of ATP7B, Metallomics. Aug. 2013;5(8):964-72. doi: 10.1039/c3mt00131h.
Samadani et al., Identification of a transthyretin enhancer site that selectively binds the hepatocyte nuclear factor-3 beta isoform, Gene Expr. 1996;6(1):23-33.
Sandig et al., HBV-derived promoters direct liver-specific expression of an adenovirally transduced LDL receptor gene, Gene Ther. Nov. 1996;3(11):1002-9.
Sasaki N et al., The gene responsible for LEC hepatitis, located on rat chromosome 16, is the homolog to the human Wilson disease gene, Biochem Biophys Res Commun. Jul. 15, 1994;202(1):512-8.
Schosinsky et al., Measurement of ceruloplasmin from its oxidase activity in serum by use of o-dianisidine dihydrochloride, Clin Chem. Dec. 1974;20(12):1556-63.
Shanmugavel et al., Probing functional roles of Wilson disease protein (ATP7B) copper-binding domains in yeast, Metallomics. Jul. 19, 2017;9(7):981-988.
Smedley R et al., Copper-associated hepatitis in Labrador Retrievers, Vet Pathol. May 2009;46(3):484-90. doi: 10.1354/vp.08-VP-0197-S-FL. Epub Jan. 27, 2009.
Sommer JM et al., Quantification of adeno-associated virus particles and empty capsids by optical density measurement, Mol Ther. Jan. 2003;7(1):122-8.
Stromeyer FW and Ishak KG, Histology of the liver in Wilson's disease: a study of 34 cases, Am J Clin Pathol. Jan. 1980;73(1):12-24.
Tanzi RE et al., The Wilson disease gene is a copper transporting ATPase with homology to the Menkes disease gene. Nat Genet. Dec. 1993;5(4):344-50.
Terada K and Sugiyama T, The Long-Evans Cinnamon rat: an animal model for Wilson's disease, Pediatr Int. Aug. 1999;41(4):414-8.
Theophilos MB et al., The toxic milk mouse is a murine model of Wilson disease, Hum Mol Genet 1996;5:1619-1624.
Thompson et al., A comprehensive comparison of multiple sequence alignments, Nucleic Acids Res. Jul. 1, 1999;27(13):2682-90.
Thornburg LP et al., Hereditary copper toxicosis in West Highland white terriers, Vet Pathol. Mar. 1986;23(2):148-54.

(56) References Cited

OTHER PUBLICATIONS

Toole JJ et al., A large region (approximately equal to 95 kDa) of human factor VIII is dispensable for in vitro procoagulant activity, Proc Natl Acad Sci U S A. Aug. 1986;83(16):5939-42.
Valencia et al., Splicing promotes rapid and efficient mRNA export in mammalian cells, Proc Natl Acad Sci U S A. Mar. 4, 2008;105(9):3386-91.
Ward NJ et al., Codon optimization of human factor VIII cDNAs leads to high-level expression, Blood. Jan. 20, 2011;117(3):798-807. doi: 10.1182/blood-2010-05-282707. Epub Nov. 1, 2010.
Wobus et al., Monoclonal antibodies against the adeno-associated virus type 2 (AAV-2) capsid: epitope mapping and identification of capsid domains involved in AAV-2-cell interaction and neutralization of AAV-2 infection, J Virol. Oct. 2000;74(19):9281-93.
Wu et al., Effect of genome size on AAV vector packaging, Mol Ther. Jan. 2010;18(1):80-6. Epub Nov. 10, 2009.
Wu et al., Optimization of self-complementary AAV vectors for liver-directed expression results in sustained correction of hemophilia B at low vector dose, Mol Ther. Feb. 2008;16(2):280-9. Epub Dec. 4, 2007.
Wu J et al., The LEC rat has a deletion in the copper transporting ATPase gene homologous to the Wilson disease gene, Nat Genet. Aug. 1994;7(4):541-5.
Yan et al. Human thyroxine binding globulin (TBG) promoter directs efficient and sustaining transgene expression in liver-specific pattern. Gene. Sep. 15, 2012;506(2):289-94.
International Search Report and Written Opinion in International Patent Application No. PCT/US2017/068919, dated May 11, 2018.
Supplementary Search Report in European Patent Application No. EP 17888104, issued Jul. 6, 2020.
International Search Report and Written Opinion in International Patent Application No. PCT/US2020/012131, mailed Mar. 30, 2020.
Office Action issued in Japanese Patent Application No. 2019-535891 on Oct. 27, 2021, with translation provided by local agent.
Restriction Requirement in U.S. Appl. No. 16/474,958, mailed Dec. 8, 2021.
Applicant's Response and Amendment in U.S. Appl. No. 16/474,958, filed Jan. 26, 2022.
Non-Final Office Action in in U.S. Appl. No. 16/474,958, mailed Mar. 15, 2022.
Applicant's Response and Amendment in U.S. Appl. No. 16/474,958, filed Jun. 10, 2022.
Notice of Allowance in U.S. Appl. No. 16/474,958, mailed Jun. 28, 2022.
Office Action dated Feb. 20, 2023 issued in corresponding Korean Patent Application No. 10-2019-7021756, with English translation provided by local agent.
Daniel E, et al. ATGme: Open-source web application for rare codon identification and custom DNA sequence optimization. BMC Bioinformatics Sep. 21, 2015;16(1):303 (6 pages).
Daya S and Berns KI. Gene therapy using adeno-associated virus vectors. Clin Microbiol Rev. Oct. 2008;21(4):583-93.
Fumoto et al., Chapter 1: Targeted Gene Delivery: Importance of Administration Routes, INTECH, Nova Gene Therapy Approaches, pp. 3-31; editors Wei and Good, publisher Books on Demand, Feb. 2013.
Greenberg B. Gene therapy for heart failure. J Cardiol, Sep. 2015;66(3):195-200.
Grote A et al. JCat: a novel tool to adapt codon usage of a target gene to its potential expression host. Nucleic Acids Res, Ju. 1, 2005;33(Web Server issue):W526-31.
Harding TC et al. Intravenous administration of an AAV-2 vector for the expression of factor IX in mice and a dog model of hemophilia B. Gene Ther. Jan. 2004;11(2):204-13.
Kattenhorn LM, Tipper CH, Stoica L, Geraghty DS, Wright TL, Clark KR, Wadsworth SC. Adeno-Associated Virus Gene Therapy for Liver Disease. Hum Gene Ther. Dec. 2016;27(12):947-961.
Leng Y et al. Long-Term Correction of Copper Metabolism in Wilson's Disease Mice with AAV8 Vector Delivering Truncated ATP7B. Hum Gene Ther. Dec. 2019;30(12):1494-1504.
Maguire CA and Corey DP. Viral vectors for gene delivery to the inner ear. Hear Res. Sep. 1, 2020;394:107927 (13 pages).
Mingozzi F and High KA. Immune responses to AAV vectors: overcoming barriers to successful gene therapy. Blood. Jul. 4, 2013;122(1):23-36.
Murillo O) et al., [Abstract] 164. Improvement of Gene Therapy for Wilson Disease. Molecular Therapy. vol. 24, Supplement 1, S64, May 2016 (1 page).
NCBI GenBank Accession No. U03464.1, Human P-type ATPase ATP7B mRNA, complete cds, Apr. 23, 1997 (3 pages).
Perrin S. Preclinical research: Make mouse studies work. Nature. Mar. 27, 2014;507(7493):423-5.
Tian LC et al. Aerosol Inhalation-mediated Delivery of an Adeno-associated Virus 5-expressed Antagonistic Interleukin-4 Mutant Ameliorates Experimental Murine Asthma. Arch Med Res. Aug. 2019;50(6):384-392.
Tobias E et al. Let's not get overexcited about any mouse study used in research, Multiple Sclerosis News Today, https://multiplesclerosisnewstoday.com/news-posts/2023/09/08/lets-not-get-overexcited-about-any-mice-study-used-research/, Sep. 8, 2023, (8 pages).
Applicant's Response to the Written Opinion in European Patent Application No. 17888104.1, filed Jan. 23, 2021.
Examination Report in European Patent Application No. 17888104.1, issued Apr. 30, 2021.
Applicant's Response to Examination Report in European Patent Application No. 17888104.1, filed Aug. 30, 2021.
Examination Report in European Patent Application No. 17888104.1, issued Nov. 5, 2021.
Applicant's Response to Examination Report in European Patent Application No. 17888104.1, filed Mar. 3, 2022.
Communication pursuant to Rule 114(2) EPC (Third Party Observation) in European Patent Application No. 17888104.1, issued Mar. 13, 2024.
Examination Report in European Patent Application No. 17888104.1, issued Mar. 19, 2024.
Applicant's Response to Examination Report in European Patent Application No. 17888104.1, filed Jul. 2, 2024.
Extended European Search Report in European Patent Application No. 24161028.6, issued Jun. 28, 2024.
Applicant's Response in European Patent Application No. 24161028.6, filed Jan. 29, 2025.

* cited by examiner

GENE THERAPY FOR TREATING WILSON'S DISEASE

CROSS-REFERENCE TO RELATED APPLICATIONS

This application is a continuation of U.S. patent application Ser. No. 16/474,958, filed Jun. 28, 2019, which is a National Stage Entry under 35 U.S.C. 371 of International Patent Application No. PCT/US2017/068919, filed Dec. 29, 2017, which claims the benefit of priority of U.S. Provisional Patent Application No. 62/440,659, filed Dec. 30, 2016, and U.S. Provisional Patent Application No. 62/473,656 filed Mar. 20, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7940PCT_ST25.txt".

1. INTRODUCTION

The application relates to embodiments useful for a gene therapy for treating Wilson's Disease.

2. BACKGROUND

The application relates to embodiments useful for a gene therapy for treating Wilson's disease. Wilson's disease is an autosomal recessive genetic disorder copper storage disorder due to mutations in the copper-transporting ATPase 2 (ATP7B) gene on chromosome 13. Copper accumulates in tissues manifesting as neurological or psychiatric symptoms and liver disease typically observed between the ages of 12 and 23. Over time without proper treatments, high copper levels can cause life-threatening organ damage.

Current treatment approaches for Wilson's disease are daily oral therapy with chelating agents (penicillamine [Cuprimine] and trientine hydrochloride [Syprine]), zinc (to block enterocyte absorption of copper), and tetrathiomolybdate (TM), a copper chelator that forms complexes with albumin in the circulation, which require the affected individual to take medicines for their whole life. Furthermore, those treatments may cause side effects, such as drug induced lupus, myasthenia, paradoxical worsening, and do not restore normal copper metabolism. Liver transplantation is curative for Wilson's disease but transplant recipients are required to maintain a constant immune suppression regimen to prevent rejection.

3. SUMMARY

The embodiments described herein relate to an AAV gene therapy vector for delivering normal human copper-transporting ATPase 2 (ATP7B) to a subject in need thereof, following intravenous (IV) administration of the vector resulting in long-term, perhaps 10 years or more, of clinically meaningful correction of Wilson's Disease ("WD"). The vector dose is intended to deliver blood levels of ATP7B to reduce circulating copper levels by about 25% or more. In one embodiment, the level of circulating copper is assessed via the excretion of copper in the urine. In another embodiment, the level of circulating copper in the plasma is assessed.

In one aspect, this application provides the use of a replication deficient adeno-associated virus (AAV) to deliver a human copper-transporting ATPase 2 (ATP7B) gene to liver cells of patients (human subjects) diagnosed with WD. The recombinant AAV vector (rAAV) used for delivering the hATP7B gene ("rAAV.hATP7B") should have a tropism for the liver (e.g., a rAAV bearing an AAV8 capsid), and the hATP7B transgene should be controlled by liver-specific expression control elements. In one embodiment, the expression control elements include one or more of the following: an enhancer; a promoter; an intron; a WPRE; and a polyA signal. Such elements are further described herein. Due to the size of the hATP7B coding sequence, selection of control elements which allow for effective expression is important. If expression of the transgene is not sufficient, the vector dosage required for correction of the defect will be too high to be practical. Thus, as described herein, selection of the e.g., enhancer, promoter and polyA is important.

In one embodiment, the hATP7B coding sequence is shown in SEQ ID NO: 1. In one embodiment, the ATP7B protein sequence is shown in SEQ ID NO: 2. The coding sequence for hATP7B is, in one embodiment, codon optimized for expression in humans. Such sequence may share less than 80% identity to the native hATP7B coding sequence (SEQ ID NO: 3). In one embodiment, the hATP7B coding sequence is that shown in SEQ ID NO: 1.

In another aspect, provided herein is an aqueous suspension suitable for administration to a WD patient which includes the rAAV described herein. In some embodiments, the suspension includes an aqueous suspending liquid and about $1\times10^{12}$ to about $1\times10^{14}$ genome copies (GC) of the rAAV/mL. The suspension is, in one embodiment, suitable for intravenous injection. In other embodiment, the suspension further includes a surfactant, preservative, and/or buffer dissolved in the aqueous suspending liquid.

In another embodiment, provided herein is a method of treating a patient having WD with a rAAV as described herein. In one embodiment, about $1\times10^{11}$ to about $3\times10^{13}$ genome copies (GC) of the rAAV/kg patient body weight are delivered the patient in an aqueous suspension.

3. BRIEF DESCRIPTION OF THE DRAWINGS

FIG. 1 is a schematic representation of AAV8.En34.TBG-S1.hATP7Bco.PA75 vector.

Figure 2A:
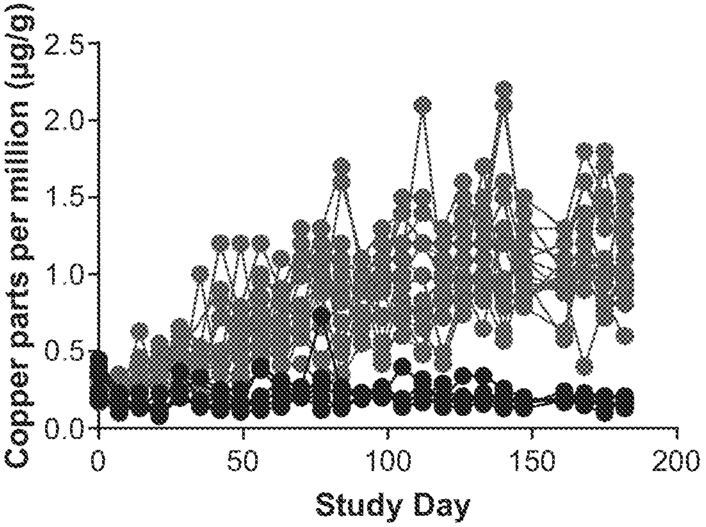
Figure 2B:
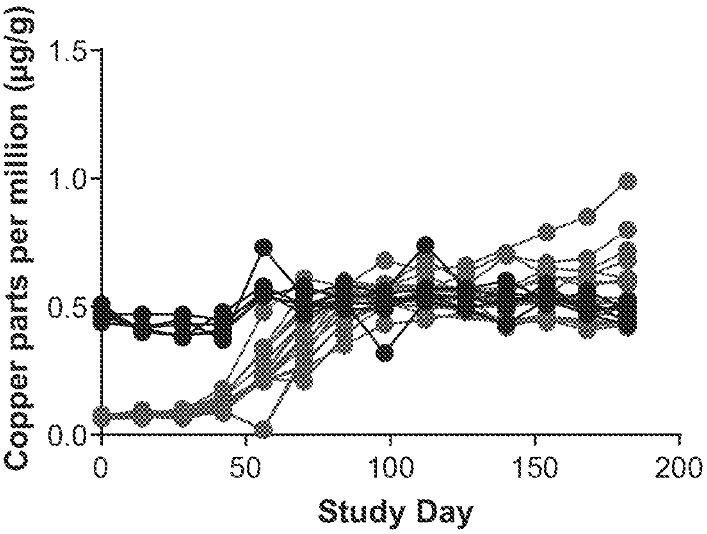

FIGS. 2A-2B demonstrate that urinary and serum copper levels increase over time in Atp7b KO mice. (A) Urine and (B) serum copper levels in Atp7b KO mice over time (black). Heterozygous littermates (Het) served as control (gray). Samples were collected weekly in the natural history study and inductively coupled plasma-mass spectrometry was performed to assess the copper level.

Figure 3A:
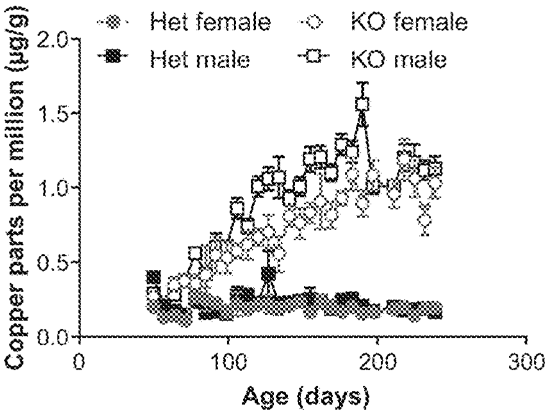
Figure 3B:
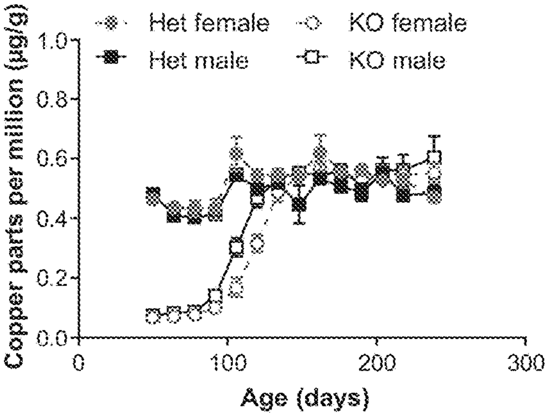
Figure 3C:
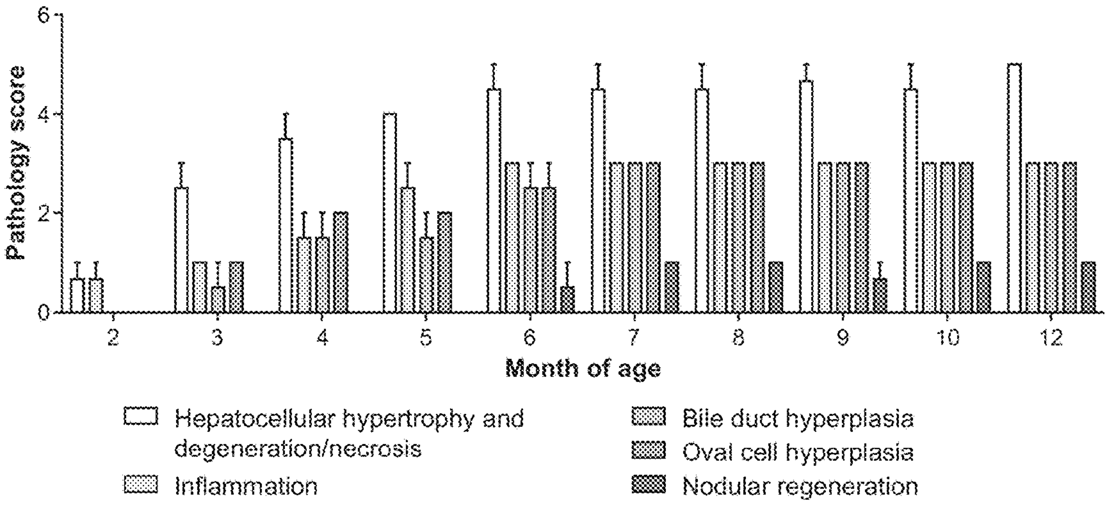

FIGS. 3A-3C demonstrate urine, copper levels, serum copper levels, and liver disease scoring in Atp7b KO mice. (A) Urine and (B) serum copper levels were evaluated by inductively coupled plasma-mass spectrometry in male and female heterozygous (Het) and Atp7b KO mice over time (KO). (C) Atp7b KO mice were necropsied at 2, 3, 4, 5, 9, 10, and 12 months of age. Liver was harvested, stained with H&E, and evaluated histologically according to the 1-5 scoring system. Values expressed as mean±SEM.

Figure 4:
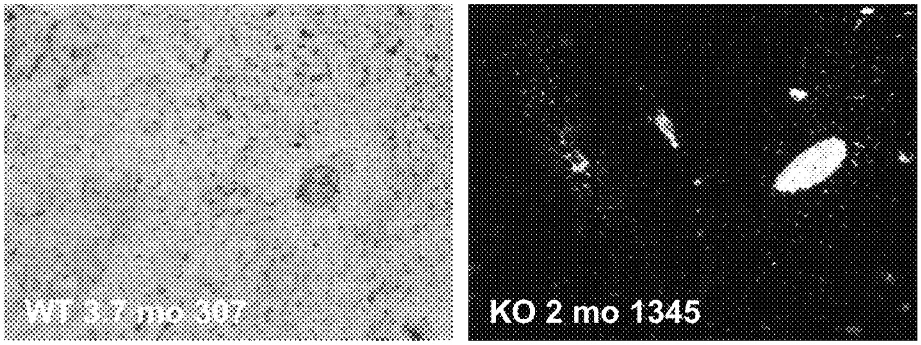

FIG. 4 demonstrates Timm's staining in Atp7b KO mice. Representative result of Timm's staining for copper in the liver of a 2 month-old Atp7b KO mouse with identification number 1345. Black deposits indicate positive staining for copper. A 3.7 month-old wild type mouse with identification number 307 served as a negative control.

Figure 5:
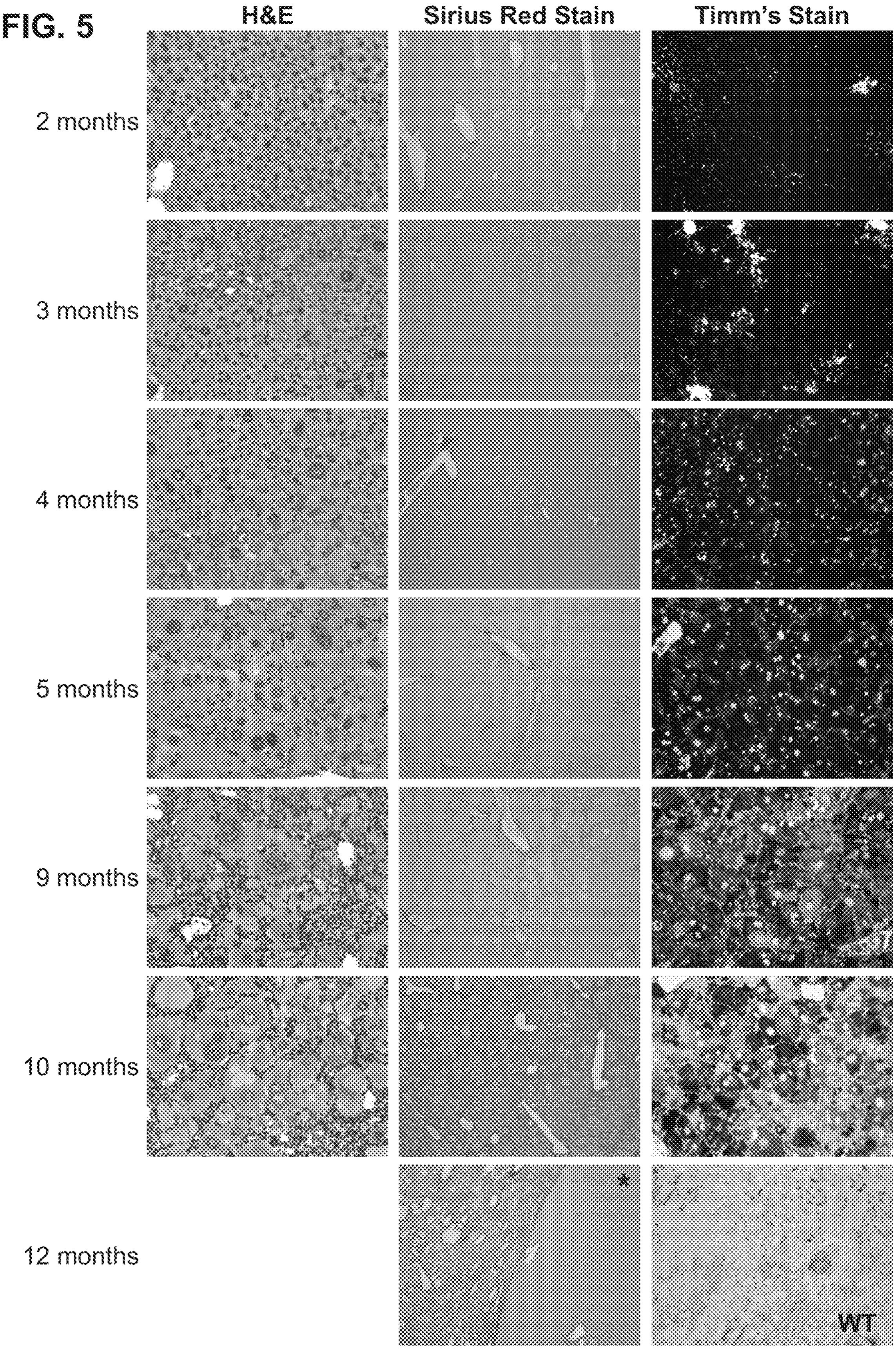

FIG. 5 demonstrates that liver disease develops over time in Atp7b KO mice. Atp7b KO mice were necropsied at 2, 3, 4, 5, 9, 10, and 12 months of age and liver was harvested to evaluate liver disease. H&E, Sirius Red, and Timm's stain were performed for histopathologic evaluation of liver lesions, including fibrosis, and copper accumulation. *, area of regeneration within the liver of a 12 month old Atp7b KO mouse. WT, section from a wild type mouse as a negative control for copper accumulation as seen by the Timm's stain.

Figure 6A:
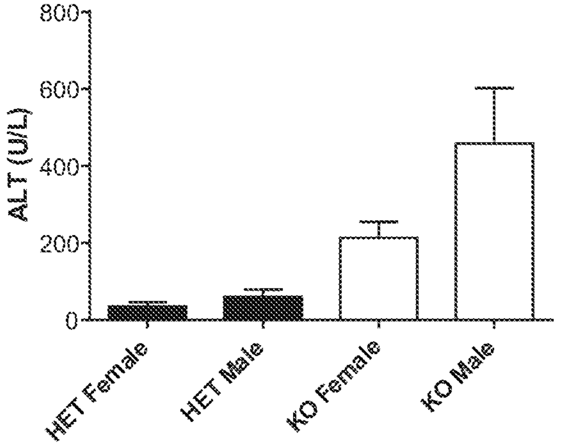
Figure 6B:
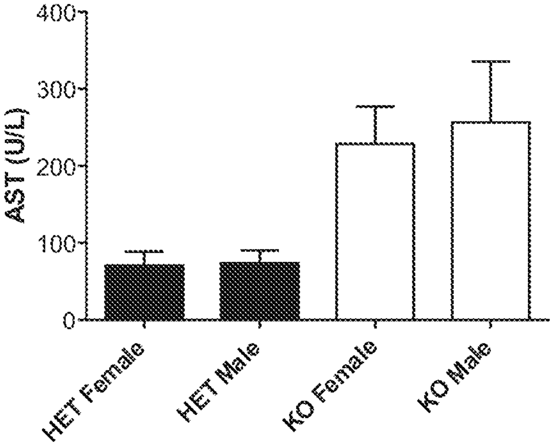
Figure 6C:
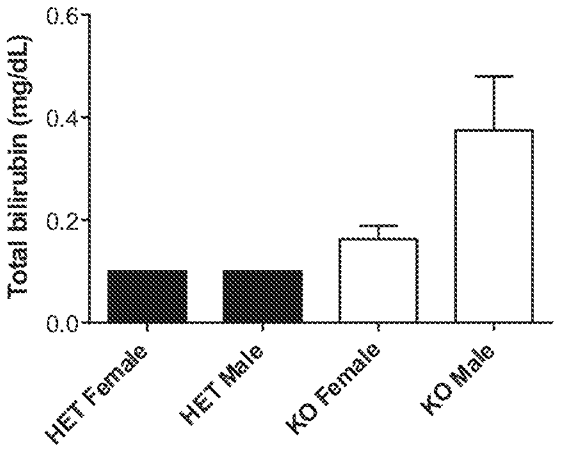

FIGS. 6A-6C demonstrate serum chemistry values in 8 month old Atp7b KO mice. (A) ALT, (B) AST, and (C) total bilirubin levels in 8 month old Atp7b KO mice (KO) and heterozygous mice (Het).

Figure 7:
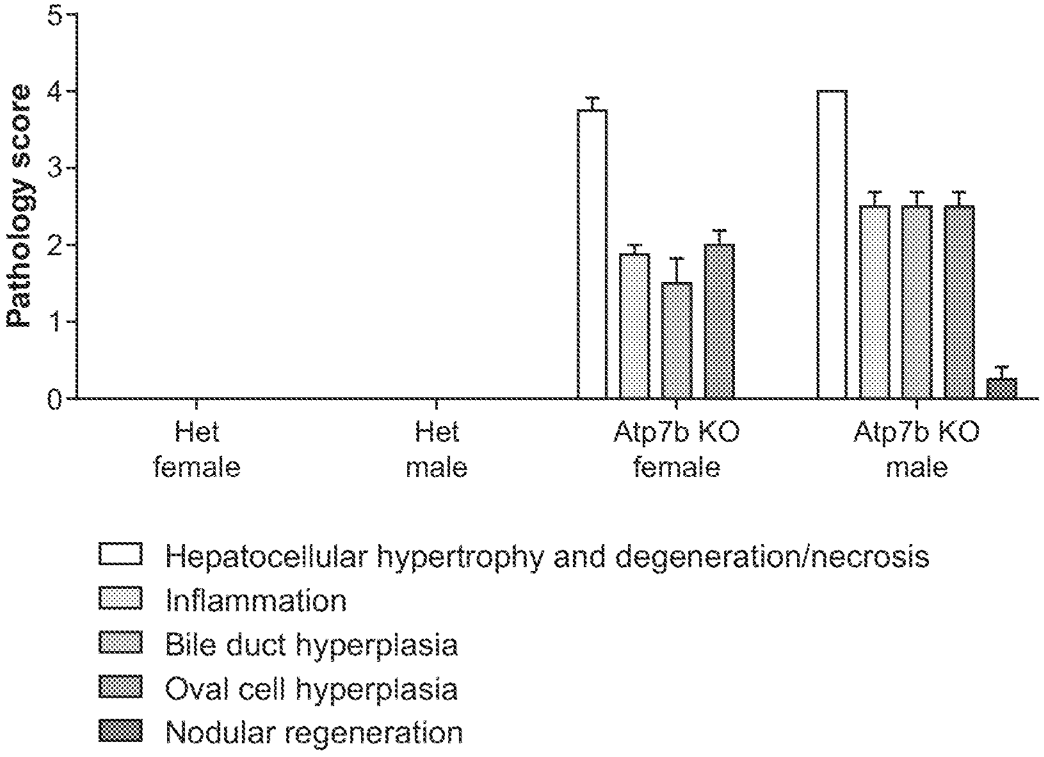

FIG. 7 demonstrates liver disease in 8 month old Atp7b KO mice. Atp7b KO and heterozygous (Het) mice were necropsied at 8 months of age. Liver was harvested, stained with H&E, and evaluated histologically according to the 1-5 scoring system. Values expressed as mean±SEM.

Figure 8A:
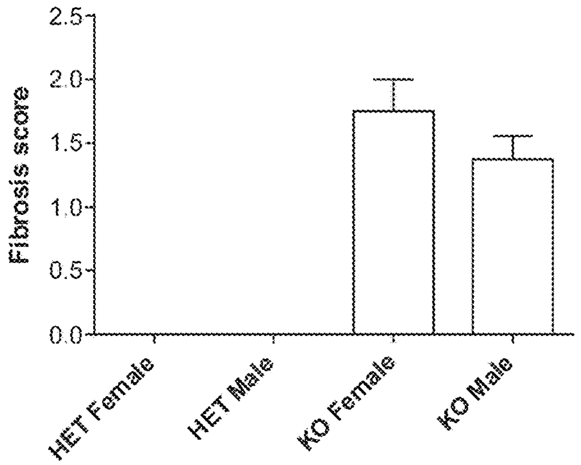
Figure 8B:
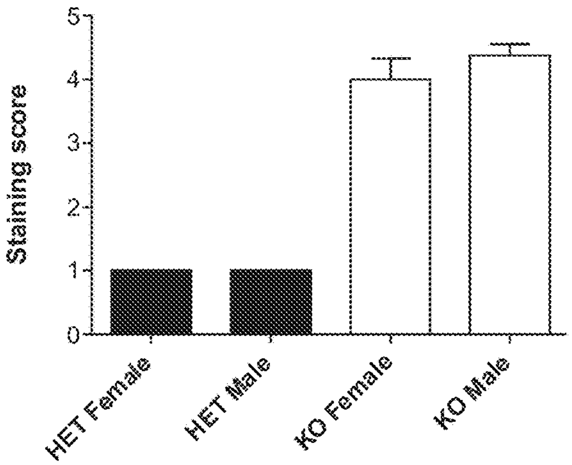

FIGS. 8A and 8B demonstrate liver fibrosis and copper accumulation in 8 month old Atp7b KO mice. Atp7b KO (KO) and heterozygous (Het) mice were necropsied at 8 months of age. Liver was harvested, stained with Sirius Red and Timm's stain for evaluation of fibrosis and copper accumulation, respectively. Histopathologic evaluation of liver lesions, including (A) fibrosis and (B) copper accumulation, was performed according to the 1-5 scoring system. Values expressed as mean±SEM.

Figure 9:
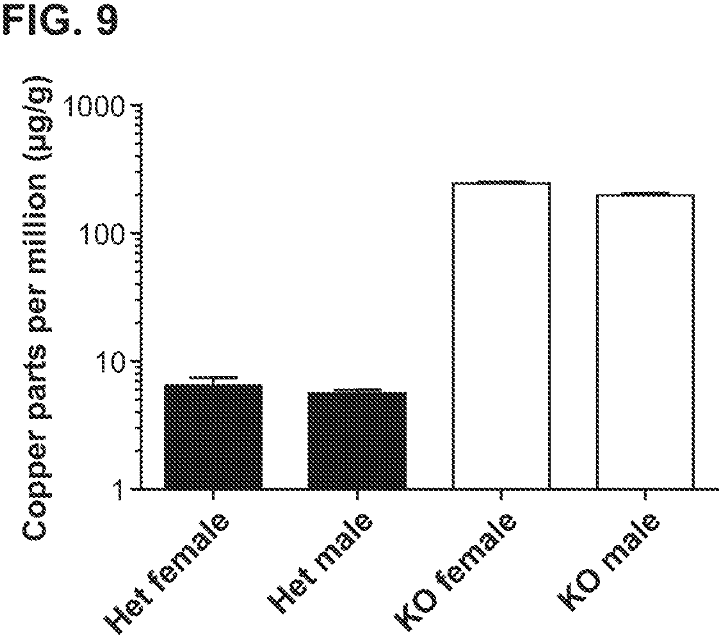

FIG. 9 demonstrates liver copper levels in 8 month old Atp7b KO mice Atp7b KO (KO) and heterozygous (Het) mice were necropsied at 8 months of age. Liver was harvested and liver copper levels were evaluated by inductively coupled plasma-mass spectrometry. Values expressed as mean±SEM.

Figure 10A:
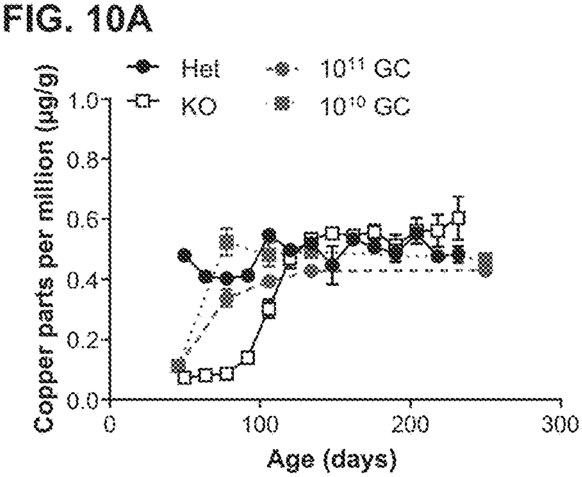
Figure 10B:
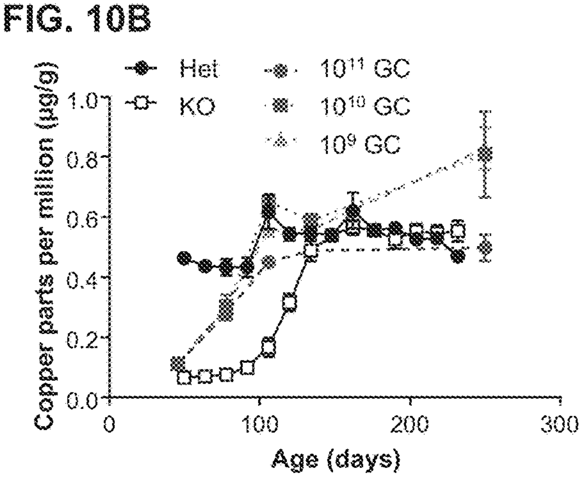
Figure 10C:
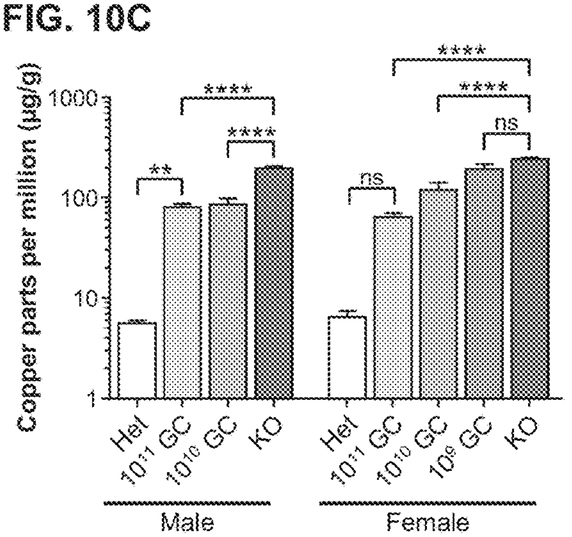

FIGS. 10A-10C demonstrates that AAV8 gene therapy can restore normal liver copper metabolism in Atp7b KO mice. Male Atp7b KO mice were injected i.v. with $10^{11}$ GC/mouse and $10^{10}$ GC/mouse of AAV8.TTR.hATP7Bco, and female Atp7b KO mice were injected i.v. with $10^{11}$, $10^{10}$, and $10^{9}$ GC/mouse of the same vector. Serum copper levels in (A) males and (B) females were evaluated by inductively coupled plasma-mass spectrometry and compared to serum copper levels from age-matched male and female heterozygous (het) and Atp7b KO mice. Mice were necropsied at 9 months of age and liver was harvested. (C) Liver copper levels were also evaluated by inductively coupled plasma-mass spectrometry and compared to age-matched uninjected heterozygous (het) and Atp7b KO mice. Values expressed as mean±SEM. ns, not significant;  $p<0.01$, ** $p<0.0001$.

Figure 11:
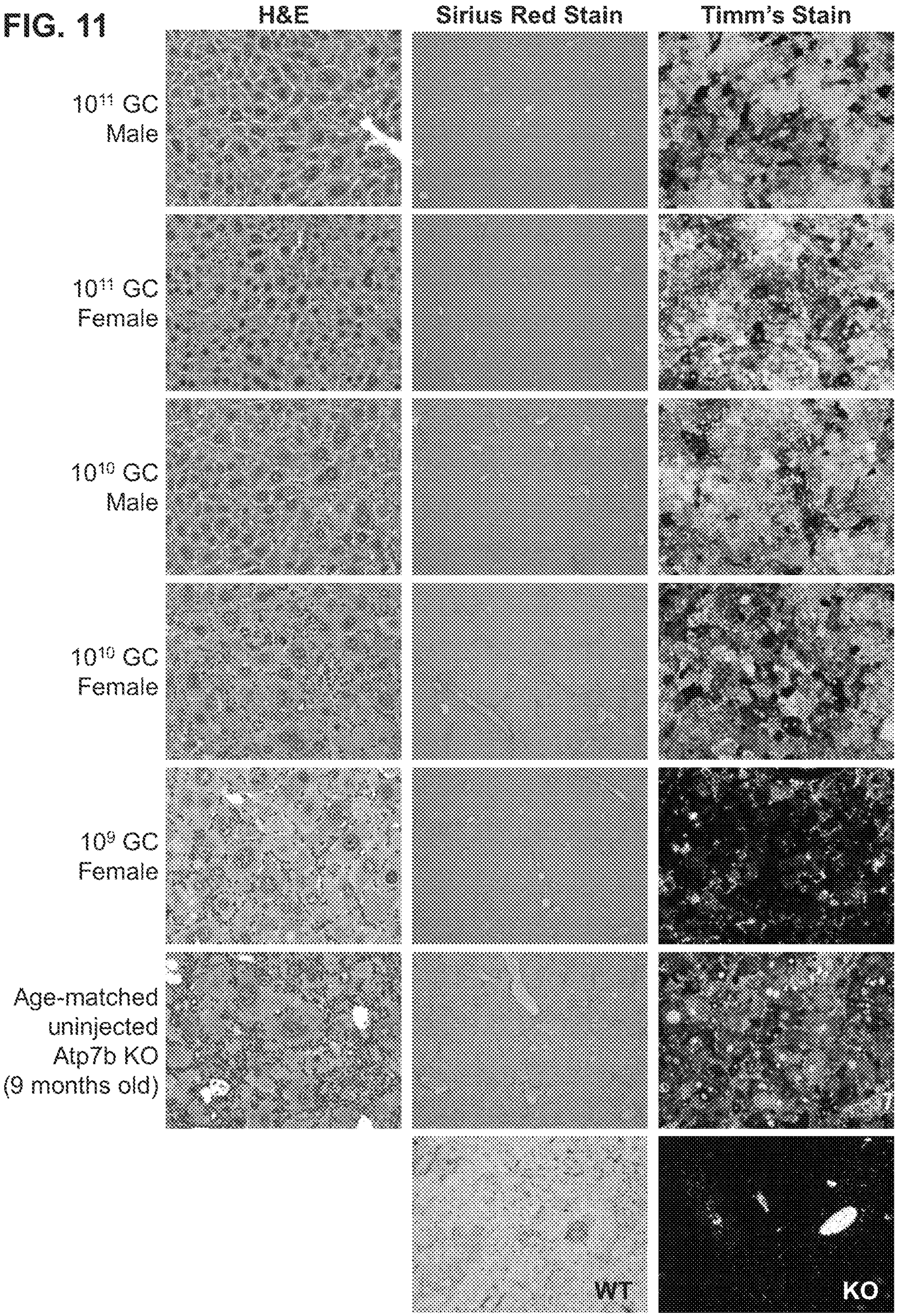

FIG. 11 demonstrates that high-dose AAV8 gene therapy prevents the development of liver disease in Atp7b KO mice. Male Atp7b KO mice were injected i.v. with $10^{11}$ GC/mouse and $10^{10}$ GC/mouse of AAV8.TTR.hATP7Bco, and female Atp7b KO mice were injected i.v. with $10^{11}$, $10^{10}$, and $10^{9}$ GC/mouse of the same vector. Mice were necropsied at 9 months of age and liver was harvested to evaluate liver disease. H&E, Sirius Red, and Timm's stain were performed to evaluate histopathological lesions of the liver, including, fibrosis and copper accumulation. Images from age-matched uninjected Atp7b KO mice are included for comparison (also presented in FIG. 2). WT, section from a wild type (WT) mouse as a negative control for copper accumulation as seen by the Timm's stain. KO, section from a two month old Atp7b KO mouse as a positive control for copper accumulation as seen by the Timm's stain.

Figure 12A:
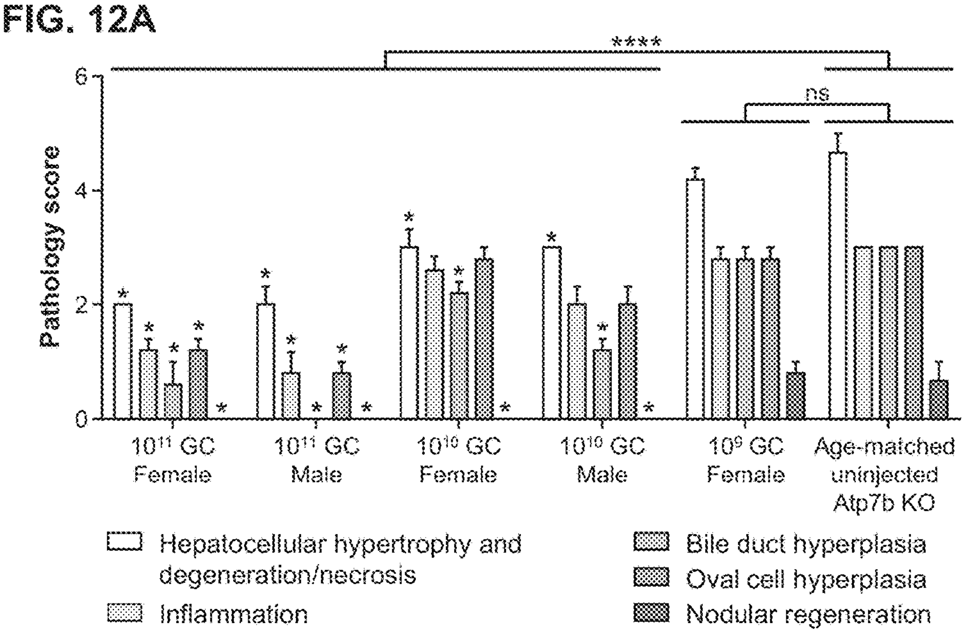
Figure 12B:
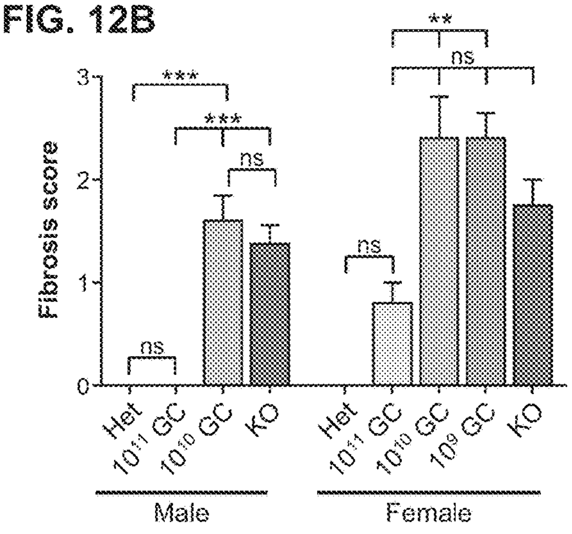
Figure 12C:
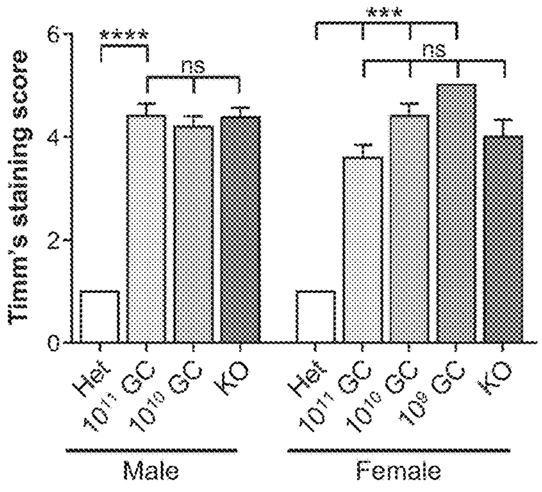

FIGS. 12A-12C demonstrates quantification of prevention of liver disease following high-dose AAV8 gene therapy in Atp7b KO mice. Male Atp7b KO mice were injected i.v. with $10^{11}$ GC/mouse and $10^{10}$ GC/mouse of AAV8.TTR.hATP7Bco and female Atp7b KO mice were injected i.v. with $10^{11}$, $10^{10}$, and $10^{9}$ GC/mouse of the same vector. Mice were necropsied at 9 months of age and liver was harvested for histologic to evaluation. (A) Liver sections were stained with H&E and evaluated histologically according to the 1-5 scoring system. (B) Liver sections were stained with Sirius Red and evaluated for fibrosis according to the 1-3 scoring system and (C) Timm's stain was performed on liver sections for evaluation of copper accumulation according to the 1-5 scoring system. Values expressed as mean±SEM were compared to age-matched uninjected heterozygous (Het) and Atp7b KO mice. ns, not significant; * $p<0.05$,  $p<0.01$, * $p<0.001$, **** $p<0.0001$.

Figure 13A:
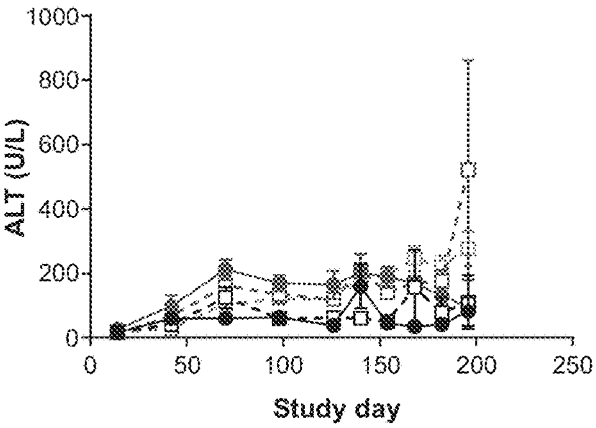
Figure 13B:
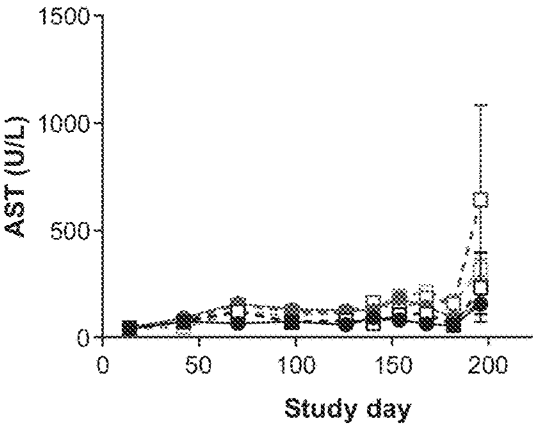
Figure 13C:
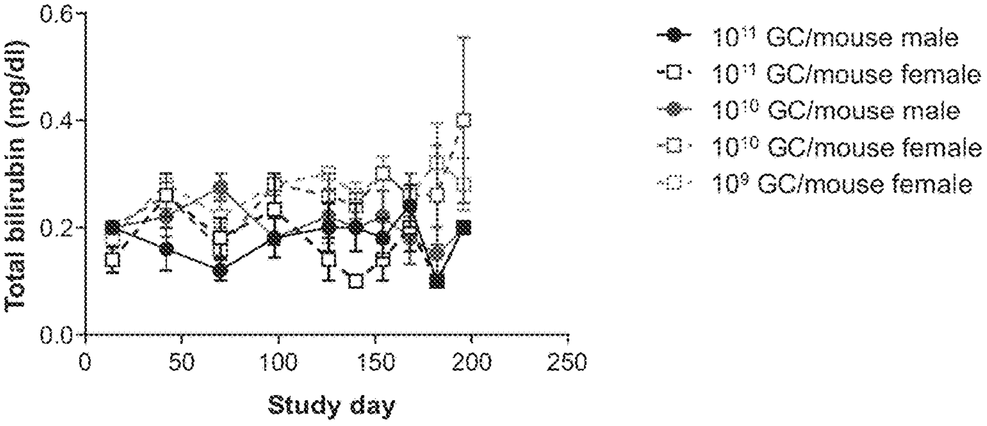

FIGS. 13A-13C demonstrate serum chemistry levels in Atp7b KO mice following AAV8 gene therapy. Male Atp7b KO mice were injected IV with $10^{11}$ GC/mouse and $10^{10}$ GC/mouse of AAV8.TTR.hATP7Bco and female Atp7b KO mice were injected i.v. with $10^{11}$, $10^{10}$, and $10^{9}$ GC/mouse of the same vector. (A) ALT, (B) AST, and (C) total bilirubin levels were evaluated in serum.

Figure 14:
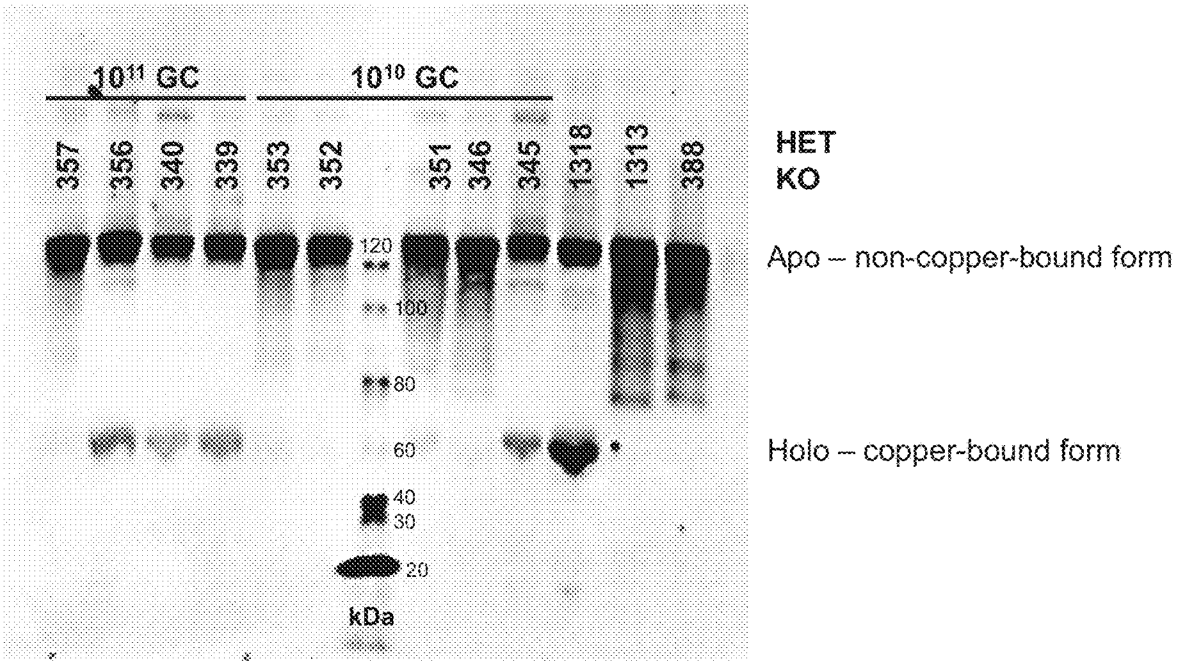

FIG. 14 demonstrates detection of ceruloplasmin by Western blot. Western blot detecting copper-bound (Holo, lower band) and non-copper-bound (Apo, upper band) forms of ceruloplasmin in Atp7b KO mice injected i.v. with $10^{10}$ or $10^{11}$ GC per mouse of AAV8.EnTTR.TTR.hATP7Bco.PA75. Blood samples were collected on Day 21 after the administration. Protein markers were provided in the center lane for comparison. Atp7b KO and heterozygous (het) littermates without vector injections served as controls (1318, 6 month old het; 1313, 6 month old Atp7b KO; 388, Atp7b KO).

Figure 15A:
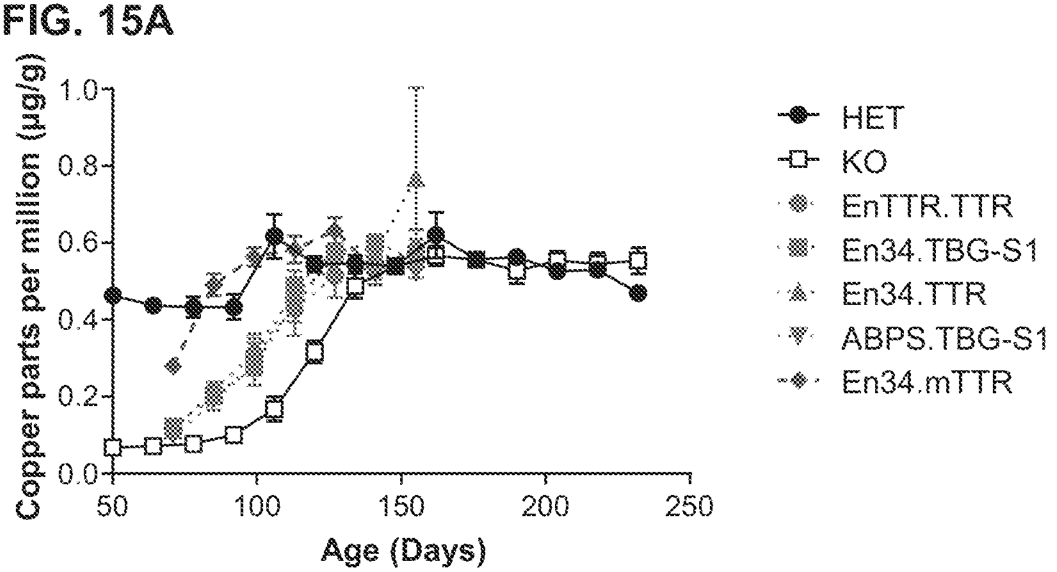
Figure 15B:
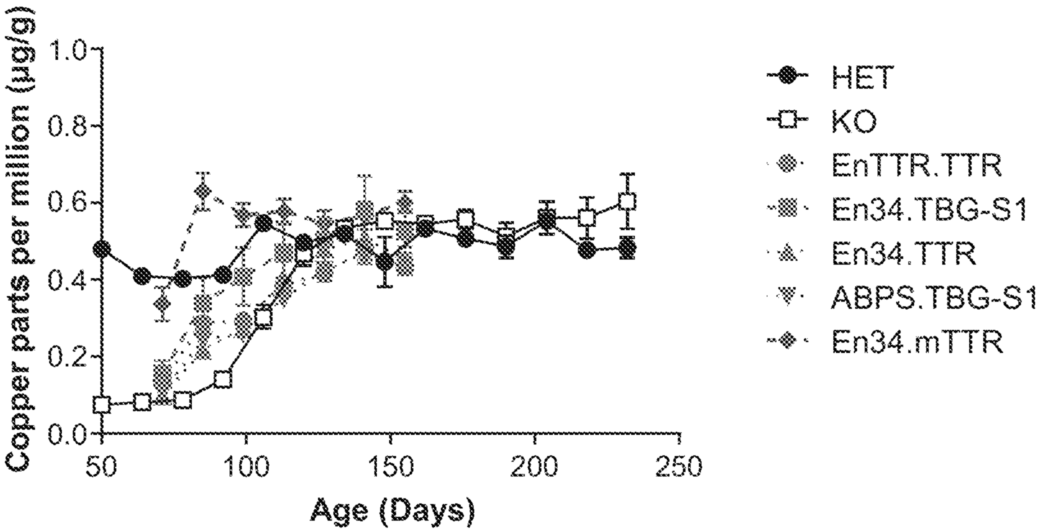

FIGS. 15A-15B demonstrates serum copper levels in female and male AAV8 vector administered Atp7b KO mice. Atp7b KO mice were administered i.v. with $3\times10^{12}$ GC/kg of AAV8 vectors for expression of hATP7Bco with different enhancer/promoter combinations (circles, EnTTR.TTR, AAV8.EnTTR.TTR.hATP7Bco.PA75; squares, En34.TBG-S1, AAV8.En34.TBG-S1.hATP7Bco.PA75; upright triangles, En34.TTR, AAV8.En34.TTR.hATP7Bco.PA75; inverted triangles, ABPS.TBG-S1, AAV8.ABPS.TBG-S1.hATP7Bco.PA75; diamonds, En34.mTTR, AAV8.En34.mTTR.hATP7Bco.PA75). Uninjected Atp7b KO and heterozygous (Het) mice served as controls. Serum copper levels were evaluated by inductively coupled plasma-mass spectrometry in (A) female and (B) male Atp7b KO mice. Values expressed as mean±SEM.

Figure 16A:
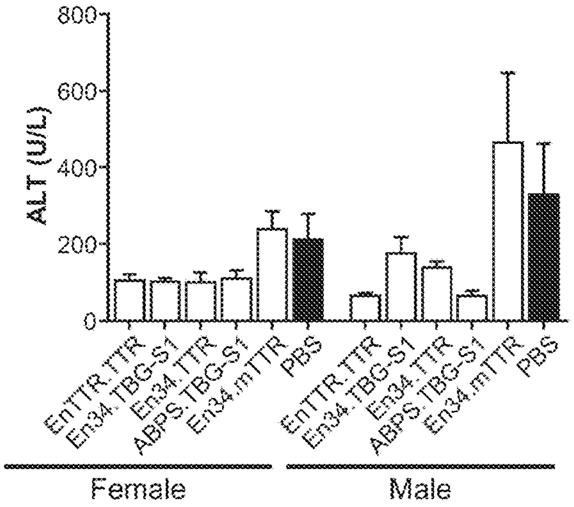
Figure 16B:
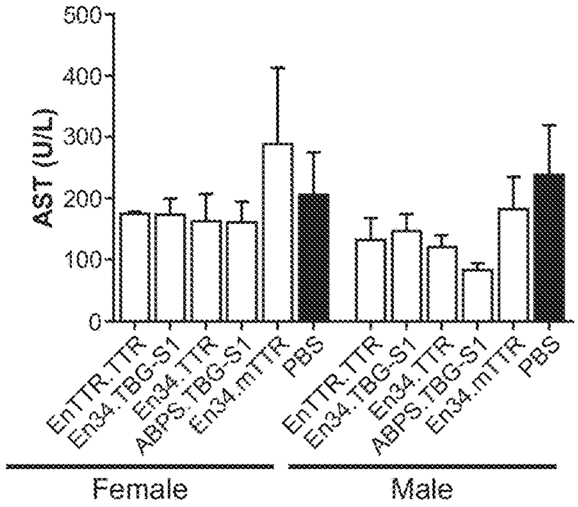
Figure 16C:
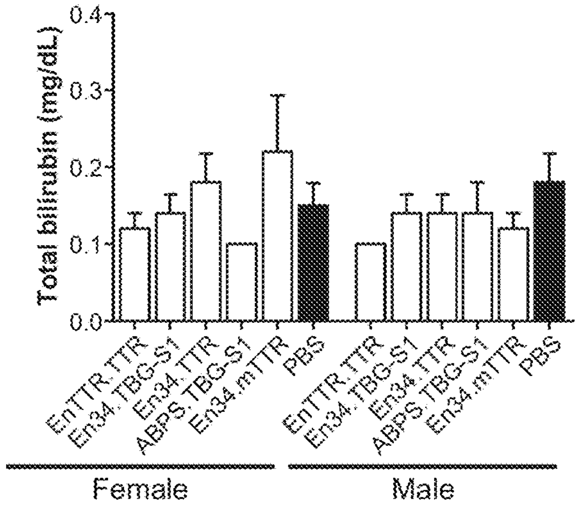

FIGS. 16A-16C demonstrates serum chemistries in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75). Vehicle control administered Atp7b KO (PBS) mice served as controls. (A) ALT, (B) AST, and (C) total bilirubin levels were evaluated in serum. Values expressed as mean±SEM.

Figure 17:
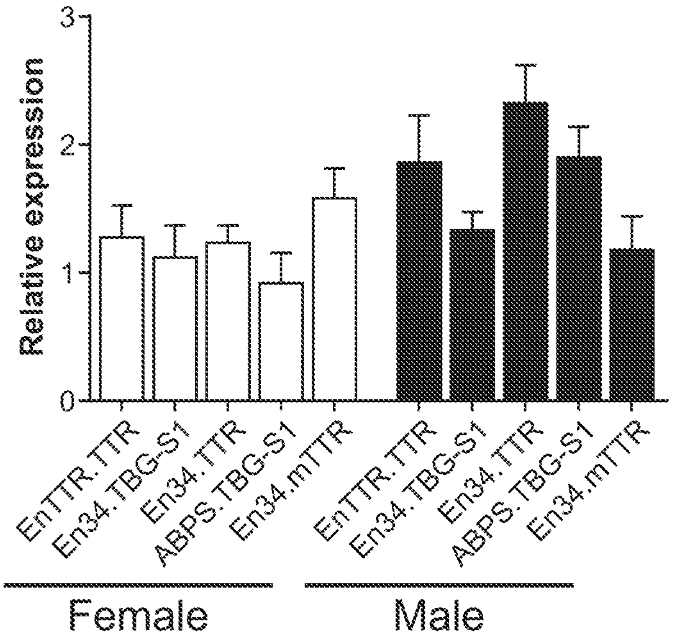

FIG. 17 demonstrates liver ATP7Bco expression determined by Western blot. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Western blot detecting ATP7B in Atp7b KO mice was quantified by band densitometry. Values expressed as mean±SEM.

Figure 18:
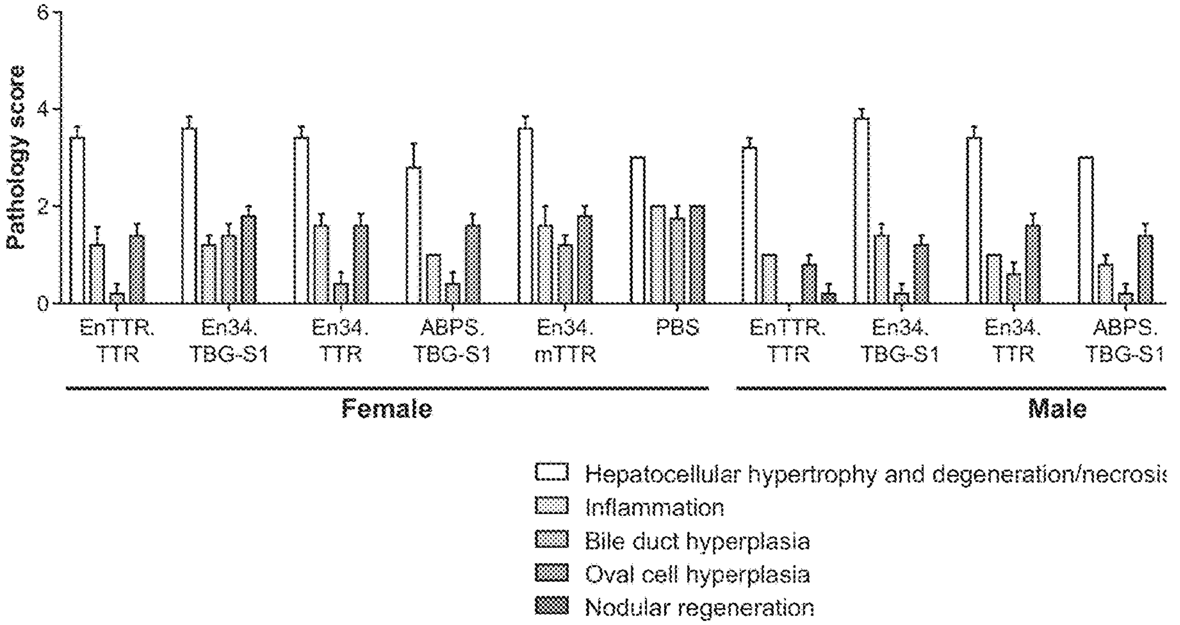

FIG. 18 demonstrates liver disease in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Vehicle control administered Atp7b KO (PBS) mice served as controls. Liver sections were stained with H&E and evaluated histologically according to the 1-5 scoring system. Values expressed as mean±SEM.

Figure 19A:
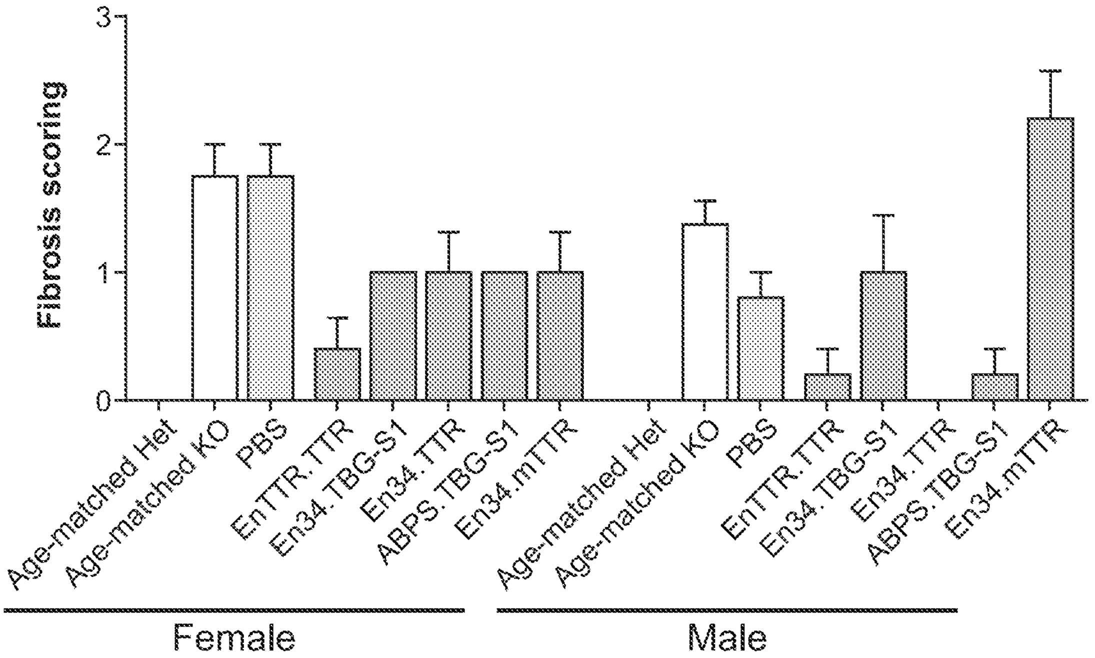
Figure 19B:
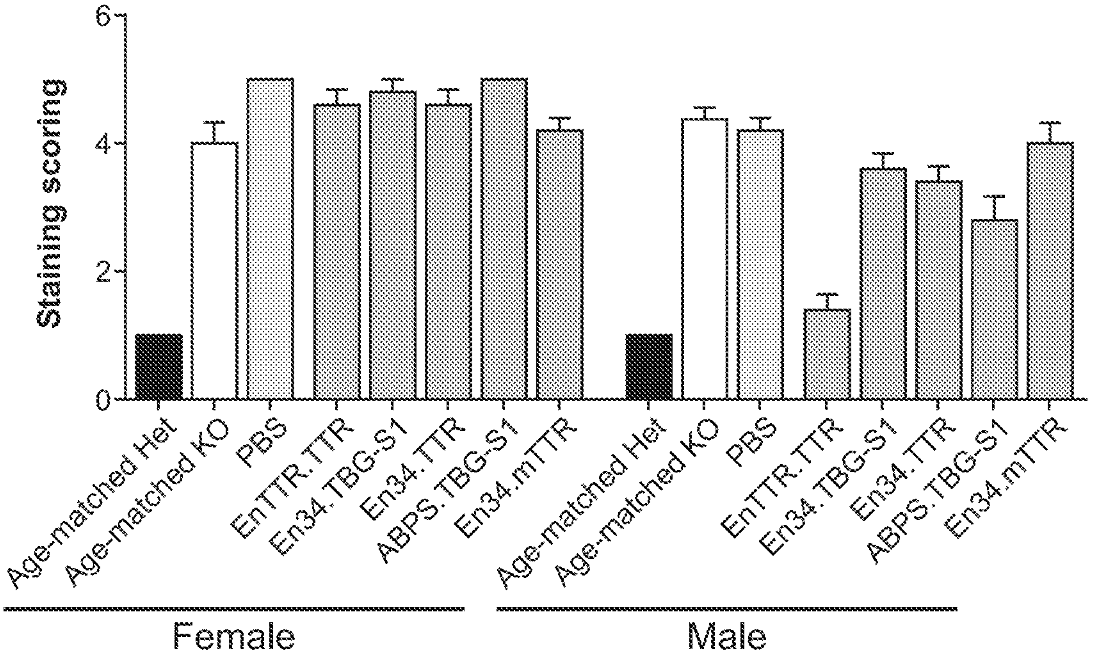

FIGS. 19A-19B demonstrate liver fibrosis and copper accumulation in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Vehicle control administered Atp7b KO (PBS) mice served as controls. (A) Liver sections were stained with Sirius Red and evaluated for fibrosis according to the 1-3 scoring system and (B) Timm's stain was performed on liver sections for evaluation of copper accumulation according to the 1-5 scoring system. Values expressed as mean±SEM were compared to age-matched uninjected heterozygous (Het) and Atp7b KO (KO) mice.

Figure 20:
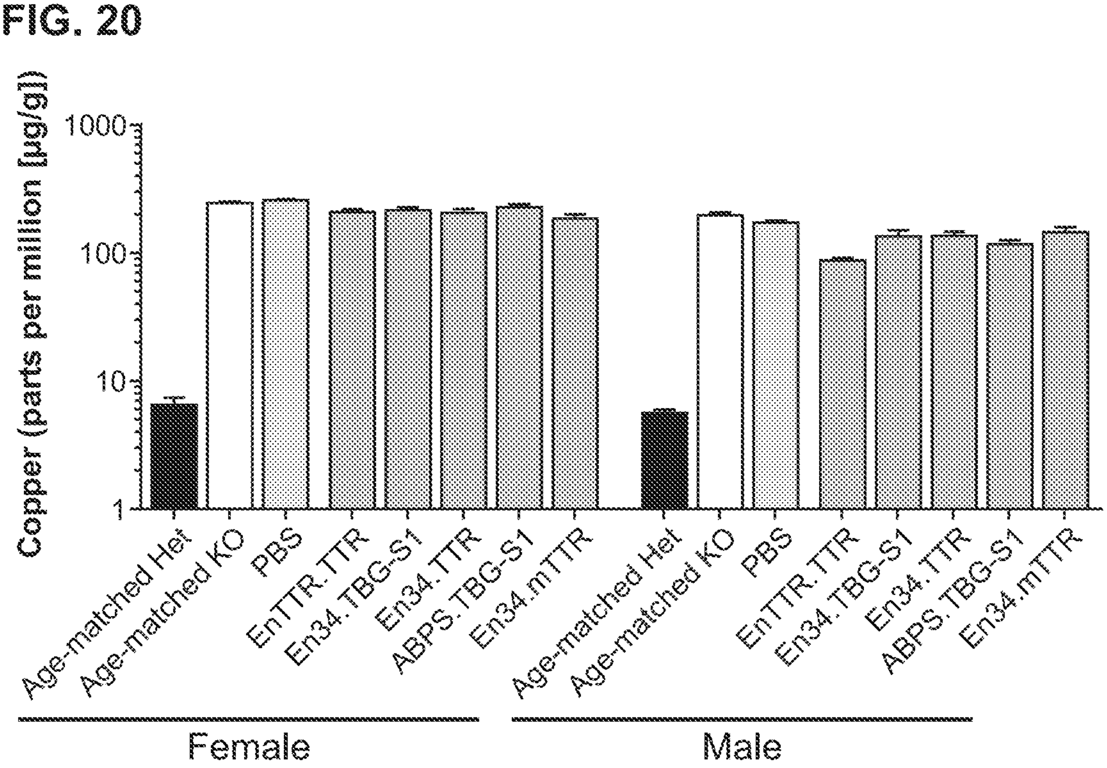

FIG. 20 demonstrates liver copper levels in female and male AAV8 vector administered Atp7b KO mice. Female and male Atp7b KO mice were administered i.v. with $3\times10^{12}$ GC/kg of AAV8 vectors for expression of hATP7Bco with different enhancer/promoter combinations (EnTTR.TTR, AAV8.EnTTR.TTR.hATP7Bco.PA75; En34.TBG-S1, AAV8.En34.TBG-S1.hATP7Bco.PA75; En34.TTR, AAV8.En34.TTR.hATP7Bco.PA75; ABPS.TBG-S1, AAV8.ABPS.TBG-S1.hATP7Bco.PA75; En34.mTTR, AAV8.En34.mTTR.hATP7Bco.PA75) and sacrificed at 6 months of age. Vehicle control administered Atp7b KO (PBS) mice served as controls. Liver copper levels were evaluated by inductively coupled plasma-mass spectrometry and compared to age-matched uninjected heterozygous (het) and Atp7b KO (KO) mice. Values expressed as mean±SEM.

Figure 21:
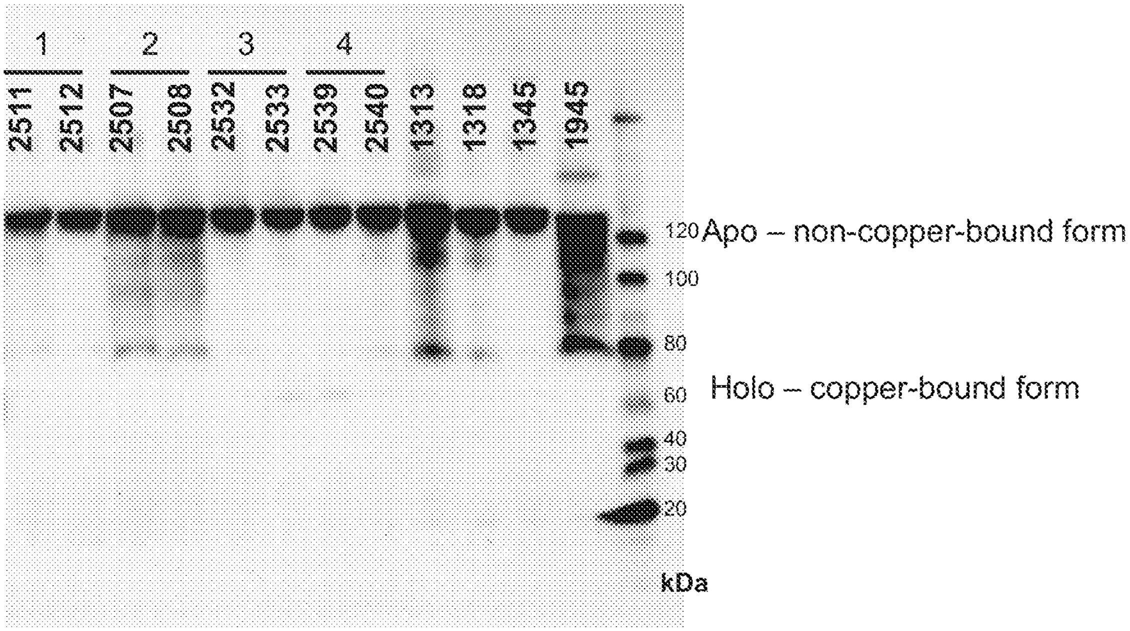

FIG. 21 demonstrates detection of ceruloplasmin by Western blot in male AAV8 vector administered Atp7b KO mice. Western blot detecting copper-bound (Holo, lower band) and non-copper-bound (Apo, upper band) forms of ceruloplasmin in male Atp7b KO mice were administered i.v. with $3\times10^{12}$ GC/kg of AAV8 vectors for expression of hATP7Bco with different enhancer/promoter combinations (1, AAV8.EnTTR.TTR.hATP7Bco.PA75; 2, AAV8.En34.TBG-S1.hATP7Bco.PA75; 3, AAV8.En34.TTR.hATP7Bco.PA75; 4, AAV8.ABPS.TBG-S1.hATP7Bco.PA75). Blood samples were collected on Day 21 after the administration. Protein markers were provided in the center lane for comparison. Atp7b KO, heterozygous (het), and wild type (WT) littermates without vector injections served as controls (1313, 6 month old Atp7b KO; 1318, 6 month old het; 1345, 2 month old Atp7b KO; 1945, WT).

Figure 22:
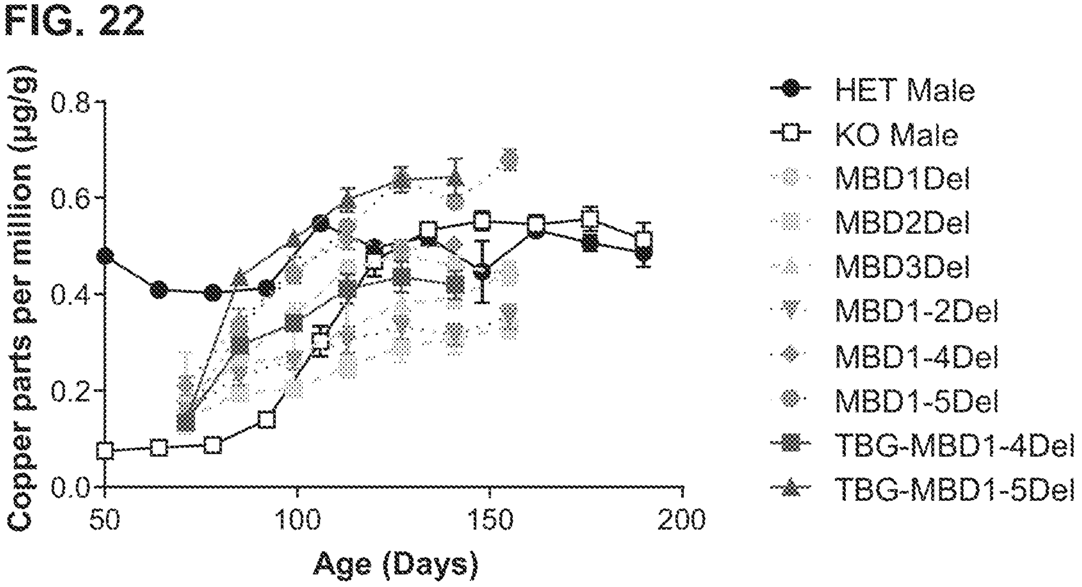

FIG. 22 demonstrates serum copper levels in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Serum copper levels were evaluated by inductively coupled plasma-mass spectrometry and compared to heterozygous (Het) and Atp7b KO mice (KO) over time. Values expressed as mean±SEM.

Figure 23A:
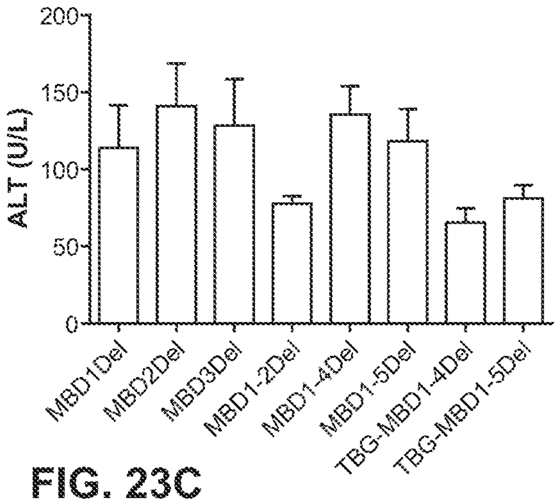
Figure 23B:
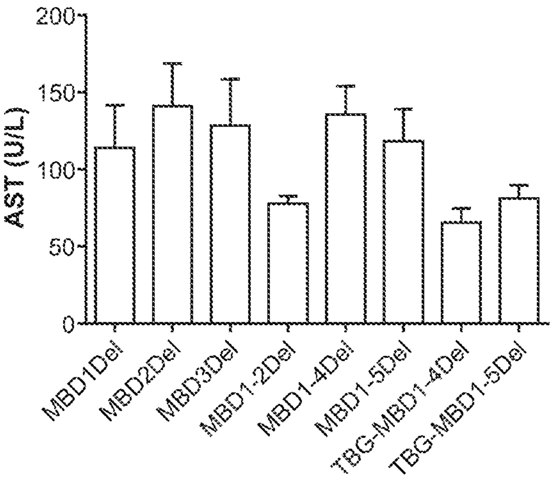
Figure 23C:
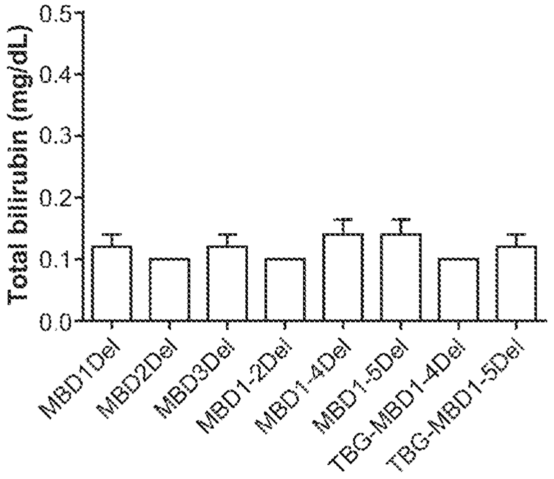

FIGS. 23A-23C demonstrates serum chemistries in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age and (A) ALT, (B) AST, and (C) total bilirubin levels were evaluated in serum. Values expressed as mean±SEM.

Figure 24:
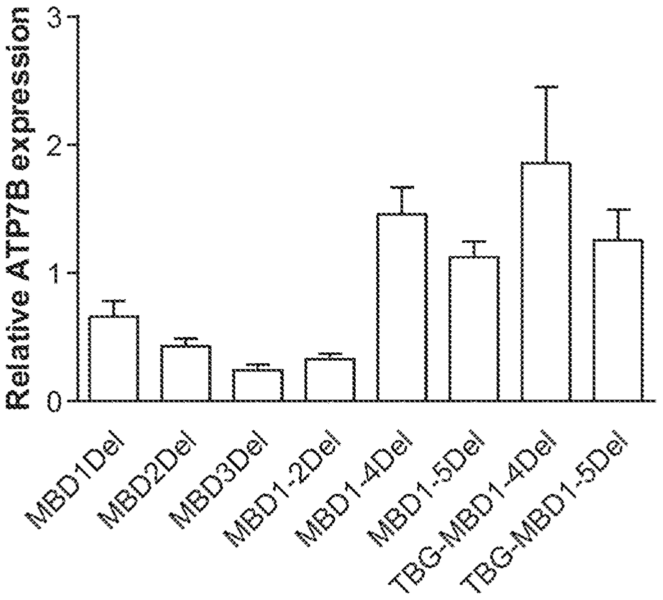

FIG. 24 demonstrates liver ATP7Bco expression determined by Western blot in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Western blot detecting ATP7B in Atp7b KO mice was quantified by band densitometry. Values expressed as mean±SEM.

Figure 25:
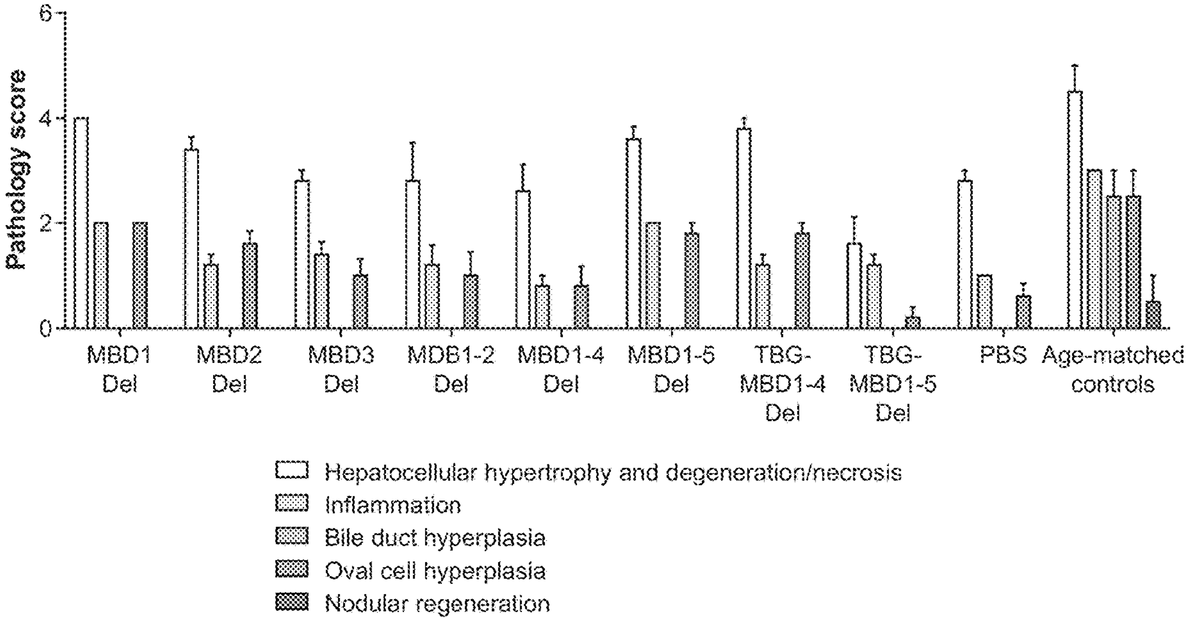

FIG. 25 demonstrates liver disease in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Vehicle control administered Atp7b KO (PBS) mice served as controls. Liver sections were stained with H&E and evaluated histologically according to the 1-5 scoring system. Values expressed as mean±SEM.

Figure 26A:
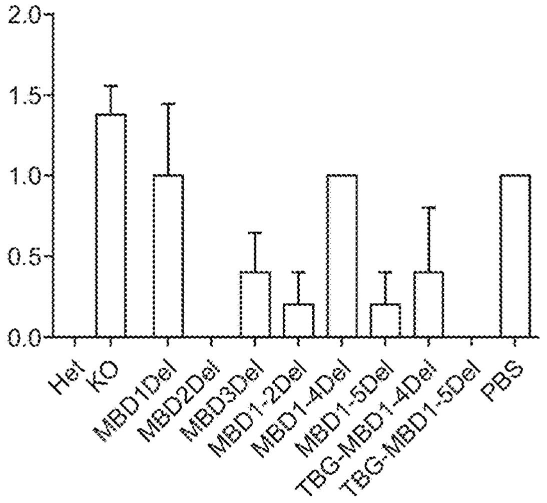
Figure 26B:
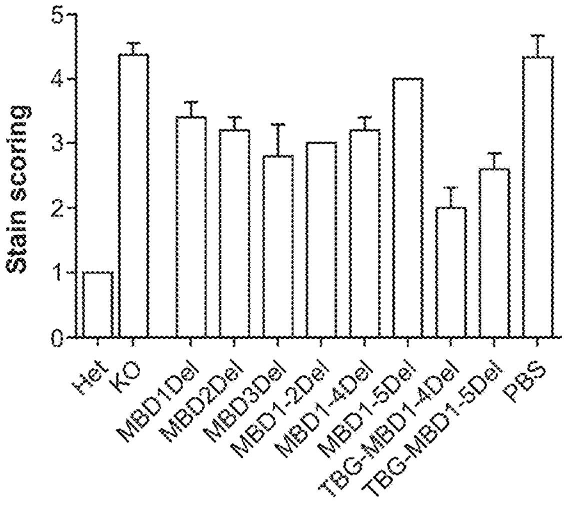

FIGS. 26A-26B demonstrate liver fibrosis and copper accumulation in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Vehicle control administered Atp7b KO (PBS) mice served as controls. (A) Liver sections were stained with Sirius Red and evaluated for fibrosis according to the 1-3 scoring system and (B) Timm's stain was performed on liver sections for evaluation of copper accumulation according to the 1-5 scoring system. Values expressed as mean±SEM were compared to age-matched uninjected heterozygous (Het) and Atp7b KO (KO) mice.

Figure 27:
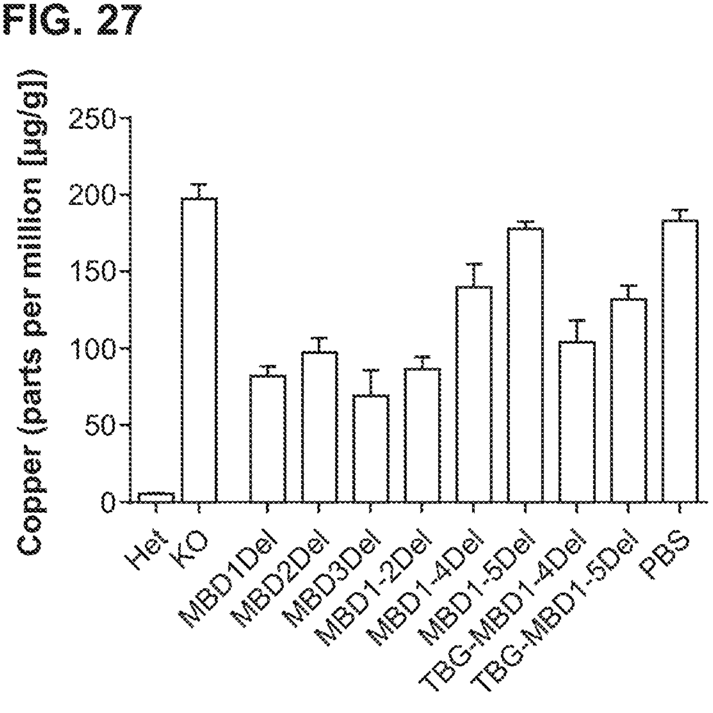

FIG. 27 demonstrates liver copper levels in male AAV8 truncated ATP7B vector administered Atp7b KO mice. Male Atp7b KO mice were administered i.v. with $3\times10^{12}$ GC/kg of AAV8 vectors for expression of different truncated versions of hATP7Bco (MBD1Del, AAV8.En34.TBG-S1.hATP7BcoMBD1Del.PA75; MBD2Del, AAV8.En34.TBG-S1.hATP7BcoMBD2Del.PA75; MBD3Del, AAV8.En34.TBG-S1.hATP7BcoMBD3Del.PA75; MBD1-2Del, AAV8.En34.TBG-S1.hATP7BcoMBD1-2Del.PA75; MBD1-4Del, AAV8.En34.TBG-S1.hATP7BcoMBD1-4Del.PA75; MBD1-5Del, AAV8.En34.TBG-S1.hATP7BcoMBD1-5Del.PA75; TBG-MBD1-4Del, AAV8.TBG.hATP7BcoMBD1-4Del.PA75; TBG-MBD1-5Del, AAV8.TBG.hATP7BcoMBD1-5Del.PA75). Mice were necropsied at 6 months of age. Vehicle control administered Atp7b KO (PBS) mice served as controls. Liver copper levels were evaluated by inductively coupled plasma-mass spectrometry and compared to age-matched uninjected heterozygous (het) and Atp7b KO (KO) mice. Values expressed as mean±SEM were compared to age-matched uninjected heterozygous (Het) and Atp7b KO (KO) mice.

4. DETAILED DESCRIPTION

The embodiments described in the application relate to the use of a replication deficient adeno-associated virus (AAV) to deliver a human copper-transporting ATPase 2 (ATP7B) gene to liver cells of patients (human subjects) diagnosed with Wilson's Disease (WD). The recombinant AAV vector (rAAV) used for delivering the hATP7B gene ("rAAV.hATP7B") should have a tropism for the liver (e.g., an rAAV bearing an AAV8 capsid), and the hATP7B transgene should be controlled by liver-specific expression control elements. In one embodiment, the expression control elements include one or more of the following: an enhancer; a promoter; an intron; a WPRE; and a polyA signal. Such elements are further described herein.

As used herein, "AAV8 capsid" refers to the AAV8 capsid having the amino acid sequence of GenBank, accession: YP_077180.1, SEQ ID NO: 16, which is incorporated by reference herein. Some variation from this encoded sequence is permitted, which may include sequences having about 99% identity to the referenced amino acid sequence in YP_077180.1 and WO 2003/052051 (which is incorporated herein by reference) (i.e., less than about 1% variation from the referenced sequence). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2015/0315612.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

5.1 Gene Therapy Vectors

In one aspect, a recombinant adeno-associated virus (rAAV) vector carrying the human ATP7B gene is provided for use in gene therapy. The rAAV.hATP7B vector should have a tropism for the liver (e.g., a rAAV bearing an AAV8 capsid) and the hATP7B transgene should be controlled by liver-specific expression control elements. The vector is formulated in a buffer/carrier suitable for infusion in human subjects. The buffer/carrier should include a component that prevents the rAAV from sticking to the infusion tubing but does not interfere with the rAAV binding activity in vivo.

5.1.1. The rAAV.hATP7B Vector 5.1.1.1. The hATP7B Sequence

Wilson's Disease is an inherited error of metabolism caused predominantly by mutations in the ATP7B gene, which encodes a copper-transporting P-type ATPase. ATP7B is responsible for transporting copper from intracellular chaperone proteins into the secretory pathway, both for excretion into bile and for incorporation into apo-ceruloplasmin for the synthesis of functional ceruloplasmin. The development of Wilson's disease is due to the accumulation of copper in affected tissues. See, EASL Clinical Practice Guidelines: Wilson's disease, EASL Journal of Hepatology, 2012, 56(671-85), which is incorporated herein by reference.

The clinical hallmark of Wilson's disease is the Kayser-Fleischer ring, which is present in 95% of patients with neurologic symptoms and somewhat over half of those without neurologic symptoms. Neurologic signs are variable, most often tremor, ataxia, and dystonia. Any type of liver disease may be encountered in patients with Wilson's disease. Clinically evident liver disease may precede neurologic manifestations by as much as 10 years and most patients with neurologic symptoms have some degree of liver disease at presentation. Presenting symptoms of liver disease can be highly variable, ranging from asymptomatic, with only biochemical abnormalities, to overt cirrhosis with all its complications. Wilson's disease may also present as acute hepatic failure sometimes associated with Coombs-negative hemolytic anemia and acute renal failure. The following table 1 provides a prognostic index in WD. (See, EASL Clinical Practice Guidelines: Wilson's disease, EASL Journal of Hepatology, 2012, 56(671-85), which is incorporated herein by reference.)

| | 1* | 2* | 3* | 4* |
|---|---|---|---|---|
| Serum bilirubin (μmol/L) | 100-150 | 151-200 | 201-300 | >300 |
| AST (U/L) | 100-150 | 151-300 | 301-400 | >400 |
| INR | 1.3-1.6 | 1.7-1.9 | 2.0-2.4 | >2.4 |
| WBC [$10^9$/L] | 6.8-8.3 | 8.4-10.3 | 10.4-15.3 | >15.3 |
| Albumin [g/L] | 34-44 | 25-33 | 21-24 | <21 |

*= score points, upper limit of normal for AST = 20 IU/ml (at King's College). A score ≥11 is associated with high probability of death without liver transplantation.

ATP7B has eight transmembrane domains that form a path through cell membranes for copper translocation; and a large N-terminus with six metal-binding domains (MBDs), each comprising approximately 70 amino acids and the highly conserved metal-binding motif GMxCxxC (where x is any amino acid). Other domains include the intramembrane CPC motif that is required for copper translocation through the membrane, the N-domain containing the ATP-binding site, the P-domain containing the conserved aspartic acid residue and the A-domain comprising the phosphatase domain. Various mutations in the hATP7B gene and/or resulting protein are known which are present in some or all patients with Wilson's Disease. A complete listing of the known mutations contributing to WB can be found at online at uniprot.org/uniprot/P35670, which is incorporated herein by reference. Further, in addition to the canonical sequence (also called isoform a, which is the longest isoform; NCBI Reference Sequence: NP_000044.2), four additional isoforms are known: NCBI Reference Sequences NP_001005918.1, NP_001230111.1, NP_001317507.1, NP_001317508.1, each of which is incorporated herein by reference. The compositions and methods described herein may be used to treat subjects having any ATP7B variant protein which causes disease.

In one embodiment, the hATP7B gene encodes the hATP7B protein shown in SEQ ID NO: 2. Thus, in one embodiment, the hATP7B transgene can include, but is not limited to, the sequence provided by SEQ ID NO:1 or SEQ ID NO: 3 which are provided in the attached Sequence Listing, which is incorporated by reference herein. SEQ ID NO: 3 provides the cDNA for native human ATP7B. SEQ ID NO: 1 provides an engineered cDNA for human ATP7B, which has been codon optimized for expression in humans (sometimes referred to herein as hATP7Bco). It is to be understood that reference to hATP7B herein may, in some embodiments, refer to the hATP7B native or codon optimized sequence, or any of the variants described herein. Alternatively or additionally, web-based or commercially available computer programs, as well as service based companies may be used to back translate the amino acid sequences to nucleic acid coding sequences, including both RNA and/or cDNA. See, e.g., backtranseq by EMBOSS, ebi.ac.uk/Tools/st/; Gene Infinity (geneinfinity.org/sms-/sms_backtranslation.html); ExPasy (expasy.org/tools/). It is intended that all nucleic acids encoding the described hATP7B polypeptide sequences are encompassed, including nucleic acid sequences which have been optimized for expression in the desired target subject (e.g., by codon optimization).

The native coding sequence of ATP7B is over 4.3 kb (SEQ ID NO: 3; Genbank Accession number XM_005266430), resulting in a 1465 amino acid protein (SEQ ID NO: 2). Due to the large size of ATP7B, and the packaging capacity of viral vectors, including the AAV vector, in some embodiments, it is desirable that the ATP7B coding sequence is shortened. It has been shown that deletion of the first 5 MBD showed a level of catalytic phosphorylation of the resulting protein consistent with wild type. See, Huster and Lutsenko, J. Biological Chem, June 2003, which is incorporated herein by reference. Thus, in one embodiment, the ATP7B coding sequence is shortened by deleting one or more MDB. In one embodiment, the ATP7B coding sequence has MBD1-2 deleted (e.g., as shown in SEQ ID NO: 17 and nt 403 to nt 4368 of SEQ ID NO: 35). In another embodiment, the ATP7B coding sequence has MBD1-3 deleted. In another embodiment, the ATP7B coding sequence has MBD1-4 deleted (e.g., as shown in SEQ ID NO: 18, and nt 403 to nt 3762 of SEQ ID NO: 34 and nt 1059 to nt 4418 of SEQ ID NO: 29). In another embodiment, the ATP7B coding sequence has MBD1-5 deleted (e.g., as shown in SEQ ID NO: 19, nt 403 to nt 3369 of SEQ ID NO: 33 and nt 1059 to nt 4025 of SEQ ID NO: 28). In another embodiment, the ATP7B coding sequence has MBD1 deleted (e.g., as shown in SEQ ID NO: 20 and nt 403 to nt 4686 of SEQ ID NO: 32). In another embodiment, the ATP7B coding sequence has MBD2 deleted (e.g., as shown in SEQ ID NO: 21 and nt 403 to nt 4617 of SEQ ID NO: 31). In another embodiment, the ATP7B coding sequence has MBD3 deleted (e.g., as shown in SEQ ID NO: 22 and nt 403 to nt 4719 of SEQ ID NO: 30). In another embodiment, the ATP7B coding sequence has MBD1-4 and 6 deleted (e.g., as described by Cater et al, Biochem J. 2004 Jun. 15; 380(Pt 3): 805-813, which is incorporated herein by reference). See also, Gourdon et al, Biol Chem. 2012 April; 393(4):205-16; Lutsenko, S., et al. (2007). "Function and regulation of human copper-transporting ATPases." Physiological reviews 87(3): 1011-1046; Safaei, R., et al. (2013). "The role of metal binding and phosphorylation domains in the regulation of cisplatin-induced trafficking of ATP7B." Metallomics 5(8): 964-972; and US Patent Publication No. 2015/0045284, each of which is incorporated herein by reference.

In one embodiment, the nucleic acid sequence encoding hATP7B shares at least 95% identity with the native hATP7B coding sequence of SEQ ID NO: 3 or SEQ ID NO: 1, or any of the variants shown in SEQ ID NO: 17, SEQ ID NO: 18, SEQ ID NO: 19, SEQ ID NO: 20, SEQ ID NO: 21, or SEQ ID NO: 22. In another embodiment, the nucleic acid sequence encoding hATP7B shares at least 90, 85, 80, 75, 70, or 65% identity with the native hATP7B coding sequence of SEQ ID NO: 3 or SEQ ID NO: 1, or any of the variants shown in SEQ ID NO: 17, SEQ ID NO: 18, SEQ ID NO: 19, SEQ ID NO: 20, SEQ ID NO: 21, or SEQ ID NO: 22. In one embodiment, the nucleic acid sequence encoding hATP7B shares about 79% identity with the native hATP7B coding sequence of SEQ ID NO: 3 or SEQ ID NO: 1, or any of the variants shown in SEQ ID NO: 17, SEQ ID NO: 18, SEQ ID NO: 19, SEQ ID NO: 20, SEQ ID NO: 21, or SEQ ID NO: 22. In one embodiment, the nucleic acid sequence encoding hATP7B is SEQ ID NO: 1. In another embodiment, the nucleic acid sequence encoding hATP7B is SEQ ID NO: 17. In another embodiment, the nucleic acid sequence encoding hATP7B is SEQ ID NO: 18. In another embodiment, the nucleic acid sequence encoding hATP7B is SEQ ID NO: 19. In another embodiment, the nucleic acid sequence encoding hATP7B is SEQ ID NO: 20. In another embodiment, the nucleic acid sequence encoding hATP7B is SEQ ID NO: 21. In another embodiment, the nucleic acid sequence encoding hATP7B is SEQ ID NO: 22.

Codon-optimized coding regions can be designed by various different methods. This optimization may be performed using methods which are available on-line (e.g., GeneArt,), published methods, or a company which provides codon optimizing services, e.g., as DNA2.0 (Menlo Park, CA). One codon optimizing approach is described, e.g., in International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Thermo Fisher Scientific Inc. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The goal of therapies described herein would provide functional ATP7B enzyme resulting in a reduction of serum copper levels of 25% or more. In one embodiment, urinary copper excretion of 3-8 μmol or less per 24 hours is desirable.

Primary/secondary goals of the therapies described herein include, without limitation:

Normalization of serum non-ceruloplasmin bound copper (NCC) (<150 microg/L)

Normalization of serum aminotransferase (liver biochemistries, ALT/AST)

Normalization of urinary Cu (<40 microg/24 hours (0.6 micromol/24 hours)ULN)

Normalization of serum ceruloplasmin (>200 mg/L) [can be inconsistent]

Improvement of Clinician Global Impression (CGI) scale [1: severity & 2: global improvement)

Incidence of AEs

Exploratory:

$^{65}$Cu, a nonradioactive isotope for copper which can be detected by mass spec Improvement in IQ, neurocognitive and psychiatric functions (Unified Wilson's Disease Rating Scale (UWDRS) & Mini International Neuropsychiatric Interview (M.I.N.I.)); and PROs (EQ5D, MMAS-8, TSQM)

In one embodiment, the "subject" or "patient" is a mammalian subject having WD as described above. It is intended that a patient having WD of any severity is the intended subject.

5.1.1.2. The rAAV Vector

Because ATP7B is natively expressed in the liver, it is desirable to use an AAV which shows tropism for liver. In one embodiment, the AAV supplying the capsid is AAV8. In another embodiment, the AAV supplying the capsid is AAVrh.10. In yet another embodiment, the AAV supplying the capsid is a Clade E AAV. Such AAV include rh.2; rh.10; rh. 25; bb.1, bb.2, pi.1, pi.2, pi.3, rh.38, rh.40, rh.43, rh.49, rh.50, rh.51, rh.52, rh.53, rh.57, rh.58, rh.61, rh.64, hu.6, hu.17, hu.37, hu.39, hu.40, hu.41, hu.42, hu.66, and hu.67. This clade further includes modified rh. 2; modified rh. 58; and modified rh.64. See, WO 2005/033321, which is incorporated herein by reference. However, any of a number of rAAV vectors with liver tropism can be used.

In a specific embodiment described in the Examples, infra, the gene therapy vector is an AAV8 vector expressing an hATP7B transgene under control of a thyroxine binding globulin (TBG-S1) promoter referred to as AAV8.En34.TBG-S1.hATP7Bco.PA75. The external AAV vector component is a serotype 8, T=1 icosahedral capsid consisting of 60 copies of three AAV viral proteins, VP1, VP2, and VP3, at a ratio of 1:1:10. The capsid contains a single-stranded DNA rAAV vector genome.

In one embodiment, the rAAV.hATP7B genome contains an hATP7B transgene flanked by two AAV inverted terminal repeats (ITRs). In one embodiment, the hATP7B transgene includes one or more of an enhancer, promoter, an hATP7B coding sequence, and polyadenylation (polyA) signal. These control sequences are "operably linked" to the hATP7B gene sequences. The expression cassette containing these sequences may be engineered onto a plasmid which is used for production of a viral vector.

The ITRs are the genetic elements responsible for the replication and packaging of the genome during vector production and are the only viral cis elements required to generate rAAV. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hATP7B coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. In one embodiment, the 5' ITR is that shown in SEQ ID NO: 14. In one embodiment, the 3' ITR is that shown in SEQ ID NO: 15.

In one embodiment, the expression control sequences include one or more enhancer. In one embodiment, the En34 enhancer is included (34 bp core enhancer from the human apolipoprotein hepatic control region), which is shown in SEQ ID NO: 4. In another embodiment, the EnTTR (100 bp enhancer sequence from transthyretin) is included. Such sequence is shown in SEQ ID NO: 5. See, Wu et al, Molecular Therapy, 16(2):280-289, February 2008, which is incorporated herein by reference. In yet another embodiment, the α1-microglobulin/bikunin precursor enhancer is included. In yet another embodiment, the ABPS (shortened version of the 100 bp distal enhancer from the α1-microglobulin/bikunin precursor [ABP] to 42 bp) enhancer is included. Such sequence is shown in SEQ ID NO: 6. In yet another embodiment, the ApoE enhancer is included. Such sequence is shown in SEQ ID NO: 7. In another embodiment, more than one enhancer is present. Such combination may include more than one copy of any of the enhancers described herein, and/or more than one type of enhancer.

Expression of the hATP7B coding sequence is driven from a liver-specific promoter. Because of the size of the ATP7B transgene, the use of promoter of relatively small size is desirable. An illustrative plasmid and vector described herein uses the modified thyroxine binding globulin (TBG-S1) promoter (SEQ ID NO: 8). In another embodiment, the TBG promoter is used. The TBG promoter sequence is shown in SEQ ID NO: 9. Alternatively, other liver-specific promoters may be used such as the transthyretin promoter (TTR promoter), as shown in SEQ ID NO: 11, or a modified transthyretin promoter (mTTR promoter), as shown in nt 21 to nt 190 of SEQ ID NO: 11. Another suitable promoter is the alpha 1 anti-trypsin (A1AT), or a modified version thereof (which sequence is shown in SEQ ID NO: 10. Various promoter and enhancer combinations are discussed in the examples below.

Other suitable promoters include human albumin (Miyatake et al., J. Virol., 71:5124 32 (1997)), humAlb; the Liver Specific promoter (LSP), and hepatitis B virus core promoter, (Sandig et al., Gene Ther., 3:1002-9 (1996). See, e.g., The Liver Specific Gene Promoter Database, Cold Spring Harbor, rulai.schl.edu/LSPDrulai.schl.edu/LSPD, which is incorporated by reference. Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, and efficient RNA processing signals. Such sequences include splicing and polyadenylation (polyA) signals; regulatory elements that enhance expression (e.g., WPRE); sequences that stabilize cytoplasmic mRNA; sequences that enhance translation efficiency (i.e., Kozak consensus sequence); sequences that enhance protein stability; and when desired, sequences that enhance secretion of the encoded product. In one embodiment, a KOZAK sequence is included. In one embodiment, a polyadenylation (polyA) signal is included to mediate termination of hATP7B mRNA transcripts. A polyA signal useful herein is an artificial polyA which is about 75 bp in size (PA75) shown in SEQ ID NO: 13. Examples of other suitable polyA sequences include, e.g., bovine growth hormone (SEQ ID NO: 12), SV40, rabbit beta globin, and TK polyA, amongst others.

In one embodiment, the regulatory sequences are selected such that the total rAAV vector genome is about 3.0 to about 5.5 kilobases in size. In one embodiment, it is desirable that the rAAV vector genome approximate the size of the native AAV genome. Thus, in one embodiment, the regulatory sequences are selected such that the total rAAV vector genome is about 4.7 kb in size. In another embodiment, the total rAAV vector genome is less about 5.2 kb in size. In a further embodiment, the total rAAV vector genome is about 5.1 kb or about 5.0 kb in size. The size of the vector genome may be manipulated based on the size of the regulatory sequences including the promoter, enhancer, intron, poly A, etc. See, Wu et al, Mol Ther, January 2010 18(1):80-6, which is incorporated herein by reference.

In one embodiment, the rAAV vector genome comprises nt 1 to nt 5134 of SEQ ID NO: 23, nt 1 to nt 5056 of SEQ ID NO: 24, nt 1 to nt 5064 of SEQ ID NO: 25, nt 1 to nt 5068 of SEQ ID NO: 26, nt 1 to nt 5048 of SEQ ID NO: 27, nt 1 to nt 4284 of SEQ ID NO: 28, nt 1 to nt 4677 of SEQ ID NO: 29, nt 1 to nt 4978 of SEQ ID NO: 30, nt 1 to nt 4876 of SEQ ID NO: 31, nt 1 to nt 4945 of SEQ ID NO: 32, nt 1 to nt 3628 of SEQ ID NO: 33, nt 1 to nt 4021 of SEQ ID NO: 34, or nt 1 to nt 4627 of SEQ ID NO: 35.

Exemplary production plasmids to generate rAAVs are shown in SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, and SEQ ID NO: 35.

5.1.2. Compositions

In one embodiment, the rAAV.hATP7B virus is provided in a pharmaceutical composition which comprises an aqueous carrier, excipient, diluent or buffer. In one embodiment, the buffer is PBS. In a specific embodiment, the rAAV.hATP7B formulation is a suspension containing an effective amount of rAAV.hATP7B vector suspended in an aqueous solution containing 0.001% Pluronic F-68 in TMN200 (200 mM sodium chloride, 1 mM magnesium chloride, 20 mM Tris, pH 8.0). However, various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

For example, a suspension as provided herein may contain both NaCl and KCl. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene (poly (propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits ×100 give the approximate molecular mass of the polyoxypropylene core, and the last digit ×10 gives the percentage polyoxyethylene content. In one embodiment Poloxamer 188 is selected. The surfactant may be present in an amount up to about 0.0005% to about 0.001% of the suspension. In another embodiment, the vector is suspended in an aqueous solution containing 180 mM sodium chloride, 10 mM sodium phosphate, 0.001% Poloxamer 188, pH 7.3.

In one embodiment, the formulation is suitable for use in human subjects and is administered intravenously. In one embodiment, the formulation is delivered via a peripheral vein by bolus injection. In one embodiment, the formulation is delivered via a peripheral vein by infusion over about 10 minutes (±5 minutes). In one embodiment, the formulation is delivered via a peripheral vein by infusion over about 20 minutes (±5 minutes). In one embodiment, the formulation is delivered via a peripheral vein by infusion over about 30 minutes (+5 minutes). In one embodiment, the formulation is delivered via a peripheral vein by infusion over about 60 minutes (+5 minutes). In one embodiment, the formulation is delivered via a peripheral vein by infusion over about 90 minutes (+10 minutes). However, this time may be adjusted as needed or desired. Any suitable method or route can be used to administer an AAV-containing composition as described herein, and optionally, to co-administer other active drugs or therapies in conjunction with the AAV-mediated delivery of hATP7B described herein. Routes of administration include, for example, systemic, oral, inhalation, intranasal, intratracheal, intraarterial, intraocular, intravenous, intramuscular, subcutaneous, intradermal, and other parental routes of administration.

In one embodiment, the formulation may contain, e.g., about $1.0\times10^{11}$ genome copies per kilogram of patient body weight (GC/kg) to about $1\times10^{14}$ GC/kg, about $5\times10^{11}$ genome copies per kilogram of patient body weight (GC/kg) to about $3\times10^{13}$ GC/kg, or about $1\times10^{12}$ to about $1\times10^{14}$ GC/kg, as measured by oqPCR or digital droplet PCR (ddPCR) as described in, e.g., M. Lock et al, Hum Gene Ther Methods. 2014 April; 25(2):115-25. doi: 10.1089/hgtb.2013.131. Epub 2014 Feb. 14, which is incorporated herein by reference. In one embodiment, the rAAV.hATP7B formulation is a suspension containing at least $1\times10^{13}$ genome copies (GC)/mL, or greater, as measured by oqPCR or digital droplet PCR (ddPCR) as described in, e.g., M. Lock et al, supra.

In order to ensure that empty capsids are removed from the dose of AAV.hATP7B that is administered to patients, empty capsids are separated from vector particles during the vector purification process, e.g., using the method discussed herein. In one embodiment, the vector particles containing packaged genomes are purified from empty capsids using the process described in WO 2017/100676 and entitled "Scalable Purification Method for AAV8", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates. Similar purification methods can be used for vectors having other capsids.

While any conventional manufacturing process can be utilized, the process described herein (and in WO 2017/100676) yields vector preparations wherein between 50 and 70% of the particles have a vector genome, i.e., 50 to 70% full particles. Thus for an exemplary dose of $1.6\times10^{12}$ GC/kg, and the total particle dose will be between $2.3\times10^{12}$ and $3\times10^{12}$ particles. In another embodiment, the proposed dose is one half log higher, or $5\times10^{12}$ GC/kg, and the total particle dose will be between $7.6\times10^{12}$ and $1.1\times10^{13}$ particles. In one embodiment, the formulation is be characterized by an rAAV stock having a ratio of "empty" to "full" of 1 or less, preferably less than 0.75, more preferably, 0.5, preferably less than 0.3.

A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

5.2 Patient Population

As discussed above, a subject having WD of any severity is the intended recipient of the compositions and methods described herein.

Subjects may be permitted to continue their standard of care treatment(s) (e.g., diet low in copper; treatment with chelating agents such as D-penicillamine and trientine. Other agents include sodium dimercaptosuccinate, dimercaptosuccinic acid, zinc, and tetrathiomolybdate) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy.

Desirable endpoints of the gene therapy regimen would provide functional ATP7B enzyme resulting in a reduction of serum copper levels of 25% or more. In one embodiment, urinary copper excretion of 3-8 μmol or less per 24 hours is desirable.

Many tests can be used to investigate patients who may have Wilson disease, including non-ceruloplasmin-bound copper (NCC; also called the "free copper" or copper index), 24-h urine copper, hepatic copper, and genetic mutation testing. Methods for measurement of copper levels are known in the art e.g, as described by McMillin et al, Am J Clin Pathol. 2009; 131(2):160-165, which is incorporated herein by reference. In one embodiment, patients achieve desired circulating ATP7B levels after treatment with rAAV.hATP7B, alone and/or combined with the use of adjunctive treatments.

5.3. Dosing & Route of Administration

In one embodiment, the rAAV.hATP7B vector is delivered as a single dose per patient. In one embodiment, the subject is delivered the minimal effective dose (MED) (as determined by preclinical study described in the Examples herein). As used herein, MED refers to the rAAV.hATP7B dose required to provide functional ATP7B enzyme resulting in a reduction of serum copper levels of 25% or more.

As is conventional, the vector titer is determined on the basis of the DNA content of the vector preparation. In one embodiment, quantitative PCR or optimized quantitative PCR as described in the Examples is used to determine the DNA content of the rAAV.hATP7B vector preparations. In one embodiment, digital droplet PCR as described above is used to determine the DNA content of the rAAV.hATP7B vector preparations. In one embodiment, the dosage is about $1\times10^{11}$ genome copies (GC)/kg body weight to about $1\times10^{13}$ GC/kg, inclusive of endpoints. In one embodiment, the dosage is $5\times10^{11}$ GC/kg. In another embodiment, the dosage is $5\times10^{12}$ GC/kg. In specific embodiments, the dose of rAAV.hATP7B administered to a patient is at least $5\times10^{11}$ GC/kg, $1\times10^{12}$ GC/kg, $1.5\times10^{12}$ GC/kg, $2.0\times10^{12}$ GC/kg, $2.5\times10^{12}$ GC/kg, $3.0\times10^{12}$ GC/kg, $3.5\times10^{12}$ GC/kg, $4.0\times10^{12}$ GC/kg, $4.5\times10^{12}$ GC/kg, $5.0\times10^{12}$ GC/kg, $5.5\times10^{12}$ GC/kg, $6.0\times10^{12}$ GC/kg, $6.5\times10^{12}$ GC/kg, $7.0\times10^{12}$ GC/kg, or $7.5\times10^{12}$ GC/kg. Also, the replication-defective virus compositions can be formulated in dosage units to contain an amount of replication-defective virus that is in the range of about $1.0\times10^{9}$ GC to about $1.0\times10^{15}$ GC. As used herein, the term "dosage" can refer to the total dosage delivered to the subject in the course of treatment, or the amount delivered in a single (of multiple) administration.

In some embodiments, rAAV.hATP7B is administered in combination with one or more therapies for the treatment of WD, such as a low copper diet or administration of D-penicillamine, trientine, sodium dimercaptosuccinate, dimercaptosuccinic acid, zinc, and/or tetrathiomolybdate.

5.4. Measuring Clinical Objectives

Measurements of efficacy of treatment can be measured by transgene expression and activity as determined by ATP7B activity and or non-ceruloplasmin-bound copper (NCC; also called the "free copper" or copper index), 24-h urine copper, or hepatic copper levels. Further assessment of efficacy can be determined by clinical assessment of dietary copper tolerance.

As used herein, the rAAV.hATP7B vector herein "functionally replaces" or "functionally supplements" the patients defective ATP7B with active ATP7B when the patient expresses a sufficient level of ATP7B to achieve ATP7B activity resulting a 25% or greater reduction in non-ceruloplasmin-bound copper, 24-h urine copper, and/or hepatic copper.

The following examples are illustrative only and are not intended to limit the present invention.

EXAMPLES

The following examples are illustrative only and are not intended to limit the present invention.

Example 1: AAV Vectors Containing hATP7B (AAV.hATP7Bco)

An exemplary gene therapy vector AAV8.En34.TBG-S1.hATP7Bco.PA75 was constructed by an AAV8 vector bearing a codon-optimized human hATP7B cDNA (hATP7Bco) under the control of a TBG-S1 promoter and an En34 enhancer (FIG. 1). The ATP7B expression cassette was flanked by AAV2 derived inverted terminal repeats (ITRs) and further included a Kozak consensus sequence and a PA75 poly (A) signal. The sequence of AAV8.En34.TBG-S1.hATP7Bco.PA75 genome is shown in nt 1 to nt 5056 of SEQ ID NO: 24.

The vector AAV8.En34.TTR.hATP7Bco.PA75 was constructed as described above with a hepatocyte specific TTR promoter instead of TBG-S1. The sequence of AAV8.En34.TTR.hATP7Bco.PA75 is shown in nt 1 to nt 5068 of SEQ ID NO: 26.

A modified TTR promoter with the sequence shown as nt 21 to nt 190 of SEQ ID NO: 11, instead of TBG-S1 was utilized to construct the vector AAV.En34.mTTR.hATP7Bco.PA75. The sequence of AAV.En34.mTTR.hATP7Bco.PA75 is shown in nt 1 to nt 5048 of SEQ ID NO: 27.

The ATP7B expression cassette of AAV8.EnTTR.TTR.hATP7Bco.PA75 vector was driven by an EnTTR enhancer and a TTR promoter with a Kozak consensus sequence and a PA75 poly (A) signal. The sequence of AAV8.EnTTR.TTR.hATP7Bco.PA75 is shown in nt 1 to nt 5134 of SEQ ID NO: 23.

The AAV8.EnABPS.TBG-S1.hATP7Bco.PA75vector encodes a codon-optimized human ATP7B cDNA (hATP7Bco) under the control of an ABP-S2 (ABPS enhancer) enhancer and a TBG-S1 promoter, with a Kozak consensus sequence and a PA75 poly (A) signal. The sequence of AAV8.ABPS.TBG-S1.hATP7Bco.PA75 is shown in nt 1 to nt 5064 of SEQ ID NO: 25.

Additionally, truncated hATP7Bco vectors, including AAV8.En34.TBG-S1.hATP7Bco(MBD1Del).PA75 (as shown in nt 1 to nt 4945 of SEQ ID NO: 32), AAV8.En34.TBG-S1.hATP7Bco(MBD2Del).PA75 (as shown in nt 1 to nt 4876 of SEQ ID NO: 31), AAV8.En34.TBG-S1.hATP7Bco(MBD3Del).PA75 (nt 1 to nt 4978 of SEQ ID NO: 30), AAV8.En34.TBG-S1.hATP7Bco(MBD1-2Del).PA75 (nt 1 to nt 4627 of SEQ ID NO: 35), AAV8.En34.TBG-S1.hATP7Bco(MBD1-4Del).PA75 (nt 1 to nt 4021 of SEQ ID NO: 34), AAV8.En34.TBG-S1.hATP7Bco(MBD1-5Del).PA75 (nt 1 to nt 3628 of SEQ ID NO: 33), AAV8.TBG.hATP7Bco(MBD1-4Del).PA75 (nt 1 to nt 4677 of SEQ ID NO: 29), and AAV8.TBG.hATP7Bco(MBD1-5Del).PA75 (nt 1 to nt 4284 of SEQ ID NO: 28) were designed, constructed and produced as the indicated truncated hATP7Bco with a Kozak consensus sequence, a PA75 Ploy (A) signal and promoters and enhancers as shown in Table 2.

Briefly, plasmids expressing a codon-optimized version of hATP7B (hATP7Bco) from a reduced sized transthyretin enhancer and promoter were packaged with the AAV8 viral capsid.

The vector was prepared using conventional triple transfection techniques in 293 cells as described e.g., by Mizukami, Hiroaki, et al. *A Protocol for AAV vector production and purification*. Diss. Division of Genetic Therapeutics, Center for Molecular Medicine, 1998, which is incorporated herein by reference. All vectors were produced by the Vector Core at the University of Pennsylvania as previously described [Lock, M., et al, Hum Gene Ther, 21: 1259-1271 (2010)].

TABLE 2

| Key elements in the vector | | | Size ITR-ITR | Mouse sex (female | Age of mice at study initiation | Difference in serum copper levels from | Percentage difference in serum copper from | Difference in serum copper levels from | Percentage difference in serum copper from |
|---|---|---|---|---|---|---|---|---|---|
| Enhancer | Promoter | Transgene | (bp) | or male) | (weeks) | W0 to W2 | W0 to W2 | W0 to W4 | W0 to W4 |
| EnTTR | TTR | hATP7Bco | 5134 | M | 12 | 0.150 | 31% | 0.158 | 33% |
| En34 | TBG-S1 | hATP7Bco | 5056 | M | 11 | 0.182 | 38% | 0.252 | 52% |
| En34 | TTR | hATP7Bco | 5069 | M | 10 | 0.120 | 25% | 0.176 | 36% |
| ABPS | TBG-S1 | hATP7Bco | 5064 | M | 9 | 0.134 | 28% | 0.154 | 32% |
| En34 | mTTR | hATP7Bco | 5084 | M | 12 | 0.294 | 61% | 0.232 | 48% |
| En34 | TBG-S1 | hATP7Bco MBD1 Del | 4945 | M | 11 | 0.106 | 22% | 0.200 | 41% |
| En34 | TBG-S1 | hATP7Bco MBD2 Del | 4876 | M | 11 | 0.052 | 11% | 0.062 | 13% |
| En34 | TBG-S1 | hATP7Bco MBD3 Del | 4978 | M | 10 | 0.058 | 12% | 0.076 | 16% |
| En34 | TBG-S1 | hATP7Bco MBD1-2 Del | 4627 | M | 11 | 0.072 | 15% | 0.106 | 22% |
| En34 | TBG-S1 | hATP7Bco MBD1-4 Del | 4021 | M | 11 | 0.132 | 27% | 0.240 | 50% |
| En34 | TBG-S1 | hATP7Bco MBD1-5 Del | 3628 | M | 10 | 0.190 | 39% | 0.302 | 63% |
| Full TBG | | hATP7Bco MBD1-4 Del | 4677 | M | 10 | 0.160 | 33% | 0.206 | 43% |
| Full TBG | | hATP7Bco MBD1-5 Del | 4284 | M | 10 | 0.300 | 62% | 0.380 | 79% |

Example 2: A Mouse Model of Wilson's Disease

Prior to the development of gene therapeutic approaches for the treatment of Wilson's disease, the animal model of the disease phenotype must be fully characterized. The studies described herein are the first detailed characterization of both the $tx^J$ mouse strain and the evaluation of copper metabolism and disease pathology following fostering of all Atp7b KO mice from birth. In the absence of the conflicting copper deficiency provided prior to weaning due to the Atp7b deficiency in the mammary glands of diseased mothers, the time line of disease progression was accurately determined. Atp7b KO mice accumulate copper in the liver from birth with severe copper accumulation evident by two months of age with concurrent liver disease.

Monogenic diseases affecting single organs are attractive targets for gene therapy approaches, especially if there is relatively little associated histologic lesions. However, for metabolic disorders affecting the liver, there can often be severe damage to the liver parenchyma as a result of the disease. One of the classical examples of this is Wilson's disease, an autosomal, recessive disease caused by mutations in the Wilson's disease protein (a copper-transporting P-type ATPase, Atp7b). Lack of functional Atp7b results in the accumulation of copper in the liver and other tissues, which manifests as liver disease with neurological or psychiatric symptoms. Wilson's disease can be treated by reducing copper absorption or removing excess copper from the body using chelation therapy, but, as for many other metabolic disorders, liver transplantation can both correct the genetic deficiency associated with disease and replace a dysfunctional organ.

Wilson's disease affects 1:30,000 people with different disease symptoms and progression. To enable the development of new therapeutic alternatives to chelation and liver transplantation, a reliable animal model of this disease must be fully characterized. There are several previously reported rat and mouse animal models of Wilson's disease, including the Long-Evans Cinnamon (LEC) rats and various transgenic mouse strains (1-6). For evaluation of the Wilson's disease phenotype in a mouse model, we selected the toxic milk mouse ($tx^J$) available from Jackson Labs (2). These mice have a Gly712Asp missense mutation in the Atp7b gene, which is located in the second putative membrane-spanning domain of the encoded protein and results in a dysfunctional Atp7b protein.

The original name for this strain, the toxic milk mouse, is a result of Atp7b also being expressed in mammary tissue in addition to liver. Therefore, the "spontaneous arising" of the toxic milk phenotype in this model is a direct result of Wilson's disease (7). Due to the deficiency in the Atp7b protein, copper cannot be transported from the mother into breastmilk (8). Diseased pups that suckle from diseased mothers will present with an inverse form of Wilson's disease (copper deficiency) as they are unable to receive any copper in their diet until they are weaned and consume normal mouse chow. This inverse form of Wilson's disease also accounts for the previously described white coat color and mental defects (9). Here, we prefer to describe this mouse model as an Atp7b knockout (KO), and not as the $tx^J$, due to the dysfunctional Atp7b protein and the fact that all mice used in these studies were fostered onto Balb/c foster mothers within 72 hours of birth to mitigate the toxic milk issue. Therefore, characterization of the Wilson's disease phenotype described here has been separated from any underlying issues related to copper deficiency prior to weaning.

All animal procedures were performed in accordance with protocols approved by the Institutional Animal Care and Use Committee (IACUC) of the University of Pennsylvania.

ATP7B KO mice do not express functional copper-transporting ATPase (Lutsenko et al, Function and Regulation of Human Copper-Transporting ATPases, Physiological Reviews, 87(3):1011-46 (July 2007), thus served as a mouse model for Wilson's disease. A natural history study was performed to evaluate the progression of Wilson's disease in ATP7B KO mice. The study was performed in two phases. In the first, the mice were necropsied at different ages for evaluation of liver disease. In the second phase, mice were followed to 9 months of age for evaluation of several biomarkers.

Atp7b heterozygous and KO mice were evaluated for urine and serum copper levels on a weekly and biweekly basis, respectively, from 2 months of age for 7 months (FIGS. 3A and 3B). Atp7b in the liver exports copper into the bile for excretion in feces (7). In the absence of Atp7b, excretion of copper will occur via the urinary tract. Urine copper levels were initially similar in both genotypes studied, but at 3 months of age the level of copper in the urine of the Atp7b KO mice started to increase compared to the heterozygous animals (FIG. 3A). At the completion of the study urine copper levels averaged 0.18 μg/g in heterozygous mice and 1.08 μg/g in Atp7b KO mice. Serum copper levels in the Atp7b KO mice at two months of age were significantly different from heterozygous animals at 0.07 μg/g compared to 0.47 μg/g ($p<0.0001$ by Student's t test, FIG. 3B). At 3-4 months of age, serum copper levels in the Atp7b KO mice began to rise, reaching levels equivalent to that of the heterozygous mice. There were little to no differences in either urine or serum copper levels in male or female mice. The results of the first phase show that accumulation of copper in the liver was observed from birth. When the Atp7b KO mice reached 2 month-old, Timm's copper stain revealed a severe copper accumulation in the liver (FIG. 4).

Monogenic diseases affecting liver metabolism can be divided into two subcategories, those with liver lesions and those without. Wilson's disease patients do exhibit moderate to severe liver disease, usually manifesting as cirrhosis (13, 14). Therefore, we wanted to evaluate the time course for development of liver pathology in this mouse model of Wilson's disease. Atp7b KO mice were necropsied at 2, 3, 4, 5, 9, 10, and 12 months of age for evaluation of liver lesions over time (FIG. 5). Sections of the liver were stained with H&E, and evaluated for histopathology according to the 1-5 scoring system (FIG. 3C). Minimal hepatocellular hypertrophy and degeneration along with single cell necrosis and inflammation were present in Atp7b KO mice from two months of age. The severity of hepatocellular hypertrophy, degeneration and necrosis was highest by 6 months of age and remained consistent thereafter. Other parameters evaluated, including inflammation, bile duct hyperplasia, and oval cell hyperplasia, increased over time from 2-3 months to 7 months of age. There was a concurrent rise in the liver transaminases, ALT and AST, from normal values at two months of age to 199 U/l and 381 U/l for ALT and AST, respectively, at 10 months (Table 3). The extent of liver damage at 10 months of age was also evident from the serum total bilirubin levels as these suddenly spiked at 2.5 mg/dl. In addition to the liver lesions, areas of hepatic nodular regeneration were evident in this mouse model from 6 months of age (an example is shown by the asterisk in FIG. 5). This is perhaps unsurprising due to the severity of the liver disease.

TABLE 3

| | Age (months) | ALT (U/l) | AST (U/l) | Total bilirubin (mg/dl) | n |
|---|---|---|---|---|---|
| ATP7B KO | 2 | 16 | 30 | 0.2 | 1 |
| | 3 | 164 | 190 | 0.2 | 1 |
| | 4 | 174 | 224 | 0.3 | 2 |
| | 5 | 279 | 175 | 0.2 | 5 |
| | 9 | 152 | 266 | 0.6 | 18 |
| | 10 | 199 | 381 | 2.5 | 2 |
| WT | 2 | 28 | 50 | 0.2 | 13 |
| | 3 | 29 | 54 | 0.2 | 8 |
| | 4 | 49 | 39 | 0.2 | 4 |
| | 5 | 30 | 41 | 0.1 | 2 |

Liver sections were also evaluated for fibrosis and copper accumulation by Sirius Red and Timm stain, respectively (FIG. 5). Focal or multifocal periportal fibrosis was seen by 3 months of age in the Atp7b KO mice. This rapidly progressed to diffuse bridging fibrosis with architectural disruption by 7 months of age. The development of liver lesions was likely due to the massive accumulation of copper in the liver as seen by the Timm's stain (FIG. 5). From two months of age, the liver of Atp7b KO mice had become saturated with copper as shown by the black staining. Accumulation of copper in the liver occurs due to disrupted export of copper into the bile in the absence of functional Atp7b. The levels of copper in the liver decreased over time, likely due to hepatocyte damage and release of copper into the serum. This has been previously shown, where copper values are significantly reduced with submassive or massive necrosis, and reduced even further with regeneration and fibrosis (1, 15-17). The fibrous connective tissue and regenerating hepatocytes do not contain excess copper concentration (18).

The copper levels in the urine of ATP7B KO mice were also monitored. Samples were collected weekly in the natural history study and then inductively coupled plasma-mass spectrometry was performed to assess the copper concentration. The results demonstrate that while the heterozygous littermates maintained a low copper level, Atp7b KO mice exhibited an overflow of copper into urine starting at about the third week followed by a steady growth of the urinary concentration of copper over the observation period (FIG. 2A, 3A), representing the high urinary copper excretion rate observed in the Wilson's disease patients.

The serum of Atp7b KO mice was collected biweekly to assess the copper concentration via inductively coupled plasma-mass spectrometry. The result showed a very low serum copper level until 2 months of age compared to heterozygous littermates suggesting a compromised ability of extracting copper from the tissue to the blood in the Atp7b KO mice. When the Atp7b KO mice were 3 to 4 month old, the serum concentration of copper significantly increased and reached the level of the heterozygous littermates (FIG. 2B, 3B).

In this Atp7b KO mouse model, the progression of disease was as follows: Severe copper accumulation in the liver was seen by Timm's copper stain at two months of age, but did decrease over time similar to that previously described by others (1, 15-17). Due to fostering of the pups, copper is likely accumulating in the liver of Atp7b KO mice from birth and reaching saturation levels around 2-3 months of age. Following development of liver disease at two months of age, copper is likely released into the serum, resulting in an apparent decrease in accumulation in hepatocytes and rising serum copper levels by 3-4 months of age. This rise in serum copper levels from initially low levels to those similar to heterozygous mice is different to what has been reported previously for another mouse model of Wilson's disease (17), where serum copper levels in the Atp7b−/− strain are similar to that seen in wild type mice at 6 weeks of age and increase over time to 2 to 3-fold higher than wild type mice by 44 weeks of age.

We observed that the overflow of copper into urine starts at ~3 months of age, which similarly could be due to hepatocellular necrosis and subsequent release of accumulated copper. Alternative mechanisms for excretion of copper via the kidney have been suggested, including lack of Atp7b activity in the kidney resulting in increased excretion (23-25), or accumulation of copper in the liver leading to downregulation of the liver copper transporter, Ctrl, and urinary excretion by a small copper carrier (26). Again, the time course of urinary copper excretion differs in this mouse model to that reported previously. Here, urinary copper excretion is initially similar in heterozygous and Atp7b KO mice, but increases in the KO mice over the course of the study. In comparison, urinary copper levels are 3-fold greater than wild type mice at 6 weeks of age in the Atp7b−/− strain, increase up until 14-20 weeks old, and then decrease substantially at 20 weeks of age (26).

Hepatocellular hypertrophy, degeneration and necrosis peak at 6 months of age with likely concomitant observation of areas of hepatic nodular regeneration from this age onwards. This progression towards regeneration has been reported for other mouse models of Wilson's disease (17). However, unlike in the other mouse models, there was no evidence of cholangiocarcinoma in the Atp7b KO mouse described here. Regions of fibrosis were seen by 3 months of age, which rapidly increased in severity over time with architectural disruption by 7 months of age. While there are marked increases in serum transaminases by 3-4 months of age, increases in serum total bilirubin levels only start to occur at 9 months, indicating advanced liver disease.

In the second phase of the natural history study, Atp7b KO and heterozygous littermates were sacrificed at 8 months of age. ALT, AST and total bilirubin levels were obtained. FIG. 6A-6C. H&E stain and then histopathology evaluated by pathologist against a scoring scheme, which is shown in FIG. 7. Fibrosis score and copper staining score by Timm's Stain are shown in FIGS. 8A and 8B, respectively. Copper levels in the liver are shown in FIG. 9.

Example 3: AAV8.hATP7Bco Vectors in the Model of Wilson's Disease

Male Atp7b KO mice were injected IV with $10^{10}$ GC/mouse and $10^{11}$ GC/mouse of AAV8.TTR.hATP7Bco, and female Atp7b KO mice were injected IV with $10^{9}$, $10^{10}$, and $10^{11}$ GC/mouse of the same vector. Serum copper levels were monitored following vector injection (FIGS. 10A and 10B). Administration of $10^{10}$ or $10^{11}$ GC/mouse in male Atp7b KO mice increased serum copper levels from an average of 0.11 μg/g to 0.52 μg/g and 0.34 μg/g by two weeks post vector administration, respectively (FIG. 10A). However, there was a lesser effect in female mice (FIG. 10B). Mice were sacrificed at 7 months post vector administration at ~9 months of age, and liver was harvested for evaluation of liver copper levels. Liver copper levels in heterozygous and Atp7b KO mice averaged 6 μg/g and 222 μg/g, respectively (FIG. 10C). AAV8 vector administration at doses $>10^{9}$ GC/mouse resulted in significant decreases in liver copper levels compared to age-matched, uninjected Atp7b KO mice. However, there were no significant differences between liver copper levels in female mice administered with $10^{9}$ GC/mouse and control Atp7b KO mice. For this measurement, there was a stronger effect of the high vector dose in female mice as liver copper levels were not significantly different from heterozygous mice (FIG. 10C).

Mice administered with AAV8 vector were necropsied at 9 months of age, and liver was histologically evaluated for parameters of copper-associated liver disease, including fibrosis and copper levels by Timm's stain (FIG. 11). Sections of the liver were stained with H&E and histologically evaluated according to the 1-5 scoring system (FIG. 12A). Similar to that seen for liver copper levels, there was no significant difference in liver lesions between age-matched, uninjected Atp7b KO mice and female mice administered with $10^{9}$ GC/mouse of AAV8 vector. There was a dose-dependent decrease in liver lesions with male mice injected with $10^{11}$ GC/mouse, which were observed to have only mild karyocytomegaly (denoting hepatocellular hypertrophy and degeneration), mild inflammation, and focal or multifocal periportal oval cell hyperplasia. There was a significant reduction in hepatocellular hypertrophy, degeneration/necrosis and as well as bile duct hyperplasia compared to the age-matched, uninjected Atp7b KO mice in mice administered with $10^{10}$ and $10^{11}$ GC/mouse ($p<0.05$). For inflammation and oval cell hyperplasia, significant reduction compared to age-matched, uninjected Atp7b KO mice was only observed at a dose of $10^{11}$ GC/mouse ($p<0.05$). When the histopathologic parameters were combined and evaluated using Fisher's combined probability test, there was a significant difference compared to age-matched, uninjected Atp7b KO mice following administration of both $10^{10}$ and $10^{11}$ GC/mouse ($p<0.0001$).

Male mice that received the highest vector dose also did not have fibrosis, which was evaluated with Sirius Red staining (FIGS. 11 and 12B). For all other vector-administered mice, there was no significant difference in fibrosis compared to age-matched, uninjected Atp7b KO mice (FIG. 12B). However, the reduction in fibrosis seen in female mice administered with $10^{11}$ GC/mouse was sufficient that there was also no significant difference between liver fibrosis score in these mice and the female Atp7b heterozygous mice. Timm's staining for copper accumulation in the liver demonstrated similar results to that seen by the quantitative liver copper levels determined by inductively coupled plasma-mass spectrometry (FIG. 12C). There were no significant differences in Timm's staining score between age-matched, uninjected Atp7b KO mice and any of the vector-administered groups. To evaluate the efficacy of AAV8.hATP7Bco vectors, Atp7b KO mice received an i.v. administration of various gene therapy vectors at $3\times10^{12}$ GC/kg, including AAV8.EnTTR.TTR.hATP7Bco.PA75 (FIG. 21, group 1), AAV8.En34.TBG-S1.hATP7Bco.PA75 (FIG. 21, group 2), AAV8.En34.TTR.hATP7Bco.PA75 (FIG. 21, group 3) and AAV8.EnABPS.TBG-S1.hATP7Bco.PA75 (FIG. 21, group 4). Heterozygous and wild type littermates and Atp7b KO mice without treatment served as controls. Blood samples were collected weekly to evaluate the levels of both copper bound and non-copper-bound forms of ceruloplasmin via Western blot. On day 21 after the administration, appearance of copper-bound ceruloplasmin was observed in the Atp7b KO mice treated with AAV8.En34.TBG-S1.hATP7Bco.PA75, indicating a promoted copper extraction into blood (FIG. 21, group 2). However, under the experimental setting described above, the other three tested vectors did not display an increase in copper-bound ceruloplasmin (FIG. 21).

To assess the copper accumulation in the liver of the ATP7B KO mice injected with the AAV8.hATP7Bco vectors described herein, Timm's copper stain was performed on the liver sections thereof. Black deposits indicate copper accumulation. The results are shown in FIG. 19B. Injection with all five vectors to male Atp7b KO mice led to a decrease in the black deposits of the liver sections compared to the samples from non-treated or PBS-only mice while the AAV8.EnTTR.TTR.hATP7Bco.PA75 vector demonstrated the least black deposits and a pattern similar to wild type (FIG. 19B). Female Atp7b KO mice (FIG. 19B) demonstrated more copper deposits in liver compared to the male, indicating a gender difference. Still compared to non-treated mice, the female Atp7b KO mice demonstrated less copper deposits in liver. Generation of antibodies against human ATP7B protein in both male and female Atp7b KO mice injected with AAV.hATP7Bco vectors described herein is under investigation.

Meanwhile, the serum samples were collected and the copper concentrations were assessed as described in Example 2. The data was plotted in FIGS. 15A and 15B for female and male mice, respectively. The result demonstrates that the treatment of $3\times10^{12}$ GC/kg of the AAV8.hATP7Bco vectors described herein successfully increased the serum copper level in the Atp7b KO mice (FIGS. 15A and 15B).

Further tests were performed as follows:

| Cohort | Vector | Dose (GC/kg) | Sex | No. of mice | Age of mice at study initiation |
|---|---|---|---|---|---|
| 1 | EnTTR.TTR | $3.0 \times 10^{12}$ | F | 5 | 11 weeks |
| 2 | EnTTR.TTR | $3.0 \times 10^{12}$ | M | 5 | 12 weeks |
| 3 | En34.TBG-S1 | $3.0 \times 10^{12}$ | F | 5 | 11 weeks |
| 4 | En34.TBG-S1 | $3.0 \times 10^{12}$ | M | 5 | 11 weeks |
| 5 | En34.TTR | $3.0 \times 10^{12}$ | F | 5 | 10 weeks |
| 6 | En34.TTR | $3.0 \times 10^{12}$ | M | 5 | 10 weeks |
| 7 | APBS.TBG-S1 | $3.0 \times 10^{12}$ | F | 5 | 9 weeks |
| 8 | APBS.TBG-S1 | $3.0 \times 10^{12}$ | M | 5 | 9 weeks |
| 1 | En34.mTTR | $3.0 \times 10^{12}$ | F | 5 | 12 weeks |
| 2 | En34.mTTR | $3.0 \times 10^{12}$ | M | 5 | 12 weeks |

Serum copper levels over time are shown in FIGS. 15A and 15B. ALT, AST and total bilirubin levels were obtained. FIG. 16A-C. Relative ATP7B expression is shown in FIG. 17. H&E stain and then histopathology evaluated by pathologist against a scoring scheme, which is shown is FIG. 18. Fibrosis score and copper staining score by Timm Stain are shown in FIGS. 19A and 19B respectively.

Example 4: Oxidase Activity of Ceruloplasmin in the Model of Wilson's Disease Injected with AAV.hATP7Bco Vectors Copper is a potentially toxic metal but it is essential for a wide number of physiological functions acting as a co-factor of a variety of enzymes. After its intestinal absorption, copper is transported to hepatocytes where it binds to ATP7B located in the membrane of the trans-Golgi network (TGN). This large transmembrane protein is in charge of transferring the metal to copper-dependent enzymes. Loading of copper into ceruloplasmin is essential for the ferroxidase activity of this enzyme and constitutes an important secretory pathway for the metal, as 95% of copper present in the plasma of healthy individuals is bound to ceruloplasmin. Please see, e.g. Murillo, Oihana, et al. "Long-term metabolic correction of Wilson's disease in a murine model by gene therapy" Journal of Hepatology 64.2 (2016): 419-426, which is incorporated by reference herein.

To measure the oxidase activity, 20 μl of serum was processed using the Sigma Ceruloplasmin Activity Colorimetric Kit (MAK177) or the BioVision Ceruloplasmin Activity Colorimetric Kit following the protocols shown in the corresponding Product Information thereof, which is incorporated by reference herein. Oxidase activity assays were also performed according to the protocols shown in Schosinsky et al, "Measurement of ceruloplasmin from its oxidase activity in serum by use of o-dianisidine dihydrochloride" Clinical Chemistry 20.12 (1974): 1556-1563 and Murillo et al. "Long-term metabolic correction of Wilson's disease in a murine model by gene therapy" Journal of Hepatology 64.2 (2016): 419-426, which are incorporated by reference herein.

The oxidase activity of serum ceruloplasmin of the Atp7b KO mice was measured using the four assays described above. Samples from wildtype and heterozygous mice were served as control. No differences between wildtype and the Atp7b KO mice were detected.

Furthermore, Atp7b KO mice were treated with or without ammonium sulphate. Wildtype mice were provided as a control. No difference in the ceruloplasmin oxidase activity assay was detected between the wildtype or Atp7b KO mice using the protocol shown in Schosinsky et al, "Measurement of ceruloplasmin from its oxidase activity in serum by use of o-dianisidine dihydrochloride" Clinical Chemistry 20.12 (1974): 1556-1563.

In another experiment, Atp7b KO mice were treated with or without copper sulphate. Wildtype mice were provided as a control. The ceruloplasmin oxidase activity assay is performed to detect differences between the mice treated with or without copper sulphate using the four methods described above. Liver homogenates of the mice described herein are also collected and tested for oxidase activity of ceruloplasmin using the four methods described above. Copper sulphate was further added to liver homogenates and served as a positive control.

Example 5: Further Testing of AAV8.TTR.hATP7Bco Vector

To determine the dose-dependent effects and minimal effective dose (MED) of the AAV8.EnTTR.TTR.hATP7Bco.PA75 vectors, both male and female 2 month-old ATP7B KO mice were injected intravenously with $1\times10^{9}$, $1\times10^{10}$ or $1\times10^{11}$ GC/mouse of the vector. The western blot for ceruloplasmin demonstrated an appearance of copper-bound ceruloplasmin in the serum of three out of four tested mice which received $1\times10^{11}$ GC of AAV8.EnTTR.TTR.hATP7Bco.PA75, suggesting an increase of copper extraction (FIG. 14). While upon treatment with $1\times10^{10}$ GC of the same vector, one out of five tested mice showed copper-bound ceruloplasmin in the blood (FIG. 14). Those date validated that a single intravenous injection of AAV8.EnTTR.TTR.hATP7Bco.PA75 at the dose of $1\times10^{11}$ GC per mouse successfully promoted the copper extraction in a murine model of Wilson's disease.

Example 6: Truncated Vectors

Monogenic diseases are excellent candidates for gene replacement therapy approaches using AAV vectors. However, there is a limit to the size of the cDNA that can be packaged inside an AAV vector capsid. The wild type AAV genome is 4,700 bp, and requests to package larger genomes can reduce the integrity of the DNA sequence encapsulated within the AAV capsid (19). Previously, extensive research has been performed to investigate ways to reduce both the size of a given transgene and the transcriptional and polyA control sequences required for expression. One example of where this has been done successfully is development of a gene therapy vector for the treatment of hemophilia A, involving generation of B domain-deleted transgene sequence for human coagulation factor VIII that is 4,374 bp in length (19-21). For the treatment of Wilson's disease, the problem is increased as the ATP7B cDNA is 4,395 bp. Therefore, we chose to use a reduced size transthyretin enhancer and promoter (TTR) sequence for expression of a codon-optimized version of the human ATP7B transgene, in combination with a 75 bp synthetic polyA sequence (PA75) (19). The resulting AAV genome is 5.1 kb and was packaged within the AAV8 capsid.

Additionally, truncated hATP7Bco vectors, including AAV8.En34.TBG-S1.hATP7Bco(MBD1Del).PA75, AAV8.En34.TBG-S1.hATP7Bco(MBD2Del).PA75, AAV8.En34.TBG-S1.hATP7Bco(MBD3Del).PA75, AAV8.En34.TBG-S1.hATP7Bco(MBD1-2Del).PA75, AAV8.En34.TBG-S1.hATP7Bco(MBD1-4Del).PA75, AAV8.En34.TBG-S1.hATP7Bco(MBD1-5Del).PA75, AAV8.TBG.PI.hATP7Bco(MBD1-4Del).PA75, and AAV8.TBG.PI.hATP7Bco(MBD1-5Del).PA75, were designed, produced and injected into ATP7B KO mice intravenously at a dose of $3\times10^{12}$ GC/kg.

Atp7b KO mice treated with the various truncated vectors described above, and heterozygous littermates were studied and sacrificed at 6 months of age. Serum copper levels over time are shown in FIG. 22. ALT, AST and total bilirubin levels were obtained. FIG. 23. Relative ATP7B expression is shown in FIG. 24. H&E stain and then histopathology evaluated by pathologist against a scoring scheme, which is shown in FIG. 25. Fibrosis score and copper staining score by Timm's Stain are shown in FIG. 26. Liver copper levels at necropsy are shown in FIG. 27.

Example 7: Materials and Methods for Above Experiments

A. AAV Vector Production

All AAV vectors were produced by the Penn Vector Core at the University of Pennsylvania as described previously (10). Briefly, plasmids expressing a codon-optimized version of hATP7B (hATP7Bco) from a reduced sized transthyretin enhancer and promoter were packaged with the AAV8 viral capsid.

B. Mice

Breeding pairs of heterozygous Atp7b/mice were obtained from The Jackson Laboratory (Bar Harbor, ME, USA) and a colony was maintained at the University of Pennsylvania under specific pathogen-free conditions. All animal procedures and protocols were approved by the Institutional Animal Care and Use Committee (IACUC) of the University of Pennsylvania. Atp7b KO were generated and used for subsequent breeding. All pups generated from Atp7b KO mating pairs were fostered on Balb/c foster mothers within 72 hours of birth. Male and female Atp7b KO mice two months of age were injected IV with $10^9$-$10^{11}$ genome copies (GC)/mouse of AAV8.TTR.hATP7Bco via the tail vein (n=5/sex/group).

C. Serum Analyses

Blood was collected at the indicated time points in serum separator tubes, allowed to clot, and serum was isolated by centrifugation at 3,500×g for 5 minutes at room temperature. Serum was analyzed for alanine aminotransferase (ALT), aspartate aminotransferase (AST), and total bilirubin levels by Antech Diagnostics (Irvine, CA, USA). Serum and urine was also analyzed for copper levels by Exova (Edinburgh, UK).

D. Liver Copper Analysis

Liver samples taken at necropsy were analyzed for copper levels by Exova (Edinburgh, UK).

E. Histopathology

Formalin-fixed paraffin-embedded tissue samples were sectioned and stained for hematoxylin and eosin (H&E) according to standard protocols. To detect liver fibrosis, Sirius Red staining was performed on paraffin sections. Sections were deparaffinized and stained for 90 minutes in a solution of 0.1% (w/v) Direct Red (Sigma), 4% (w/v) picric acid (Sigma), washed with 0.01 N HCl (2×1 min), dehydrated through an ethanol and xylene series, and cover slips applied.

F. Timm's Copper Stain

Sections from formalin-fixed paraffin-embedded livers were dewaxed and incubated sequentially in 0.5% ammonium sulfide (5 min), deionized water (1 min rinse), 0.1N HCl (2-3 min), deionized water (2-3 min rinse), and developer (1 part 5% silver nitrate, 5 parts 2% (w/v) hydroquinone/5% (w/v) citric acid, for approximately 10 min). Liver sections from control animals (wild type and ATP7B KO) were included in each run and monitored for consistent staining intensity. Sections were finally washed in water, counterstained with Nuclear Fast Red, dehydrated, and cover slips applied.

G. Histopathology Scoring

The histopathologic lesions were scored based on the following criteria. Hepatocellular hypertrophy and degeneration: 0, no significant lesions; 1, minimal karyocytomegaly (rare to occasional, 1-2 hepatocytes within a lobule), 2, mild karyocytomegaly (<10% of hepatocytes within a lobule); 3, moderate karyocytomegaly (10-50% of hepatocytes within a lobule) with hepatocyte dissociation and rare to few single cell necrosis; 4, severe karyocytomegaly (51-90% of hepatocytes within a lobule) with extensive hepatocyte dissociation and frequent single cell necrosis; relatively normal hepatic architecture is maintained; 5, marked karyocytomegaly (>90% of hepatocytes within a lobule) with lobular collapse and numerous single cell necrosis. Inflammation: 0, none; 1, mild—few aggregates within portal areas and rare foci within parenchyma; considered within normal limits; 2, moderate—extending into surrounding periportal hepatocytes or multifocally within parenchyma; 3, marked—bridging or dissecting hepatocytes or multifocal to coalescing within parenchyma. Bile duct hyperplasia: 0, none; 1, focal or multifocal within portal areas; 2, dissecting hepatocytes in periportal region; 3, bridging or dissecting hepatocytes with architectural distortion. Oval cell hyperplasia: 0, none; 1, focal or multifocal (periportal); 2, bridging or dissecting hepatocytes; 3, bridging or dissecting hepatoytes with architectural distortion. Nodular regeneration: 0, absent; 1, present.

The grading scheme for fibrosis based on Sirius red staining was derived from those reported in the literature (11): 0, none; 1, focal or multifocal; 2, bridging; 3, bridging with architectural disruption, with notation on whether the distribution was centrilobular, midzonal, periportal, or diffuse.

H. The grading scheme for copper accumulation based on Timm's staining was the same as has been previously described in the literature (12): 1, absence or few copper-containing granules in the cytoplasm of an occasional hepatocyte; considered within normal limits; 2, obvious copper-containing granules in some centrilobular hepatocytes; considered within normal limits; 3, mild—numerous granules in most centrilobular hepatocytes (one-third of each lobule); 4, moderate—presence of numerous granules in all centrilobular and midzonal hepatocytes (approximately two-thirds of the hepatocytes in all lobules); 5 marked—abundant granules in more than two-thirds of the liver cells in all lobules. Statistical analysis For all data, group average and standard error of the mean (SEM) was calculated and reported. Student's t test was performed to compare two groups and a one-way analysis of variance (AVOVA) with Tukey's multiple comparisons test was performed across groups and stratified by sex. The five pathology parameters were analyzed in vector administration and compared with those in age-matched uninjected Atp7b KO mice. Comparisons were carried out using the Wilcoxon rank sum test within the R program (version 3.3.1; cran.r-project.org). The difference in combined pathology parameters was also evaluated for each dose group compared to age-matched uninjected ATP7B KO mice using Fisher's combined probability test within the R program using function "sumlog" in the "metap" package. Ap value of 0.05 was considered to be significant.

Example 8: Discussion

Before a mouse model of disease can be used to assess the translatability of a therapeutic approach to the clinic, the model must be extensively characterized. While characterization of other mouse models of Wilson's disease have been performed (1, 15, 17), this study is the first detailed characterization of both the $tx^J$ mouse strain and the evaluation of copper metabolism and liver disease following fostering of all Atp7b KO mice from birth. In the absence of the conflicting copper deficiency that occurs prior to weaning due to the Atp7b deficiency in the mammary glands of diseased mothers, the time line of disease progression in these mice can be more accurately determined by ensuring separation of the disease phenotype from any underlying issues related to copper deficiency prior to weaning. The development of liver disease and nodular regeneration in this mouse model was similar to what has been previously reported for the $Atp7b^{-/-}$ strain developed by others (1, 17). However, the time line was slightly increased in this mouse strain, likely due to the fostering of pups from birth resulting in a continuous supply of copper.

In this Atp7b KO mouse model, the progression of disease was as follows: Severe copper accumulation in the liver was seen by Timm's copper stain at two months of age, but did decrease over time similar to that previously described by others (1, 15-17). Due to fostering of the pups, copper is likely accumulating in the liver of Atp7b KO mice from birth and reaching saturation levels around 2-3 months of age. Following development of liver disease at two months of age, copper is likely released into the serum, resulting in an apparent decrease in accumulation in hepatocytes and rising serum copper levels by 3-4 months of age. This rise in serum copper levels from initially low levels to those similar to heterozygous mice is different to what has been reported previously for another mouse model of Wilson's disease (17), where serum copper levels in the $Atp7b^{-/-}$ strain are similar to that seen in wild type mice at 6 weeks of age and increase over time to 2 to 3-fold higher than wild type mice by 44 weeks of age.

We observed that the overflow of copper into urine starts at ~3 months of age, which similarly could be due to hepatocellular necrosis and subsequent release of accumulated copper. Alternative mechanisms for excretion of copper via the kidney have been suggested, including lack of Atp7b activity in the kidney resulting in increased excretion (23-25), or accumulation of copper in the liver leading to downregulation of the liver copper transporter, Ctrl, and urinary excretion by a small copper carrier (26). Again, the time course of urinary copper excretion differs in this mouse model to that reported previously. Here, urinary copper excretion is initially similar in heterozygous and Atp7b KO mice, but increases in the KO mice over the course of the study. In comparison, urinary copper levels are 3-fold greater than wild type mice at 6 weeks of age in the $Atp7b^{-/-}$ strain, increase up until 14-20 weeks old, and then decrease substantially at 20 weeks of age (26).

Hepatocellular hypertrophy, degeneration and necrosis peak at 6 months of age with likely concomitant observation of areas of hepatic nodular regeneration from this age onwards. This progression towards regeneration has been reported for other mouse models of Wilson's disease (17). However, unlike in the other mouse models, there was no evidence of cholangiocarcinoma in the Atp7b KO mouse described here. Regions of fibrosis were seen by 3 months of age, which rapidly increased in severity over time with architectural disruption by 7 months of age. While there are marked increases in serum transaminases by 3-4 months of age, increases in serum total bilirubin levels only start to occur at 9 months, indicating advanced liver disease.

Following characterization of this Atp7b KO mouse model, we developed a gene therapy approach for treatment of Wilson's disease. IV administration of an AAV8 vector expressing a codon-optimized version of the human ATP7B transgene into Atp7b KO mice at two months of age resulted in an increase in serum copper levels by two weeks post vector administration. The higher doses of vector evaluated here ($>10^9$ GC/mouse) resulted in significant decreases in liver copper levels compared to age-matched, uninjected Atp7b KO mice. There was a significant, dose-dependent decrease in liver lesions, with only mild histopathological findings present in male mice injected with $10^{11}$ GC/mouse and a complete lack of liver fibrosis. Therefore, administration of a gene therapy approach during the early stages of disease onset prevented liver damage and corrected copper metabolism in a mouse model of Wilson's disease.

All publications cited in this specification, as well as U.S. Provisional Patent Application Nos. 62/440,659 and 62/473,656, are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

Sequence Listing Free Text

| Seq ID NO | Free Text |
|---|---|
| 4-15 | <213> Artificial Sequence<br><223> constructed sequence |
| 17-35 | <213> Artificial Sequence<br><223> constructed sequence |

REFERENCES

1. Buiakova O I, Xu J, Lutsenko S, Zeitlin S, Das K, Das S, Ross B M, et al. Null mutation of the murine ATP7B (Wilson disease) gene results in intracellular copper accumulation and late-onset hepatic nodular transformation. Hum Mol Genet 1999; 8:1665-1671.
2. Coronado V, Nanji M, Cox D W. The Jackson toxic milk mouse as a model for copper loading. Mamm Genome 2001; 12:793-795.
3. Theophilos M B, Cox D W, Mercer J F. The toxic milk mouse is a murine model of Wilson disease. Hum Mol Genet 1996; 5:1619-1624.
4. Sasaki N, Hayashizaki Y, Muramatsu M, Matsuda Y, Ando Y, Kuramoto T, Serikawa T, et al. The gene responsible for LEC hepatitis, located on rat chromosome 16, is the homolog to the human Wilson disease gene. Biochem Biophys Res Commun 1994; 202:512-518.
5. Wu J, Forbes J R, Chen H S, Cox D W. The LEC rat has a deletion in the copper transporting ATPase gene homologous to the Wilson disease gene. Nat Genet 1994; 7:541-545.
6. Terada K, Sugiyama T. The Long-Evans Cinnamon rat: an animal model for Wilson's disease. Pediatr Int 1999; 41:414-418.
7. Lutsenko S, Barnes N L, Bartee M Y, Dmitriev O Y. Function and regulation of human copper-transporting ATPases. Physiol Rev 2007; 87:1011-1046.

8. Michalczyk A, Bastow E, Greenough M, Camakaris J, Freestone D, Taylor P, Linder M, et al. ATP7B expression in human breast epithelial cells is mediated by lactational hormones. J Histochem Cytochem 2008; 56:389-399.
9. Bronson R T, Sweet H O, Davisson M T. Acute cerebral neuronal necrosis in copper deficient offspring of female mice with the toxic milk mutation. Mouse Genome 1995; 93:152-154.
10. Gao G, Lu Y, Calcedo R, Grant R L, Bell P, Wang L, Figueredo J, et al. Biology of AAV serotype vectors in liver-directed gene transfer to nonhuman primates. Mol Ther 2006; 13:77-87.
11. Bernard J M, Newkirk K M, McRee A E, Whittemore J C, Ramsay E C. Hepatic lesions in 90 captive nondomestic felids presented for autopsy. Vet Pathol 2015; 52:369-376.
12. Thornburg L P, Shaw D, Dolan M, Raisbeck M, Crawford S, Dennis G L, Olwin D B. Hereditary copper toxicosis in West Highland white terriers. Vet Pathol 1986; 23:148-154.
13. Stromeyer F W, Ishak K G. Histology of the liver in Wilson's disease: a study of 34 cases. Am J Clin Pathol 1980; 73:12-24.
14. Roberts E A, Schilsky M L, American Association for Study of Liver D. Diagnosis and treatment of Wilson disease: an update. Hepatology 2008; 47:2089-2111.
15. Biempica L, Rauch H, Quintana N, Sternlieb I. Morphologic and chemical studies on a murine mutation (toxic milk mice) resulting in hepatic copper toxicosis. Lab Invest 1988; 59:500-508.
16. Haywood S, Loughran M, Batt R M. Copper toxicosis and tolerance in the rat. III. Intracellular localization of copper in the liver and kidney. Exp Mol Pathol 1985; 43:209-219.
17. Huster D, Finegold M J, Morgan C T, Burkhead J L, Nixon R, Vanderwerf S M, Gilliam C T, et al. Consequences of copper accumulation in the livers of the Atp7b−/− (Wilson disease gene) knockout mice. Am J Pathol 2006; 168:423-434.
18. Smedley R, Mullaney T, Rumbeiha W. Copper-associated hepatitis in Labrador Retrievers. Vet Pathol 2009; 46:484-490.
19. Greig J A, Wang Q, Reicherter A L, Chen S J, Hanlon A L, Tipper C H, Clark K R, et al. Characterization of Adeno-Associated Viral Vector-Mediated Human Factor VIII Gene Therapy in Hemophilia A Mice. Hum Gene Ther 2017; 28:392-402.
20. Toole J J, Pittman D D, Orr E C, Murtha P, Wasley L C, Kaufman R J. A large region (approximately equal to 95 kDa) of human factor VIII is dispensable for in vitro procoagulant activity. Proc Natl Acad Sci USA 1986; 83:5939-5942.
21. Ward N J, Buckley S M, Waddington S N, Vandendriessche T, Chuah M K, Nathwani A C, McIntosh J, et al. Codon optimization of human factor VIII cDNAs leads to high-level expression. Blood 2011; 117:798-807.
22. Davidoff A M, Ng C Y, Zhou J, Spence Y, Nathwani A C. Sex significantly influences transduction of murine liver by recombinant adeno-associated viral vectors through an androgen-dependent pathway. Blood 2003; 102:480-488.
23. Bull P C, Thomas G R, Rommens J M, Forbes J R, Cox D W. The Wilson disease gene is a putative copper transporting P-type ATPase similar to the Menkes gene. Nat Genet 1993; 5:327-337.
24. Petrukhin K, Fischer S G, Pirastu M, Tanzi R E, Chernov I, Devoto M, Brzustowicz L M, et al. Mapping, cloning and genetic characterization of the region containing the Wilson disease gene. Nat Genet 1993; 5:338-343.
25. Tanzi R E, Petrukhin K, Chernov I, Pellequer J L, Wasco W, Ross B, Romano D M, et al. The Wilson disease gene is a copper transporting ATPase with homology to the Menkes disease gene. Nat Genet 1993; 5:344-350.
26. Gray L W, Peng F, Molloy S A, Pendyala V S, Muchenditsi A, Muzik O, Lee J, et al. Urinary copper elevation in a mouse model of Wilson's disease is a regulated process to specifically decrease the hepatic copper load. PLoS One 2012; 7:e38327.

The invention claimed is:

1. A recombinant nucleic acid construct comprising a recombinant adeno-associated virus (AAV) vector genome, said vector genome comprising:

(a) an AAV 5' inverted terminal repeat (ITR) sequence;

(b) a promoter;

(c) a codon optimized coding sequence encoding a truncated human copper-transporting ATPase 2 (ATP7B) polypeptide comprising metal-binding domains (MBD) 4-6 and comprising a deletion of MBD 1-3; and (d) an AAV 3' ITR sequence.

2. The recombinant nucleic acid construct of claim 1, wherein the AAV 5' ITR and/or the AAV 3' ITR is from AAV2.

3. The recombinant nucleic acid construct of claim 1, wherein the promoter comprises a liver-specific promoter.

4. The recombinant nucleic acid construct of claim 3, wherein the liver-specific promoter is a transthyretin (TTR) promoter.

5. The recombinant nucleic acid construct of claim 1, wherein the codon optimized coding sequence comprises SEQ ID NO: 1 truncated to encode the ATP7B polypeptide comprising metal-binding domains (MBD) 4-6 and a deletion of MBD 1-3.

6. The recombinant nucleic acid construct of claim 1, wherein the vector genome further comprises an enhancer.

7. The recombinant nucleic acid construct of claim 6, wherein the enhancer is a TTR enhancer.

8. The recombinant nucleic acid construct of claim 1, wherein the vector genome further comprises a polyA signal.

9. The recombinant nucleic acid construct of claim 8, wherein the poly A signal is from SV40.

10. The recombinant nucleic acid construct of claim 1, wherein the vector genome further comprises an intron.

11. The recombinant nucleic acid construct of claim 10, wherein the intron is from SV40.

12. The recombinant nucleic acid construct of claim 1, wherein the recombinant nucleic acid construct is packaged in an AAV capsid.

13. The recombinant nucleic acid construct of claim 12, wherein the AAV capsid has tropism for liver.

14. A host cell comprising a recombinant nucleic acid construct, said nucleic acid construct comprising a recombinant adeno-associated virus (AAV) vector genome, said vector genome comprising:

(a) an AAV 5' inverted terminal repeat (ITR) sequence;

(b) a promoter;

(c) a codon optimized coding sequence encoding a truncated human copper-transporting ATPase 2 (ATP7B) polypeptide comprising metal-binding domains (MBD) 4-6 and comprising a deletion of MBD 1-3; and (d) an AAV 3' ITR sequence.

15. A method of treating a subject having Wilson's Disease, the method comprising administering to the subject a recombinant adeno-associated virus (AAV) useful as a liver-directed therapeutic for Wilson's Disease (WD), said recombinant AAV comprising an AAV capsid, and a vector genome packaged therein, said vector genome comprising:

(a) an AAV 5' inverted terminal repeat (ITR) sequence;

(b) a promoter;

(c) a codon optimized coding sequence encoding a human copper-transporting ATPase 2 (ATP7B) polypeptide comprising metal-binding domains (MBD) 4-6 and comprising a deletion of MBD 1-3; and (d) an AAV 3' ITR sequence.

16. The method of claim 15, comprising administering about $1\times10^{11}$ to about $1\times10^{14}$ genome copies (GC)/kg of the recombinant AAV to the subject.

17. The method of claim 15, comprising administering about $5\times10^{12}$ to about $2\times10^{13}$ genome copies (GC)/kg of the recombinant AAV to the subject.

18. The method of claim 15, wherein the recombinant AAV is administered to the subject intravenously.

19. The method of claim 15, wherein the recombinant AAV is administered in combination with one or more additional therapies for the treatment of Wilson's Disease.

20. The method of claim 19, wherein the one or more additional therapies comprise low copper diet, administration of D-penicillamine, trientine, sodium dimercaptosuccinate, dimercaptosuccinic acid, zinc, and/or tetrathiomolybdate.

* * * * *

SEQUENCE LISTING

```
Sequence total quantity: 35
SEQ ID NO: 1           moltype = DNA  length = 4395
FEATURE                Location/Qualifiers
misc_feature           1..4395
                       note = constructed sequence
source                 1..4395
                       mol_type = other DNA
                       organism = synthetic construct
SEQUENCE: 1
atgcccgagc aggaaagaca gatcaccgcc agagagggcg ccagccggaa gatcctgagc  60
aagctgagcc tgcccaccag agcctgggag cccgccatga agaagtcctt cgccttcgac  120
aacgtgggct acgagggcgg cctggacgga ctgggaccat cttctcaggt ggccacaagc  180
accgtgcgca tcctgggcat gacctgccag agctgcgtga agtccatcga ggaccggatc  240
agcaacctga agggcatcat cagcatgaag gtgtccctgg aacagggcag cgccaccgtg  300
aaatacgtgc cctctgtcgt gtgcctgcag caggtgtgcc accagatcgg cgacatgggc  360
ttcgaggcct ctatcgccga gggaaaggcc gcctcttggc cctctagaag cctgcctgct  420
caggaagccg tcgtgaagct gcgggtggaa gggatgacct gtcagtcctg cgtgtccagc  480
atcgagggca aagtgcggaa gctgcagggc gtggtgcgcg tgaaagtgtc tctgagcaac  540
caggaagctg tgatcaccta ccagccctac ctgatccagc ccgaggacct gagggaccac  600
gtgaacgata tgggatttga ggccgccatc aagagcaagg tggcccctct gtctctgggc  660
cccatcgaca tcgagagact gcagagcacc aaccccaagc ggcctctgag cagcgccaac  720
cagaacttca acaacagcga gacactgggc caccagggca gccacgtcgt gacactgcag  780
ctgcggatcg acggaatgca ctgcaagagc tgtgtgctga acatcgagga aaacatcggc  840
cagctgctgg gagtgcagag catccaggtg tcactggaaa acaagaccgc ccaggtgaag  900
tacgacccca gctgcacaag ccccgtggcc ctgcagagag ccattgaagc tctgcccccct  960
ggcaacttca aagtgtccct gcctgacgga gccgagggct ccggaacaga tcacagaagc  1020
agcagcagcc acagccctgg cagcccccct agaaatcagg tgcagggcac ctgtagcacc  1080
accctgatcg ccattgccgg catgacatgc gccagctgcg tgcactctat tgagggcatg  1140
```

-continued

```
atctcccagc tggaaggcgt gcagcagatc agtgtgtctc tggccgaggg caccgccaca  1200
gtgctgtaca accctagcgt gatcagcccc gaagaactga gagccgccat tgaggacatg  1260
ggattcgaag ccagcgtggt gtccgagagc tgctccacca accctctggg caatcacagc  1320
gccggcaaca gcatggtgca gaccaccgac ggcacccccca ccagcgtgca ggaagtggcc  1380
ccacatacag gcagactgcc cgccaatcac gcccccgata tcctggccaa gagcccccag  1440
agtacaagag ccgtggcccc ccagaagtgc ttcctgcaga tcaagggcat gacttgtgcc  1500
tcttgtgtgt ccaatatcga gcggaacctg cagaaagagg ccggcgtgct gtctgtgctg  1560
gtggctctga tggccggcaa ggccgagatc aaatacgacc ccgaagtgat tcagcccctg  1620
gaaatcgccc agtttatcca ggacctgggc tttgaagccg ccgtgatgga agattacgcc  1680
ggctccgacg gcaacatcga gctgaccatc accggaatga cctgcgcctc ctgtgtgcac  1740
aacattgagt ccaagctgac ccggaccaac ggcatcacct acgcctctgt ggctctggcc  1800
acctccaagg ccctcgtgaa gttcgatccc gagatcatcg gccccaggga catcatcaag  1860
atcatcgaag agatcggctt ccacgccagc ctggcccaga ggaaccctaa cgcccaccac  1920
ctggaccaca agatggaaat caagcagtgg aagaaaagct tcctgtgcag cctggtgttc  1980
ggcatccccg tgatggccct gatgatctac atgctgatcc ccagcaacga gccccaccag  2040
tccatggtgc tggatcacaa catcatcccc ggcctgtcta tcctgaacct gatcttcttc  2100
atcctgtgca ccttcgtgca gctgctgggc ggctggtact tctacgtgca ggcctacaag  2160
tccctgcggc acagatccgc caacatggac gtgctgatcg tgctggccac atctatcgcc  2220
tacgtgtact ccctcgtgat cctggtggtg gccgtggccg agaaagccga gagaagccct  2280
gtgaccttct tcgacacccc ccctatgctg ttcgtgttta tcgccctggg ccggtggctg  2340
gaacacctgg ccaaaagcaa gaccagcgag gccctggcta agctgatgag tctgcaggcc  2400
accgaggcca cagtcgtgac cctgggcgag gacaacctga tcatccgcga ggaacaggtg  2460
ccaatggaac tggtgcagcg gggcgacatc gtgaaggtgg tgcctggcgg caagttcccc  2520
gtggacggaa aagtgctgga agggaatacc atggccgacg agagcctgat cacaggcgag  2580
gccatgcccg tgaccaagaa acctggcagc acagtgatcg ccggcagcat caatgcccac  2640
ggcagcgtgc tgattaaggc cacacacgtg ggcaacgata ccaccctggc tcagattgtg  2700
aagctggtgg aagaggccca gatgagcaag gcccccattc agcagctggc tgaccggttc  2760
agcggctact tcgtgccctt tatcatcatc atgagcaccc tgacactggt cgtgtggatc  2820
gtgatcggct ttatcgactt cggagtggtg cagagatact tccccaaccc taacaagcac  2880
atcagccaga cagaagtgat catcagattc gcctttcaga ccagcatcac cgtgctgtgt  2940
atcgcctgcc cctgtagcct gggactggcc acacctaccg ctgtgatggt gggaacaggc  3000
gtggccgctc agaacggcat cctgatcaag gggggcaagc ctctggaaat ggctcacaag  3060
atcaagaccg tgatgttcga caagaccggc accatcaccc acggcgtgcc cagagtgatg  3120
agagtgctgc tgctggggga tgtggccacc ctgcctctga gaaaggtgct ggctgtcgtg  3180
ggcacagccg aggctagctc tgaacaccca ctgggagtgg ccgtgacaaa gtactgcaaa  3240
gaggaactgg gcaccgaaac cctgggctac tgcaccgact ttcaggccgt gcctggctgt  3300
ggcatcggct gcaaggtgtc caacgtggaa ggcatcctgg cccacagcga gaggccactg  3360
tctgcccctg ccagccacct gaacgaggcc ggatctctgc ccgccgaaaa ggacgctgtg  3420
ccccagacct tctctgtgct gattggcaac agagagtggc tgcggcggaa cggcctgacc  3480
atctcctccg atgtgtccga cgccatgacc gaccacgaga tgaagggcca gaccgccatt  3540
ctggtggcca ttgacggggt gctgtgcggc atgatcgcaa tcgccgatgc cgtgaaacag  3600
gaagcagcac tggccgtgca caccctgcag tctatgggag tggatgtggt gctgatcacc  3660
ggcgacaaca gaaagaccgc cagggccatt gccacccagg tgggcatcaa caaggtgttc  3720
gccgaggtgc tgcccagcca caaagtggcc aaggtgcagg aactgcagaa caaaggcaaa  3780
aaggtggcca tggtgggaga tggcgtgaac gactctcctg ctctggccca ggcagatatg  3840
ggcgtggcca tcggcacagg caccgacgtg gcaattgagg ctgctgacgt ggtgctgatt  3900
cggaacgacc tgctggacgt ggtggcctcc atccacctgt ccaagagaac cgtgcggcgg  3960
atcagaatca acctggtgct ggcactgatc tataacctcg tgggcatccc tatcgccgct  4020
ggcgtgttca tgcctatcgg aatcgtgctg cagccctgga tgggctctgc cgccatggct  4080
gcaagctccg tgtctgtggt gctgtccagc ctgcagctga agtgctacaa gaagcccgac  4140
ctggaaagat acgaggccca ggcccacgga cacatgaagc ctctgacagc ctcccaggtg  4200
tccgtgcaca tcggcatgga cgacagatgg cgggacagcc ctagagccac cccttgggat  4260
caggtgtcat acgtgtcaca ggtgtccctg agcagcctga ccagcgacaa gcccagcaga  4320
catagcgccg ctgccgacga cgatggggac aagtggtccc tgctgctgaa cggccgggat  4380
gaggaacagt acatc                                                    4395

SEQ ID NO: 2           moltype = AA  length = 1465
FEATURE                Location/Qualifiers
source                 1..1465
                       mol_type = protein
                       organism = Homo sapiens
SEQUENCE: 2
MPEQERQITA REGASRKILS KLSLPTRAWE PAMKKSFAFD NVGYEGGLDG LGPSSQVATS  60
TVRILGMTCQ SCVKSIEDRI SNLKGIISMK VSLEQGSATV KYVPSVVCLQ QVCHQIGDMG  120
FEASIAEGKA ASWPSRSLPA QEAVVKLRVE GMTCQSCVSS IEGKVRKLQG VVRVKVSLSN  180
QEAVITYQPY LIQPEDLRDH VNDMGFEAAI KSKVAPLSLG PIDIERLQST NPKRPLSSAN  240
QNFNNSETLG HQGSHVVTLQ LRIDGMHCKS CVLNIEENIG QLLGVQSIQV SLENKTAQVK  300
YDPSCTSPVA LQRAIEALPP GNFKVSLPDG AEGSGTDHRS SSHSPGSPP RNQVQGTCST  360
TLIAIAGMTC ASCVHSIEGM ISQLEGVQQI SVSLAEGTAT VLYNPSVISP EELRAAIEDM  420
GFEASVVSES CSTNPLGNHS AGNSMVQTTD GTPTSVQEVA PHTGRLPANH APDILAKSPQ  480
STRAVAPQKC FLQIKGMTCA SCVSNIERNL QKEAGVLSVL VALMAGKAEI KYDPEVIQPL  540
EIAQFIQDLG FEAAVMEDYA GSDGNIELTI TGMTCASCVH NIESKLTRTN GITYASVALA  600
TSKALVKFDP EIIGPRDIIK IIEEIGFHAS LAQRNPNAHH LDHKMEIKQW KKSFLCSLVF  660
GIPVMALMIY MLIPSNEPHQ SMVLDHNIIP GLSILNLIFF ILCTFVQLLG GWYFYVQAYK  720
SLRHRSANMD VLIVLATSIA YVYSLVILVV AVAEKAERSP VTFFDTPPML FVFIALGRWL  780
EHLAKSKTSE ALAKLMSLQA TEATVVTLGE DNLIIREEQV PMELVQRGDI VKVVPGGKFP  840
VDGKVLEGNT MADESLITGE AMPVTKKPGS TVIAGSINAH GSVLIKATHV GNDTTLAQIV  900
KLVEEAQMSK APIQQLADRF SGYFVPFIII MSTLTLVVWI VIGFIDFGVV QRYFPNPNKH  960
ISQTEVIIRF AFQTSITVLC IACPCSLGLA TPTAVMVGTG VAAQNGILIK GGKPLEMAHK  1020
```

-continued

```
IKTVMFDKTG TITHGVPRVM RVLLLGDVAT LPLRKVLAVV GTAEASSEHP LGVAVTKYCK  1080
EELGTETLGY CTDFQAVPGC GIGCKVSNVE GILAHSERPL SAPASHLNEA GSLPAEKDAV  1140
PQTFSVLIGN REWLRRNGLT ISSDVSDAMT DHEMKGQTAI LVAIDGVLCG MIAIADAVKQ  1200
EAALAVHTLQ SMGVDVVLIT GDNRKTARAI ATQVGINKVF AEVLPSHKVA KVQELQNKGK  1260
KVAMVGDGVN DSPALAQADM GVAIGTGTDV AIEAADVVLI RNDLLDVVAS IHLSKRTVRR  1320
IRINLVLALI YNLVGIPIAA GVFMPIGIVL QPWMGSAAMA ASSVSVVLSS LQLKCYKKPD  1380
LERYEAQAHG HMKPLTASQV SVHIGMDDRW RDSPRATPWD QVSYVSQVSL SSLTSDKPSR  1440
HSAAADDDGD KWSLLLNGRD EEQYI                                       1465

SEQ ID NO: 3           moltype = DNA  length = 4395
FEATURE                Location/Qualifiers
source                 1..4395
                       mol_type = genomic DNA
                       organism = Homo sapiens
SEQUENCE: 3
atgcctgagc aggagagaca gatcacagcc agagaagggg ccagtcggaa aatcttatct  60
aagctttctt tgcctacccg tgcctgggaa ccagcaatga agaagagttt tgcttttgac  120
aatgttggct atgaaggtgg tctggatggc ctgggccctt cttctcaggt ggccaccagc  180
acagtcagga tcttgggcat gacttgccag tcatgtgtga agtccattga ggacaggatt  240
tccaatttga aaggcatcat cagcatgaag gtttccctgg aacaaggcag tgccactgtg  300
aaatatgtgc catcggttgt gtgcctgcaa caggtttgcc atcaaattgg ggacatgggc  360
ttcgaggcca gcattgcaga aggaaaggca gcctcctggc cctcaaggtc cttgcctgcc  420
caggaggctg tggtcaagct ccgggtggag ggcatgacct gccagtcctg tgtcagctcc  480
attgaaggca aggtccggaa actgcaagga gtagtgagag tcaaagtctc actcagcaac  540
caagaggccg tcatcactta tcagccttat ctcattcagc ccgaagacct cagggaccat  600
gtaaatgaca tgggatttga agctgccatc aagagcaaag tggctccctt aagcctggga  660
ccaattgata ttgagcggtt acaaagcact aacccaaaga gacctttatc ttctgctaac  720
cagaatttta ataattctga gaccttgggg caccaaggaa gccatgtggt caccctccaa  780
ctgagaatag atggaatgca ttgtaagtct tgcgtcttga atattgaaga aaatattggc  840
cagctcctag ggtttcaaag tattcaagtg tccttggaga acaaaactgc ccaagtaaag  900
tatgacccct cttgtaccag cccagtggct ctgcagaggg ctatcgaggc acttccacct  960
gggaatttta aagtttctct tcctgatgga gccgaaggga gtgggacaga tcacaggtct  1020
tccagttctc attcccctgg ctccccaccg agaaaccagg tccagggcac atgcagtacc  1080
actctgattg ccattgccgg catgacctgt gcatcctgtg tccattccat tgaaggcatg  1140
atctcccaac tggaaggggt gcagcaaata tcggtgtctt tggccgaagg gactgcaaca  1200
gttctttata atccctctgt aattagccca gaagaactca gagctgctat agaagacatg  1260
ggatttgagg cttcagtcgt ttctgaaagc tgttctacta accctcttgg aaaccacagt  1320
gctgggaatt ccatggtgca aactacagat ggtacaccta catctgtgca ggaagtggct  1380
ccccacactg ggaggctccc tgcaaaccat gccccggaca tcttggcaaa gtccccacaa  1440
tcaaccagag cagtggcacc gcagaagtgc ttcttacaga tcaaaggcat gacctgtgca  1500
tcctgtgtgt ctaacataga aaggaatctg cagaaagaag ctggtgttct ctccgtgttg  1560
gttgccttga tggcaggaaa ggcagagatc aagtatgacc cagaggtcat ccagcccctc  1620
gagatagctc agttcatcca ggacctgggt tttgaggcag cagtcatgga ggactacgca  1680
ggctccgatg gcaacattga gctgacaatc acagggatga cctgcgcgtc ctgtgtccac  1740
aacatagagt ccaaactcac gaggacaaat ggcatcactt atgcctccgt tgcccttgcc  1800
accagcaaag cccttgttaa gtttgacccg gaaattatcg gtccacggga tattatcaaa  1860
attattgagg aaattggctt tcatgcttcc ctggcccaga gaaaccccaa cgctcatcac  1920
ttggaccaca agatggaaat aaagcagtgg aagaagtctt tcctgtgcag cctggtgttt  1980
ggcatccctg tcatggcctt aatgatctat atgctgatac ccagcaacga gccccaccag  2040
tccatggtcc tggaccacaa catcattcca ggactgtcca ttctaaatct catcttcttt  2100
atcttgtgta cctttgtcca gctcctcggt gggtggtact tctacgttca ggcctacaaa  2160
tctctgagac acaggtcagc caacatggac gtgctcatcg tcctggccac aagcattgct  2220
tatgtttatt ctctggtcat cctggtggtt gctgtggctg agaaggcgga gaggagccct  2280
gtgacattct tcgacacgcc ccccatgctc tttgtgttca ttgccctggg ccggtggctg  2340
gaacacttgg caaagagcaa aacctcagaa gccctggcta aactcatgtc tctccaagcc  2400
acagaagcca ccgttgtgac ccttggtgag gacaatttaa tcatcaggga ggagcaagtc  2460
cccatggagc tggtgcagcg gggcgatatc gtcaaggtgg tccctggggg aaagtttcca  2520
gtggatggga aagtcctgga aggcaatacc atggctgatg agtccctcat cacaggagaa  2580
gccatgccag tcactaagaa acccggaagc actgtaattg cggggtctat aaatgcacat  2640
ggctctgtgc tcattaaagc tacccacgtg ggcaatgaca ccactttggc tcagattgtg  2700
aaactggtgg aagaggctca gatgtcaaag gcacccattc agcagctggc tgaccggttt  2760
agtggatatt ttgtcccatt tatcatcatc atgtcaactt tgacgttggt ggtatggatt  2820
gtaatcggtt ttatcgattt tggtgttgtt cagagatact ttcctaaccc caacaagcac  2880
atctcccaga cagaggtgat catccggttt gctttccaga cgtccatcac ggtgctgtgc  2940
attgcctgcc cctgctccct ggggctggcc acgcccacgg ctgtcatggt gggcaccggg  3000
gtggccgcgc agaacggcat cctcatcaag ggaggcaagc ccctggagat ggcgcacaag  3060
ataaagactg tgatgtttga caagactggc accattaccc atggcgtccc cagggtcatg  3120
cgggtgctcc tgctggggga tgtggccaca ctgcccctca ggaaggttct ggctgtggtg  3180
gggactgcgg aggccagcag tgaacacccc ttgggcgtgg cagtcaccaa atactgtaaa  3240
gaggaacttg gaacagagac cttgggatac tgcacggact tccaggcagt gccaggctgt  3300
ggaattgggt gcaaagtcag caacgtggaa ggcatcctgg cccacagtga gcgccctttg  3360
agtgcaccgg ccagtcacct gaatgaggct ggcagccttc ccgcagaaaa agatgcagtc  3420
ccccagacct tctctgtgct gattggaaac cgtgagtggc tgaggcgcaa cggtttaacc  3480
atttctagcg atgtcagtga cgctatgaca gaccacgaga tgaaaggaca gacagccatc  3540
ctggtggcta ttgacggtgt gctctgtggg atgatcgcaa tcgcagacgc tgtcaagcag  3600
gaggctgccc tggctgtgca cacgctgcag agcatgggtg tggacgtggt tctgatcacg  3660
ggggacaacc ggaagacagc cagagctatt gccacccagg ttggcatcaa caaagtcttt  3720
gcagaggtgc tgccttcgca caaggtggcc aaggtccagg agctccagaa taaagggaag  3780
aaagtcgcca tggtggggga tggggtcaat gactccccgg ccttggccca ggcagacatg  3840
```

-continued

```
ggtgtggcca ttggcaccgg cacggatgtg gccatcgagg cagccgacgt cgtccttatc  3900
agaaatgatt tgctggatgt ggtggctagc attcaccttt ccaagaggac tgtccgaagg  3960
atacgcatca acctggtcct ggcactgatt tataacctgg ttgggatacc cattgcagca  4020
ggtgtcttca tgcccatcgg cattgtgctg cagccctgga tgggctcagc ggccatggca  4080
gcctcctctg tgtctgtggt gctctcatcc ctgcagctca agtgctataa gaagcctgac  4140
ctggagaggt atgaggcaca ggcgcatggc cacatgaagc ccctgacggc atcccaggtc  4200
agtgtgcaca taggcatgga tgacaggtgg cgggactccc ccagggccac accatgggac  4260
caggtcagct atgtcagcca ggtgtcgctg tcctccctga cgtccgacaa gccatctcgg  4320
cacagcgctg cagcagacga tgatggggac aagtggtctc tgctcctgaa tggcagggat  4380
gaggagcagt acatc                                                   4395

SEQ ID NO: 4            moltype = DNA  length = 34
FEATURE                 Location/Qualifiers
misc_feature            1..34
                        note = constructed sequence
source                  1..34
                        mol_type = other DNA
                        organism = synthetic construct
SEQUENCE: 4
tgtttgctgc ttgcaatgtt tgcccatttt aggg                              34

SEQ ID NO: 5            moltype = DNA  length = 100
FEATURE                 Location/Qualifiers
misc_feature            1..100
                        note = constructed sequence
source                  1..100
                        mol_type = other DNA
                        organism = synthetic construct
SEQUENCE: 5
ctacctcgtg atcgcccggc ccctgttcaa acatgtccta atactctgtc tctgcaaggg  60
tcatcagtag ttttccatct tactcaacat cctcccagtg                        100

SEQ ID NO: 6            moltype = DNA  length = 42
FEATURE                 Location/Qualifiers
misc_feature            1..42
                        note = constructed sequence
source                  1..42
                        mol_type = other DNA
                        organism = synthetic construct
SEQUENCE: 6
aggttaattt ttaaactgtt tgctctggtt aataatctca gg                     42

SEQ ID NO: 7            moltype = DNA  length = 322
FEATURE                 Location/Qualifiers
misc_feature            1..322
                        note = constructed sequence
source                  1..322
                        mol_type = other DNA
                        organism = synthetic construct
SEQUENCE: 7
aaggctcaga ggcacacagg agtttctggg ctcaccctgc cccctccaa cccctcagtt  60
cccatcctcc agcagctgtt tgtgtgctgc ctctgaagtc cacactgaac aaacttcagc  120
ctactcatgt ccctaaaatg ggcaaacatt gcaagcagca aacagcaaac acacagccct  180
ccctgcctgc tgaccttgga gctggggcag aggtcagaga cctctctggg cccatgccac  240
ctccaacatc cactcgaccc cttggaattt cggtggagag gagcagaggt tgtcctggcg  300
tggtttaggt agtgtgagag gg                                           322

SEQ ID NO: 8            moltype = DNA  length = 178
FEATURE                 Location/Qualifiers
misc_feature            1..178
                        note = constructed sequence
source                  1..178
                        mol_type = other DNA
                        organism = synthetic construct
SEQUENCE: 8
actcaaagtt caaaccttat catttttgc tttgttcctc ttggccttgg ttttgtacat  60
cagctttgaa aataccatcc cagggttaat gctggggtta atttataact aagagtgctc  120
tagttttgca atacaggaca tgctataaaa atggaaagat gttgctttct gagagaca    178

SEQ ID NO: 9            moltype = DNA  length = 477
FEATURE                 Location/Qualifiers
misc_feature            1..477
                        note = constructed sequence
source                  1..477
                        mol_type = other DNA
                        organism = synthetic construct
SEQUENCE: 9
agggctggaa gctacctttg acatcatttc ctctgcgaat gcatgtataa tttctacaga  60
acctattaga aaggatcacc cagcctctgc ttttgtacaa ctttccctta aaaaactgcc  120
```

```
aattccactg ctgtttggcc caatagtgag aactttttcc tgctgcctct tggtgctttt  180
gcctatggcc cctattctgc ctgctgaaga cactcttgcc agcatggact taaacccctc  240
cagctctgac aatcctcttt ctcttttgtt ttacatgaag ggtctggcag ccaaagcaat  300
cactcaaagt tcaaacctta tcattttttg ctttgttcct cttggccttg gttttgtaca  360
tcagctttga aaataccatc ccagggttaa tgctggggtt aatttataac taagagtgct  420
ctagttttgc aatacaggac atgctataaa aatggaaaga tgttgctttc tgagaga     477

SEQ ID NO: 10          moltype = DNA  length = 218
FEATURE                Location/Qualifiers
misc_feature           1..218
                       note = constructed sequence
source                 1..218
                       mol_type = other DNA
                       organism = synthetic construct
SEQUENCE: 10
tggacacagg acgctgtggt ttctgagcca gggggcgact cagatcccag ccagtggact  60
tagcccctgt ttgctcctcc gataactggg gtgaccttgg ttaatattca ccagcagcct  120
cccccgttgc ccctctggat ccactgctta aatacggacg aggacagggc cctgtctcct  180
cagcttcagg caccaccact gacctgggac agtgaata                          218

SEQ ID NO: 11          moltype = DNA  length = 190
FEATURE                Location/Qualifiers
misc_feature           1..190
                       note = constructed sequence
source                 1..190
                       mol_type = other DNA
                       organism = synthetic construct
SEQUENCE: 11
atttcataga acgaatgttc cgatgctcta atctctctag acaaggttca tatttgtatg  60
ggttacttat tctctctttg ttgactaagt caataatcag aatcagcagg tttgcagtca  120
gattggcagg gataagcagc ctagctcagg agaagtgagt ataaaagccc caggctggga  180
gcagccatca                                                         190

SEQ ID NO: 12          moltype = DNA  length = 215
FEATURE                Location/Qualifiers
misc_feature           1..215
                       note = constructed sequence
source                 1..215
                       mol_type = other DNA
                       organism = synthetic construct
SEQUENCE: 12
gcctcgactg tgccttctag ttgccagcca tctgttgttt gcccctcccc cgtgccttcc  60
ttgaccctgg aaggtgccac tcccactgtc ctttcctaat aaaatgagga aattgcatcg  120
cattgtctga gtaggtgtca ttctattctg gggggtgggg tggggcagga cagcaagggg  180
gaggattggg aagacaatag caggcatgct gggga                             215

SEQ ID NO: 13          moltype = DNA  length = 75
FEATURE                Location/Qualifiers
misc_feature           1..75
                       note = constructed sequence
source                 1..75
                       mol_type = other DNA
                       organism = synthetic construct
SEQUENCE: 13
aataaagtct gagtgggcgg cagcctgtgt gtgcctgggt tctctctgtc ccggaatgtg  60
caaacaatgg aggtg                                                   75

SEQ ID NO: 14          moltype = DNA  length = 168
FEATURE                Location/Qualifiers
misc_feature           1..168
                       note = constructed sequence
source                 1..168
                       mol_type = other DNA
                       organism = synthetic construct
SEQUENCE: 14
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacg               168

SEQ ID NO: 15          moltype = DNA  length = 168
FEATURE                Location/Qualifiers
misc_feature           1..168
                       note = constructed sequence
source                 1..168
                       mol_type = other DNA
                       organism = synthetic construct
SEQUENCE: 15
cgtagataag tagcatggcg ggttaatcat taactacaag gaacccctag tgatggagtt  60
ggccactccc tctctgcgcg ctcgctcgct cactgaggcc gggcgaccaa aggtcgcccg  120
```

```
acgcccgggc tttgcccggg cggcctcagt gagcgagcga gcgcgcag             168

SEQ ID NO: 16          moltype = AA  length = 738
FEATURE                Location/Qualifiers
source                 1..738
                       mol_type = protein
                       organism = adeno-associated virus 8
SEQUENCE: 16
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                              738

SEQ ID NO: 17          moltype = DNA  length = 3966
FEATURE                Location/Qualifiers
misc_feature           1..3966
                       note = constructed sequence
source                 1..3966
                       mol_type = other DNA
                       organism = synthetic construct
SEQUENCE: 17
atgcccgagc aggaaagaca gatcaccgcc agagagggcg ccagccggaa gatcctgagc  60
aagctgagcc tgcccaccag agcctgggag cccgccatga agaagtcctt cgccttcgac  120
aacgtgggct acgagggcgg cctggacgga ctgggaccat cttctcaggt ggccacaagc  180
accgtgcgcg aggccgccat caagagcaag gtggcccctc tgtctctggg ccccatcgac  240
atcgagagac tgcagagcac caaccccaag cggcctctga gcagcgccaa ccagaacttc  300
aacaacagcg agacactggg ccaccagggc agccacgtcg tgacactgca gctgcggatc  360
gacggaatgc actgcaagag ctgtgtgctg aacatcgagg aaaacatcgg ccagctgctg  420
ggagtgcaga gcatccaggt gtcactggaa aacaagaccg cccaggtgaa gtacgacccc  480
agctgcacaa gccccgtggc cctgcagaga gccattgaag ctctgccccc tggcaacttc  540
aaagtgtccc tgcctgacgg agccgagggc tccggaacag atcacagaag cagcagcagc  600
cacagccctg gcagcccccc tagaaatcag gtgcagggca cctgtagcac caccctgatc  660
gccattgccg gcatgacatg cgccagctgc gtgcactcta ttgagggcat gatctcccag  720
ctggaaggcg tgcagcagat cagtgtgtct ctggccgagg gcaccgccac agtgctgtac  780
aaccctagcg tgatcagccc cgaagaactg agagccgcca ttgaggacat gggattcgaa  840
gccagcgtgg tgtccgagag ctgctccacc aaccctctgg gcaatcacag cgccggcaac  900
agcatggtgc agaccaccga cggcaccccc accagcgtgc aggaagtggc cccacataca  960
ggcagactgc ccgccaatca cgcccccgat atcctggcca agagccccca gagtacaaga  1020
gccgtggccc cccagaagtg cttcctgcag atcaagggca tgacttgtgc ctcttgtgtg  1080
tccaatatcg agcggaacct gcagaaagag gccggcgtgc tgtctgtgct ggtggctctg  1140
atggccggca aggccgagat caaatacgac cccgaagtga ttcagcccct ggaaatcgcc  1200
cagtttatcc aggacctggg ctttgaagcc gccgtgatgg aagattacgc cggctccgac  1260
ggcaacatcg agctgaccat caccggaatg acctgcgcct cctgtgtgca caacattgag  1320
tccaagctga cccggaccaa cggcatcacc tacgcctctg tggctctggc cacctccaag  1380
gccctcgtga agttcgatcc cgagatcatc ggccccaggg acatcatcaa gatcatcgaa  1440
gagatcggct tccacgccag cctggcccag aggaacccta acgcccacca cctggaccac  1500
aagatggaaa tcaagcagtg gaagaaaagc ttcctgtgca gcctggtgtt cggcatcccc  1560
gtgatggccc tgatgatcta catgctgatc cccagcaacg agccccacca gtccatggtg  1620
ctggatcaca acatcatccc cggcctgtct atcctgaacc tgatcttctt catcctgtgc  1680
accttcgtgc agctgctggg cggctggtac ttctacgtgc aggcctacaa gtccctgcgg  1740
cacagatccg ccaacatgga cgtgctgatc gtgctggcca catctatcgc ctacgtgtac  1800
tccctcgtga tcctggtggt ggccgtggcc gagaaagccg agagaagccc tgtgaccttc  1860
ttcgacaccc cccctatgct gttcgtgttt atcgccctgg gccggtggct ggaacacctg  1920
gccaaaagca agaccagcga ggccctggct aagctgatga gtctgcaggc caccgaggcc  1980
acagtcgtga ccctgggcga ggacaacctg atcatccgcg aggaacaggt gccaatggaa  2040
ctggtgcagc ggggcgacat cgtgaaggtg gtgcctggcg gcaagttccc cgtggacgga  2100
aaagtgctgg aagggaatac catggccgac gagagcctga tcacaggcga ggccatgccc  2160
gtgaccaaga aacctggcag cacagtgatc gccggcagca tcaatgccca cggcagcgtg  2220
ctgattaagg ccacacacgt gggcaacgat accaccctgg ctcagattgt gaagctggtg  2280
gaagaggccc agatgagcaa ggcccccatt cagcagctgg ctgaccggtt cagcggctac  2340
ttcgtgccct ttatcatcat catgagcacc ctgacactgg tcgtgtggat cgtgatcggc  2400
tttatcgact tcggagtggt gcagagatac ttccccaacc ctaacaagca catcagccag  2460
acagaagtga tcatcagatt cgcctttcag accagcatca ccgtgctgtg tatcgcctgc  2520
ccctgtagcc tgggactggc cacacctacc gctgtgatgg tgggaacagg cgtggccgct  2580
cagaacggca tcctgatcaa ggggggcaag cctctggaaa tggctcacaa gatcaagacc  2640
gtgatgttcg acaagaccgg caccatcacc cacggcgtgc ccagagtgat gagagtgctg  2700
ctgctggggg atgtggccac cctgcctctg agaaaggtgc tggctgtcgt gggcacagcc  2760
gaggctagct ctgaacaccc actgggagtg gccgtgacaa agtactgcaa agaggaactg  2820
ggcaccgaaa ccctgggcta ctgcaccgac tttcaggccg tgcctggctg tggcatcggc  2880
tgcaaggtgt ccaacgtgga aggcatcctg gcccacagcg agaggccact gtctgcccct  2940
```

```
gccagccacc tgaacgaggc cggatctctg cccgccgaaa aggacgctgt gccccagacc  3000
ttctctgtgc tgattggcaa cagagagtgg ctgcggcgga acggcctgac catctcctcc  3060
gatgtgtccg acgccatgac cgaccacgag atgaagggcc agaccgccat tctggtggcc  3120
attgacgggg tgctgtgcgg catgatcgca atcgccgatg ccgtgaaaca ggaagcagca  3180
ctggccgtgc acaccctgca gtctatggga gtggatgtgg tgctgatcac cggcgacaac  3240
agaaagaccg ccagggccat tgccacccag gtgggcatca acaaggtgtt cgccgaggtg  3300
ctgcccagcc acaaagtggc caaggtgcag gaactgcaga acaaaggcaa aaaggtggcc  3360
atggtgggag atggcgtgaa cgactctcct gctctggccc aggcagatat gggcgtggcc  3420
atcggcacag gcaccgacgt ggcaattgag gctgctgacg tggtgctgat tcggaacgac  3480
ctgctggacg tggtggcctc catccacctg tccaagagaa ccgtgcggcg gatcagaatc  3540
aacctggtgc tggcactgat ctataacctc gtgggcatcc ctatcgccgc tggcgtgttc  3600
atgcctatcg gaatcgtgct gcagccctgg atgggctctg ccgccatggc tgcaagctcc  3660
gtgtctgtgg tgctgtccag cctgcagctg aagtgctaca agaagcccga cctggaaaga  3720
tacgaggccc aggcccacgg acacatgaag cctctgacag cctcccaggt gtccgtgcac  3780
atcggcatgg acgacagatg gcgggacagc cctagagcca ccccttggga tcaggtgtca  3840
tacgtgtcac aggtgtccct gagcagcctg accagcgaca agcccagcag acatagcgcc  3900
gctgccgacg acgatgggga caagtggtcc ctgctgctga acggccggga tgaggaacag  3960
tacatc                                                             3966

SEQ ID NO: 18          moltype = DNA  length = 3360
FEATURE                Location/Qualifiers
misc_feature           1..3360
                       note = constructed sequence
source                 1..3360
                       mol_type = other DNA
                       organism = synthetic construct
SEQUENCE: 18
atgcccgagc aggaaagaca gatcaccgcc agagagggcg ccagccggaa gatcctgagc  60
aagctgagcc tgcccaccag agcctgggag cccgccatga agaagtcctt cgccttcgac  120
aacgtgggct acgagggcgg cctggacgga ctgggaccat cttctcaggt ggccacaagc  180
accgtgcgca gccccgaaga actgagagcc gccattgagg acatgggatt cgaagccagc  240
gtggtgtccg agagctgctc caccaaccct ctgggcaatc acagcgccgg caacagcatg  300
gtgcagacca ccgacggcac ccccaccagc gtgcaggaag tggccccaca tacaggcaga  360
ctgcccgcca atcacgcccc cgatatcctg gccaagagcc cccagagtac aagagccgtg  420
gccccccaga agtgcttcct gcagatcaag ggcatgactt gtgcctcttg tgtgtccaat  480
atcgagcgga acctgcagaa agaggccggc gtgctgtctg tgctggtggc tctgatggcc  540
ggcaaggccg agatcaaata cgaccccgaa gtgattcagc ccctggaaat cgcccagttt  600
atccaggacc tgggctttga agccgccgtg atggaagatt acgccggctc cgacggcaac  660
atcgagctga ccatcaccgg aatgacctgc gcctcctgtg tgcacaacat tgagtccaag  720
ctgacccgga ccaacggcat cacctacgcc tctgtggctc tggccacctc caaggccctc  780
gtgaagttcg atcccgagat catcggcccc agggacatca tcaagatcat cgaagagatc  840
ggcttccacg ccagcctggc ccagaggaac cctaacgccc accacctgga ccacaagatg  900
gaaatcaagc agtggaagaa aagcttcctg tgcagcctgg tgttcggcat ccccgtgatg  960
gccctgatga tctacatgct gatccccagc aacgagcccc accagtccat ggtgctggat  1020
cacaacatca tccccggcct gtctatcctg aacctgatct tcttcatcct gtgcaccttc  1080
gtgcagctgc tgggcggctg gtacttctac gtgcaggcct acaagtccct gcggcacaga  1140
tccgccaaca tggacgtgct gatcgtgctg gccacatcta tcgcctacgt gtactccctc  1200
gtgatcctgg tggtggccgt ggccgagaaa gccgagagaa gccctgtgac cttcttcgac  1260
accccccccta tgctgttcgt gtttatcgcc ctgggccggt ggctggaaca cctggccaaa  1320
agcaagacca gcgaggccct ggctaagctg atgagtctgc aggccaccga ggccacagtc  1380
gtgaccctgg gcgaggacaa cctgatcatc cgcgaggaac aggtgccaat ggaactggtg  1440
cagcggggcg acatcgtgaa ggtggtgcct ggcggcaagt tccccgtgga cggaaaagtg  1500
ctggaaggga ataccatggc cgacgagagc ctgatcacag gcgaggccat gcccgtgacc  1560
aagaaacctg gcagcacagt gatcgccggc agcatcaatg cccacggcag cgtgctgatt  1620
aaggccacac acgtgggcaa cgataccacc ctggctcaga ttgtgaagct ggtggaagag  1680
gcccagatga gcaaggcccc cattcagcag ctggctgacc ggttcagcgg ctacttcgtg  1740
ccctttatca tcatcatgag caccctgaca ctggtcgtgt ggatcgtgat cggctttatc  1800
gacttcggag tggtgcagag atacttcccc aaccctaaca agcacatcag ccagacagaa  1860
gtgatcatca gattcgcctt tcagaccagc atcaccgtgc tgtgtatcgc ctgcccctgt  1920
agcctgggac tggccacacc taccgctgtg atggtgggaa caggcgtggc cgctcagaac  1980
ggcatcctga tcaagggggg caagcctctg gaaatggctc acaagatcaa gaccgtgatg  2040
ttcgacaaga ccggcaccat cacccacggc gtgcccagag tgatgagagt gctgctgctg  2100
ggggatgtgg ccaccctgcc tctgagaaag gtgctggctg tcgtgggcac agccgaggct  2160
agctctgaac acccactggg agtggccgtg acaaagtact gcaaagagga actgggcacc  2220
gaaaccctgg gctactgcac cgactttcag gccgtgcctg gctgtggcat cggctgcaag  2280
gtgtccaacg tggaaggcat cctggcccac agcgagaggc cactgtctgc ccctgccagc  2340
cacctgaacg aggccggatc tctgcccgcc gaaaaggacg ctgtgcccca gaccttctct  2400
gtgctgattg gcaacagaga gtggctgcgg cggaacggcc tgaccatctc ctccgatgtg  2460
tccgacgcca tgaccgacca cgagatgaag ggccagaccg ccattctggt ggccattgac  2520
ggggtgctgt gcggcatgat cgcaatcgcc gatgccgtga aacaggaagc agcactggcc  2580
gtgcacaccc tgcagtctat gggagtggat gtggtgctga tcaccggcga caacagaaag  2640
accgccaggg ccattgccac ccaggtgggc atcaacaagg tgttcgccga ggtgctgccc  2700
agccacaaag tggccaaggt gcaggaactg cagaacaaag gcaaaaaggt ggccatggtg  2760
ggagatggcg tgaacgactc tcctgctctg gcccaggcag atatgggcgt ggccatcggc  2820
acaggcaccg acgtggcaat tgaggctgct gacgtggtgc tgattcggaa cgacctgctg  2880
gacgtggtgg cctccatcca cctgtccaag agaaccgtgc ggcggatcag aatcaacctg  2940
gtgctggcac tgatctataa cctcgtgggc atccctatcg ccgctggcgt gttcatgcct  3000
atcggaatcg tgctgcagcc ctggatgggc tctgccgcca tggctgcaag ctccgtgtct  3060
gtggtgctgt ccagcctgca gctgaagtgc tacaagaagc ccgacctgga aagatacgag  3120
```

```
gcccaggccc acggacacat gaagcctctg acagcctccc aggtgtccgt gcacatcggc  3180
atggacgaca gatggcggga cagccctaga gccacccctt gggatcaggt gtcatacgtg  3240
tcacaggtgt ccctgagcag cctgaccagc gacaagccca gcagacatag cgccgctgcc  3300
gacgacgatg ggacaagtg gtccctgctg ctgaacggcc gggatgagga acagtacatc  3360

SEQ ID NO: 19          moltype = DNA  length = 2967
FEATURE                Location/Qualifiers
misc_feature           1..2967
                       note = constructed sequence
source                 1..2967
                       mol_type = other DNA
                       organism = synthetic construct
SEQUENCE: 19
atgcccgagc aggaaagaca gatcaccgcc agagagggcg ccagccggaa gatcctgagc  60
aagctgagcc tgcccaccag agcctgggag cccgccatga agaagtcctt cgccttcgac  120
aacgtgggct acgagggcgg cctggacgga ctgggaccat cttctcaggt ggccacaagc  180
accgtgcgcc tggaaatcgc ccagtttatc caggacctgg gctttgaagc cgccgtgatg  240
gaagattacg ccggctccga cggcaacatc gagctgacca tcaccggaat gacctgcgcc  300
tcctgtgtgc acaacattga gtccaagctg acccggacca acggcatcac ctacgcctct  360
gtggctctgg ccacctccaa ggccctcgtg aagttcgatc ccgagatcat cggccccagg  420
gacatcatca agatcatcga agagatcggc ttccacgcca gcctggccca gaggaaccct  480
aacgcccacc acctggacca caagatggaa atcaagcagt ggaagaaaag cttcctgtgc  540
agcctggtgt tcggcatccc cgtgatggcc ctgatgatct acatgctgat ccccagcaac  600
gagccccacc agtccatggt gctggatcac aacatcatcc ccggcctgtc tatcctgaac  660
ctgatcttct tcatcctgtg caccttcgtg cagctgctgg gcggctggta cttctacgtg  720
caggcctaca agtccctgcg gcacagatcc gccaacatgg acgtgctgat cgtgctggcc  780
acatctatcg cctacgtgta ctccctcgtg atcctggtgg tggccgtggc cgagaaagcc  840
gagagaagcc ctgtgacctt cttcgacacc ccccctatgc tgttcgtgtt tatcgccctg  900
ggccggtggc tggaacacct ggccaaaagc aagaccagcg aggccctggc taagctgatg  960
agtctgcagg ccaccgaggc cacagtcgtg accctgggcg aggacaacct gatcatccgc  1020
gaggaacagg tgccaatgga actggtgcag cggggcgaca tcgtgaaggt ggtgcctggc  1080
ggcaagttcc ccgtggacgg aaaagtgctg gaagggaata ccatggccga cgagagcctg  1140
atcacaggcg aggccatgcc cgtgaccaag aaacctggca gcacagtgat cgccggcagc  1200
atcaatgccc acggcagcgt gctgattaag gccacacacg tgggcaacga taccaccctg  1260
gctcagattg tgaagctggt ggaagaggcc cagatgagca aggcccccat tcagcagctg  1320
gctgaccggt tcagcggcta cttcgtgccc tttatcatca tcatgagcac cctgacactg  1380
gtcgtgtgga tcgtgatcgg ctttatcgac ttcggagtgg tgcagagata cttccccaac  1440
cctaacaagc acatcagcca gacagaagtg atcatcagat tcgcctttca gaccagcatc  1500
accgtgctgt gtatcgcctg cccctgtagc ctgggactgg ccacacctac cgctgtgatg  1560
gtgggaacag gcgtggccgc tcagaacggc atcctgatca agggggcaa gcctctggaa  1620
atggctcaca agatcaagac cgtgatgttc gacaagaccg gcaccatcac ccacggcgtg  1680
cccagagtga tgagagtgct gctgctgggg gatgtggcca ccctgcctct gagaaaggtg  1740
ctggctgtcg tgggcacagc cgaggctagc tctgaacacc cactgggagt ggccgtgaca  1800
aagtactgca aagaggaact gggcaccgaa accctgggct actgcaccga ctttcaggcc  1860
gtgcctggct gtggcatcgg ctgcaaggtg tccaacgtgg aaggcatcct ggcccacagc  1920
gagaggccac tgtctgcccc tgccagccac ctgaacgagg ccggatctct gcccgccgaa  1980
aaggacgctg tgccccagac cttctctgtg ctgattggca acagagagtg gctgcggcgg  2040
aacggcctga ccatctcctc cgatgtgtcc gacgccatga ccgaccacga gatgaagggc  2100
cagaccgcca ttctggtggc cattgacggg gtgctgtgcg gcatgatcgc aatcgccgat  2160
gccgtgaaac aggaagcagc actggccgtg cacaccctgc agtctatggg agtggatgtg  2220
gtgctgatca ccggcgacaa cagaaagacc gccagggcca ttgccaccca ggtgggcatc  2280
aacaaggtgt tcgccgaggt gctgcccagc cacaaagtgg ccaaggtgca ggaactgcag  2340
aacaaaggca aaaaggtggc catggtggga gatggcgtga acgactctcc tgctctggcc  2400
caggcagata tgggcgtggc catcggcaca ggcaccgacg tggcaattga ggctgctgac  2460
gtggtgctga ttcggaacga cctgctggac gtggtggcct ccatccacct gtccaagaga  2520
accgtgcggc ggatcagaat caacctggtg ctggcactga tctataacct cgtgggcatc  2580
cctatcgccg ctggcgtgtt catgcctatc ggaatcgtgc tgcagccctg gatgggctct  2640
gccgccatgg ctgcaagctc cgtgtctgtg gtgctgtcca gcctgcagct gaagtgctac  2700
aagaagcccg acctggaaag atacgaggcc caggcccacg gacacatgaa gcctctgaca  2760
gcctcccagg tgtccgtgca catcggcatg gacgacagat ggcgggacag ccctagagcc  2820
acccccttggg atcaggtgtc atacgtgtca caggtgtccc tgagcagcct gaccagcgac  2880
aagcccagca gacatagcgc cgctgccgac gacgatgggg acaagtggtc cctgctgctg  2940
aacggccggg atgaggaaca gtacatc                                      2967

SEQ ID NO: 20          moltype = DNA  length = 4284
FEATURE                Location/Qualifiers
misc_feature           1..4284
                       note = constructed sequence
source                 1..4284
                       mol_type = other DNA
                       organism = synthetic construct
SEQUENCE: 20
atgcccgagc aggaaagaca gatcaccgcc agagagggcg ccagccggaa gatcctgagc  60
aagctgagcc tgcccaccag agcctgggag cccgccatga agaagtcctt cgccttcgac  120
aacgtgggct acgagggcgg cctggacgga ctgggaccat cttctcaggt ggccacaagc  180
accgtgcgca aatacgtgcc ctctgtcgtg tgcctgcagc aggtgtgcca ccagatcggc  240
gacatgggct tcgaggcctc tatcgccgag ggaaaggccg cctcttggcc ctctagaagc  300
ctgcctgctc aggaagccgt cgtgaagctg cgggtggaag ggatgacctg tcagtcctgc  360
gtgtccagca tcgagggcaa agtgcggaag ctgcagggcg tggtgcgcgt gaaagtgtct  420
```

```
ctgagcaacc aggaagctgt gatcacctac cagccctacc tgatccagcc cgaggacctg  480
agggaccacg tgaacgatat gggatttgag gccgccatca agagcaaggt ggcccctctg  540
tctctgggcc ccatcgacat cgagagactg cagagcacca accccaagcg gcctctgagc  600
agcgccaacc agaacttcaa caacagcgag acactgggcc accagggcag ccacgtcgtg  660
acactgcagc tgcggatcga cggaatgcac tgcaagagct gtgtgctgaa catcgaggaa  720
aacatcggcc agctgctggg agtgcagagc atccaggtgt cactggaaaa caagaccgcc  780
caggtgaagt acgaccccag ctgcacaagc cccgtggccc tgcagagagc cattgaagct  840
ctgccccctg gcaacttcaa agtgtccctg cctgacggag ccgagggctc cggaacagat  900
cacagaagca gcagcagcca cagccctggc agcccccccta gaaatcaggt gcagggcacc  960
tgtagcacca ccctgatcgc cattgccggc atgacatgcg ccagctgcgt gcactctatt  1020
gagggcatga tctcccagct ggaaggcgtg cagcagatca gtgtgtctct ggccgagggc  1080
accgccacag tgctgtacaa ccctagcgtg atcagccccg aagaactgag agccgccatt  1140
gaggacatgg gattcgaagc cagcgtggtg tccgagagct gctccaccaa ccctctgggc  1200
aatcacagcg ccggcaacag catggtgcag accaccgacg gcaccccccac cagcgtgcag  1260
gaagtggccc cacatacagg cagactgccc gccaatcacg cccccgatat cctggccaag  1320
agcccccaga gtacaagagc cgtggccccc cagaagtgct tcctgcagat caagggcatg  1380
acttgtgcct cttgtgtgtc caatatcgag cggaacctgc agaaagaggc cggcgtgctg  1440
tctgtgctgg tggctctgat ggccggcaag gccgagatca aatacgaccc cgaagtgatt  1500
cagcccctgg aaatcgccca gtttatccag gacctgggct ttgaagccgc cgtgatggaa  1560
gattacgccg gctccgacgg caacatcgag ctgaccatca ccggaatgac ctgcgcctcc  1620
tgtgtgcaca acattgagtc caagctgacc cggaccaacg gcatcaccta cgcctctgtg  1680
gctctggcca cctccaaggc cctcgtgaag ttcgatcccg agatcatcgg ccccagggac  1740
atcatcaaga tcatcgaaga gatcggcttc cacgccagcc tggcccagag gaaccctaac  1800
gcccaccacc tggaccacaa gatggaaatc aagcagtgga agaaaagctt cctgtgcagc  1860
ctggtgttcg gcatccccgt gatggccctg atgatctaca tgctgatccc cagcaacgag  1920
ccccaccagt ccatggtgct ggatcacaac atcatccccg gcctgtctat cctgaacctg  1980
atcttcttca tcctgtgcac cttcgtgcag ctgctgggcg gctggtactt ctacgtgcag  2040
gcctacaagt ccctgcggca cagatccgcc aacatggacg tgctgatcgt gctggccaca  2100
tctatcgcct acgtgtactc cctcgtgatc ctggtggtgg ccgtggccga gaaagccgag  2160
agaagccctg tgaccttctt cgacaccccc cctatgctgt tcgtgtttat cgccctgggc  2220
cggtggctgg aacacctggc caaaagcaag accagcgagg ccctggctaa gctgatgagt  2280
ctgcaggcca ccgaggccac agtcgtgacc ctgggcgagg acaacctgat catccgcgag  2340
gaacaggtgc caatggaact ggtgcagcgg ggcgacatcg tgaaggtggt gcctggcggc  2400
aagttccccg tggacggaaa agtgctggaa gggaatacca tggccgacga gagcctgatc  2460
acaggcgagg ccatgcccgt gaccaagaaa cctggcagca cagtgatcgc cggcagcatc  2520
aatgcccacg gcagcgtgct gattaaggcc acacacgtgg gcaacgatac caccctggct  2580
cagattgtga agctggtgga agaggcccag atgagcaagg cccccattca gcagctggct  2640
gaccggttca gcggctactt cgtgcccttt atcatcatca tgagcaccct gacactggtc  2700
gtgtggatcg tgatcggctt tatcgacttc ggagtggtgc agagatactt ccccaaccct  2760
aacaagcaca tcagccagac agaagtgatc atcagattcg cctttcagac cagcatcacc  2820
gtgctgtgta tcgcctgccc ctgtagcctg ggactggcca cacctaccgc tgtgatggtg  2880
ggaacaggcg tggccgctca gaacggcatc ctgatcaagg ggggcaagcc tctggaaatg  2940
gctcacaaga tcaagaccgt gatgttcgac aagaccggca ccatcaccca cggcgtgccc  3000
agagtgatga gagtgctgct gctgggggat gtggccaccc tgcctctgag aaaggtgctg  3060
gctgtcgtgg gcacagccga ggctagctct gaacacccac tgggagtggc cgtgacaaag  3120
tactgcaaag aggaactggg caccgaaacc ctgggctact gcaccgactt tcaggccgtg  3180
cctggctgtg gcatcggctg caaggtgtcc aacgtggaag gcatcctggc ccacagcgag  3240
aggccactgt ctgcccctgc cagccacctg aacgaggccg gatctctgcc cgccgaaaag  3300
gacgctgtgc cccagacctt ctctgtgctg attggcaaca gagagtggct gcggcggaac  3360
ggcctgacca tctcctccga tgtgtccgac gccatgaccg accacgagat gaagggccag  3420
accgccattc tggtggccat tgacggggtg ctgtgcggca tgatcgcaat cgccgatgcc  3480
gtgaaacagg aagcagcact ggccgtgcac accctgcagt ctatgggagt ggatgtggtg  3540
ctgatcaccg gcgacaacag aaagaccgcc agggccattg ccacccaggt gggcatcaac  3600
aaggtgttcg ccgaggtgct gcccagccac aaagtggcca aggtgcagga actgcagaac  3660
aaaggcaaaa aggtggccat ggtgggagat ggcgtgaacg actctcctgc tctggcccag  3720
gcagatatgg gcgtggccat cggcacaggc accgacgtgg caattgaggc tgctgacgtg  3780
gtgctgattc ggaacgacct gctggacgtg gtggcctcca tccacctgtc caagagaacc  3840
gtgcggcgga tcagaatcaa cctggtgctg gcactgatct ataacctcgt gggcatccct  3900
atcgccgctg gcgtgttcat gcctatcgga atcgtgctgc agccctggat gggctctgcc  3960
gccatggctg caagctccgt gtctgtggtg ctgtccagcc tgcagctgaa gtgctacaag  4020
aagcccgacc tggaaagata cgaggcccag gcccacggac acatgaagcc tctgacagcc  4080
tcccaggtgt ccgtgcacat cggcatggac gacagatggc gggacagccc tagagccacc  4140
ccttgggatc aggtgtcata cgtgtcacag gtgtccctga gcagcctgac cagcgacaag  4200
cccagcagac atagcgccgc tgccgacgac gatggggaca agtggtccct gctgctgaac  4260
ggccgggatg aggaacagta catc                                       4284
```

```
SEQ ID NO: 21          moltype = DNA  length = 4215
FEATURE                Location/Qualifiers
misc_feature           1..4215
                       note = constructed sequence
source                 1..4215
                       mol_type = other DNA
                       organism = synthetic construct
SEQUENCE: 21
atgcccgagc aggaaagaca gatcaccgcc agagagggcg ccagccggaa gatcctgagc  60
aagctgagcc tgcccaccag agcctgggag cccgccatga agaagtcctt cgccttcgac  120
aacgtgggct acgagggcgg cctggacgga ctgggaccat cttctcaggt ggccacaagc  180
accgtgcgca tcctgggcat gacctgccag agctgcgtga agtccatcga ggaccggatc  240
agcaacctga agggcatcat cagcatgaag gtgtccctgg aacagggcag cgccaccgtg  300
```

```
aaatacgtgc cctctgtcgt gtgcctgcag caggtgtgcc accagatcgg cgacatgggc  360
ttcgaggcct ctatcgccga gggaaaggcc gcctcttggc cctctagaag cctgcctgct  420
caggaagccg tcgtgaagga ggccgccatc aagagcaagg tggcccctct gtctctgggc  480
cccatcgaca tcgagagact gcagagcacc aaccccaagc ggcctctgag cagcgccaac  540
cagaacttca acaacagcga gacactgggc caccagggca gccacgtcgt gacactgcag  600
ctgcggatcg acggaatgca ctgcaagagc tgtgtgctga acatcgagga aaacatcggc  660
cagctgctgg gagtgcagag catccaggtg tcactggaaa acaagaccgc ccaggtgaag  720
tacgacccca gctgcacaag ccccgtggcc ctgcagagag ccattgaagc tctgccccct  780
ggcaacttca aagtgtccct gcctgacgga gccgagggct ccggaacaga tcacagaagc  840
agcagcagcc acagccctgg cagcccccct agaaatcagg tgcagggcac ctgtagcacc  900
accctgatcg ccattgccgg catgacatgc gccagctgcg tgcactctat tgagggcatg  960
atctcccagc tggaaggcgt gcagcagatc agtgtgtctc tggccgaggg caccgccaca  1020
gtgctgtaca accctagcgt gatcagcccc gaagaactga gagccgccat tgaggacatg  1080
ggattcgaag ccagcgtggt gtccgagagc tgctccacca accctctggg caatcacagc  1140
gccggcaaca gcatggtgca gaccaccgac ggcaccccca ccagcgtgca ggaagtggcc  1200
ccacatacag gcagactgcc cgccaatcac gcccccgata tcctggccaa gagcccccag  1260
agtacaagag ccgtggcccc ccagaagtgc ttcctgcaga tcaagggcat gacttgtgcc  1320
tcttgtgtgt ccaatatcga gcggaacctg cagaaagagg ccggcgtgct gtctgtgctg  1380
gtggctctga tggccggcaa ggccgagatc aaatacgacc ccgaagtgat tcagcccctg  1440
gaaatcgccc agtttatcca ggacctgggc tttgaagccg ccgtgatgga agattacgcc  1500
ggctccgacg gcaacatcga gctgaccatc accggaatga cctgcgcctc ctgtgtgcac  1560
aacattgagt ccaagctgac ccggaccaac ggcatcacct acgcctctgt ggctctggcc  1620
acctccaagg ccctcgtgaa gttcgatccc gagatcatcg gccccaggga catcatcaag  1680
atcatcgaag agatcggctt ccacgccagc ctggcccaga ggaaccctaa cgcccaccac  1740
ctggaccaca agatggaaat caagcagtgg aagaaaagct tcctgtgcag cctggtgttc  1800
ggcatccccg tgatggccct gatgatctac atgctgatcc ccagcaacga gccccaccag  1860
tccatggtgc tggatcacaa catcatcccc ggcctgtcta tcctgaacct gatcttcttc  1920
atcctgtgca ccttcgtgca gctgctgggc ggctggtact tctacgtgca ggcctacaag  1980
tccctgcggc acagatccgc caacatggac gtgctgatcg tgctggccac atctatcgcc  2040
tacgtgtact ccctcgtgat cctggtggtg gccgtggccg agaaagccga gagaagccct  2100
gtgaccttct tcgacacccc ccctatgctg ttcgtgttta tcgccctggg ccggtggctg  2160
gaacacctgg ccaaaagcaa gaccagcgag gccctggcta agctgatgag tctgcaggcc  2220
accgaggcca cagtcgtgac cctgggcgag gacaacctga tcatccgcga ggaacaggtg  2280
ccaatggaac tggtgcagcg gggcgacatc gtgaaggtgg tgcctggcgg caagttcccc  2340
gtggacggaa aagtgctgga agggaatacc atggccgacg agagcctgat cacaggcgag  2400
gccatgcccg tgaccaagaa acctggcagc acagtgatcg ccggcagcat caatgcccac  2460
ggcagcgtgc tgattaaggc cacacacgtg ggcaacgata ccaccctggc tcagattgtg  2520
aagctggtgg aagaggccca gatgagcaag gcccccattc agcagctggc tgaccggttc  2580
agcggctact tcgtgccctt tatcatcatc atgagcaccc tgacactggt cgtgtggatc  2640
gtgatcggct ttatcgactt cggagtggtg cagagatact tccccaaccc taacaagcac  2700
atcagccaga cagaagtgat catcagattc gcctttcaga ccagcatcac cgtgctgtgt  2760
atcgcctgcc cctgtagcct gggactggcc acacctaccg ctgtgatggt gggaacaggc  2820
gtggccgctc agaacggcat cctgatcaag gggggcaagc ctctggaaat ggctcacaag  2880
atcaagaccg tgatgttcga caagaccggc accatcaccc acggcgtgcc cagagtgatg  2940
agagtgctgc tgctgggga tgtggccacc ctgcctctga gaaaggtgct ggctgtcgtg  3000
ggcacagccg aggctagctc tgaacaccca ctgggagtgg ccgtgacaaa gtactgcaaa  3060
gaggaactgg gcaccgaaac cctgggctac tgcaccgact ttcaggccgt gcctggctgt  3120
ggcatcggct gcaaggtgtc caacgtggaa ggcatcctgg cccacagcga gaggccactg  3180
tctgcccctg ccagccacct gaacgaggcc ggatctctgc ccgccgaaaa ggacgctgtg  3240
ccccagacct tctctgtgct gattggcaac agagagtggc tgcggcggaa cggcctgacc  3300
atctcctccg atgtgtccga cgccatgacc gaccacgaga tgaagggcca gaccgccatt  3360
ctggtggcca ttgacggggt gctgtgcggc atgatcgcaa tcgccgatgc cgtgaaacag  3420
gaagcagcac tggccgtgca caccctgcag tctatgggag tggatgtggt gctgatcacc  3480
ggcgacaaca gaaagaccgc cagggccatt gccacccagg tgggcatcaa caaggtgttc  3540
gccgaggtgc tgcccagcca caaagtggcc aaggtgcagg aactgcagaa caaaggcaaa  3600
aaggtggcca tggtgggaga tggcgtgaac gactctcctg ctctggccca ggcagatatg  3660
ggcgtggcca tcggcacagg caccgacgtg gcaattgagg ctgctgacgt ggtgctgatt  3720
cggaacgacc tgctggacgt ggtggcctcc atccacctgt ccaagagaac cgtgcggcgg  3780
atcagaatca acctggtgct ggcactgatc tataacctcg tgggcatccc tatcgccgct  3840
ggcgtgttca tgcctatcgg aatcgtgctg cagccctgga tgggctctgc cgccatggct  3900
gcaagctccg tgtctgtggt gctgtccagc ctgcagctga agtgctacaa gaagcccgac  3960
ctggaaagat acgaggccca ggcccacgga cacatgaagc ctctgacagc ctcccaggtg  4020
tccgtgcaca tcggcatgga cgacagatgg cgggacagcc ctagagccac cccttgggat  4080
caggtgtcat acgtgtcaca ggtgtccctg agcagcctga ccagcgacaa gcccagcaga  4140
catagcgccg ctgccgacga cgatggggac aagtggtccc tgctgctgaa cggccgggat  4200
gaggaacagt acatc                                                   4215
```

```
SEQ ID NO: 22          moltype = DNA  length = 4317
FEATURE                Location/Qualifiers
misc_feature           1..4317
                       note = constructed sequence
source                 1..4317
                       mol_type = other DNA
                       organism = synthetic construct
SEQUENCE: 22
atgcccgagc aggaaagaca gatcaccgcc agagagggcg ccagccggaa gatcctgagc  60
aagctgagcc tgcccaccag agcctgggag cccgccatga agaagtcctt cgccttcgac  120
aacgtgggct acgagggcgg cctggacgga ctgggaccat cttctcaggt ggccacaagc  180
accgtgcgca tcctgggcat gacctgccag agctgcgtga agtccatcga ggaccggatc  240
```

```
agcaacctga agggcatcat cagcatgaag gtgtccctgg aacagggcag cgccaccgtg  300
aaatacgtgc cctctgtcgt gtgcctgcag caggtgtgcc accagatcgg cgacatgggc  360
ttcgaggcct ctatcgccga gggaaaggcc gcctcttggc cctctagaag cctgcctgct  420
caggaagccg tcgtgaagct gcgggtggaa gggatgacct gtcagtcctg cgtgtccagc  480
atcgagggca aagtgcggaa gctgcagggc gtggtgcgcg tgaaagtgtc tctgagcaac  540
caggaagctg tgatcaccta ccagccctac ctgatccagc ccgaggacct gagggaccac  600
gtgaacgata tgggatttga ggccgccatc aagagcaagg tggcccctct gtctctgggc  660
cccatcgaca tcgagagact gcagagcacc aaccccaagc ggcctctgag cagcgccaac  720
cagaacttca acaacagcga gacactgggc caccagggca gccacgtcgt gacactgcag  780
agcatccagg tgtcactgga aaacaagacc gcccaggtga agtacgaccc cagctgcaca  840
agccccgtgg ccctgcagag agccattgaa gctctgcccc ctggcaactt caaagtgtcc  900
ctgcctgacg gagccgaggg ctccggaaca gatcacagaa gcagcagcag ccacagccct  960
ggcagccccc ctagaaatca ggtgcagggc acctgtagca ccaccctgat cgccattgcc  1020
ggcatgacat gcgccagctg cgtgcactct attgagggca tgatctccca gctggaaggc  1080
gtgcagcaga tcagtgtgtc tctggccgag ggcaccgcca cagtgctgta caaccctagc  1140
gtgatcagcc ccgaagaact gagagccgcc attgaggaca tgggattcga agccagcgtg  1200
gtgtccgaga gctgctccac caaccctctg ggcaatcaca gcgccggcaa cagcatggtg  1260
cagaccaccg acggcacccc caccagcgtg caggaagtgg ccccacatac aggcagactg  1320
cccgccaatc acgcccccga tatcctggcc aagagccccc agagtacaag agccgtggcc  1380
ccccagaagt gcttcctgca gatcaagggc atgacttgtg cctcttgtgt gtccaatatc  1440
gagcggaacc tgcagaaaga ggccggcgtg ctgtctgtgc tggtggctct gatggccggc  1500
aaggccgaga tcaaatacga ccccgaagtg attcagcccc tggaaatcgc ccagtttatc  1560
caggacctgg gctttgaagc cgccgtgatg gaagattacg ccggctccga cggcaacatc  1620
gagctgacca tcaccggaat gacctgcgcc tcctgtgtgc acaacattga gtccaagctg  1680
acccggacca acggcatcac ctacgcctct gtggctctgg ccacctccaa ggccctcgtg  1740
aagttcgatc ccgagatcat cggccccagg gacatcatca agatcatcga agagatcggc  1800
ttccacgcca gcctggccca gaggaaccct aacgcccacc acctggacca caagatggaa  1860
atcaagcagt ggaagaaaag cttcctgtgc agcctggtgt tcggcatccc cgtgatggcc  1920
ctgatgatct acatgctgat ccccagcaac gagccccacc agtccatggt gctggatcac  1980
aacatcatcc ccggcctgtc tatcctgaac ctgatcttct tcatcctgtg caccttcgtg  2040
cagctgctgg gcggctggta cttctacgtg caggcctaca agtccctgcg gcacagatcc  2100
gccaacatgg acgtgctgat cgtgctggcc acatctatcg cctacgtgta ctccctcgtg  2160
atcctggtgg tggccgtggc cgagaaagcc gagagaagcc ctgtgacctt cttcgacacc  2220
ccccctatgc tgttcgtgtt tatcgccctg ggccggtggc tggaacacct ggccaaaagc  2280
aagaccagcg aggccctggc taagctgatg agtctgcagg ccaccgaggc cacagtcgtg  2340
accctgggcg aggacaacct gatcatccgc gaggaacagg tgccaatgga actggtgcag  2400
cggggcgaca tcgtgaaggt ggtgcctggc ggcaagttcc ccgtggacgg aaaagtgctg  2460
gaagggaata ccatggccga cgagagcctg atcacaggcg aggccatgcc cgtgaccaag  2520
aaacctggca gcacagtgat cgccggcagc atcaatgccc acggcagcgt gctgattaag  2580
gccacacacg tgggcaacga taccaccctg gctcagattg tgaagctggt ggaagaggcc  2640
cagatgagca aggcccccat tcagcagctg gctgaccggt tcagcggcta cttcgtgccc  2700
tttatcatca tcatgagcac cctgacactg gtcgtgtgga tcgtgatcgg ctttatcgac  2760
ttcggagtgg tgcagagata cttccccaac cctaacaagc acatcagcca gacagaagtg  2820
atcatcagat tcgcctttca gaccagcatc accgtgctgt gtatcgcctg cccctgtagc  2880
ctgggactgg ccacacctac cgctgtgatg gtgggaacag gcgtggccgc tcagaacggc  2940
atcctgatca agggggcaa gcctctggaa atggctcaca agatcaagac cgtgatgttc  3000
gacaagaccg gcaccatcac ccacggcgtg cccagagtga tgagagtgct gctgctgggg  3060
gatgtggcca ccctgcctct gagaaaggtg ctggctgtcg tgggcacagc cgaggctagc  3120
tctgaacacc cactgggagt ggccgtgaca aagtactgca aagaggaact gggcaccgaa  3180
accctgggct actgcaccga ctttcaggcc gtgcctggct gtggcatcgg ctgcaaggtg  3240
tccaacgtgg aaggcatcct ggcccacagc gagaggccac tgtctgcccc tgccagccac  3300
ctgaacgagg ccggatctct gcccgccgaa aaggacgctg tgccccagac cttctctgtg  3360
ctgattggca acagagagtg gctgcggcgg aacggcctga ccatctcctc cgatgtgtcc  3420
gacgccatga ccgaccacga gatgaagggc cagaccgcca ttctggtggc cattgacggg  3480
gtgctgtgcg gcatgatcgc aatcgccgat gccgtgaaac aggaagcagc actggccgtg  3540
cacaccctgc agtctatggg agtggatgtg gtgctgatca ccggcgacaa cagaaagacc  3600
gccagggcca ttgccaccca ggtgggcatc aacaaggtgt tcgccgaggt gctgcccagc  3660
cacaaagtgg ccaaggtgca ggaactgcag aacaaaggca aaaaggtggc catggtggga  3720
gatggcgtga acgactctcc tgctctggcc caggcagata tgggcgtggc catcggcaca  3780
ggcaccgacg tggcaattga ggctgctgac gtggtgctga ttcggaacga cctgctggac  3840
gtggtggcct ccatccacct gtccaagaga accgtgcggc ggatcagaat caacctggtg  3900
ctggcactga tctataacct cgtgggcatc cctatcgccg ctggcgtgtt catgcctatc  3960
ggaatcgtgc tgcagccctg gatgggctct gccgccatgg ctgcaagctc cgtgtctgtg  4020
gtgctgtcca gcctgcagct gaagtgctac aagaagcccg acctggaaag atacgaggcc  4080
caggcccacg gacacatgaa gcctctgaca gcctcccagg tgtccgtgca catcggcatg  4140
gacgacagat ggcgggacag ccctagagcc accccttggg atcaggtgtc atacgtgtca  4200
caggtgtccc tgagcagcct gaccagcgac aagcccagca gacatagcgc cgctgccgac  4260
gacgatgggg acaagtggtc cctgctgctg aacggccggg atgaggaaca gtacatc     4317
```

```
SEQ ID NO: 23           moltype = DNA  length = 7944
FEATURE                 Location/Qualifiers
misc_feature            1..7944
                        note = constructed sequence
source                  1..7944
                        mol_type = other DNA
                        organism = synthetic construct
SEQUENCE: 23
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
```

-continued

```
aggggttcct tgtagttaat gattaacccg ccatgctact tatctactta agctacctcg  180
tgatcgcccg gcccctgttc aaacatgtcc taatactctg tctctgcaag ggtcatcagt  240
agttttccat cttactcaac atcctcccag tggaattcat ttcatagaac gaatgttccg  300
atgctctaat ctctctagac aaggttcata tttgtatggg ttacttattc tctctttgtt  360
gactaagtca ataatcagaa tcagcaggtt tgcagtcaga ttggcaggga taagcagcct  420
agctcaggag aagtgagtat aaaagcccca ggctgggagc agccatcagc ggccgccacc  480
atgcccgagc aggaaagaca gatcaccgcc agagagggcg ccagccggaa gatcctgagc  540
aagctgagcc tgcccaccag agcctgggag cccgccatga agaagtcctt cgccttcgac  600
aacgtgggct acgagggcgg cctggatgga ctgggaccat cttctcaggt ggccacaagc  660
accgtgcgca tcctgggcat gacctgccag agctgcgtga agtccatcga ggaccggatc  720
agcaacctga agggcatcat cagcatgaag gtgtccctgg aacagggcag cgccaccgtg  780
aaatacgtgc cctctgtcgt gtgcctgcag caagtgtgcc accagatcgg cgacatgggc  840
ttcgaggcct ctatcgccga gggaaaggcc gcctcttggc cctctagaag cctgcctgct  900
caggaagccg tcgtgaagct gcgggtggaa gggatgacct gtcagtcctg cgtgtccagc  960
atcgagggca aagtgcggaa gctgcagggc gtggtgcgcg tgaaagtgtc tctgagcaac  1020
caggaagctg tgatcaccta ccagccctac ctgatccagc ccgaggacct gagggaccac  1080
gtgaacgata tgggatttga ggccgccatc aagagcaagg tggcccctct gtctctgggc  1140
cccatcgaca tcgagagact gcagagcacc aaccccaagc ggcctctgag cagcgccaac  1200
cagaacttca acaacagcga gacactgggc caccagggca gccacgtcgt gacactgcag  1260
ctgcggatcg acggaatgca ctgcaagagc tgtgtgctga acatcgagga aaacatcggc  1320
cagctgctgg gagtgcagag catccaggtg tcactggaaa acaagaccgc ccaagtgaag  1380
tacgacccca gctgcacaag ccccgtggcc ctgcagagag ccattgaagc tctgccccct  1440
ggcaacttca aagtgtccct gcctgatggc gccgagggct ccggaacaga tcacagaagc  1500
agcagcagcc acagccctgg cagccccccct agaaatcagg tgcagggcac ctgtagcacc  1560
accctgatcg ccattgccgg catgacatgc gccagctgcg tgcactctat tgagggcatg  1620
atctcccagc tggaaggcgt gcagcagatc agtgtgtctc tggccgaggg caccgccaca  1680
gtgctgtaca accctagcgt gatcagcccc gaagaactga gagccgccat tgaggacatg  1740
ggattcgaag ccagcgtggt gtccgagagc tgctccacca accctctggg caatcacagc  1800
gccggcaaca gcatggtgca gaccaccgat ggcaccccca ccagcgtgca ggaagtggcc  1860
ccacatacag gcagactgcc cgccaatcac gcccccgata tcctggccaa gagcccccag  1920
agtacaagag ccgtggcccc ccagaagtgc ttcctgcaga tcaagggcat gacttgtgcc  1980
tcttgtgtgt ccaatatcga gcggaacctg cagaaagagg ccggcgtgct gtctgtgctg  2040
gtggctctga tggccggcaa ggccgagatc aaatacgacc ccgaagtgat tcagcccctg  2100
gaaatcgccc agtttatcca ggacctgggc tttgaagccg ccgtgatgga agattacgcc  2160
ggctccgacg gcaacatcga gctgaccatc accggaatga cctgcgcctc ctgtgtgcac  2220
aacattgagt ccaagctgac ccggaccaac ggcatcacct acgcctctgt ggctctggcc  2280
acctccaagg ccctcgtgaa gttcgatccc gagatcatcg gccccaggga catcatcaag  2340
atcatcgaag agatcggctt ccacgccagc ctggcccaga ggaaccctaa tgcccaccac  2400
ctggaccaca agatggaaat caagcagtgg aagaaaagct tcctgtgcag cctggtgttc  2460
ggcatccccg tgatggccct gatgatctac atgctgatcc ccagcaacga gccccaccag  2520
tccatggtgc tggatcacaa catcatcccc ggcctgtcta tcctgaacct gatcttcttc  2580
atcctgtgca ccttcgtgca gctgctgggc ggctggtact tctatgtgca agcctacaag  2640
tccctgcggc acagatccgc caacatggac gtgctgatcg tgctggccac atctatcgcc  2700
tacgtgtact ccctcgtgat cctggtggtg gccgtggccg agaaagccga gagaagccct  2760
gtgaccttct tcgacacccc ccctatgctg ttcgtgttta tcgccctggg ccggtggctg  2820
gaacacctgg ccaaaagcaa gaccagcgag gccctggcta agctgatgag tctgcaggcc  2880
accgaggcca cagtcgtgac cctgggcgag gacaacctga tcatccgcga ggaacaggtg  2940
ccaatggaac tggtgcagcg gggcgacatc gtgaaggtgg tgcctggcgg caagttcccc  3000
gtggacggaa aagtgctgga agggaatacc atggccgacg agagcctgat cacaggcgag  3060
gccatgcccg tgaccaagaa acctggcagc acagtgatcg ccggcagcat caatgcccac  3120
ggcagcgtgc tgattaaggc cacacacgtg ggcaacgata ccaccctggc tcagattgtg  3180
aagctggtgg aagaggccca gatgagcaag gcccccattc agcagctggc tgaccggttc  3240
agcggctact tcgtgccctt tatcatcatc atgagcaccc tgacactggt cgtgtggatc  3300
gtgatcggct ttatcgactt cggagtggtg cagagatact tccccaaccc taacaagcac  3360
atcagccaga cagaagtgat catcagattc gcctttcaga ccagcatcac cgtgctgtgt  3420
atcgcctgcc cctgtagcct gggactggcc acacctaccg ctgtgatggt gggaacaggc  3480
gtggccgctc agaacggcat cctgatcaag gggggcaagc ctctggaaat ggctcacaag  3540
atcaagaccg tgatgttcga caagaccggc accatcaccc acggcgtgcc cagagtgatg  3600
agagtgctgc tgctggggga tgtggccacc ctgcctctga gaaaggtgct ggctgtcgtg  3660
ggcacagccg aggctagctc tgaacaccca ctgggagtgg ccgtgacaaa gtactgcaaa  3720
gaggaactgg gcaccgaaac cctgggctac tgcaccgact ttcaggccgt gcctggctgt  3780
ggcatcggct gcaaggtgtc caacgtggaa ggcatcctgg cccacagcga gaggccactg  3840
tctgcccctg ccagccacct gaatgaggcc ggatctctgc ccgccgaaaa ggacgctgtg  3900
ccccagacct tctctgtgct gattggcaac agagagtggc tgcggcggaa cggcctgacc  3960
atctcctccg atgtgtccga cgccatgacc gaccacgaga tgaagggcca gaccgccatt  4020
ctggtggcca ttgacggggt gctgtgcggc atgatcgcaa tcgccgatgc cgtgaaacag  4080
gaagcagcac tggccgtgca caccctgcag tctatgggag tggatgtggt gctgatcacc  4140
ggcgacaaca gaaagaccgc cagggccatt gccacccaag tgggcatcaa caaggtgttc  4200
gccgaggtgc tgcccagcca caaagtggcc aaggtgcagg aactgcagaa caaaggcaaa  4260
aaggtggcca tggtgggaga tggcgtgaac gactctcctg ctctggccca ggcagatatg  4320
ggcgtggcca tcggcacagg caccgacgtg gcaattgagg ctgctgacgt ggtgctgatt  4380
cggaacgacc tgctggacgt ggtggcctcc atccacctgt ccaagagaac cgtgcggcgg  4440
atcagaatca acctggtgct ggcactgatc tataacctcg tgggcatccc tatcgccgct  4500
ggcgtgttca tgcctatcgg aatcgtgctg cagccctgga tgggctctgc cgccatggct  4560
gcaagctccg tgtctgtggt gctgtccagc ctgcagctga agtgctacaa gaagcccgac  4620
ctggaaagat acgaggccca ggcccacgga cacatgaagc ctctgacagc ctcccaggtg  4680
tccgtgcaca tcggcatgga cgacagatgg cgggacagcc ctagagccac cccttgggat  4740
caggtgtcat acgtgtcaca ggtgtccctg agcagcctga ccagcgacaa gcccagcaga  4800
catagcgccg ctgccgacga cgatggggac aaatggtccc tgctgctgaa cggccgggat  4860
```

```
gaggaacagt acatctgata agcatgcaat aaagtctgag tgggcggcag cctgtgtgtg  4920
cctgggttct ctctgtcccg gaatgtgcaa acaatggagg tgctcgagta gataagtagc  4980
atggcgggtt aatcattaac tacaaggaac ccctagtgat ggagttggcc actccctctc  5040
tgcgcgctcg ctcgctcact gaggccgggc gaccaaaggt cgcccgacgc ccgggctttg  5100
cccgggcggc ctcagtgagc gagcgagcgc gcagccttaa ttaacctaat tcactggccg  5160
tcgttttaca acgtcgtgac tgggaaaacc ctggcgttac ccaacttaat cgccttgcag  5220
cacatccccc tttcgccagc tggcgtaata gcgaagaggc ccgcaccgat cgcccttccc  5280
aacagttgcg cagcctgaat ggcgaatggg acgcgccctg tagcggcgca ttaagcgcgg  5340
cgggtgtggt ggttacgcgc agcgtgaccg ctacacttgc cagcgcccta gcgcccgctc  5400
ctttcgcttt cttcccttcc tttctcgcca cgttcgccgg ctttccccgt caagctctaa  5460
atcgggggct ccctttaggg ttccgattta gtgctttacg gcacctcgac cccaaaaaac  5520
ttgattaggg tgatggttca cgtagtgggc catcgccctg atagacggtt tttcgccctt  5580
tgacgttgga gtccacgttc tttaatagtg gactcttgtt ccaaactgga acaacactca  5640
accctatctc ggtctattct tttgatttat aagggatttt gccgatttcg gcctattggt  5700
taaaaaatga gctgatttaa caaaaattta acgcgaattt taacaaaata ttaacgctta  5760
caatttaggt ggcacttttc ggggaaatgt gcgcggaacc cctatttgtt tatttttcta  5820
aatacattca aatatgtatc cgctcatgag acaataaccc tgataaatgc ttcaataata  5880
ttgaaaaagg aagagtatga gtattcaaca tttccgtgtc gcccttattc ccttttttgc  5940
ggcattttgc cttcctgttt ttgctcaccc agaaacgctg gtgaaagtaa aagatgctga  6000
agatcagttg ggtgcacgag tgggttacat cgaactggat ctcaacagcg gtaagatcct  6060
tgagagtttt cgccccgaag aacgttttcc aatgatgagc acttttaaag ttctgctatg  6120
tggcgcggta ttatcccgta ttgacgccgg gcaagagcaa ctcggtcgcc gcatacacta  6180
ttctcagaat gacttggttg agtactcacc agtcacagaa aagcatctta cggatggcat  6240
gacagtaaga gaattatgca gtgctgccat aaccatgagt gataacactg cggccaactt  6300
acttctgaca acgatcggag gaccgaagga gctaaccgct tttttgcaca acatggggga  6360
tcatgtaact cgccttgatc gttgggaacc ggagctgaat gaagccatac caaacgacga  6420
gcgtgacacc acgatgcctg tagcaatggc aacaacgttg cgcaaactat taactggcga  6480
actacttact ctagcttccc ggcaacaatt aatagactgg atggaggcgg ataaagttgc  6540
aggaccactt ctgcgctcgg cccttccggc tggctggttt attgctgata aatctggagc  6600
cggtgagcgt gggtctcgcg gtatcattgc agcactgggg ccagatggta agccctcccg  6660
tatcgtagtt atctacacga cggggagtca ggcaactatg gatgaacgaa atagacagat  6720
cgctgagata ggtgcctcac tgattaagca ttggtaactg tcagaccaag tttactcata  6780
tatactttag attgatttaa aacttcattt ttaatttaaa aggatctagg tgaagatcct  6840
ttttgataat ctcatgacca aaatccctta acgtgagttt tcgttccact gagcgtcaga  6900
ccccgtagaa aagatcaaag gatcttcttg agatcctttt tttctgcgcg taatctgctg  6960
cttgcaaaca aaaaaaccac cgctaccagc ggtggtttgt ttgccggatc aagagctacc  7020
aactcttttt ccgaaggtaa ctggcttcag cagagcgcag ataccaaata ctgttcttct  7080
agtgtagccg tagttaggcc accacttcaa gaactctgta gcaccgccta catacctcgc  7140
tctgctaatc ctgttaccag tggctgctgc cagtggcgat aagtcgtgtc ttaccgggtt  7200
ggactcaaga cgatagttac cggataaggc gcagcggtcg ggctgaacgg ggggttcgtg  7260
cacacagccc agcttggagc gaacgaccta caccgaactg agatacctac agcgtgagct  7320
atgagaaagc gccacgcttc ccgaagggag aaaggcggac aggtatccgg taagcggcag  7380
ggtcggaaca ggagagcgca cgagggagct tccaggggga aacgcctggt atctttatag  7440
tcctgtcggg tttcgccacc tctgacttga gcgtcgattt ttgtgatgct cgtcaggggg  7500
gcggagccta tggaaaaacg ccagcaacgc ggccttttta cggttcctgg ccttttgctg  7560
gccttttgct cacatgttct ttcctgcgtt atcccctgat tctgtggata accgtattac  7620
cgcctttgag tgagctgata ccgctcgccg cagccgaacg accgagcgca gcgagtcagt  7680
gagcgaggaa gcggaagagc gcccaatacg caaaccgcct ctccccgcgc gttggccgat  7740
tcattaatgc agctggcacg acaggtttcc cgactggaaa gcgggcagtg agcgcaacgc  7800
aattaatgtg agttagctca ctcattaggc accccaggct ttacacttta tgcttccggc  7860
tcgtatgttg tgtggaattg tgagcggata acaatttcac acaggaaaca gctatgacca  7920
tgattacgcc agatttaatt aagg                                         7944

SEQ ID NO: 24          moltype = DNA  length = 7866
FEATURE                Location/Qualifiers
misc_feature           1..7866
                       note = constructed sequence
source                 1..7866
                       mol_type = other DNA
                       organism = synthetic construct
SEQUENCE: 24
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttaggggaat tcactcaaag ttcaaacctt atcatttttt  240
gctttgttcc tcttggcctt ggttttgtac atcagctttg aaaataccat cccagggtta  300
atgctggggt taatttataa ctaagagtgc tctagttttg caatacagga catgctataa  360
aaatggaaag atgttgcttt ctgagagaca gcggccgcca ccatgcccga gcaggaaaga  420
cagatcaccg ccagagaggg cgccagccgg aagatcctga gcaagctgag cctgccccacc  480
agagcctggg agcccgccat gaagaagtcc ttcgccttcg acaacgtggg ctacgagggc  540
ggcctggacg gactgggacc atcttctcag gtggccacaa gcaccgtgcg catcctgggc  600
atgacctgcc agagctgcgt gaagtccatc gaggaccgga tcagcaacct gaagggcatc  660
atcagcatga aggtgtccct ggaacagggc agcgccaccg tgaaatacgt gccctctgtc  720
gtgtgcctgc agcaggtgtg ccaccagatc ggcgacatgg gcttcgaggc ctctatcgcc  780
gagggaaagg ccgcctcttg gccctctaga agcctgcctg ctcaggaagc cgtcgtgaag  840
ctgcgggtgg aagggatgac ctgtcagtcc tgcgtgtcca gcatcgaggg caaagtgcgg  900
aagctgcagg gcgtggtgcg cgtgaaagtg tctctgagca accaggaagc tgtgatcacc  960
taccagccct acctgatcca gcccgaggac ctgagggacc acgtgaacga tatgggattt  1020
gaggccgcca tcaagagcaa ggtggcccct ctgtctctgg gccccatcga catcgagaga  1080
```

-continued

```
ctgcagagca ccaaccccaa gcggcctctg agcagcgcca accagaactt caacaacagc  1140
gagacactgg gccaccaggg cagccacgtc gtgacactgc agctgcggat cgacggaatg  1200
cactgcaaga gctgtgtgct gaacatcgag gaaaacatcg gccagctgct gggagtgcag  1260
agcatccagg tgtcactgga aaacaagacc gcccaggtga agtacgaccc cagctgcaca  1320
agccccgtgg ccctgcagag agccattgaa gctctgcccc ctggcaactt caaagtgtcc  1380
ctgcctgacg gagccgaggg ctccggaaca gatcacagaa gcagcagcag ccacagccct  1440
ggcagccccc ctagaaatca ggtgcagggc acctgtagca ccaccctgat cgccattgcc  1500
ggcatgacat gcgccagctg cgtgcactct attgagggca tgatctccca gctggaaggc  1560
gtgcagcaga tcagtgtgtc tctggccgag ggcaccgcca cagtgctgta caaccctagc  1620
gtgatcagcc ccgaagaact gagagccgcc attgaggaca tgggattcga agccagcgtg  1680
gtgtccgaga gctgctccac caaccctctg ggcaatcaca gcgccggcaa cagcatggtg  1740
cagaccaccg acggcacccc caccagcgtg caggaagtgg ccccacatac aggcagactg  1800
cccgccaatc acgcccccga tatcctggcc aagagccccc agagtacaag agccgtggcc  1860
ccccagaagt gcttcctgca gatcaagggc atgacttgtg cctcttgtgt gtccaatatc  1920
gagcggaacc tgcagaaaga ggccggcgtg ctgtctgtgc tggtggctct gatggccggc  1980
aaggccgaga tcaaatacga ccccgaagtg attcagcccc tggaaatcgc ccagtttatc  2040
caggacctgg gctttgaagc cgccgtgatg gaagattacg ccggctccga cggcaacatc  2100
gagctgacca tcaccggaat gacctgcgcc tcctgtgtgc acaacattga gtccaagctg  2160
acccggacca acggcatcac ctacgcctct gtggctctgg ccacctccaa ggccctcgtg  2220
aagttcgatc ccgagatcat cggccccagg gacatcatca agatcatcga agagatcggc  2280
ttccacgcca gcctggccca gaggaaccct aacgcccacc acctggacca caagatggaa  2340
atcaagcagt ggaagaaaag cttcctgtgc agcctggtgt tcggcatccc cgtgatggcc  2400
ctgatgatct acatgctgat ccccagcaac gagccccacc agtccatggt gctggatcac  2460
aacatcatcc ccggcctgtc tatcctgaac ctgatcttct tcatcctgtg caccttcgtg  2520
cagctgctgg gcggctggta cttctacgtg caggcctaca agtccctgcg gcacagatcc  2580
gccaacatgg acgtgctgat cgtgctggcc acatctatcg cctacgtgta ctccctcgtg  2640
atcctggtgg tggccgtggc cgagaaagcc gagagaagcc ctgtgacctt cttcgacacc  2700
ccccctatgc tgttcgtgtt tatcgccctg ggccggtggc tggaacacct ggccaaaagc  2760
aagaccagcg aggccctggc taagctgatg agtctgcagg ccaccgaggc cacagtcgtg  2820
accctgggcg aggacaacct gatcatccgc gaggaacagg tgccaatgga actggtgcag  2880
cggggcgaca tcgtgaaggt ggtgcctggc ggcaagttcc ccgtggacgg aaaagtgctg  2940
gaagggaata ccatggccga cgagagcctg atcacaggcg aggccatgcc cgtgaccaag  3000
aaacctggca gcacagtgat cgccggcagc atcaatgccc acggcagcgt gctgattaag  3060
gccacacacg tgggcaacga taccaccctg gctcagattg tgaagctggt ggaagaggcc  3120
cagatgagca aggcccccat tcagcagctg gctgaccggt tcagcggcta cttcgtgccc  3180
tttatcatca tcatgagcac cctgacactg gtcgtgtgga tcgtgatcgg ctttatcgac  3240
ttcggagtgg tgcagagata cttccccaac cctaacaagc acatcagcca gacagaagtg  3300
atcatcagat tcgcctttca gaccagcatc accgtgctgt gtatcgcctg cccctgtagc  3360
ctgggactgg ccacacctac cgctgtgatg gtgggaacag gcgtggccgc tcagaacggc  3420
atcctgatca agggggcaa gcctctggaa atggctcaca agatcaagac cgtgatgttc  3480
gacaagaccg gcaccatcac ccacggcgtg cccagagtga tgagagtgct gctgctgggg  3540
gatgtggcca ccctgcctct gagaaaggtg ctggctgtcg tgggcacagc cgaggctagc  3600
tctgaacacc cactgggagt ggccgtgaca aagtactgca aagaggaact gggcaccgaa  3660
accctgggct actgcaccga ctttcaggcc gtgcctggct gtggcatcgg ctgcaaggtg  3720
tccaacgtgg aaggcatcct ggcccacagc gagaggccac tgtctgcccc tgccagccac  3780
ctgaacgagg ccggatctct gcccgccgaa aaggacgctg tgccccagac cttctctgtg  3840
ctgattggca acagagagtg gctgcggcgg aacggcctga ccatctcctc cgatgtgtcc  3900
gacgccatga ccgaccacga gatgaagggc cagaccgcca ttctggtggc cattgacggg  3960
gtgctgtgcg gcatgatcgc aatcgccgat gccgtgaaac aggaagcagc actggccgtg  4020
cacaccctgc agtctatggg agtggatgtg gtgctgatca ccggcgacaa cagaaagacc  4080
gccagggcca ttgccaccca ggtgggcatc aacaaggtgt tcgccgaggt gctgcccagc  4140
cacaaagtgg ccaaggtgca ggaactgcag aacaaaggca aaaaggtggc catggtggga  4200
gatggcgtga acgactctcc tgctctggcc caggcagata tgggcgtggc catcggcaca  4260
ggcaccgacg tggcaattga ggctgctgac gtggtgctga ttcggaacga cctgctggac  4320
gtggtggcct ccatccacct gtccaagaga accgtgcggc ggatcagaat caacctggtg  4380
ctggcactga tctataacct cgtgggcatc cctatcgccg ctggcgtgtt catgcctatc  4440
ggaatcgtgc tgcagccctg gatgggctct gccgccatgg ctgcaagctc cgtgtctgtg  4500
gtgctgtcca gcctgcagct gaagtgctac aagaagcccg acctggaaag atacgaggcc  4560
caggcccacg gacacatgaa gcctctgaca gcctcccagg tgtccgtgca catcggcatg  4620
gacgacagat ggcgggacag ccctagagcc accccttggg atcaggtgtc atacgtgtca  4680
caggtgtccc tgagcagcct gaccagcgac aagcccagca gacatagcgc cgctgccgac  4740
gacgatgggg acaagtggtc cctgctgctg aacggccggg atgaggaaca gtacatctga  4800
taagcatgca ataaagtctg agtgggcggc agcctgtgtg tgcctgggtt ctctctgtcc  4860
cggaatgtgc aaacaatgga ggtgctcgag tagataagta gcatggcggg ttaatcatta  4920
actacaagga acccctagtg atggagttgg ccactccctc tctgcgcgct cgctcgctca  4980
ctgaggccgg gcgaccaaag gtcgcccgac gcccgggctt tgcccgggcg gcctcagtga  5040
gcgagcgagc gcgcagcctt aattaaccta attcactggc cgtcgtttta caacgtcgtg  5100
actgggaaaa ccctggcgtt acccaactta atcgccttgc agcacatccc cctttcgcca  5160
gctggcgtaa tagcgaagag gcccgcaccg atcgcccttc ccaacagttg cgcagcctga  5220
atggcgaatg ggacgcgccc tgtagcggcg cattaagcgc ggcgggtgtg gtggttacgc  5280
gcagcgtgac cgctacactt gccagcgccc tagcgcccgc tcctttcgct ttcttccctt  5340
cctttctcgc cacgttcgcc ggctttcccc gtcaagctct aaatcggggg ctccctttag  5400
ggttccgatt tagtgcttta cggcacctcg accccaaaaa acttgattag ggtgatggtt  5460
cacgtagtgg gccatcgccc tgatagacgg tttttcgccc tttgacgttg gagtccacgt  5520
tctttaatag tggactcttg ttccaaactg gaacaacact caaccctatc tcggtctatt  5580
cttttgattt ataagggatt ttgccgattt cggcctattg gttaaaaaat gagctgattt  5640
aacaaaaatt taacgcgaat tttaacaaaa tattaacgct tacaatttag gtggcacttt  5700
tcggggaaat gtgcgcggaa cccctatttg tttatttttc taaatacatt caaatatgta  5760
tccgctcatg agacaataac cctgataaat gcttcaataa tattgaaaaa ggaagagtat  5820
```

```
gagtattcaa catttccgtg tcgcccttat tccctttttt gcggcatttt gccttcctgt  5880
ttttgctcac ccagaaacgc tggtgaaagt aaaagatgct gaagatcagt tgggtgcacg  5940
agtgggttac atcgaactgg atctcaacag cggtaagatc cttgagagtt ttcgccccga  6000
agaacgtttt ccaatgatga gcacttttaa agttctgcta tgtggcgcgg tattatcccg  6060
tattgacgcc gggcaagagc aactcggtcg ccgcatacac tattctcaga atgacttggt  6120
tgagtactca ccagtcacag aaaagcatct tacggatggc atgacagtaa gagaattatg  6180
cagtgctgcc ataaccatga gtgataacac tgcggccaac ttacttctga caacgatcgg  6240
aggaccgaag gagctaaccg cttttttgca caacatgggg gatcatgtaa ctcgccttga  6300
tcgttgggaa ccggagctga atgaagccat accaaacgac gagcgtgaca ccacgatgcc  6360
tgtagcaatg gcaacaacgt tgcgcaaact attaactggc gaactactta ctctagcttc  6420
ccggcaacaa ttaatagact ggatggaggc ggataaagtt gcaggaccac ttctgcgctc  6480
ggcccttccg gctggctggt ttattgctga taaatctgga gccggtgagc gtgggtctcg  6540
cggtatcatt gcagcactgg ggccagatgg taagccctcc cgtatcgtag ttatctacac  6600
gacggggagt caggcaacta tggatgaacg aaatagacag atcgctgaga taggtgcctc  6660
actgattaag cattggtaac tgtcagacca agtttactca tatatacttt agattgattt  6720
aaaacttcat ttttaattta aaaggatcta ggtgaagatc ctttttgata atctcatgac  6780
caaaatccct taacgtgagt tttcgttcca ctgagcgtca gaccccgtag aaaagatcaa  6840
aggatcttct tgagatcctt tttttctgcg cgtaatctgc tgcttgcaaa caaaaaaacc  6900
accgctacca gcggtggttt gtttgccgga tcaagagcta ccaactcttt ttccgaaggt  6960
aactggcttc agcagagcgc agataccaaa tactgttctt ctagtgtagc cgtagttagg  7020
ccaccacttc aagaactctg tagcaccgcc tacatacctc gctctgctaa tcctgttacc  7080
agtggctgct gccagtggcg ataagtcgtg tcttaccggg ttggactcaa gacgatagtt  7140
accggataag gcgcagcggt cggctgaac  gggggggttcg tgcacacagc ccagcttgga  7200
gcgaacgacc tacaccgaac tgagatacct acagcgtgag ctatgagaaa gcgccacgct  7260
tcccgaaggg agaaaggcgg acaggtatcc ggtaagcggc agggtcggaa caggagagcg  7320
cacgagggag cttccagggg gaaacgcctg gtatctttat agtcctgtcg ggtttcgcca  7380
cctctgactt gagcgtcgat ttttgtgatg ctcgtcaggg gggcggagcc tatggaaaaa  7440
cgccagcaac gcggcctttt tacggttcct ggccttttgc tggccttttg ctcacatgtt  7500
ctttcctgcg ttatcccctg attctgtgga taaccgtatt accgcctttg agtgagctga  7560
taccgctcgc cgcagccgaa cgaccgagcg cagcgagtca gtgagcgagg aagcggaaga  7620
gcgcccaata cgcaaaccgc ctctccccgc gcgttggccg attcattaat gcagctggca  7680
cgacaggttt cccgactgga aagcgggcag tgagcgcaac gcaattaatg tgagttagct  7740
cactcattag gcaccccagg ctttacactt tatgcttccg gctcgtatgt tgtgtggaat  7800
tgtgagcgga taacaatttc acacaggaaa cagctatgac catgattacg ccagatttaa  7860
ttaagg                                                             7866

SEQ ID NO: 25           moltype = DNA  length = 7874
FEATURE                 Location/Qualifiers
misc_feature            1..7874
                        note = constructed sequence
source                  1..7874
                        mol_type = other DNA
                        organism = synthetic construct
SEQUENCE: 25
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agaggttaat  180
ttttaaactg tttgctctgg ttaataatct cagggaattc actcaaagtt caaaccttat  240
cattttttgc tttgttcctc ttggccttgg ttttgtacat cagctttgaa aataccatcc  300
cagggttaat gctggggtta atttataact aagagtgctc tagttttgca atacaggaca  360
tgctataaaa atggaaagat gttgctttct gagagacagc ggccgccacc atgcccgagc  420
aggaaagaca gatcaccgcc agagagggcg ccagccggaa gatcctgagc aagctgagcc  480
tgcccaccag agcctgggag cccgccatga agaagtcctt cgccttcgac aacgtgggct  540
acgagggcgg cctggacgga ctgggaccat cttctcaggt ggccacaagc accgtgcgca  600
tcctgggcat gacctgccag agctgcgtga agtccatcga ggaccggatc agcaacctga  660
agggcatcat cagcatgaag gtgtccctgg aacagggcag cgccaccgtg aaatacgtgc  720
cctctgtcgt gtgcctgcag caggtgtgcc accagatcgg cgacatgggc ttcgaggcct  780
ctatcgccga gggaaaggcc gcctcttggc cctctagaag cctgcctgct caggaagccg  840
tcgtgaagct gcgggtggaa gggatgacct gtcagtcctg cgtgtccagc atcgagggca  900
aagtgcggaa gctgcagggc gtggtgcgcg tgaaagtgtc tctgagcaac caggaagctg  960
tgatcaccta ccagccctac ctgatccagc ccgaggacct gagggaccac gtgaacgata  1020
tgggatttga ggccgccatc aagagcaagg tggcccctct gtctctgggc cccatcgaca  1080
tcgagagact gcagagcacc aaccccaagc ggcctctgag cagcgccaac cagaacttca  1140
acaacagcga gacactgggc caccagggca gccacgtcgt gacactgcag ctgcggatcg  1200
acggaatgca ctgcaagagc tgtgtgctga acatcgagga aaacatcggc cagctgctgg  1260
gagtgcagag catccaggtg tcactggaaa acaagaccgc ccaggtgaag tacgacccca  1320
gctgcacaag ccccgtggcc ctgcagagag ccattgaagc tctgcccccct ggcaacttca  1380
aagtgtccct gcctgacgga gccgagggct ccggaacaga tcacagaagc agcagcagcc  1440
acagccctgg cagcccccct agaaatcagg tgcagggcac ctgtagcacc accctgatcg  1500
ccattgccgg catgacatgc gccagctgcg tgcactctat tgagggcatg atctcccagc  1560
tggaaggcgt gcagcagatc agtgtgtctc tggccgaggg caccgccaca gtgctgtaca  1620
accctagcgt gatcagcccc gaagaactga gagccgccat tgaggacatg ggattcgaag  1680
ccagcgtggt gtccgagagc tgctccacca accctctggg caatcacagc gccggcaaca  1740
gcatggtgca gaccaccgac ggcacccccca ccagcgtgca ggaagtggcc cccacatacag  1800
gcagactgcc cgccaatcac gcccccgata tcctggccaa gagcccccag agtacaagag  1860
ccgtggcccc ccagaagtgc ttcctgcaga tcaagggcat gacttgtgcc tcttgtgtgt  1920
ccaatatcga gcggaacctg cagaaagagg ccggcgtgct gtctgtgctg gtggctctga  1980
tggccggcaa ggccgagatc aaatacgacc ccgaagtgat tcagcccctg gaaatcgccc  2040
agtttatcca ggacctgggc tttgaagccg ccgtgatgga agattacgcc ggctccgacg  2100
```

```
gcaacatcga gctgaccatc accggaatga cctgcgcctc ctgtgtgcac aacattgagt  2160
ccaagctgac ccggaccaac ggcatcacct acgcctctgt ggctctggcc acctccaagg  2220
ccctcgtgaa gttcgatccc gagatcatcg gccccaggga catcatcaag atcatcgaag  2280
agatcggctt ccacgccagc ctggcccaga ggaaccctaa cgcccaccac ctggaccaca  2340
agatggaaat caagcagtgg aagaaaagct tcctgtgcag cctggtgttc ggcatccccg  2400
tgatggccct gatgatctac atgctgatcc ccagcaacga gccccaccag tccatggtgc  2460
tggatcacaa catcatcccc ggcctgtcta tcctgaacct gatcttcttc atcctgtgca  2520
ccttcgtgca gctgctgggc ggctggtact tctacgtgca ggcctacaag tccctgcggc  2580
acagatccgc caacatggac gtgctgatcg tgctggccac atctatcgcc tacgtgtact  2640
ccctcgtgat cctggtggtg gccgtggccg agaaagccga gagaagccct gtgaccttct  2700
tcgacacccc ccctatgctg ttcgtgttta tcgccctggg ccggtggctg gaacacctgg  2760
ccaaaagcaa gaccagcgag gccctggcta agctgatgag tctgcaggcc accgaggcca  2820
cagtcgtgac cctgggcgag gacaacctga tcatccgcga ggaacaggtg ccaatggaac  2880
tggtgcagcg gggcgacatc gtgaaggtgg tgcctggcgg caagttcccc gtggacggaa  2940
aagtgctgga agggaatacc atggccgacg agagcctgat cacaggcgag gccatgcccg  3000
tgaccaagaa acctggcagc acagtgatcg ccggcagcat caatgcccac ggcagcgtgc  3060
tgattaaggc cacacacgtg ggcaacgata ccaccctggc tcagattgtg aagctggtgg  3120
aagaggccca gatgagcaag gcccccattc agcagctggc tgaccggttc agcggctact  3180
tcgtgccctt tatcatcatc atgagcaccc tgacactggt cgtgtggatc gtgatcggct  3240
ttatcgactt cggagtggtg cagagatact tccccaaccc taacaagcac atcagccaga  3300
cagaagtgat catcagattc gcctttcaga ccagcatcac cgtgctgtgt atcgcctgcc  3360
cctgtagcct gggactggcc acacctaccg ctgtgatggt gggaacaggc gtggccgctc  3420
agaacggcat cctgatcaag gggggcaagc ctctggaaat ggctcacaag atcaagaccg  3480
tgatgttcga caagaccggc accatcaccc acggcgtgcc cagagtgatg agagtgctgc  3540
tgctggggga tgtggccacc ctgcctctga gaaaggtgct ggctgtcgtg ggcacagccg  3600
aggctagctc tgaacaccca ctgggagtgg ccgtgacaaa gtactgcaaa gaggaactgg  3660
gcaccgaaac cctgggctac tgcaccgact ttcaggccgt gcctggctgt ggcatcggct  3720
gcaaggtgtc caacgtggaa ggcatcctgg cccacagcga gaggccactg tctgcccctg  3780
ccagccacct gaacgaggcc ggatctctgc ccgccgaaaa ggacgctgtg ccccagacct  3840
tctctgtgct gattggcaac agagagtggc tgcggcggaa cggcctgacc atctcctccg  3900
atgtgtccga cgccatgacc gaccacgaga tgaagggcca gaccgccatt ctggtggcca  3960
ttgacggggt gctgtgcggc atgatcgcaa tcgccgatgc cgtgaaacag gaagcagcac  4020
tggccgtgca caccctgcag tctatgggag tggatgtggt gctgatcacc ggcgacaaca  4080
gaaagaccgc cagggccatt gccacccagg tgggcatcaa caaggtgttc gccgaggtgc  4140
tgcccagcca caaagtggcc aaggtgcagg aactgcagaa caaaggcaaa aaggtggcca  4200
tggtgggaga tggcgtgaac gactctcctg ctctggccca ggcagatatg ggcgtggcca  4260
tcggcacagg caccgacgtg gcaattgagg ctgctgacgt ggtgctgatt cggaacgacc  4320
tgctggacgt ggtggcctcc atccacctgt ccaagagaac cgtgcggcgg atcagaatca  4380
acctggtgct ggcactgatc tataacctcg tgggcatccc tatcgccgct ggcgtgttca  4440
tgcctatcgg aatcgtgctg cagccctgga tgggctctgc cgccatggct gcaagctccg  4500
tgtctgtggt gctgtccagc ctgcagctga agtgctacaa gaagcccgac ctggaaagat  4560
acgaggccca ggcccacgga cacatgaagc ctctgacagc ctcccaggtg tccgtgcaca  4620
tcggcatgga cgacagatgg cgggacagcc ctagagccac cccttgggat caggtgtcat  4680
acgtgtcaca ggtgtccctg agcagcctga ccagcgacaa gcccagcaga catagcgccg  4740
ctgccgacga cgatggggac aagtggtccc tgctgctgaa cggccgggat gaggaacagt  4800
acatctgata agcatgcaat aaagtctgag tgggcggcag cctgtgtgtg cctgggttct  4860
ctctgtcccg gaatgtgcaa acaatggagg tgctcgagta gataagtagc atggcgggtt  4920
aatcattaac tacaaggaac ccctagtgat ggagttggcc actccctctc tgcgcgctcg  4980
ctcgctcact gaggccgggc gaccaaaggt cgcccgacgc ccgggctttg cccgggcggc  5040
ctcagtgagc gagcgagcgc gcagccttaa ttaacctaat tcactggccg tcgttttaca  5100
acgtcgtgac tgggaaaacc ctggcgttac ccaacttaat cgccttgcag cacatccccc  5160
tttcgccagc tggcgtaata gcgaagaggc ccgcaccgat cgcccttccc aacagttgcg  5220
cagcctgaat ggcgaatggg acgcgccctg tagcggcgca ttaagcgcgg cgggtgtggt  5280
ggttacgcgc agcgtgaccg ctacacttgc cagcgcccta gcgcccgctc ctttcgcttt  5340
cttcccttcc tttctcgcca cgttcgccgg ctttccccgt caagctctaa atcgggggct  5400
ccctttaggg ttccgattta gtgctttacg gcacctcgac cccaaaaaac ttgattaggg  5460
tgatggttca cgtagtgggc catcgccctg atagacggtt tttcgccctt tgacgttgga  5520
gtccacgttc tttaatagtg gactcttgtt ccaaactgga acaacactca accctatctc  5580
ggtctattct tttgatttat aagggatttt gccgatttcg gcctattggt taaaaaatga  5640
gctgatttaa caaaaattta acgcgaattt taacaaaata ttaacgctta caatttaggt  5700
ggcacttttc ggggaaatgt gcgcggaacc cctatttgtt tatttttcta aatacattca  5760
aatatgtatc cgctcatgag acaataaccc tgataaatgc ttcaataata ttgaaaaagg  5820
aagagtatga gtattcaaca tttccgtgtc gcccttattc ccttttttgc ggcattttgc  5880
cttcctgttt ttgctcaccc agaaacgctg gtgaaagtaa aagatgctga agatcagttg  5940
ggtgcacgag tgggttacat cgaactggat ctcaacagcg gtaagatcct tgagagtttt  6000
cgccccgaag aacgttttcc aatgatgagc acttttaaag ttctgctatg tggcgcggta  6060
ttatcccgta ttgacgccgg gcaagagcaa ctcggtcgcc gcatacacta ttctcagaat  6120
gacttggttg agtactcacc agtcacagaa aagcatctta cggatggcat gacagtaaga  6180
gaattatgca gtgctgccat aaccatgagt gataacactg cggccaactt acttctgaca  6240
acgatcggag gaccgaagga gctaaccgct tttttgcaca acatgggggga tcatgtaact  6300
cgccttgatc gttgggaacc ggagctgaat gaagccatac caaacgacga gcgtgacacc  6360
acgatgcctg tagcaatggc aacaacgttg cgcaaactat taactggcga actacttact  6420
ctagcttccc ggcaacaatt aatagactgg atggaggcgg ataaagttgc aggaccactt  6480
ctgcgctcgg cccttccggc tggctggttt attgctgata aatctggagc cggtgagcgt  6540
gggtctcgcg gtatcattgc agcactgggg ccagatggta agccctcccg tatcgtagtt  6600
atctacacga cggggagtca ggcaactatg gatgaacgaa atagacagat cgctgagata  6660
ggtgcctcac tgattaagca ttggtaactg tcagaccaag tttactcata tatactttag  6720
attgatttaa aacttcattt ttaatttaaa aggatctagg tgaagatcct ttttgataat  6780
ctcatgacca aaatccctta acgtgagttt tcgttccact gagcgtcaga ccccgtagaa  6840
```

```
aagatcaaag gatcttcttg agatcctttt tttctgcgcg taatctgctg cttgcaaaca  6900
aaaaaaccac cgctaccagc ggtggtttgt ttgccggatc aagagctacc aactcttttt  6960
ccgaaggtaa ctggcttcag cagagcgcag ataccaaata ctgttcttct agtgtagccg  7020
tagttaggcc accacttcaa gaactctgta gcaccgccta catacctcgc tctgctaatc  7080
ctgttaccag tggctgctgc cagtggcgat aagtcgtgtc ttaccgggtt ggactcaaga  7140
cgatagttac cggataaggc gcagcggtcg ggctgaacgg ggggttcgtg cacacagccc  7200
agcttggagc gaacgaccta caccgaactg agatacctac agcgtgagct atgagaaagc  7260
gccacgcttc ccgaagggag aaaggcggac aggtatccgg taagcggcag ggtcggaaca  7320
ggagagcgca cgagggagct tccaggggga aacgcctggt atctttatag tcctgtcggg  7380
tttcgccacc tctgacttga gcgtcgattt ttgtgatgct cgtcaggggg gcggagccta  7440
tggaaaaacg ccagcaacgc ggccttttta cggttcctgg ccttttgctg gccttttgct  7500
cacatgttct ttcctgcgtt atcccctgat tctgtggata accgtattac cgcctttgag  7560
tgagctgata ccgctcgccg cagccgaacg accgagcgca gcgagtcagt gagcgaggaa  7620
gcggaagagc gcccaatacg caaaccgcct ctccccgcgc gttggccgat tcattaatgc  7680
agctggcacg acaggtttcc cgactggaaa gcgggcagtg agcgcaacgc aattaatgtg  7740
agttagctca ctcattaggc accccaggct ttacacttta tgcttccggc tcgtatgttg  7800
tgtggaattg tgagcggata acaatttcac acaggaaaca gctatgacca tgattacgcc  7860
agatttaatt aagg                                                    7874

SEQ ID NO: 26          moltype = DNA  length = 7878
FEATURE                Location/Qualifiers
misc_feature           1..7878
                       note = constructed sequence
source                 1..7878
                       mol_type = other DNA
                       organism = synthetic construct
SEQUENCE: 26
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttaggggaat tcatttcata gaacgaatgt tccgatgctc  240
taatctctct agacaaggtt catatttgta tgggttactt attctctctt tgttgactaa  300
gtcaataatc agaatcagca ggtttgcagt cagattggca gggataagca gcctagctca  360
ggagaagtga gtataaaagc cccaggctgg gagcagccat cagcggccgc caccatgccc  420
gagcaggaaa gacagatcac cgccagagag ggcgccagcc ggaagatcct gagcaagctg  480
agcctgccca ccagagcctg ggagcccgcc atgaagaagt ccttcgcctt cgacaacgtg  540
ggctacgagg gcggcctgga cggactggga ccatcttctc aggtggccac aagcaccgtg  600
cgcatcctgg gcatgacctg ccagagctgc gtgaagtcca tcgaggaccg gatcagcaac  660
ctgaagggca tcatcagcat gaaggtgtcc ctggaacagg gcagcgccac cgtgaaatac  720
gtgccctctg tcgtgtgcct gcagcaggtg tgccaccaga tcggcgacat gggcttcgag  780
gcctctatcg ccgagggaaa ggccgcctct tggccctcta gaagcctgcc tgctcaggaa  840
gccgtcgtga agctgcgggt ggaagggatg acctgtcagt cctgcgtgtc cagcatcgag  900
ggcaaagtgc ggaagctgca gggcgtggtg cgcgtgaaag tgtctctgag caaccaggaa  960
gctgtgatca cctaccagcc ctacctgatc cagcccgagg acctgaggga ccacgtgaac  1020
gatatgggat ttgaggccgc catcaagagc aaggtggccc ctctgtctct gggccccatc  1080
gacatcgaga gactgcagag caccaacccc aagcggcctc tgagcagcgc caaccagaac  1140
ttcaacaaca gcgagacact gggccaccag ggcagccacg tcgtgacact gcagctgcgg  1200
atcgacggaa tgcactgcaa gagctgtgtg ctgaacatcg aggaaaacat cggccagctg  1260
ctgggagtgc agagcatcca ggtgtcactg gaaaacaaga ccgcccaggt gaagtacgac  1320
cccagctgca caagccccgt ggccctgcag agagccattg aagctctgcc ccctggcaac  1380
ttcaaagtgt ccctgcctga cggagccgag ggctccggaa cagatcacag aagcagcagc  1440
agccacagcc ctggcagccc ccctagaaat caggtgcagg gcacctgtag caccaccctg  1500
atcgccattg ccggcatgac atgcgccagc tgcgtgcact ctattgaggg catgatctcc  1560
cagctggaag gcgtgcagca gatcagtgtg tctctggccg agggcaccgc cacagtgctg  1620
tacaacccta gcgtgatcag ccccgaagaa ctgagagccg ccattgagga catgggattc  1680
gaagccagcg tggtgtccga gagctgctcc accaaccctc tgggcaatca cagcgccggc  1740
aacagcatgg tgcagaccac cgacggcacc cccaccagcg tgcaggaagt ggccccacat  1800
acaggcagac tgcccgccaa tcacgccccc gatatcctgg ccaagagccc ccagagtaca  1860
agagccgtgg ccccccagaa gtgcttcctg cagatcaagg gcatgacttg tgcctcttgt  1920
gtgtccaata tcgagcggaa cctgcagaaa gaggccggcg tgctgtctgt gctggtggct  1980
ctgatggccg gcaaggccga gatcaaatac gaccccgaag tgattcagcc cctggaaatc  2040
gcccagttta tccaggacct gggctttgaa gccgccgtga tggaagatta cgccggctcc  2100
gacggcaaca tcgagctgac catcaccgga atgacctgcg cctcctgtgt gcacaacatt  2160
gagtccaagc tgacccggac caacggcatc acctacgcct ctgtggctct ggccacctcc  2220
aaggccctcg tgaagttcga tcccgagatc atcggcccca gggacatcat caagatcatc  2280
gaagagatcg gcttccacgc cagcctggcc cagaggaacc ctaacgccca ccacctggac  2340
cacaagatgg aaatcaagca gtggaagaaa agcttcctgt gcagcctggt gttcggcatc  2400
cccgtgatgg ccctgatgat ctacatgctg atccccagca acgagcccca ccagtccatg  2460
gtgctggatc acaacatcat ccccggcctg tctatcctga acctgatctt cttcatcctg  2520
tgcaccttcg tgcagctgct gggcggctgg tacttctacg tgcaggccta caagtccctg  2580
cggcacagat ccgccaacat ggacgtgctg atcgtgctgg ccacatctat cgcctacgtg  2640
tactccctcg tgatcctggt ggtggccgtg gccgagaaag ccgagagaag ccctgtgacc  2700
ttcttcgaca cccccccctat gctgttcgtg tttatcgccc tgggccggtg gctggaacac  2760
ctggccaaaa gcaagaccag cgaggccctg gctaagctga tgagtctgca ggccaccgag  2820
gccacagtcg tgaccctggg cgaggacaac ctgatcatcc gcgaggaaca ggtgccaatg  2880
gaactggtgc agcggggcga catcgtgaag gtggtgcctg gcggcaagtt ccccgtggac  2940
ggaaaagtgc tggaagggaa taccatggcc gacgagagcc tgatcacagg cgaggccatg  3000
cccgtgacca agaaacctgg cagcacagtg atcgccggca gcatcaatgc ccacggcagc  3060
gtgctgatta aggccacaca cgtgggcaac gataccaccc tggctcagat tgtgaagctg  3120
```

-continued

```
gtggaagagg cccagatgag caaggccccc attcagcagc tggctgaccg gttcagcggc  3180
tacttcgtgc cctttatcat catcatgagc accctgacac tggtcgtgtg gatcgtgatc  3240
ggctttatcg acttcggagt ggtgcagaga tacttcccca accctaacaa gcacatcagc  3300
cagacagaag tgatcatcag attcgccttt cagaccagca tcaccgtgct gtgtatcgcc  3360
tgcccctgta gcctgggact ggccacacct accgctgtga tggtgggaac aggcgtggcc  3420
gctcagaacg gcatcctgat caaggggggc aagcctctgg aaatggctca caagatcaag  3480
accgtgatgt tcgacaagac cggcaccatc acccacggcg tgcccagagt gatgagagtg  3540
ctgctgctgg gggatgtggc caccctgcct ctgagaaagg tgctggctgt cgtgggcaca  3600
gccgaggcta gctctgaaca cccactggga gtggccgtga caaagtactg caaagaggaa  3660
ctgggcaccg aaaccctggg ctactgcacc gactttcagg ccgtgcctgg ctgtggcatc  3720
ggctgcaagg tgtccaacgt ggaaggcatc ctggcccaca gcgagaggcc actgtctgcc  3780
cctgccagcc acctgaacga ggccggatct ctgcccgccg aaaaggacgc tgtgccccag  3840
accttctctg tgctgattgg caacagagag tggctgcggc ggaacggcct gaccatctcc  3900
tccgatgtgt ccgacgccat gaccgaccac gagatgaagg gccagaccgc cattctggtg  3960
gccattgacg gggtgctgtg cggcatgatc gcaatcgccg atgccgtgaa acaggaagca  4020
gcactggccg tgcacaccct gcagtctatg ggagtggatg tggtgctgat caccggcgac  4080
aacagaaaga ccgccagggc cattgccacc caggtgggca tcaacaaggt gttcgccgag  4140
gtgctgccca gccacaaagt ggccaaggtg caggaactgc agaacaaagg caaaaaggtg  4200
gccatggtgg gagatggcgt gaacgactct cctgctctgg cccaggcaga tatgggcgtg  4260
gccatcggca caggcaccga cgtggcaatt gaggctgctg acgtggtgct gattcggaac  4320
gacctgctgg acgtggtggc ctccatccac ctgtccaaga gaaccgtgcg gcggatcaga  4380
atcaacctgg tgctggcact gatctataac ctcgtgggca tccctatcgc cgctggcgtg  4440
ttcatgccta tcggaatcgt gctgcagccc tggatgggct ctgccgccat ggctgcaagc  4500
tccgtgtctg tggtgctgtc cagcctgcag ctgaagtgct acaagaagcc cgacctggaa  4560
agatacgagg cccaggccca cggacacatg aagcctctga cagcctccca ggtgtccgtg  4620
cacatcggca tggacgacag atggcgggac agccctagag ccaccccttg ggatcaggtg  4680
tcatacgtgt cacaggtgtc cctgagcagc ctgaccagcg acaagcccag cagacatagc  4740
gccgctgccg acgacgatgg ggacaagtgg tccctgctgc tgaacggccg ggatgaggaa  4800
cagtacatct gataagcatg caataaagtc tgagtgggcg gcagcctgtg tgtgcctggg  4860
ttctctctgt cccggaatgt gcaaacaatg gaggtgctcg agtagataag tagcatggcg  4920
ggttaatcat taactacaag gaacccctag tgatggagtt ggccactccc tctctgcgcg  4980
ctcgctcgct cactgaggcc gggcgaccaa aggtcgcccg acgcccgggc tttgcccggg  5040
cggcctcagt gagcgagcga gcgcgcagcc ttaattaacc taattcactg gccgtcgttt  5100
tacaacgtcg tgactgggaa aaccctggcg ttacccaact taatcgcctt gcagcacatc  5160
ccccttttcgc cagctggcgt aatagcgaag aggcccgcac cgatcgccct tcccaacagt  5220
tgcgcagcct gaatggcgaa tgggacgcgc cctgtagcgg cgcattaagc gcggcgggtg  5280
tggtggttac gcgcagcgtg accgctacac ttgccagcgc cctagcgccc gctcctttcg  5340
ctttcttccc ttcctttctc gccacgttcg ccggctttcc ccgtcaagct ctaaatcggg  5400
ggctcccttt agggttccga tttagtgctt tacggcacct cgaccccaaa aaacttgatt  5460
agggtgatgg ttcacgtagt gggccatcgc cctgatagac ggtttttcgc cctttgacgt  5520
tggagtccac gttctttaat agtggactct tgttccaaac tggaacaaca ctcaacccta  5580
tctcggtcta ttcttttgat ttataaggga ttttgccgat ttcggcctat tggttaaaaa  5640
atgagctgat ttaacaaaaa tttaacgcga attttaacaa aatattaacg cttacaattt  5700
aggtggcact tttcggggaa atgtgcgcgg aacccctatt tgtttatttt tctaaataca  5760
ttcaaatatg tatccgctca tgagacaata accctgataa atgcttcaat aatattgaaa  5820
aaggaagagt atgagtattc aacatttccg tgtcgccctt attccctttt ttgcggcatt  5880
ttgccttcct gtttttgctc acccagaaac gctggtgaaa gtaaaagatg ctgaagatca  5940
gttgggtgca cgagtgggtt acatcgaact ggatctcaac agcggtaaga tccttgagag  6000
ttttcgcccc gaagaacgtt ttccaatgat gagcactttt aaagttctgc tatgtggcgc  6060
ggtattatcc cgtattgacg ccgggcaaga gcaactcggt cgccgcatac actattctca  6120
gaatgacttg gttgagtact caccagtcac agaaaagcat cttacggatg gcatgacagt  6180
aagagaatta tgcagtgctg ccataaccat gagtgataac actgcggcca acttacttct  6240
gacaacgatc ggaggaccga aggagctaac cgcttttttg cacaacatgg gggatcatgt  6300
aactcgcctt gatcgttggg aaccggagct gaatgaagcc ataccaaacg acgagcgtga  6360
caccacgatg cctgtagcaa tggcaacaac gttgcgcaaa ctattaactg gcgaactact  6420
tactctagct tcccggcaac aattaataga ctggatggag gcggataaag ttgcaggacc  6480
acttctgcgc tcggcccttc cggctggctg gtttattgct gataaatctg gagccggtga  6540
gcgtgggtct cgcggtatca ttgcagcact ggggccagat ggtaagccct cccgtatcgt  6600
agttatctac acgacgggga gtcaggcaac tatggatgaa cgaaatagac agatcgctga  6660
gataggtgcc tcactgatta agcattggta actgtcagac caagtttact catatatact  6720
ttagattgat ttaaaacttc atttttaatt taaaaggatc taggtgaaga tcctttttga  6780
taatctcatg accaaaatcc cttaacgtga gttttcgttc cactgagcgt cagaccccgt  6840
agaaaagatc aaaggatctt cttgagatcc tttttttctg cgcgtaatct gctgcttgca  6900
aacaaaaaaa ccaccgctac cagcggtggt ttgtttgccg gatcaagagc taccaactct  6960
ttttccgaag gtaactggct tcagcagagc gcagatacca aatactgttc ttctagtgta  7020
gccgtagtta ggccaccact tcaagaactc tgtagcaccg cctacatacc tcgctctgct  7080
aatcctgtta ccagtggctg ctgccagtgg cgataagtcg tgtcttaccg ggttggactc  7140
aagacgatag ttaccggata aggcgcagcg gtcgggctga acggggggtt cgtgcacaca  7200
gcccagcttg gagcgaacga cctacaccga actgagatac ctacagcgtg agctatgaga  7260
aagcgccacg cttcccgaag ggagaaaggc ggacaggtat ccggtaagcg gcagggtcgg  7320
aacaggagag cgcacgaggg agcttccagg gggaaacgcc tggtatcttt atagtcctgt  7380
cgggtttcgc cacctctgac ttgagcgtcg atttttgtga tgctcgtcag gggggcggag  7440
cctatggaaa aacgccagca acgcggcctt tttacggttc ctggcctttt gctggccttt  7500
tgctcacatg ttctttcctg cgttatcccc tgattctgtg gataaccgta ttaccgcctt  7560
tgagtgagct gataccgctc gccgcagccg aacgaccgag cgcagcgagt cagtgagcga  7620
ggaagcggaa gagcgcccaa tacgcaaacc gcctctcccc gcgcgttggc cgattcatta  7680
atgcagctgg cacgacaggt ttcccgactg gaaagcgggc agtgagcgca acgcaattaa  7740
tgtgagttag ctcactcatt aggcacccca ggctttacac tttatgcttc cggctcgtat  7800
gttgtgtgga attgtgagcg gataacaatt tcacacagga aacagctatg accatgatta  7860
```

```
cgccagattt aattaagg                                              7878

SEQ ID NO: 27          moltype = DNA  length = 7858
FEATURE                Location/Qualifiers
misc_feature           1..7858
                       note = constructed sequence
source                 1..7858
                       mol_type = other DNA
                       organism = synthetic construct
SEQUENCE: 27
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttaggggaat tccgatgctc taatctctct agacaaggtt  240
catatttgta tgggttactt attctctctt tgttgactaa gtcaataatc agaatcagca  300
ggtttgcagt cagattggca gggataagca gcctagctca ggagaagtga gtataaaagc  360
cccaggctgg gagcagccat cagcggccgc caccatgccc gagcaggaaa gacagatcac  420
cgccagagag ggcgccagcc ggaagatcct gagcaagctg agcctgccca ccagagcctg  480
ggagcccgcc atgaagaagt ccttcgcctt cgacaacgtg ggctacgagg gcggcctgga  540
cggactggga ccatcttctc aggtggccac aagcaccgtg cgcatcctgg gcatgacctg  600
ccagagctgc gtgaagtcca tcgaggaccg gatcagcaac ctgaagggca tcatcagcat  660
gaaggtgtcc ctggaacagg gcagcgccac cgtgaaatac gtgccctctg tcgtgtgcct  720
gcagcaggtg tgccaccaga tcggcgacat gggcttcgag gcctctatcg ccgagggaaa  780
ggccgcctct tggccctcta gaagcctgcc tgctcaggaa gccgtcgtga agctgcgggt  840
ggaagggatg acctgtcagt cctgcgtgtc cagcatcgag ggcaaagtgc ggaagctgca  900
gggcgtggtg cgcgtgaaag tgtctctgag caaccaggaa gctgtgatca cctaccagcc  960
ctacctgatc cagcccgagg acctgaggga ccacgtgaac gatatgggat ttgaggccgc  1020
catcaagagc aaggtggccc ctctgtctct gggccccatc gacatcgaga gactgcagag  1080
caccaacccc aagcggcctc tgagcagcgc caaccagaac ttcaacaaca gcgagacact  1140
gggccaccag ggcagccacg tcgtgacact gcagctgcgg atcgacggaa tgcactgcaa  1200
gagctgtgtg ctgaacatcg aggaaaacat cggccagctg ctgggagtgc agagcatcca  1260
ggtgtcactg gaaaacaaga ccgcccaggt gaagtacgac cccagctgca caagccccgt  1320
ggccctgcag agagccattg aagctctgcc ccctggcaac ttcaaagtgt ccctgcctga  1380
cggagccgag ggctccggaa cagatcacag aagcagcagc agccacagcc ctggcagccc  1440
ccctagaaat caggtgcagg gcacctgtag caccaccctg atcgccattg ccggcatgac  1500
atgcgccagc tgcgtgcact ctattgaggg catgatctcc cagctggaag gcgtgcagca  1560
gatcagtgtg tctctggccg agggcaccgc cacagtgctg tacaacccta gcgtgatcag  1620
ccccgaagaa ctgagagccg ccattgagga catgggattc gaagccagcg tggtgtccga  1680
gagctgctcc accaaccctc tgggcaatca cagcgccggc aacagcatgg tgcagaccac  1740
cgacggcacc cccaccagcg tgcaggaagt ggccccacat acaggcagac tgcccgccaa  1800
tcacgccccc gatatcctgg ccaagagccc ccagagtaca agagccgtgg ccccccagaa  1860
gtgcttcctg cagatcaagg gcatgacttg tgcctcttgt gtgtccaata tcgagcggaa  1920
cctgcagaaa gaggccggcg tgctgtctgt gctggtggct ctgatggccg gcaaggccga  1980
gatcaaatac gaccccgaag tgattcagcc cctggaaatc gcccagttta tccaggacct  2040
gggctttgaa gccgccgtga tggaagatta cgccggctcc gacggcaaca tcgagctgac  2100
catcaccgga atgacctgcg cctcctgtgt gcacaacatt gagtccaagc tgacccggac  2160
caacggcatc acctacgcct ctgtggctct ggccacctcc aaggccctcg tgaagttcga  2220
tcccgagatc atcggcccca gggacatcat caagatcatc gaagagatcg gcttccacgc  2280
cagcctggcc cagaggaacc ctaacgccca ccacctggac cacaagatgg aaatcaagca  2340
gtggaagaaa agcttcctgt gcagcctggt gttcggcatc cccgtgatgg ccctgatgat  2400
ctacatgctg atccccagca acgagcccca ccagtccatg gtgctggatc acaacatcat  2460
ccccggcctg tctatcctga acctgatctt cttcatcctg tgcaccttcg tgcagctgct  2520
gggcggctgg tacttctacg tgcaggccta caagtccctg cggcacagat ccgccaacat  2580
ggacgtgctg atcgtgctgg ccacatctat cgcctacgtg tactccctcg tgatcctggt  2640
ggtggccgtg gccgagaaag ccgagagaag ccctgtgacc ttcttcgaca cccccccctat  2700
gctgttcgtg tttatcgccc tgggccggtg gctggaacac ctggccaaaa gcaagaccag  2760
cgaggccctg gctaagctga tgagtctgca ggccaccgag gccacagtcg tgaccctggg  2820
cgaggacaac ctgatcatcc gcgaggaaca ggtgccaatg gaactggtgc agcggggcga  2880
catcgtgaag gtggtgcctg gcggcaagtt ccccgtggac ggaaaagtgc tggaagggaa  2940
taccatggcc gacgagagcc tgatcacagg cgaggccatg cccgtgacca agaaacctgg  3000
cagcacagtg atcgccggca gcatcaatgc ccacggcagc gtgctgatta aggccacaca  3060
cgtgggcaac gataccaccc tggctcagat tgtgaagctg gtggaagagg cccagatgag  3120
caaggccccc attcagcagc tggctgaccg gttcagcggc tacttcgtgc cctttatcat  3180
catcatgagc accctgacac tggtcgtgtg gatcgtgatc ggctttatcg acttcggagt  3240
ggtgcagaga tacttcccca accctaacaa gcacatcagc cagacagaag tgatcatcag  3300
attcgccttt cagaccagca tcaccgtgct gtgtatcgcc tgcccctgta gcctgggact  3360
ggccacacct accgctgtga tggtgggaac aggcgtggcc gctcagaacg gcatcctgat  3420
caagggggc aagcctctgg aaatggctca caagatcaag accgtgatgt tcgacaagac  3480
cggcaccatc acccacggcg tgcccagagt gatgagagtg ctgctgctgg gggatgtggc  3540
caccctgcct ctgagaaagg tgctggctgt cgtgggcaca gccgaggcta gctctgaaca  3600
cccactggga gtggccgtga caaagtactg caaagaggaa ctgggcaccg aaaccctggg  3660
ctactgcacc gactttcagg ccgtgcctgg ctgtggcatc ggctgcaagg tgtccaacgt  3720
ggaaggcatc ctggcccaca gcgagaggcc actgtctgcc cctgccagcc acctgaacga  3780
ggccggatct ctgcccgccg aaaaggacgc tgtgccccag accttctctg tgctgattgg  3840
caacagagag tggctgcggc ggaacggcct gaccatctcc tccgatgtgt ccgacgccat  3900
gaccgaccac gagatgaagg gccagaccgc cattctggtg gccattgacg gggtgctgtg  3960
cggcatgatc gcaatcgccg atgccgtgaa acaggaagca gcactggccg tgcacaccct  4020
gcagtctatg ggagtggatg tggtgctgat caccggcgac aacagaaaga ccgccagggc  4080
cattgccacc caggtgggca tcaacaaggt gttcgccgag gtgctgccca gccacaaagt  4140
```

```
ggccaaggtg caggaactgc agaacaaagg caaaaaggtg gccatggtgg gagatggcgt  4200
gaacgactct cctgctctgg cccaggcaga tatgggcgtg gccatcggca caggcaccga  4260
cgtggcaatt gaggctgctg acgtggtgct gattcggaac gacctgctgg acgtggtggc  4320
ctccatccac ctgtccaaga gaaccgtgcg gcggatcaga atcaacctgg tgctggcact  4380
gatctataac ctcgtgggca tccctatcgc cgctggcgtg ttcatgccta tcggaatcgt  4440
gctgcagccc tggatgggct ctgccgccat ggctgcaagc tccgtgtctg tggtgctgtc  4500
cagcctgcag ctgaagtgct acaagaagcc cgacctggaa agatacgagg cccaggccca  4560
cggacacatg aagcctctga cagcctccca ggtgtccgtg cacatcggca tggacgacag  4620
atggcgggac agccctagag ccaccccttg ggatcaggtg tcatacgtgt cacaggtgtc  4680
cctgagcagc ctgaccagcg acaagcccag cagacatagc gccgctgccg acgacgatgg  4740
ggacaagtgg tccctgctgc tgaacggccg ggatgaggaa cagtacatct gataagcatg  4800
caataaagtc tgagtgggcg gcagcctgtg tgtgcctggg ttctctctgt cccggaatgt  4860
gcaaacaatg gaggtgctcg agtagataag tagcatggcg ggttaatcat taactacaag  4920
gaacccctag tgatggagtt ggccactccc tctctgcgcg ctcgctcgct cactgaggcc  4980
gggcgaccaa aggtcgcccg acgcccgggc tttgcccggg cggcctcagt gagcgagcga  5040
gcgcgcagcc ttaattaacc taattcactg gccgtcgttt tacaacgtcg tgactgggaa  5100
aaccctggcg ttacccaact taatcgcctt gcagcacatc ccccttcgc cagctggcgt  5160
aatagcgaag aggcccgcac cgatcgccct tcccaacagt tgcgcagcct gaatggcgaa  5220
tgggacgcgc cctgtagcgg cgcattaagc gcggcgggtg tggtggttac gcgcagcgtg  5280
accgctacac ttgccagcgc cctagcgccc gctcctttcg ctttcttccc ttcctttctc  5340
gccacgttcg ccggctttcc ccgtcaagct ctaaatcggg ggctcccttt agggttccga  5400
tttagtgctt tacggcacct cgaccccaaa aaacttgatt agggtgatgg ttcacgtagt  5460
gggccatcgc cctgatagac ggtttttcgc cctttgacgt tggagtccac gttctttaat  5520
agtggactct tgttccaaac tggaacaaca ctcaacccta tctcggtcta ttcttttgat  5580
ttataaggga ttttgccgat ttcggcctat tggttaaaaa atgagctgat ttaacaaaaa  5640
tttaacgcga attttaacaa aatattaacg cttacaattt aggtggcact tttcggggaa  5700
atgtgcgcgg aacccctatt tgtttatttt tctaaataca ttcaaatatg tatccgctca  5760
tgagacaata accctgataa atgcttcaat aatattgaaa aaggaagagt atgagtattc  5820
aacatttccg tgtcgccctt attccctttt ttgcggcatt ttgccttcct gtttttgctc  5880
acccagaaac gctggtgaaa gtaaaagatg ctgaagatca gttgggtgca cgagtgggtt  5940
acatcgaact ggatctcaac agcggtaaga tccttgagag ttttcgcccc gaagaacgtt  6000
ttccaatgat gagcactttt aaagttctgc tatgtggcgc ggtattatcc cgtattgacg  6060
ccgggcaaga gcaactcggt cgccgcatac actattctca gaatgacttg gttgagtact  6120
caccagtcac agaaaagcat cttacggatg gcatgacagt aagagaatta tgcagtgctg  6180
ccataaccat gagtgataac actgcggcca acttacttct gacaacgatc ggaggaccga  6240
aggagctaac cgcttttttg cacaacatgg gggatcatgt aactcgcctt gatcgttggg  6300
aaccggagct gaatgaagcc ataccaaacg acgagcgtga caccacgatg cctgtagcaa  6360
tggcaacaac gttgcgcaaa ctattaactg gcgaactact tactctagct tcccggcaac  6420
aattaataga ctggatggag gcggataaag ttgcaggacc acttctgcgc tcggcccttc  6480
cggctggctg gtttattgct gataaatctg gagccggtga gcgtgggtct cgcggtatca  6540
ttgcagcact ggggccagat ggtaagccct cccgtatcgt agttatctac acgacgggga  6600
gtcaggcaac tatggatgaa cgaaatagac agatcgctga gataggtgcc tcactgatta  6660
agcattggta actgtcagac caagtttact catatatact ttagattgat ttaaaacttc  6720
atttttaatt taaaaggatc taggtgaaga tcctttttga taatctcatg accaaaatcc  6780
cttaacgtga gttttcgttc cactgagcgt cagaccccgt agaaaagatc aaaggatctt  6840
cttgagatcc tttttttctg cgcgtaatct gctgcttgca aacaaaaaaa ccaccgctac  6900
cagcggtggt ttgtttgccg gatcaagagc taccaactct ttttccgaag gtaactggct  6960
tcagcagagc gcagatacca aatactgttc ttctagtgta gccgtagtta ggccaccact  7020
tcaagaactc tgtagcaccg cctacatacc tcgctctgct aatcctgtta ccagtggctg  7080
ctgccagtgg cgataagtcg tgtcttaccg ggttggactc aagacgatag ttaccggata  7140
aggcgcagcg gtcgggctga acggggggtt cgtgcacaca gcccagcttg gagcgaacga  7200
cctacaccga actgagatac ctacagcgtg agctatgaga aagcgccacg cttcccgaag  7260
ggagaaaggc ggacaggtat ccggtaagcg gcagggtcgg aacaggagag cgcacgaggg  7320
agcttccagg gggaaacgcc tggtatcttt atagtcctgt cgggtttcgc cacctctgac  7380
ttgagcgtcg atttttgtga tgctcgtcag gggggcggag cctatggaaa aacgccagca  7440
acgcggcctt tttacggttc ctggcctttt gctggccttt tgctcacatg ttctttcctg  7500
cgttatcccc tgattctgtg gataaccgta ttaccgcctt tgagtgagct gataccgctc  7560
gccgcagccg aacgaccgag cgcagcgagt cagtgagcga ggaagcggaa gagcgcccaa  7620
tacgcaaacc gcctctcccc gcgcgttggc cgattcatta atgcagctgg cacgacaggt  7680
ttcccgactg gaaagcgggc agtgagcgca acgcaattaa tgtgagttag ctcactcatt  7740
aggcacccca ggctttacac tttatgcttc cggctcgtat gttgtgtgga attgtgagcg  7800
gataacaatt tcacacagga aacagctatg accatgatta cgccagattt aattaagg    7858
```

```
SEQ ID NO: 28          moltype = DNA  length = 7094
FEATURE                Location/Qualifiers
misc_feature           1..7094
                       note = constructed sequence
source                 1..7094
                       mol_type = other DNA
                       organism = synthetic construct
SEQUENCE: 28
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agctagcagg  180
ttaattttta aaaagcagtc aaaagtccaa gtggcccttg gcagcattta ctctctctgt  240
ttgctctggt taataatctc aggagcacaa acattccaga tccaggttaa tttttaaaaa  300
gcagtcaaaa gtccaagtgg ccccttggcag catttactct ctctgtttgc tctggttaat  360
aatctcagga gcacaaacat tccagatccg gcgcgccagg gctggaagct acctttgaca  420
tcatttcctc tgcgaatgca tgtataattt ctacagaacc tattagaaag gatcacccag  480
```

```
cctctgcttt tgtacaactt tcccttaaaa aactgccaat tccactgctg tttggcccaa  540
tagtgagaac tttttcctgc tgcctcttgg tgcttttgcc tatggcccct attctgcctg  600
ctgaagacac tcttgccagc atggacttaa accectccag ctctgacaat cctctttctc  660
ttttgtttta catgaagggt ctggcagcca aagcaatcac tcaaagttca aaccttatca  720
ttttttgctt tgttcctctt ggccttggtt ttgtacatca gctttgaaaa taccatccca  780
gggttaatgc tggggttaat ttataactaa gagtgctcta gttttgcaat acaggacatg  840
ctataaaaat ggaaagatgt tgctttctga gagactgcag aagttggtcg tgaggcactg  900
ggcaggtaag tatcaaggtt acaagacagg tttaaggaga ccaatagaaa ctgggcttgt  960
cgagacagag aagactcttg cgtttctgat aggcacctat tggtcttact gacatccact  1020
ttgcctttct ctccacaggt gtccaggcgg ccgccaccat gcccgagcag gaaagacaga  1080
tcaccgccag agagggcgcc agccggaaga tcctgagcaa gctgagcctg cccaccagag  1140
cctgggagcc cgccatgaag aagtccttcg ccttcgacaa cgtgggctac gagggcggcc  1200
tggacggact gggaccatct tctcaggtgg ccacaagcac cgtgcgcctg gaaatcgccc  1260
agtttatcca ggacctgggc tttgaagccg ccgtgatgga agattacgcc ggctccgacg  1320
gcaacatcga gctgaccatc accggaatga cctgcgcctc ctgtgtgcac aacattgagt  1380
ccaagctgac ccggaccaac ggcatcacct acgcctctgt ggctctggcc acctccaagg  1440
ccctcgtgaa gttcgatccc gagatcatcg gccccaggga catcatcaag atcatcgaag  1500
agatcggctt ccacgccagc ctggcccaga ggaaccctaa cgcccaccac ctggaccaca  1560
agatggaaat caagcagtgg aagaaaagct tcctgtgcag cctggtgttc ggcatccccg  1620
tgatggccct gatgatctac atgctgatcc ccagcaacga gccccaccag tccatggtgc  1680
tggatcacaa catcatcccc ggcctgtcta tcctgaacct gatcttcttc atcctgtgca  1740
ccttcgtgca gctgctgggc ggctggtact tctacgtgca ggcctacaag tccctgcggc  1800
acagatccgc caacatggac gtgctgatcg tgctggccac atctatcgcc tacgtgtact  1860
ccctcgtgat cctggtggtg gccgtggccg agaaagccga gagaagccct gtgaccttct  1920
tcgacacccc ccctatgctg ttcgtgttta tcgccctggg ccggtggctg gaacacctgg  1980
ccaaaagcaa gaccagcgag gccctggcta agctgatgag tctgcaggcc accgaggcca  2040
cagtcgtgac cctgggcgag gacaacctga tcatccgcga ggaacaggtg ccaatggaac  2100
tggtgcagcg gggcgacatc gtgaaggtgg tgcctggcgg caagttcccc gtggacggaa  2160
aagtgctgga agggaatacc atggccgacg agagcctgat cacaggcgag gccatgcccg  2220
tgaccaagaa acctggcagc acagtgatcg ccggcagcat caatgcccac ggcagcgtgc  2280
tgattaaggc cacacacgtg ggcaacgata ccaccctggc tcagattgtg aagctggtgg  2340
aagaggccca gatgagcaag gcccccattc agcagctggc tgaccggttc agcggctact  2400
tcgtgccctt tatcatcatc atgagcaccc tgacactggt cgtgtggatc gtgatcggct  2460
ttatcgactt cggagtggtg cagagatact tccccaaccc taacaagcac atcagccaga  2520
cagaagtgat catcagattc gcctttcaga ccagcatcac cgtgctgtgt atcgcctgcc  2580
cctgtagcct gggactggcc acacctaccg ctgtgatggt gggaacaggc gtggccgctc  2640
agaacggcat cctgatcaag gggggcaagc ctctggaaat ggctcacaag atcaagaccg  2700
tgatgttcga caagaccggc accatcaccc acggcgtgcc cagagtgatg agagtgctgc  2760
tgctggggga tgtggccacc ctgcctctga gaaaggtgct ggctgtcgtg ggcacagccg  2820
aggctagctc tgaacaccca ctgggagtgg ccgtgacaaa gtactgcaaa gaggaactgg  2880
gcaccgaaac cctgggctac tgcaccgact ttcaggccgt gcctggctgt ggcatcggct  2940
gcaaggtgtc caacgtggaa ggcatcctgg cccacagcga gaggccactg tctgcccctg  3000
ccagccacct gaacgaggcc ggatctctgc ccgccgaaaa ggacgctgtg ccccagacct  3060
tctctgtgct gattggcaac agagagtggc tgcggcggaa cggcctgacc atctcctccg  3120
atgtgtccga cgccatgacc gaccacgaga tgaagggcca gaccgccatt ctggtggcca  3180
ttgacggggt gctgtgcggc atgatcgcaa tcgccgatgc cgtgaaacag gaagcagcac  3240
tggccgtgca caccctgcag tctatgggag tggatgtggt gctgatcacc ggcgacaaca  3300
gaaagaccgc cagggccatt gccacccagg tgggcatcaa caaggtgttc gccgaggtgc  3360
tgcccagcca caaagtggcc aaggtgcagg aactgcagaa caaaggcaaa aaggtggcca  3420
tggtgggaga tggcgtgaac gactctcctg ctctggccca ggcagatatg ggcgtggcca  3480
tcggcacagg caccgacgtg gcaattgagg ctgctgacgt ggtgctgatt cggaacgacc  3540
tgctggacgt ggtggcctcc atccacctgt ccaagagaac cgtgcggcgg atcagaatca  3600
acctggtgct ggcactgatc tataacctcg tgggcatccc tatcgccgct ggcgtgttca  3660
tgcctatcgg aatcgtgctg cagccctgga tgggctctgc cgccatggct gcaagctccg  3720
tgtctgtggt gctgtccagc ctgcagctga agtgctacaa gaagcccgac ctggaaagat  3780
acgaggccca ggcccacgga cacatgaagc ctctgacagc ctcccaggtg tccgtgcaca  3840
tcggcatgga cgacagatgg cgggacagcc ctagagccac cccttgggat caggtgtcat  3900
acgtgtcaca ggtgtccctg agcagcctga ccagcgacaa gcccagcaga catagcgccg  3960
ctgccgacga cgatggggac aagtggtccc tgctgctgaa cggccgggat gaggaacagt  4020
acatctgata agcatgcaat aaagtctgag tgggcggcag cctgtgtgtg cctgggttct  4080
ctctgtcccg gaatgtgcaa acaatggagg tgctcgagta gataagtagc atggcgggtt  4140
aatcattaac tacaaggaac ccctagtgat ggagttggcc actccctctc tgcgcgctcg  4200
ctcgctcact gaggccgggc gaccaaaggt cgcccgacgc ccgggctttg cccgggcggc  4260
ctcagtgagc gagcgagcgc gcagccttaa ttaacctaat tcactggccg tcgttttaca  4320
acgtcgtgac tgggaaaacc ctggcgttac ccaacttaat cgccttgcag cacatccccc  4380
tttcgccagc tggcgtaata gcgaagaggc ccgcaccgat cgcccttccc aacagttgcg  4440
cagcctgaat ggcgaatggg acgcgccctg tagcggcgca ttaagcgcgg cgggtgtggt  4500
ggttacgcgc agcgtgaccg ctacacttgc cagcgcccta gcgcccgctc ctttcgcttt  4560
cttcccttcc tttctcgcca cgttcgccgg ctttccccgt caagctctaa atcgggggct  4620
ccctttaggg ttccgattta gtgctttacg gcacctcgac cccaaaaaac ttgattaggg  4680
tgatggttca cgtagtgggc catcgccctg atagacggtt tttcgccctt tgacgttgga  4740
gtccacgttc tttaatagtg gactcttgtt ccaaactgga acaacactca accctatctc  4800
ggtctattct tttgatttat aagggatttt gccgatttcg gcctattggt taaaaaatga  4860
gctgatttaa caaaaattta acgcgaattt taacaaaata ttaacgctta caatttaggt  4920
ggcacttttc ggggaaatgt gcgcggaacc cctatttgtt tatttttcta aatacattca  4980
aatatgtatc cgctcatgag acaataaccc tgataaatgc ttcaataata ttgaaaaagg  5040
aagagtatga gtattcaaca tttccgtgtc gcccttattc ccttttttgc ggcattttgc  5100
cttcctgttt ttgctcaccc agaaacgctg gtgaaagtaa aagatgctga agatcagttg  5160
ggtgcacgag tgggttacat cgaactggat ctcaacagcg gtaagatcct tgagagtttt  5220
```

```
cgccccgaag aacgttttcc aatgatgagc acttttaaag ttctgctatg tggcgcggta  5280
ttatcccgta ttgacgccgg gcaagagcaa ctcggtcgcc gcatacacta ttctcagaat  5340
gacttggttg agtactcacc agtcacagaa aagcatctta cggatggcat gacagtaaga  5400
gaattatgca gtgctgccat aaccatgagt gataacactg cggccaactt acttctgaca  5460
acgatcggag gaccgaagga gctaaccgct tttttgcaca acatggggga tcatgtaact  5520
cgccttgatc gttgggaacc ggagctgaat gaagccatac caaacgacga gcgtgacacc  5580
acgatgcctg tagcaatggc aacaacgttg cgcaaactat taactggcga actacttact  5640
ctagcttccc ggcaacaatt aatagactgg atggaggcgg ataaagttgc aggaccactt  5700
ctgcgctcgg cccttccggc tggctggttt attgctgata aatctggagc cggtgagcgt  5760
gggtctcgcg gtatcattgc agcactgggg ccagatggta agccctcccg tatcgtagtt  5820
atctacacga cggggagtca ggcaactatg gatgaacgaa atagacagat cgctgagata  5880
ggtgcctcac tgattaagca ttggtaactg tcagaccaag tttactcata tatactttag  5940
attgatttaa aacttcattt ttaatttaaa aggatctagg tgaagatcct ttttgataat  6000
ctcatgacca aaatccctta acgtgagttt tcgttccact gagcgtcaga ccccgtagaa  6060
aagatcaaag gatcttcttg agatcctttt tttctgcgcg taatctgctg cttgcaaaca  6120
aaaaaaccac cgctaccagc ggtggtttgt ttgccggatc aagagctacc aactcttttt  6180
ccgaaggtaa ctggcttcag cagagcgcag ataccaaata ctgttcttct agtgtagccg  6240
tagttaggcc accacttcaa gaactctgta gcaccgccta catacctcgc tctgctaatc  6300
ctgttaccag tggctgctgc cagtggcgat aagtcgtgtc ttaccgggtt ggactcaaga  6360
cgatagttac cggataaggc gcagcggtcg ggctgaacgg ggggttcgtg cacacagccc  6420
agcttggagc gaacgaccta caccgaactg agatacctac agcgtgagct atgagaaagc  6480
gccacgcttc ccgaagggag aaaggcggac aggtatccgg taagcggcag ggtcggaaca  6540
ggagagcgca cgagggagct tccaggggga aacgcctggt atctttatag tcctgtcggg  6600
tttcgccacc tctgacttga gcgtcgattt ttgtgatgct cgtcaggggg gcggagccta  6660
tggaaaaacg ccagcaacgc ggccttttta cggttcctgg ccttttgctg gccttttgct  6720
cacatgttct ttcctgcgtt atcccctgat tctgtggata accgtattac cgcctttgag  6780
tgagctgata ccgctcgccg cagccgaacg accgagcgca gcgagtcagt gagcgaggaa  6840
gcggaagagc gcccaatacg caaaccgcct ctccccgcgc gttggccgat tcattaatgc  6900
agctggcacg acaggtttcc cgactggaaa gcgggcagtg agcgcaacgc aattaatgtg  6960
agttagctca ctcattaggc accccaggct ttacacttta tgcttccggc tcgtatgttg  7020
tgtggaattg tgagcggata acaatttcac acaggaaaca gctatgacca tgattacgcc  7080
agatttaatt aagg                                                    7094

SEQ ID NO: 29           moltype = DNA  length = 7487
FEATURE                 Location/Qualifiers
misc_feature            1..7487
                        note = constructed sequence
source                  1..7487
                        mol_type = other DNA
                        organism = synthetic construct
SEQUENCE: 29
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agctagcagg  180
ttaattttta aaaagcagtc aaaagtccaa gtggcccttg gcagcattta ctctctctgt  240
ttgctctggt taataatctc aggagcacaa acattccaga tccaggttaa tttttaaaaa  300
gcagtcaaaa gtccaagtgg cccttggcag catttactct ctctgtttgc tctggttaat  360
aatctcagga gcacaaacat tccagatccg gcgcgccagg gctggaagct acctttgaca  420
tcatttcctc tgcgaatgca tgtataattt ctacagaacc tattagaaag gatcacccag  480
cctctgcttt tgtacaactt tcccttaaaa aactgccaat tccactgctg tttggcccaa  540
tagtgagaac tttttcctgc tgcctcttgg tgcttttgcc tatggcccct attctgcctg  600
ctgaagacac tcttgccagc atggacttaa acccctccag ctctgacaat cctctttctc  660
ttttgtttta catgaagggt ctggcagcca aagcaatcac tcaaagttca aaccttatca  720
ttttttgctt tgttcctctt ggccttggtt ttgtacatca gctttgaaaa taccatccca  780
gggttaatgc tggggttaat ttataactaa gagtgctcta gttttgcaat acaggacatg  840
ctataaaaat ggaaagatgt tgctttctga gagactgcag aagttggtcg tgaggcactg  900
ggcaggtaag tatcaaggtt acaagacagg tttaaggaga ccaatagaaa ctgggcttgt  960
cgagacagag aagactcttg cgtttctgat aggcacctat tggtcttact gacatccact  1020
ttgcctttct ctccacaggt gtccaggcgg ccgccaccat gcccgagcag gaaagacaga  1080
tcaccgccag agagggcgcc agccggaaga tcctgagcaa gctgagcctg cccaccagag  1140
cctgggagcc cgccatgaag aagtccttcg ccttcgacaa cgtgggctac gagggcggcc  1200
tggacggact gggaccatct tctcaggtgg ccacaagcac cgtgcgcagc cccgaagaac  1260
tgagagccgc cattgaggac atgggattcg aagccagcgt ggtgtccgag agctgctcca  1320
ccaaccctct gggcaatcac agcgccggca acagcatggt gcagaccacc gacggcaccc  1380
ccaccagcgt gcaggaagtg gccccacata caggcagact gcccgccaat cacgcccccg  1440
atatcctggc caagagcccc cagagtacaa gagccgtggc cccccagaag tgcttcctgc  1500
agatcaaggg catgacttgt gcctcttgtg tgtccaatat cgagcggaac ctgcagaaag  1560
aggccggcgt gctgtctgtg ctggtggctc tgatggccgg caaggccgag atcaaatacg  1620
accccgaagt gattcagccc ctggaaatcg cccagtttat ccaggacctg ggctttgaag  1680
ccgccgtgat ggaagattac gccggctccg acggcaacat cgagctgacc atcaccggaa  1740
tgacctgcgc ctcctgtgtg cacaacattg agtccaagct gacccggacc aacggcatca  1800
cctacgcctc tgtggctctg gccacctcca aggccctcgt gaagttcgat cccgagatca  1860
tcggccccag ggacatcatc aagatcatcg aagagatcgg cttccacgcc agcctggccc  1920
agaggaaccc taacgcccac cacctggacc acaagatgga aatcaagcag tggaagaaaa  1980
gcttcctgtg cagcctggtg ttcggcatcc ccgtgatggc cctgatgatc tacatgctga  2040
tccccagcaa cgagccccac cagtccatgg tgctggatca caacatcatc cccggcctgt  2100
ctatcctgaa cctgatcttc ttcatcctgt gcaccttcgt gcagctgctg ggcggctggt  2160
acttctacgt gcaggcctac aagtccctgc ggcacagatc cgccaacatg gacgtgctga  2220
tcgtgctggc cacatctatc gcctacgtgt actccctcgt gatcctggtg gtggccgtgg  2280
```

```
ccgagaaagc cgagagaagc cctgtgacct tcttcgacac ccccccctatg ctgttcgtgt  2340
ttatcgccct gggccggtgg ctggaacacc tggccaaaag caagaccagc gaggccctgg  2400
ctaagctgat gagtctgcag gccaccgagg ccacagtcgt gaccctgggc gaggacaacc  2460
tgatcatccg cgaggaacag gtgccaatgg aactggtgca gcggggcgac atcgtgaagg  2520
tggtgcctgg cggcaagttc cccgtggacg gaaaagtgct ggaagggaat accatggccg  2580
acgagagcct gatcacaggc gaggccatgc ccgtgaccaa gaaacctggc agcacagtga  2640
tcgccggcag catcaatgcc cacggcagcg tgctgattaa ggccacacac gtgggcaacg  2700
ataccaccct ggctcagatt gtgaagctgg tggaagaggc ccagatgagc aaggccccca  2760
ttcagcagct ggctgaccgg ttcagcggct acttcgtgcc ctttatcatc atcatgagca  2820
ccctgacact ggtcgtgtgg atcgtgatcg gctttatcga cttcggagtg gtgcagagat  2880
acttccccaa ccctaacaag cacatcagcc agacagaagt gatcatcaga ttcgcctttc  2940
agaccagcat caccgtgctg tgtatcgcct gcccctgtag cctgggactg gccacaccta  3000
ccgctgtgat ggtgggaaca ggcgtggccg ctcagaacgg catcctgatc aagggggggca  3060
agcctctgga aatggctcac aagatcaaga ccgtgatgtt cgacaagacc ggcaccatca  3120
cccacggcgt gcccagagtg atgagagtgc tgctgctggg ggatgtggcc accctgcctc  3180
tgagaaaggt gctggctgtc gtgggcacag ccgaggctag ctctgaacac ccactgggag  3240
tggccgtgac aaagtactgc aaagaggaac tgggcaccga aaccctgggc tactgcaccg  3300
actttcaggc cgtgcctggc tgtggcatcg gctgcaaggt gtccaacgtg gaaggcatcc  3360
tggcccacag cgagaggcca ctgtctgccc ctgccagcca cctgaacgag gccggatctc  3420
tgcccgccga aaaggacgct gtgccccaga ccttctctgt gctgattggc aacagagagt  3480
ggctgcggcg gaacggcctg accatctcct ccgatgtgtc cgacgccatg accgaccacg  3540
agatgaaggg ccagaccgcc attctggtgg ccattgacgg ggtgctgtgc ggcatgatcg  3600
caatcgccga tgccgtgaaa caggaagcag cactggccgt gcacaccctg cagtctatgg  3660
gagtggatgt ggtgctgatc accggcgaca acagaaagac cgccagggcc attgccaccc  3720
aggtgggcat caacaaggtg ttcgccgagg tgctgcccag ccacaaagtg gccaaggtgc  3780
aggaactgca gaacaaaggc aaaaaggtgg ccatggtggg agatggcgtg aacgactctc  3840
ctgctctggc ccaggcagat atgggcgtgg ccatcggcac aggcaccgac gtggcaattg  3900
aggctgctga cgtggtgctg attcggaacg acctgctgga cgtggtggcc tccatccacc  3960
tgtccaagag aaccgtgcgg cggatcagaa tcaacctggt gctggcactg atctataacc  4020
tcgtgggcat ccctatcgcc gctggcgtgt tcatgcctat cggaatcgtg ctgcagccct  4080
ggatgggctc tgccgccatg gctgcaagct ccgtgtctgt ggtgctgtcc agcctgcagc  4140
tgaagtgcta caagaagccc gacctggaaa gatacgaggc ccaggcccac ggacacatga  4200
agcctctgac agcctcccag gtgtccgtgc acatcggcat ggacgacaga tggcgggaca  4260
gccctagagc cacccccttgg gatcaggtgt catacgtgtc acaggtgtcc ctgagcagcc  4320
tgaccagcga caagcccagc agacatagcg ccgctgccga cgacgatggg gacaagtggt  4380
ccctgctgct gaacggccgg gatgaggaac agtacatctg ataagcatgc aataaagtct  4440
gagtgggcgg cagcctgtgt gtgcctgggt tctctctgtc ccggaatgtg caaacaatgg  4500
aggtgctcga gtagataagt agcatggcgg gttaatcatt aactacaagg aacccctagt  4560
gatggagttg gccactccct ctctgcgcgc tcgctcgctc actgaggccg ggcgaccaaa  4620
ggtcgcccga cgcccgggct ttgcccgggc ggcctcagtg agcgagcgag cgcgcagcct  4680
taattaacct aattcactgg ccgtcgtttt acaacgtcgt gactgggaaa accctggcgt  4740
tacccaactt aatcgccttg cagcacatcc ccctttcgcc agctggcgta atagcgaaga  4800
ggcccgcacc gatcgccctt cccaacagtt gcgcagcctg aatggcgaat gggacgcgcc  4860
ctgtagcggc gcattaagcg cggcgggtgt ggtggttacg cgcagcgtga ccgctacact  4920
tgccagcgcc ctagcgcccg ctcctttcgc tttcttccct tcctttctcg ccacgttcgc  4980
cggctttccc cgtcaagctc taaatcgggg gctcccttta gggttccgat ttagtgcttt  5040
acggcacctc gaccccaaaa aacttgatta gggtgatggt tcacgtagtg ggccatcgcc  5100
ctgatagacg gtttttcgcc ctttgacgtt ggagtccacg ttctttaata gtggactctt  5160
gttccaaact ggaacaacac tcaaccctat ctcggtctat tcttttgatt tataagggat  5220
tttgccgatt tcggcctatt ggttaaaaaa tgagctgatt taacaaaaat ttaacgcgaa  5280
ttttaacaaa atattaacgc ttacaattta ggtggcactt ttcggggaaa tgtgcgcgga  5340
acccctattt gtttattttt ctaaatacat tcaaatatgt atccgctcat gagacaataa  5400
ccctgataaa tgcttcaata atattgaaaa aggaagagta tgagtattca acatttccgt  5460
gtcgccctta ttcccttttt tgcggcattt tgccttcctg tttttgctca cccagaaacg  5520
ctggtgaaag taaaagatgc tgaagatcag ttgggtgcac gagtgggtta catcgaactg  5580
gatctcaaca gcggtaagat ccttgagagt tttcgccccg aagaacgttt tccaatgatg  5640
agcactttta aagttctgct atgtggcgcg gtattatccc gtattgacgc cgggcaagag  5700
caactcggtc gccgcataca ctattctcag aatgacttgg ttgagtactc accagtcaca  5760
gaaaagcatc ttacggatgg catgacagta agagaattat gcagtgctgc cataaccatg  5820
agtgataaca ctgcggccaa cttacttctg acaacgatcg gaggaccgaa ggagctaacc  5880
gcttttttgc acaacatggg ggatcatgta actcgccttg atcgttggga accggagctg  5940
aatgaagcca taccaaacga cgagcgtgac accacgatgc ctgtagcaat ggcaacaacg  6000
ttgcgcaaac tattaactgg cgaactactt actctagctt cccggcaaca attaatagac  6060
tggatggagg cggataaagt tgcaggacca cttctgcgct cggcccttcc ggctggctgg  6120
tttattgctg ataaatctgg agccggtgag cgtgggtctc gcggtatcat tgcagcactg  6180
gggccagatg gtaagccctc ccgtatcgta gttatctaca cgacggggag tcaggcaact  6240
atggatgaac gaaatagaca gatcgctgag ataggtgcct cactgattaa gcattggtaa  6300
ctgtcagacc aagtttactc atatatactt tagattgatt taaaacttca tttttaattt  6360
aaaaggatct aggtgaagat cctttttgat aatctcatga ccaaaatccc ttaacgtgag  6420
ttttcgttcc actgagcgtc agaccccgta gaaaagatca aaggatcttc ttgagatcct  6480
ttttttctgc gcgtaatctg ctgcttgcaa acaaaaaaac caccgctacc agcggtggtt  6540
tgtttgccgg atcaagagct accaactctt tttccgaagg taactggctt cagcagagcg  6600
cagataccaa atactgttct tctagtgtag ccgtagttag gccaccactt caagaactct  6660
gtagcaccgc ctacatacct cgctctgcta atcctgttac cagtggctgc tgccagtggc  6720
gataagtcgt gtcttaccgg gttggactca agacgatagt taccggataa ggcgcagcgg  6780
tcgggctgaa cggggggttc gtgcacacag cccagcttgg agcgaacgac ctacaccgaa  6840
ctgagatacc tacagcgtga gctatgagaa agcgccacgc ttcccgaagg gagaaaggcg  6900
gacaggtatc cggtaagcgg cagggtcgga acaggagagc gcacgaggga gcttccaggg  6960
ggaaacgcct ggtatcttta tagtcctgtc gggtttcgcc acctctgact tgagcgtcga  7020
```

```
tttttgtgat gctcgtcagg ggggcggagc ctatggaaaa acgccagcaa cgcggccttt  7080
ttacggttcc tggccttttg ctggcctttt gctcacatgt tctttcctgc gttatcccct  7140
gattctgtgg ataaccgtat taccgccttt gagtgagctg ataccgctcg ccgcagccga  7200
acgaccgagc gcagcgagtc agtgagcgag gaagcggaag agcgcccaat acgcaaaccg  7260
cctctccccg cgcgttggcc gattcattaa tgcagctggc acgacaggtt tcccgactgg  7320
aaagcgggca gtgagcgcaa cgcaattaat gtgagttagc tcactcatta ggcaccccag  7380
gctttacact ttatgcttcc ggctcgtatg ttgtgtggaa ttgtgagcgg ataacaattt  7440
cacacaggaa acagctatga ccatgattac gccagattta attaagg                7487

SEQ ID NO: 30           moltype = DNA  length = 7788
FEATURE                 Location/Qualifiers
misc_feature            1..7788
                        note = constructed sequence
source                  1..7788
                        mol_type = other DNA
                        organism = synthetic construct
SEQUENCE: 30
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttaggggaat tcactcaaag ttcaaacctt atcatttttt  240
gctttgttcc tcttggcctt ggttttgtac atcagctttg aaaataccat cccagggtta  300
atgctggggt taatttataa ctaagagtgc tctagttttg caatacagga catgctataa  360
aaatggaaag atgttgcttt ctgagagaca gcggccgcca ccatgcccga gcaggaaaga  420
cagatcaccg ccagagaggg cgccagccgg aagatcctga gcaagctgag cctgccccacc  480
agagcctggg agcccgccat gaagaagtcc ttcgccttcg acaacgtggg ctacgagggc  540
ggcctggacg gactgggacc atcttctcag gtggccacaa gcaccgtgcg catcctgggc  600
atgacctgcc agagctgcgt gaagtccatc gaggaccgga tcagcaacct gaagggcatc  660
atcagcatga aggtgtccct ggaacagggc agcgccaccg tgaaatacgt gccctctgtc  720
gtgtgcctgc agcaggtgtg ccaccagatc ggcgacatgg gcttcgaggc ctctatcgcc  780
gagggaaagg ccgcctcttg gccctctaga agcctgcctg ctcaggaagc cgtcgtgaag  840
ctgcgggtgg aagggatgac ctgtcagtcc tgcgtgtcca gcatcgaggg caaagtgcgg  900
aagctgcagg gcgtggtgcg cgtgaaagtg tctctgagca accaggaagc tgtgatcacc  960
taccagccct acctgatcca gcccgaggac ctgagggacc acgtgaacga tatgggattt  1020
gaggccgcca tcaagagcaa ggtggcccct ctgtctctgg gccccatcga catcgagaga  1080
ctgcagagca ccaaccccaa gcggcctctg agcagcgcca accagaactt caacaacagc  1140
gagacactgg gccaccaggg cagccacgtc gtgacactgc agagcatcca ggtgtcactg  1200
gaaaacaaga ccgcccaggt gaagtacgac cccagctgca caagccccgt ggccctgcag  1260
agagccattg aagctctgcc ccctggcaac ttcaaagtgt ccctgcctga cggagccgag  1320
ggctccggaa cagatcacag aagcagcagc agccacagcc ctggcagccc ccctagaaat  1380
caggtgcagg gcacctgtag caccaccctg atcgccattg ccggcatgac atgcgccagc  1440
tgcgtgcact ctattgaggg catgatctcc cagctggaag gcgtgcagca gatcagtgtg  1500
tctctggccg agggcaccgc cacagtgctg tacaacccta gcgtgatcag ccccgaagaa  1560
ctgagagccg ccattgagga catgggattc gaagccagcg tggtgtccga gagctgctcc  1620
accaaccctc tgggcaatca cagcgccggc aacagcatgg tgcagaccac cgacggcacc  1680
cccaccagcg tgcaggaagt ggccccacat acaggcagac tgcccgccaa tcacgccccc  1740
gatatcctgg ccaagagccc ccagagtaca agagccgtgg cccccagaa gtgcttcctg  1800
cagatcaagg gcatgacttg tgcctcttgt gtgtccaata tcgagcggaa cctgcagaaa  1860
gaggccggcg tgctgtctgt gctggtggct ctgatggccg gcaaggccga gatcaaatac  1920
gaccccgaag tgattcagcc cctggaaatc gcccagttta tccaggacct gggctttgaa  1980
gccgccgtga tggaagatta cgccggctcc gacggcaaca tcgagctgac catcaccgga  2040
atgacctgcg cctcctgtgt gcacaacatt gagtccaagc tgacccggac caacggcatc  2100
acctacgcct ctgtggctct ggccacctcc aaggccctcg tgaagttcga tcccgagatc  2160
atcggcccca gggacatcat caagatcatc gaagagatcg gcttccacgc cagcctggcc  2220
cagaggaacc ctaacgccca ccacctggac cacaagatgg aaatcaagca gtggaagaaa  2280
agcttcctgt gcagcctggt gttcggcatc cccgtgatgg ccctgatgat ctacatgctg  2340
atccccagca acgagcccca ccagtccatg gtgctggatc acaacatcat ccccggcctg  2400
tctatcctga acctgatctt cttcatcctg tgcaccttcg tgcagctgct gggcggctgg  2460
tacttctacg tgcaggccta caagtccctg cggcacagat ccgccaacat ggacgtgctg  2520
atcgtgctgg ccacatctat cgcctacgtg tactccctcg tgatcctggt ggtggccgtg  2580
gccgagaaag ccgagagaag ccctgtgacc ttcttcgaca ccccccctat gctgttcgtg  2640
tttatcgccc tgggccggtg gctggaacac ctggccaaaa gcaagaccag cgaggccctg  2700
gctaagctga tgagtctgca ggccaccgag gccacagtcg tgaccctggg cgaggacaac  2760
ctgatcatcc gcgaggaaca ggtgccaatg gaactggtgc agcggggcga catcgtgaag  2820
gtggtgcctg gcggcaagtt ccccgtggac ggaaaagtgc tggaagggaa taccatggcc  2880
gacgagagcc tgatcacagg cgaggccatg cccgtgacca agaaacctgg cagcacagtg  2940
atcgccggca gcatcaatgc ccacggcagc gtgctgatta aggccacaca cgtgggcaac  3000
gataccaccc tggctcagat tgtgaagctg gtggaagagg cccagatgag caaggccccc  3060
attcagcagc tggctgaccg gttcagcggc tacttcgtgc cctttatcat catcatgagc  3120
accctgacac tggtcgtgtg gatcgtgatc ggctttatcg acttcggagt ggtgcagaga  3180
tacttcccca accctaacaa gcacatcagc cagacagaag tgatcatcag attcgccttt  3240
cagaccagca tcaccgtgct gtgtatcgcc tgcccctgta gcctgggact ggccacacct  3300
accgctgtga tggtgggaac aggcgtggcc gctcagaacg gcatcctgat caagggggggc  3360
aagcctctgg aaatggctca caagatcaag accgtgatgt tcgacaagac cggcaccatc  3420
acccacggcg tgcccagagt gatgagagtg ctgctgctgg gggatgtggc caccctgcct  3480
ctgagaaagg tgctggctgt cgtgggcaca gccgaggcta gctctgaaca cccactggga  3540
gtggccgtga caaagtactg caaagaggaa ctgggcaccg aaaccctggg ctactgcacc  3600
gactttcagg ccgtgcctgg ctgtggcatc ggctgcaagg tgtccaacgt ggaaggcatc  3660
ctggcccaca gcgagaggcc actgtctgcc cctgccagcc acctgaacga ggccggatct  3720
```

```
ctgcccgccg aaaaggacgc tgtgccccag accttctctg tgctgattgg caacagagag  3780
tggctgcggc ggaacggcct gaccatctcc tccgatgtgt ccgacgccat gaccgaccac  3840
gagatgaagg gccagaccgc cattctggtg gccattgacg gggtgctgtg cggcatgatc  3900
gcaatcgccg atgccgtgaa acaggaagca gcactggccg tgcacaccct gcagtctatg  3960
ggagtggatg tggtgctgat caccggcgac aacagaaaga ccgccagggc cattgccacc  4020
caggtgggca tcaacaaggt gttcgccgag gtgctgccca gccacaaagt ggccaaggtg  4080
caggaactgc agaacaaagg caaaaaggtg gccatggtgg gagatggcgt gaacgactct  4140
cctgctctgg cccaggcaga tatgggcgtg gccatcggca caggcaccga cgtggcaatt  4200
gaggctgctg acgtggtgct gattcggaac gacctgctgg acgtggtggc ctccatccac  4260
ctgtccaaga gaaccgtgcg gcggatcaga atcaacctgg tgctggcact gatctataac  4320
ctcgtgggca tccctatcgc cgctggcgtg ttcatgccta tcggaatcgt gctgcagccc  4380
tggatgggct ctgccgccat ggctgcaagc tccgtgtctg tggtgctgtc cagcctgcag  4440
ctgaagtgct acaagaagcc cgacctggaa agatacgagg cccaggccca cggacacatg  4500
aagcctctga cagcctccca ggtgtccgtg cacatcggca tggacgacag atggcgggac  4560
agccctagag ccaccccttg ggatcaggtg tcatacgtgt cacaggtgtc cctgagcagc  4620
ctgaccagcg acaagcccag cagacatagc gccgctgccg acgacgatgg ggacaagtgg  4680
tccctgctgc tgaacggccg ggatgaggaa cagtacatct gataagcatg caataaagtc  4740
tgagtgggcg gcagcctgtg tgtgcctggg ttctctctgt cccggaatgt gcaaacaatg  4800
gaggtgctcg agtagataag tagcatggcg ggttaatcat taactacaag gaacccctag  4860
tgatggagtt ggccactccc tctctgcgcg ctcgctcgct cactgaggcc gggcgaccaa  4920
aggtcgcccg acgcccgggc tttgcccggg cggcctcagt gagcgagcga gcgcgcagcc  4980
ttaattaacc taattcactg gccgtcgttt tacaacgtcg tgactgggaa aaccctggcg  5040
ttacccaact taatcgcctt gcagcacatc ccccttttcgc cagctggcgt aatagcgaag  5100
aggcccgcac cgatcgccct tcccaacagt tgcgcagcct gaatggcgaa tgggacgcgc  5160
cctgtagcgg cgcattaagc gcggcgggtg tggtggttac gcgcagcgtg accgctacac  5220
ttgccagcgc cctagcgccc gctcctttcg ctttcttccc ttcctttctc gccacgttcg  5280
ccggctttcc ccgtcaagct ctaaatcggg ggctcccttt agggttccga tttagtgctt  5340
tacggcacct cgaccccaaa aaacttgatt agggtgatgg ttcacgtagt gggccatcgc  5400
cctgatagac ggtttttcgc cctttgacgt tggagtccac gttctttaat agtggactct  5460
tgttccaaac tggaacaaca ctcaacccta tctcggtcta ttcttttgat ttataaggga  5520
ttttgccgat ttcggcctat tggttaaaaa atgagctgat ttaacaaaaa tttaacgcga  5580
attttaacaa aatattaacg cttacaattt aggtggcact tttcggggaa atgtgcgcgg  5640
aacccctatt tgtttatttt tctaaataca ttcaaatatg tatccgctca tgagacaata  5700
accctgataa atgcttcaat aatattgaaa aaggaagagt atgagtattc aacatttccg  5760
tgtcgccctt attccctttt ttgcggcatt ttgccttcct gtttttgctc acccagaaac  5820
gctggtgaaa gtaaaagatg ctgaagatca gttgggtgca cgagtgggtt acatcgaact  5880
ggatctcaac agcggtaaga tccttgagag ttttcgcccc gaagaacgtt ttccaatgat  5940
gagcactttt aaagttctgc tatgtggcgc ggtattatcc cgtattgacg ccgggcaaga  6000
gcaactcggt cgccgcatac actattctca gaatgacttg gttgagtact caccagtcac  6060
agaaaagcat cttacggatg gcatgacagt aagagaatta tgcagtgctg ccataaccat  6120
gagtgataac actgcggcca acttacttct gacaacgatc ggaggaccga aggagctaac  6180
cgcttttttg cacaacatgg gggatcatgt aactcgcctt gatcgttggg aaccggagct  6240
gaatgaagcc ataccaaacg acgagcgtga caccacgatg cctgtagcaa tggcaacaac  6300
gttgcgcaaa ctattaactg gcgaactact tactctagct tcccggcaac aattaataga  6360
ctggatggag gcggataaag ttgcaggacc acttctgcgc tcggcccttc cggctggctg  6420
gtttattgct gataaatctg gagccggtga gcgtgggtct cgcggtatca ttgcagcact  6480
ggggccagat ggtaagccct cccgtatcgt agttatctac acgacgggga gtcaggcaac  6540
tatggatgaa cgaaatagac agatcgctga gataggtgcc tcactgatta agcattggta  6600
actgtcagac caagtttact catatatact ttagattgat ttaaaacttc atttttaatt  6660
taaaaggatc taggtgaaga tcctttttga taatctcatg accaaaatcc cttaacgtga  6720
gttttcgttc cactgagcgt cagaccccgt agaaaagatc aaaggatctt cttgagatcc  6780
tttttttctg cgcgtaatct gctgcttgca aacaaaaaaa ccaccgctac cagcggtggt  6840
ttgtttgccg gatcaagagc taccaactct ttttccgaag gtaactggct tcagcagagc  6900
gcagatacca aatactgttc ttctagtgta gccgtagtta ggccaccact tcaagaactc  6960
tgtagcaccg cctacatacc tcgctctgct aatcctgtta ccagtggctg ctgccagtgg  7020
cgataagtcg tgtcttaccg ggttggactc aagacgatag ttaccggata aggcgcagcg  7080
gtcgggctga acggggggtt cgtgcacaca gcccagcttg gagcgaacga cctacaccga  7140
actgagatac ctacagcgtg agctatgaga aagcgccacg cttcccgaag ggagaaaggc  7200
ggacaggtat ccggtaagcg gcagggtcgg aacaggagag cgcacgaggg agcttccagg  7260
gggaaacgcc tggtatcttt atagtcctgt cgggtttcgc cacctctgac ttgagcgtcg  7320
atttttgtga tgctcgtcag gggggcggag cctatggaaa aacgccagca acgcggcctt  7380
tttacggttc ctggcctttt gctggccttt tgctcacatg ttctttcctg cgttatcccc  7440
tgattctgtg gataaccgta ttaccgcctt tgagtgagct gataccgctc gccgcagccg  7500
aacgaccgag cgcagcgagt cagtgagcga ggaagcggaa gagcgcccaa tacgcaaacc  7560
gcctctcccc gcgcgttggc cgattcatta atgcagctgg cacgacaggt ttcccgactg  7620
gaaagcgggc agtgagcgca acgcaattaa tgtgagttag ctcactcatt aggcacccca  7680
ggctttacac tttatgcttc cggctcgtat gttgtgtgga attgtgagcg gataacaatt  7740
tcacacagga aacagctatg accatgatta cgccagattt aattaagg              7788
```

```
SEQ ID NO: 31          moltype = DNA  length = 7686
FEATURE                Location/Qualifiers
misc_feature           1..7686
                       note = constructed sequence
source                 1..7686
                       mol_type = other DNA
                       organism = synthetic construct
SEQUENCE: 31
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
```

-continued

```
aggggttcct tgtagttaat gattaacccg ccatgctact tatctactta agtgtttgct  180
gcttgcaatg tttgcccatt ttaggggaat tcactcaaag ttcaaacctt atcatttttt  240
gctttgttcc tcttggcctt ggttttgtac atcagctttg aaaataccat cccagggtta  300
atgctggggt taatttataa ctaagagtgc tctagttttg caatacagga catgctataa  360
aaatggaaag atgttgcttt ctgagagaca gcggccgcca ccatgcccga gcaggaaaga  420
cagatcaccg ccagagaggg cgccagccgg aagatcctga gcaagctgag cctgcccacc  480
agagcctggg agcccgccat gaagaagtcc ttcgccttcg acaacgtggg ctacgagggc  540
ggcctggacg gactgggacc atcttctcag gtggccacaa gcaccgtgcg catcctgggc  600
atgacctgcc agagctgcgt gaagtccatc gaggaccgga tcagcaacct gaagggcatc  660
atcagcatga aggtgtccct ggaacagggc agcgccaccg tgaaatacgt gccctctgtc  720
gtgtgcctgc agcaggtgtg ccaccagatc ggcgacatgg gcttcgaggc ctctatcgcc  780
gagggaaagg ccgcctcttg gccctctaga agcctgcctg ctcaggaagc cgtcgtgaag  840
gaggccgcca tcaagagcaa ggtggcccct ctgtctctgg gccccatcga catcgagaga  900
ctgcagagca ccaaccccaa gcggcctctg agcagcgcca accagaactt caacaacagc  960
gagacactgg gccaccaggg cagccacgtc gtgacactgc agctgcggat cgacggaatg  1020
cactgcaaga gctgtgtgct gaacatcgag gaaaacatcg gccagctgct gggagtgcag  1080
agcatccagg tgtcactgga aaacaagacc gcccaggtga agtacgaccc cagctgcaca  1140
agccccgtgg ccctgcagag agccattgaa gctctgcccc ctggcaactt caaagtgtcc  1200
ctgcctgacg gagccgaggg ctccggaaca gatcacagaa gcagcagcag ccacagccct  1260
ggcagccccc ctagaaatca ggtgcagggc acctgtagca ccaccctgat cgccattgcc  1320
ggcatgacat gcgccagctg cgtgcactct attgagggca tgatctccca gctggaaggc  1380
gtgcagcaga tcagtgtgtc tctggccgag ggcaccgcca cagtgctgta caaccctagc  1440
gtgatcagcc ccgaagaact gagagccgcc attgaggaca tgggattcga agccagcgtg  1500
gtgtccgaga gctgctccac caaccctctg ggcaatcaca gcgccggcaa cagcatggtg  1560
cagaccaccg acggcacccc caccagcgtg caggaagtgg ccccacatac aggcagactg  1620
cccgccaatc acgcccccga tatcctggcc aagagccccc agagtacaag agccgtggcc  1680
ccccagaagt gcttcctgca gatcaagggc atgacttgtg cctcttgtgt gtccaatatc  1740
gagcggaacc tgcagaaaga ggccggcgtg ctgtctgtgc tggtggctct gatggccggc  1800
aaggccgaga tcaaatacga ccccgaagtg attcagcccc tggaaatcgc ccagtttatc  1860
caggacctgg gctttgaagc cgccgtgatg gaagattacg ccggctccga cggcaacatc  1920
gagctgacca tcaccggaat gacctgcgcc tcctgtgtgc acaacattga gtccaagctg  1980
acccggacca acggcatcac ctacgcctct gtggctctgg ccacctccaa ggccctcgtg  2040
aagttcgatc ccgagatcat cggccccagg gacatcatca agatcatcga agagatcggc  2100
ttccacgcca gcctggccca gaggaaccct aacgcccacc acctggacca caagatggaa  2160
atcaagcagt ggaagaaaag cttcctgtgc agcctggtgt tcggcatccc cgtgatggcc  2220
ctgatgatct acatgctgat ccccagcaac gagccccacc agtccatggt gctggatcac  2280
aacatcatcc ccggcctgtc tatcctgaac ctgatcttct tcatcctgtg caccttcgtg  2340
cagctgctgg gcggctggta cttctacgtg caggcctaca agtccctgcg gcacagatcc  2400
gccaacatgg acgtgctgat cgtgctggcc acatctatcg cctacgtgta ctccctcgtg  2460
atcctggtgg tggccgtggc cgagaaagcc gagagaagcc ctgtgacctt cttcgacacc  2520
ccccctatgc tgttcgtgtt tatcgccctg ggccggtggc tggaacacct ggccaaaagc  2580
aagaccagcg aggccctggc taagctgatg agtctgcagg ccaccgaggc cacagtcgtg  2640
accctgggcg aggacaacct gatcatccgc gaggaacagg tgccaatgga actggtgcag  2700
cggggcgaca tcgtgaaggt ggtgcctggc ggcaagttcc ccgtggacgg aaaagtgctg  2760
gaagggaata ccatggccga cgagagcctg atcacaggcg aggccatgcc cgtgaccaag  2820
aaacctggca gcacagtgat cgccggcagc atcaatgccc acggcagcgt gctgattaag  2880
gccacacacg tgggcaacga taccaccctg gctcagattg tgaagctggt ggaagaggcc  2940
cagatgagca aggcccccat tcagcagctg gctgaccggt tcagcggcta cttcgtgccc  3000
tttatcatca tcatgagcac cctgacactg gtcgtgtgga tcgtgatcgg ctttatcgac  3060
ttcggagtgg tgcagagata cttccccaac cctaacaagc acatcagcca gacagaagtg  3120
atcatcagat tcgcctttca gaccagcatc accgtgctgt gtatcgcctg cccctgtagc  3180
ctgggactgg ccacacctac cgctgtgatg gtgggaacag gcgtggccgc tcagaacggc  3240
atcctgatca agggggggcaa gcctctggaa atggctcaca agatcaagac cgtgatgttc  3300
gacaagaccg gcaccatcac ccacggcgtg cccagagtga tgagagtgct gctgctgggg  3360
gatgtggcca ccctgcctct gagaaaggtg ctggctgtcg tgggcacagc cgaggctagc  3420
tctgaacacc cactgggagt ggccgtgaca aagtactgca aagaggaact gggcaccgaa  3480
accctgggct actgcaccga ctttcaggcc gtgcctggct gtggcatcgg ctgcaaggtg  3540
tccaacgtgg aaggcatcct ggcccacagc gagaggccac tgtctgcccc tgccagccac  3600
ctgaacgagg ccggatctct gcccgccgaa aaggacgctg tgccccagac cttctctgtg  3660
ctgattggca acagagagtg gctgcggcgg aacggcctga ccatctcctc cgatgtgtcc  3720
gacgccatga ccgaccacga gatgaagggc cagaccgcca ttctggtggc cattgacggg  3780
gtgctgtgcg gcatgatcgc aatcgccgat gccgtgaaac aggaagcagc actggccgtg  3840
cacaccctgc agtctatggg agtggatgtg gtgctgatca ccggcgacaa cagaaagacc  3900
gccagggcca ttgccaccca ggtgggcatc aacaaggtgt tcgccgaggt gctgcccagc  3960
cacaaagtgg ccaaggtgca ggaactgcag aacaaaggca aaaaggtggc catggtggga  4020
gatggcgtga acgactctcc tgctctggcc caggcagata tgggcgtggc catcggcaca  4080
ggcaccgacg tggcaattga ggctgctgac gtggtgctga ttcggaacga cctgctggac  4140
gtggtggcct ccatccacct gtccaagaga accgtgcggc ggatcagaat caacctggtg  4200
ctggcactga tctataacct cgtgggcatc cctatcgccg ctggcgtgtt catgcctatc  4260
ggaatcgtgc tgcagccctg gatgggctct gccgccatgg ctgcaagctc cgtgtctgtg  4320
gtgctgtcca gcctgcagct gaagtgctac aagaagcccg acctggaaag atacgaggcc  4380
caggcccacg gacacatgaa gcctctgaca gcctcccagg tgtccgtgca catcggcatg  4440
gacgacagat ggcgggacag ccctagagcc accccttggg atcaggtgtc atacgtgtca  4500
caggtgtccc tgagcagcct gaccagcgac aagcccagca gacatagcgc cgctgccgac  4560
gacgatgggg acaagtggtc cctgctgctg aacggccggg atgaggaaca gtacatctga  4620
taagcatgca ataaagtctg agtgggcggc agcctgtgtg tgcctgggtt ctctctgtcc  4680
cggaatgtgc aaacaatgga ggtgctcgag tagataagta gcatggcggg ttaatcatta  4740
actacaagga acccctagtg atggagttgg ccactccctc tctgcgcgct cgctcgctca  4800
ctgaggccgg gcgaccaaag gtcgcccgac gcccgggctt tgcccgggcg gcctcagtga  4860
```

```
gcgagcgagc gcgcagcctt aattaaccta attcactggc cgtcgtttta caacgtcgtg  4920
actgggaaaa ccctggcgtt acccaactta atcgccttgc agcacatccc cctttcgcca  4980
gctggcgtaa tagcgaagag gcccgcaccg atcgcccttc ccaacagttg cgcagcctga  5040
atggcgaatg ggacgcgccc tgtagcggcg cattaagcgc ggcgggtgtg gtggttacgc  5100
gcagcgtgac cgctacactt gccagcgccc tagcgcccgc tcctttcgct ttcttccctt  5160
cctttctcgc cacgttcgcc ggctttcccc gtcaagctct aaatcggggg ctccctttag  5220
ggttccgatt tagtgcttta cggcacctcg accccaaaaa acttgattag ggtgatggtt  5280
cacgtagtgg gccatcgccc tgatagacgg tttttcgccc tttgacgttg gagtccacgt  5340
tctttaatag tggactcttg ttccaaactg gaacaacact caaccctatc tcggtctatt  5400
cttttgattt ataagggatt ttgccgattt cggcctattg gttaaaaaat gagctgattt  5460
aacaaaaatt taacgcgaat tttaacaaaa tattaacgct tacaatttag gtggcacttt  5520
tcggggaaat gtgcgcggaa cccctatttg tttatttttc taaatacatt caaatatgta  5580
tccgctcatg agacaataac cctgataaat gcttcaataa tattgaaaaa ggaagagtat  5640
gagtattcaa catttccgtg tcgcccttat tccctttttt gcggcatttt gccttcctgt  5700
ttttgctcac ccagaaacgc tggtgaaagt aaaagatgct gaagatcagt tgggtgcacg  5760
agtgggttac atcgaactgg atctcaacag cggtaagatc cttgagagtt ttcgccccga  5820
agaacgtttt ccaatgatga gcacttttaa agttctgcta tgtggcgcgg tattatcccg  5880
tattgacgcc gggcaagagc aactcggtcg ccgcatacac tattctcaga atgacttggt  5940
tgagtactca ccagtcacag aaaagcatct tacggatggc atgacagtaa gagaattatg  6000
cagtgctgcc ataaccatga gtgataacac tgcggccaac ttacttctga caacgatcgg  6060
aggaccgaag gagctaaccg cttttttgca caacatgggg gatcatgtaa ctcgccttga  6120
tcgttgggaa ccggagctga atgaagccat accaaacgac gagcgtgaca ccacgatgcc  6180
tgtagcaatg gcaacaacgt tgcgcaaact attaactggc gaactactta ctctagcttc  6240
ccggcaacaa ttaatagact ggatggaggc ggataaagtt gcaggaccac ttctgcgctc  6300
ggcccttccg gctggctggt ttattgctga taaatctgga gccggtgagc gtgggtctcg  6360
cggtatcatt gcagcactgg ggccagatgg taagccctcc cgtatcgtag ttatctacac  6420
gacggggagt caggcaacta tggatgaacg aaatagacag atcgctgaga taggtgcctc  6480
actgattaag cattggtaac tgtcagacca agtttactca tatatacttt agattgattt  6540
aaaacttcat ttttaattta aaaggatcta ggtgaagatc ctttttgata atctcatgac  6600
caaaatccct taacgtgagt tttcgttcca ctgagcgtca gaccccgtag aaaagatcaa  6660
aggatcttct tgagatcctt tttttctgcg cgtaatctgc tgcttgcaaa caaaaaaacc  6720
accgctacca gcggtggttt gtttgccgga tcaagagcta ccaactcttt ttccgaaggt  6780
aactggcttc agcagagcgc agataccaaa tactgttctt ctagtgtagc cgtagttagg  6840
ccaccacttc aagaactctg tagcaccgcc tacatacctc gctctgctaa tcctgttacc  6900
agtggctgct gccagtggcg ataagtcgtg tcttaccggg ttggactcaa gacgatagtt  6960
accggataag gcgcagcggt cgggctgaac ggggggttcg tgcacacagc ccagcttgga  7020
gcgaacgacc tacaccgaac tgagatacct acagcgtgag ctatgagaaa gcgccacgct  7080
tcccgaaggg agaaaggcgg acaggtatcc ggtaagcggc agggtcggaa caggagagcg  7140
cacgagggag cttccagggg gaaacgcctg gtatctttat agtcctgtcg ggtttcgcca  7200
cctctgactt gagcgtcgat ttttgtgatg ctcgtcaggg gggcggagcc tatggaaaaa  7260
cgccagcaac gcggcctttt tacggttcct ggccttttgc tggccttttg ctcacatgtt  7320
ctttcctgcg ttatcccctg attctgtgga taaccgtatt accgcctttg agtgagctga  7380
taccgctcgc cgcagccgaa cgaccgagcg cagcgagtca gtgagcgagg aagcggaaga  7440
gcgcccaata cgcaaaccgc ctctccccgc gcgttggccg attcattaat gcagctggca  7500
cgacaggttt cccgactgga aagcgggcag tgagcgcaac gcaattaatg tgagttagct  7560
cactcattag gcaccccagg ctttacactt tatgcttccg gctcgtatgt tgtgtggaat  7620
tgtgagcgga taacaatttc acacaggaaa cagctatgac catgattacg ccagatttaa  7680
ttaagg                                                             7686

SEQ ID NO: 32          moltype = DNA  length = 7755
FEATURE                Location/Qualifiers
misc_feature           1..7755
                       note = constructed sequence
source                 1..7755
                       mol_type = other DNA
                       organism = synthetic construct
SEQUENCE: 32
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttaggggaat tcactcaaag ttcaaacctt atcatttttt  240
gctttgttcc tcttggcctt ggttttgtac atcagctttg aaaataccat cccagggtta  300
atgctggggt taatttataa ctaagagtgc tctagttttg caatacagga catgctataa  360
aaatggaaag atgttgcttt ctgagagaca gcggccgcca ccatgcccga gcaggaaaga  420
cagatcaccg ccagagaggg cgccagccgg aagatcctga gcaagctgag cctgccccacc  480
agagcctggg agcccgccat gaagaagtcc ttcgccttcg acaacgtggg ctacgagggc  540
ggcctggacg gactgggacc atcttctcag gtggccacaa gcaccgtgcg caaatacgtg  600
ccctctgtcg tgtgcctgca gcaggtgtgc caccagatcg gcgacatggg cttcgaggcc  660
tctatcgccg agggaaaggc cgcctcttgg ccctctagaa gcctgcctgc tcaggaagcc  720
gtcgtgaagc tgcgggtgga agggatgacc tgtcagtcct gcgtgtccag catcgagggc  780
aaagtgcgga agctgcaggg cgtggtgcgc gtgaaagtgt ctctgagcaa ccaggaagct  840
gtgatcacct accagcccta cctgatccag cccgaggacc tgagggacca cgtgaacgat  900
atgggatttg aggccgccat caagagcaag gtggcccctc tgtctctggg ccccatcgac  960
atcgagagac tgcagagcac caaccccaag cggcctctga gcagcgccaa ccagaacttc  1020
aacaacagcg agacactggg ccaccagggc agccacgtcg tgacactgca gctgcggatc  1080
gacggaatgc actgcaagag ctgtgtgctg aacatcgagg aaaacatcgg ccagctgctg  1140
ggagtgcaga gcatccaggt gtcactggaa aacaagaccg cccaggtgaa gtacgacccc  1200
agctgcacaa gccccgtggc cctgcagaga gccattgaag ctctgccccc tggcaacttc  1260
aaagtgtccc tgcctgacgg agccgagggc tccggaacag atcacagaag cagcagcagc  1320
```

```
cacagccctg gcagcccccc tagaaatcag gtgcagggca cctgtagcac caccctgatc  1380
gccattgccg gcatgacatg cgccagctgc gtgcactcta ttgagggcat gatctcccag  1440
ctggaaggcg tgcagcagat cagtgtgtct ctggccgagg gcaccgccac agtgctgtac  1500
aaccctagcg tgatcagccc cgaagaactg agagccgcca ttgaggacat gggattcgaa  1560
gccagcgtgg tgtccgagag ctgctccacc aaccctctgg gcaatcacag cgccggcaac  1620
agcatggtgc agaccaccga cggcaccccc accagcgtgc aggaagtggc cccacataca  1680
ggcagactgc ccgccaatca cgcccccgat atcctggcca agagccccca gagtacaaga  1740
gccgtggccc cccagaagtg cttcctgcag atcaagggca tgacttgtgc ctcttgtgtg  1800
tccaatatcg agcggaacct gcagaaagag gccggcgtgc tgtctgtgct ggtggctctg  1860
atggccggca aggccgagat caaatacgac cccgaagtga ttcagcccct ggaaatcgcc  1920
cagtttatcc aggacctggg ctttgaagcc gccgtgatgg aagattacgc cggctccgac  1980
ggcaacatcg agctgaccat caccggaatg acctgcgcct cctgtgtgca caacattgag  2040
tccaagctga cccggaccaa cggcatcacc tacgcctctg tggctctggc cacctccaag  2100
gccctcgtga agttcgatcc cgagatcatc ggccccaggg acatcatcaa gatcatcgaa  2160
gagatcggct tccacgccag cctggcccag aggaacccta acgcccacca cctggaccac  2220
aagatggaaa tcaagcagtg gaagaaaagc ttcctgtgca gcctggtgtt cggcatcccc  2280
gtgatggccc tgatgatcta catgctgatc cccagcaacg agccccacca gtccatggtg  2340
ctggatcaca acatcatccc cggcctgtct atcctgaacc tgatcttctt catcctgtgc  2400
accttcgtgc agctgctggg cggctggtac ttctacgtgc aggcctacaa gtccctgcgg  2460
cacagatccg ccaacatgga cgtgctgatc gtgctggcca catctatcgc ctacgtgtac  2520
tccctcgtga tcctggtggt ggccgtggcc gagaaagccg agagaagccc tgtgaccttc  2580
ttcgacaccc cccctatgct gttcgtgttt atcgccctgg gccggtggct ggaacacctg  2640
gccaaaagca agaccagcga ggccctggct aagctgatga gtctgcaggc caccgaggcc  2700
acagtcgtga ccctgggcga ggacaacctg atcatccgcg aggaacaggt gccaatggaa  2760
ctggtgcagc ggggcgacat cgtgaaggtg gtgcctggcg gcaagttccc cgtggacgga  2820
aaagtgctgg aagggaatac catggccgac gagagcctga tcacaggcga ggccatgccc  2880
gtgaccaaga aacctggcag cacagtgatc gccggcagca tcaatgccca cggcagcgtg  2940
ctgattaagg ccacacacgt gggcaacgat accaccctgg ctcagattgt gaagctggtg  3000
gaagaggccc agatgagcaa ggcccccatt cagcagctgg ctgaccggtt cagcggctac  3060
ttcgtgccct ttatcatcat catgagcacc ctgacactgg tcgtgtggat cgtgatcggc  3120
tttatcgact tcggagtggt gcagagatac ttccccaacc ctaacaagca catcagccag  3180
acagaagtga tcatcagatt cgcctttcag accagcatca ccgtgctgtg tatcgcctgc  3240
ccctgtagcc tgggactggc cacacctacc gctgtgatgg tgggaacagg cgtggccgct  3300
cagaacggca tcctgatcaa gggggggcaag cctctggaaa tggctcacaa gatcaagacc  3360
gtgatgttcg acaagaccgg caccatcacc cacggcgtgc ccagagtgat gagagtgctg  3420
ctgctggggg atgtggccac cctgcctctg agaaaggtgc tggctgtcgt gggcacagcc  3480
gaggctagct ctgaacaccc actgggagtg gccgtgacaa agtactgcaa agaggaactg  3540
ggcaccgaaa ccctgggcta ctgcaccgac tttcaggccg tgcctggctg tggcatcggc  3600
tgcaaggtgt ccaacgtgga aggcatcctg gcccacagcg agaggccact gtctgcccct  3660
gccagccacc tgaacgaggc cggatctctg cccgccgaaa aggacgctgt gccccagacc  3720
ttctctgtgc tgattggcaa cagagagtgg ctgcggcgga acggcctgac catctcctcc  3780
gatgtgtccg acgccatgac cgaccacgag atgaagggcc agaccgccat tctggtggcc  3840
attgacgggg tgctgtgcgg catgatcgca atcgccgatg ccgtgaaaca ggaagcagca  3900
ctggccgtgc acaccctgca gtctatggga gtggatgtgg tgctgatcac cggcgacaac  3960
agaaagaccg ccagggccat tgccacccag gtgggcatca acaaggtgtt cgccgaggtg  4020
ctgcccagcc acaaagtggc caaggtgcag gaactgcaga acaaaggcaa aaaggtggcc  4080
atggtgggag atggcgtgaa cgactctcct gctctggccc aggcagatat gggcgtggcc  4140
atcggcacag gcaccgacgt ggcaattgag gctgctgacg tggtgctgat tcggaacgac  4200
ctgctggacg tggtggcctc catccacctg tccaagagaa ccgtgcggcg gatcagaatc  4260
aacctggtgc tggcactgat ctataacctc gtgggcatcc ctatcgccgc tggcgtgttc  4320
atgcctatcg gaatcgtgct gcagccctgg atgggctctg ccgccatggc tgcaagctcc  4380
gtgtctgtgg tgctgtccag cctgcagctg aagtgctaca agaagcccga cctggaaaga  4440
tacgaggccc aggcccacgg acacatgaag cctctgacag cctcccaggt gtccgtgcac  4500
atcggcatgg acgacagatg gcgggacagc cctagagcca ccccttggga tcaggtgtca  4560
tacgtgtcac aggtgtccct gagcagcctg accagcgaca agcccagcag acatagcgcc  4620
gctgccgacg acgatgggga caagtggtcc ctgctgctga acggccggga tgaggaacag  4680
tacatctgat aagcatgcaa taaagtctga gtgggcggca gcctgtgtgt gcctgggttc  4740
tctctgtccc ggaatgtgca aacaatggag gtgctcgagt agataagtag catggcgggt  4800
taatcattaa ctacaaggaa cccctagtga tggagttggc cactccctct ctgcgcgctc  4860
gctcgctcac tgaggccggg cgaccaaagg tcgcccgacg cccgggcttt gcccgggcgg  4920
cctcagtgag cgagcgagcg cgcagcctta attaacctaa ttcactggcc gtcgttttac  4980
aacgtcgtga ctgggaaaac cctggcgtta cccaacttaa tcgccttgca gcacatcccc  5040
ctttcgccag ctggcgtaat agcgaagagg cccgcaccga tcgcccttcc caacagttgc  5100
gcagcctgaa tggcgaatgg gacgcgccct gtagcggcgc attaagcgcg gcgggtgtgg  5160
tggttacgcg cagcgtgacc gctacacttg ccagcgccct agcgcccgct cctttcgctt  5220
tcttcccttc ctttctcgcc acgttcgccg gctttccccg tcaagctcta aatcgggggc  5280
tccctttagg gttccgattt agtgctttac ggcacctcga ccccaaaaaa cttgattagg  5340
gtgatggttc acgtagtggg ccatcgccct gatagacggt ttttcgccct ttgacgttgg  5400
agtccacgtt ctttaatagt ggactcttgt tccaaactgg aacaacactc aaccctatct  5460
cggtctattc ttttgattta taagggattt tgccgatttc ggcctattgg ttaaaaaatg  5520
agctgattta acaaaaattt aacgcgaatt ttaacaaaat attaacgctt acaatttagg  5580
tggcactttt cggggaaatg tgcgcggaac ccctatttgt ttatttttct aaatacattc  5640
aaatatgtat ccgctcatga gacaataacc ctgataaatg cttcaataat attgaaaaag  5700
gaagagtatg agtattcaac atttccgtgt cgcccttatt cccttttttg cggcattttg  5760
ccttcctgtt tttgctcacc cagaaacgct ggtgaaagta aaagatgctg aagatcagtt  5820
gggtgcacga gtgggttaca tcgaactgga tctcaacagc ggtaagatcc ttgagagttt  5880
tcgccccgaa gaacgttttc caatgatgag cacttttaaa gttctgctat gtggcgcggt  5940
attatcccgt attgacgccg ggcaagagca actcggtcgc cgcatacact attctcagaa  6000
tgacttggtt gagtactcac cagtcacaga aaagcatctt acggatggca tgacagtaag  6060
```

```
agaattatgc agtgctgcca taaccatgag tgataacact gcggccaact tacttctgac  6120
aacgatcgga ggaccgaagg agctaaccgc tttttgcac aacatggggg atcatgtaac  6180
tcgccttgat cgttgggaac cggagctgaa tgaagccata ccaaacgacg agcgtgacac  6240
cacgatgcct gtagcaatgg caacaacgtt gcgcaaacta ttaactggcg aactacttac  6300
tctagcttcc cggcaacaat taatagactg gatggaggcg gataaagttg caggaccact  6360
tctgcgctcg gcccttccgg ctggctggtt tattgctgat aaatctggag ccggtgagcg  6420
tgggtctcgc ggtatcattg cagcactggg gccagatggt aagccctccc gtatcgtagt  6480
tatctacacg acggggagtc aggcaactat ggatgaacga aatagacaga tcgctgagat  6540
aggtgcctca ctgattaagc attggtaact gtcagaccaa gtttactcat atatacttta  6600
gattgattta aaacttcatt tttaatttaa aaggatctag gtgaagatcc tttttgataa  6660
tctcatgacc aaaatccctt aacgtgagtt ttcgttccac tgagcgtcag accccgtaga  6720
aaagatcaaa ggatcttctt gagatccttt ttttctgcgc gtaatctgct gcttgcaaac  6780
aaaaaaacca ccgctaccag cggtggtttg tttgccggat caagagctac caactctttt  6840
tccgaaggta actggcttca gcagagcgca gataccaaat actgttcttc tagtgtagcc  6900
gtagttaggc caccacttca agaactctgt agcaccgcct acatacctcg ctctgctaat  6960
cctgttacca gtggctgctg ccagtggcga taagtcgtgt cttaccgggt tggactcaag  7020
acgatagtta ccggataagg cgcagcggtc gggctgaacg gggggttcgt gcacacagcc  7080
cagcttggag cgaacgacct acaccgaact gagataccta cagcgtgagc tatgagaaag  7140
cgccacgctt cccgaaggga gaaaggcgga caggtatccg gtaagcggca gggtcggaac  7200
aggagagcgc acgagggagc ttccaggggg aaacgcctgg tatctttata gtcctgtcgg  7260
gtttcgccac ctctgacttg agcgtcgatt tttgtgatgc tcgtcagggg ggcggagcct  7320
atggaaaaac gccagcaacg cggccttttt acggttcctg gccttttgct ggccttttgc  7380
tcacatgttc tttcctgcgt tatcccctga ttctgtggat aaccgtatta ccgcctttga  7440
gtgagctgat accgctcgcc gcagccgaac gaccgagcgc agcgagtcag tgagcgagga  7500
agcggaagag cgcccaatac gcaaaccgcc tctccccgcg cgttggccga ttcattaatg  7560
cagctggcac gacaggtttc ccgactggaa agcgggcagt gagcgcaacg caattaatgt  7620
gagttagctc actcattagg caccccaggc tttacacttt atgcttccgg ctcgtatgtt  7680
gtgtggaatt gtgagcggat aacaatttca cacaggaaac agctatgacc atgattacgc  7740
cagatttaat taagg                                                    7755
```

```
SEQ ID NO: 33          moltype = DNA  length = 6438
FEATURE                Location/Qualifiers
misc_feature           1..6438
                       note = constructed sequence
source                 1..6438
                       mol_type = other DNA
                       organism = synthetic construct
SEQUENCE: 33
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttaggggaat tcactcaaag ttcaaacctt atcatttttt  240
gctttgttcc tcttggcctt ggttttgtac atcagctttg aaaataccat cccagggtta  300
atgctggggt taatttataa ctaagagtgc tctagttttg caatacagga catgctataa  360
aaatggaaag atgttgcttt ctgagagaca gcggccgcca ccatgcccga gcaggaaaga  420
cagatcaccg ccagagaggg cgccagccgg aagatcctga gcaagctgag cctgccccacc  480
agagcctggg agcccgccat gaagaagtcc ttcgccttcg acaacgtggg ctacgagggc  540
ggcctggacg gactgggacc atcttctcag gtggccacaa gcaccgtgcg cctggaaatc  600
gcccagttta tccaggacct gggctttgaa gccgccgtga tggaagatta cgccggctcc  660
gacggcaaca tcgagctgac catcaccgga atgacctgcg cctcctgtgt gcacaacatt  720
gagtccaagc tgacccggac caacggcatc acctacgcct ctgtggctct ggccacctcc  780
aaggccctcg tgaagttcga tcccgagatc atcggcccca gggacatcat caagatcatc  840
gaagagatcg gcttccacgc cagcctggcc cagaggaacc ctaacgccca ccacctggac  900
cacaagatgg aaatcaagca gtggaagaaa agcttcctgt gcagcctggt gttcggcatc  960
cccgtgatgg ccctgatgat ctacatgctg atccccagca acgagcccca ccagtccatg  1020
gtgctggatc acaacatcat ccccggcctg tctatcctga acctgatctt cttcatcctg  1080
tgcaccttcg tgcagctgct gggcggctgg tacttctacg tgcaggccta caagtccctg  1140
cggcacagat ccgccaacat ggacgtgctg atcgtgctgg ccacatctat cgcctacgtg  1200
tactccctcg tgatcctggt ggtggccgtg gccgagaaag ccgagagaag ccctgtgacc  1260
ttcttcgaca cccccccctat gctgttcgtg tttatcgccc tgggccggtg gctggaacac  1320
ctggccaaaa gcaagaccag cgaggccctg gctaagctga tgagtctgca ggccaccgag  1380
gccacagtcg tgaccctggg cgaggacaac ctgatcatcc gcgaggaaca ggtgccaatg  1440
gaactggtgc agcggggcga catcgtgaag gtggtgcctg gcggcaagtt ccccgtggac  1500
ggaaaagtgc tggaagggaa taccatggcc gacgagagcc tgatcacagg cgaggccatg  1560
cccgtgacca agaaacctgg cagcacagtg atcgccggca gcatcaatgc ccacggcagc  1620
gtgctgatta aggccacaca cgtgggcaac gataccaccc tggctcagat tgtgaagctg  1680
gtggaagagg cccagatgag caaggccccc attcagcagc tggctgaccg gttcagcggc  1740
tacttcgtgc cctttatcat catcatgagc accctgacac tggtcgtgtg gatcgtgatc  1800
ggctttatcg acttcggagt ggtgcagaga tacttcccca accctaacaa gcacatcagc  1860
cagacagaag tgatcatcag attcgccttt cagaccagca tcaccgtgct gtgtatcgcc  1920
tgcccctgta gcctgggact ggccacacct accgctgtga tggtgggaac aggcgtggcc  1980
gctcagaacg gcatcctgat caaggggggc aagcctctgg aaatggctca caagatcaag  2040
accgtgatgt tcgacaagac cggcaccatc acccacggcg tgcccagagt gatgagagtg  2100
ctgctgctgg gggatgtggc caccctgcct ctgagaaagg tgctggctgt cgtgggcaca  2160
gccgaggcta gctctgaaca cccactggga gtggccgtga caaagtactg caaagaggaa  2220
ctgggcaccg aaaccctggg ctactgcacc gactttcagg ccgtgcctgg ctgtggcatc  2280
ggctgcaagg tgtccaacgt ggaaggcatc ctggcccaca gcgagaggcc actgtctgcc  2340
cctgccagcc acctgaacga ggccggatct ctgcccgccg aaaaggacgc tgtgccccag  2400
accttctctg tgctgattgg caacagagag tggctgcggc ggaacggcct gaccatctcc  2460
```

```
tccgatgtgt ccgacgccat gaccgaccac gagatgaagg gccagaccgc cattctggtg  2520
gccattgacg gggtgctgtg cggcatgatc gcaatcgccg atgccgtgaa acaggaagca  2580
gcactggccg tgcacaccct gcagtctatg ggagtggatg tggtgctgat caccggcgac  2640
aacagaaaga ccgccagggc cattgccacc caggtgggca tcaacaaggt gttcgccgag  2700
gtgctgccca gccacaaagt ggccaaggtg caggaactgc agaacaaagg caaaaaggtg  2760
gccatggtgg gagatggcgt gaacgactct cctgctctgg cccaggcaga tatgggcgtg  2820
gccatcggca caggcaccga cgtggcaatt gaggctgctg acgtggtgct gattcggaac  2880
gacctgctgg acgtggtggc ctccatccac ctgtccaaga gaaccgtgcg gcggatcaga  2940
atcaacctgg tgctggcact gatctataac ctcgtgggca tccctatcgc cgctggcgtg  3000
ttcatgccta tcggaatcgt gctgcagccc tggatgggct ctgccgccat ggctgcaagc  3060
tccgtgtctg tggtgctgtc cagcctgcag ctgaagtgct acaagaagcc cgacctggaa  3120
agatacgagg cccaggccca cggacacatg aagcctctga cagcctccca ggtgtccgtg  3180
cacatcggca tggacgacag atggcgggac agccctagag ccacccccttg ggatcaggtg  3240
tcatacgtgt cacaggtgtc cctgagcagc ctgaccagcg acaagcccag cagacatagc  3300
gccgctgccg acgacgatgg ggacaagtgg tccctgctgc tgaacggccg ggatgaggaa  3360
cagtacatct gataagcatg caataaagtc tgagtgggcg gcagcctgtg tgtgcctggg  3420
ttctctctgt cccggaatgt gcaaacaatg gaggtgctcg agtagataag tagcatggcg  3480
ggttaatcat taactacaag gaacccctag tgatggagtt ggccactccc tctctgcgcg  3540
ctcgctcgct cactgaggcc gggcgaccaa aggtcgcccg acgcccgggc tttgcccggg  3600
cggcctcagt gagcgagcga gcgcgcagcc ttaattaacc taattcactg gccgtcgttt  3660
tacaacgtcg tgactgggaa aaccctggcg ttacccaact taatcgcctt gcagcacatc  3720
ccccttttcgc cagctggcgt aatagcgaag aggcccgcac cgatcgccct tcccaacagt  3780
tgcgcagcct gaatggcgaa tggacgcgcc cctgtagcgg cgcattaagc gcggcgggtg  3840
tggtggttac gcgcagcgtg accgctacac ttgccagcgc cctagcgccc gctcctttcg  3900
ctttcttccc ttcctttctc gccacgttcg ccggctttcc ccgtcaagct ctaaatcggg  3960
ggctcccttt agggttccga tttagtgctt tacggcacct cgaccccaaa aaacttgatt  4020
agggtgatgg ttcacgtagt gggccatcgc cctgatagac ggtttttcgc cctttgacgt  4080
tggagtccac gttctttaat agtggactct tgttccaaac tggaacaaca ctcaacccta  4140
tctcggtcta ttcttttgat ttataaggga ttttgccgat ttcggcctat tggttaaaaa  4200
atgagctgat ttaacaaaaa tttaacgcga attttaacaa aatattaacg cttacaattt  4260
aggtggcact tttcggggaa atgtgcgcgg aacccctatt tgtttatttt tctaaataca  4320
ttcaaatatg tatccgctca tgagacaata accctgataa atgcttcaat aatattgaaa  4380
aaggaagagt atgagtattc aacatttccg tgtcgccctt attccctttt ttgcggcatt  4440
ttgccttcct gtttttgctc acccagaaac gctggtgaaa gtaaaagatg ctgaagatca  4500
gttgggtgca cgagtgggtt acatcgaact ggatctcaac agcggtaaga tccttgagag  4560
ttttcgcccc gaagaacgtt ttccaatgat gagcactttt aaagttctgc tatgtggcgc  4620
ggtattatcc cgtattgacg ccgggcaaga gcaactcggt cgccgcatac actattctca  4680
gaatgacttg gttgagtact caccagtcac agaaaagcat cttacggatg gcatgacagt  4740
aagagaatta tgcagtgctg ccataaccat gagtgataac actgcggcca acttacttct  4800
gacaacgatc ggaggaccga aggagctaac cgcttttttg cacaacatgg gggatcatgt  4860
aactcgcctt gatcgttggg aaccggagct gaatgaagcc ataccaaacg acgagcgtga  4920
caccacgatg cctgtagcaa tggcaacaac gttgcgcaaa ctattaactg gcgaactact  4980
tactctagct tcccggcaac aattaataga ctggatggag gcggataaag ttgcaggacc  5040
acttctgcgc tcggcccttc cggctggctg gtttattgct gataaatctg gagccggtga  5100
gcgtgggtct cgcggtatca ttgcagcact ggggccagat ggtaagccct cccgtatcgt  5160
agttatctac acgacgggga gtcaggcaac tatggatgaa cgaaatagac agatcgctga  5220
gataggtgcc tcactgatta agcattggta actgtcagac caagtttact catatatact  5280
ttagattgat ttaaaacttc atttttaatt taaaaggatc taggtgaaga tcctttttga  5340
taatctcatg accaaaatcc cttaacgtga gttttcgttc cactgagcgt cagaccccgt  5400
agaaaagatc aaaggatctt cttgagatcc tttttttctg cgcgtaatct gctgcttgca  5460
aacaaaaaaa ccaccgctac cagcggtggt ttgtttgccg gatcaagagc taccaactct  5520
ttttccgaag gtaactggct tcagcagagc gcagatacca aatactgttc ttctagtgta  5580
gccgtagtta ggccaccact tcaagaactc tgtagcaccg cctacatacc tcgctctgct  5640
aatcctgtta ccagtggctg ctgccagtgg cgataagtcg tgtcttaccg ggttggactc  5700
aagacgatag ttaccggata aggcgcagcg gtcgggctga acggggggtt cgtgcacaca  5760
gcccagcttg gagcgaacga cctacaccga actgagatac ctacagcgtg agctatgaga  5820
aagcgccacg cttcccgaag ggagaaaggc ggacaggtat ccggtaagcg gcagggtcgg  5880
aacaggagag cgcacgaggg agcttccagg gggaaacgcc tggtatcttt atagtcctgt  5940
cgggtttcgc cacctctgac ttgagcgtcg atttttgtga tgctcgtcag gggggcggag  6000
cctatggaaa aacgccagca acgcggcctt tttacggttc ctggcctttt gctggccttt  6060
tgctcacatg ttctttcctg cgttatcccc tgattctgtg gataaccgta ttaccgcctt  6120
tgagtgagct gataccgctc gccgcagccg aacgaccgag cgcagcgagt cagtgagcga  6180
ggaagcggaa gagcgcccaa tacgcaaacc gcctctcccc gcgcgttggc cgattcatta  6240
atgcagctgg cacgacaggt ttcccgactg gaaagcgggc agtgagcgca acgcaattaa  6300
tgtgagttag ctcactcatt aggcacccca ggctttacac tttatgcttc cggctcgtat  6360
gttgtgtgga attgtgagcg gataacaatt tcacacagga aacagctatg accatgatta  6420
cgccagattt aattaagg                                                 6438
```

```
SEQ ID NO: 34          moltype = DNA  length = 6831
FEATURE                Location/Qualifiers
misc_feature           1..6831
                       note = constructed sequence
source                 1..6831
                       mol_type = other DNA
                       organism = synthetic construct
SEQUENCE: 34
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
```

-continued

```
gcttgcaatg tttgcccatt ttaggggaat tcactcaaag ttcaaacctt atcatttttt  240
gctttgttcc tcttggcctt ggttttgtac atcagctttg aaaataccat cccagggtta  300
atgctggggt taatttataa ctaagagtgc tctagttttg caatacagga catgctataa  360
aaatggaaag atgttgcttt ctgagagaca gcggccgcca ccatgcccga gcaggaaaga  420
cagatcaccg ccagagaggg cgccagccgg aagatcctga gcaagctgag cctgcccacc  480
agagcctggg agcccgccat gaagaagtcc ttcgccttcg acaacgtggg ctacgagggc  540
ggcctggacg gactgggacc atcttctcag gtggccacaa gcaccgtgcg cagccccgaa  600
gaactgagag ccgccattga ggacatggga ttcgaagcca gcgtggtgtc cgagagctgc  660
tccaccaacc ctctgggcaa tcacagcgcc ggcaacagca tggtgcagac caccgacggc  720
acccccacca gcgtgcagga agtggcccca catacaggca gactgcccgc caatcacgcc  780
cccgatatcc tggccaagag cccccagagt acaagagccg tggcccccca gaagtgcttc  840
ctgcagatca agggcatgac ttgtgcctct tgtgtgtcca atatcgagcg gaacctgcag  900
aaagaggccg gcgtgctgtc tgtgctggtg gctctgatgg ccggcaaggc cgagatcaaa  960
tacgaccccg aagtgattca gcccctggaa atcgcccagt ttatccagga cctgggcttt  1020
gaagccgccg tgatggaaga ttacgccggc tccgacggca acatcgagct gaccatcacc  1080
ggaatgacct gcgcctcctg tgtgcacaac attgagtcca agctgacccg gaccaacggc  1140
atcacctacg cctctgtggc tctggccacc tccaaggccc tcgtgaagtt cgatcccgag  1200
atcatcggcc ccagggacat catcaagatc atcgaagaga tcggcttcca cgccagcctg  1260
gcccagagga accctaacgc ccaccacctg gaccacaaga tggaaatcaa gcagtggaag  1320
aaaagcttcc tgtgcagcct ggtgttcggc atccccgtga tggccctgat gatctacatg  1380
ctgatcccca gcaacgagcc ccaccagtcc atggtgctgg atcacaacat catccccggc  1440
ctgtctatcc tgaacctgat cttcttcatc ctgtgcacct tcgtgcagct gctgggcggc  1500
tggtacttct acgtgcaggc ctacaagtcc ctgcggcaca gatccgccaa catggacgtg  1560
ctgatcgtgc tggccacatc tatcgcctac gtgtactccc tcgtgatcct ggtggtggcc  1620
gtggccgaga aagccgagag aagccctgtg accttcttcg acaccccccc tatgctgttc  1680
gtgtttatcg ccctgggccg gtggctggaa cacctggcca aaagcaagac cagcgaggcc  1740
ctggctaagc tgatgagtct gcaggccacc gaggccacag tcgtgaccct gggcgaggac  1800
aacctgatca tccgcgagga acaggtgcca atggaactgg tgcagcgggg cgacatcgtg  1860
aaggtggtgc ctggcggcaa gttccccgtg gacggaaaag tgctggaagg gaataccatg  1920
gccgacgaga gcctgatcac aggcgaggcc atgcccgtga ccaagaaacc tggcagcaca  1980
gtgatcgccg gcagcatcaa tgcccacggc agcgtgctga ttaaggccac acacgtgggc  2040
aacgatacca ccctggctca gattgtgaag ctggtggaag aggcccagat gagcaaggcc  2100
cccattcagc agctggctga ccggttcagc ggctacttcg tgccctttat catcatcatg  2160
agcaccctga cactggtcgt gtggatcgtg atcggcttta tcgacttcgg agtggtgcag  2220
agatacttcc ccaaccctaa caagcacatc agccagacag aagtgatcat cagattcgcc  2280
tttcagacca gcatcaccgt gctgtgtatc gcctgcccct gtagcctggg actggccaca  2340
cctaccgctg tgatggtggg aacaggcgtg gccgctcaga acggcatcct gatcaagggg  2400
ggcaagcctc tggaaatggc tcacaagatc aagaccgtga tgttcgacaa gaccggcacc  2460
atcacccacg gcgtgcccag agtgatgaga gtgctgctgc tgggggatgt ggccaccctg  2520
cctctgagaa aggtgctggc tgtcgtgggc acagccgagg ctagctctga acacccactg  2580
ggagtggccg tgacaaagta ctgcaaagag gaactgggca ccgaaaccct gggctactgc  2640
accgactttc aggccgtgcc tggctgtggc atcggctgca aggtgtccaa cgtggaaggc  2700
atcctggccc acagcgagag gccactgtct gcccctgcca gccacctgaa cgaggccgga  2760
tctctgcccg ccgaaaagga cgctgtgccc cagaccttct ctgtgctgat tggcaacaga  2820
gagtggctgc ggcggaacgg cctgaccatc tcctccgatg tgtccgacgc catgaccgac  2880
cacgagatga agggccagac cgccattctg gtggccattg acggggtgct gtgcggcatg  2940
atcgcaatcg ccgatgccgt gaaacaggaa gcagcactgg ccgtgcacac cctgcagtct  3000
atgggagtgg atgtggtgct gatcaccggc gacaacagaa agaccgccag ggccattgcc  3060
acccaggtgg gcatcaacaa ggtgttcgcc gaggtgctgc ccagccacaa agtggccaag  3120
gtgcaggaac tgcagaacaa aggcaaaaag gtggccatgg tgggagatgg cgtgaacgac  3180
tctcctgctc tggcccaggc agatatgggc gtggccatcg gcacaggcac cgacgtggca  3240
attgaggctg ctgacgtggt gctgattcgg aacgacctgc tggacgtggt ggcctccatc  3300
cacctgtcca agagaaccgt gcggcggatc agaatcaacc tggtgctggc actgatctat  3360
aacctcgtgg gcatccctat cgccgctggc gtgttcatgc ctatcggaat cgtgctgcag  3420
ccctggatgg gctctgccgc catggctgca agctccgtgt ctgtggtgct gtccagcctg  3480
cagctgaagt gctacaagaa gcccgacctg gaaagatacg aggcccaggc ccacggacac  3540
atgaagcctc tgacagcctc ccaggtgtcc gtgcacatcg gcatggacga cagatggcgg  3600
gacagcccta gagccacccc ttgggatcag gtgtcatacg tgtcacaggt gtccctgagc  3660
agcctgacca gcgacaagcc cagcagacat agcgccgctg ccgacgacga tggggacaag  3720
tggtccctgc tgctgaacgg ccgggatgag gaacagtaca tctgataagc atgcaataaa  3780
gtctgagtgg gcggcagcct gtgtgtgcct gggttctctc tgtcccggaa tgtgcaaaca  3840
atggaggtgc tcgagtagat aagtagcatg gcgggttaat cattaactac aaggaacccc  3900
tagtgatgga gttggccact ccctctctgc gcgctcgctc gctcactgag gccgggcgac  3960
caaaggtcgc ccgacgcccg ggctttgccc gggcggcctc agtgagcgag cgagcgcgca  4020
gccttaatta acctaattca ctggccgtcg ttttacaacg tcgtgactgg gaaaaccctg  4080
gcgttaccca acttaatcgc cttgcagcac atcccccttt cgccagctgg cgtaatagcg  4140
aagaggcccg caccgatcgc ccttcccaac agttgcgcag cctgaatggc gaatgggacg  4200
cgccctgtag cggcgcatta agcgcggcgg gtgtggtggt tacgcgcagc gtgaccgcta  4260
cacttgccag cgccctagcg cccgctcctt tcgctttctt cccttccttt ctcgccacgt  4320
tcgccggctt tccccgtcaa gctctaaatc gggggctccc tttagggttc cgatttagtg  4380
ctttacggca cctcgacccc aaaaaacttg attagggtga tggttcacgt agtgggccat  4440
cgccctgata gacggttttt cgccctttga cgttggagtc cacgttcttt aatagtggac  4500
tcttgttcca aactggaaca acactcaacc ctatctcggt ctattctttt gatttataag  4560
ggattttgcc gatttcggcc tattggttaa aaaatgagct gatttaacaa aaatttaacg  4620
cgaattttaa caaaatatta acgcttacaa tttaggtggc acttttcggg gaaatgtgcg  4680
cggaacccct atttgtttat ttttctaaat acattcaaat atgtatccgc tcatgagaca  4740
ataaccctga taaatgcttc aataatattg aaaaaggaag agtatgagta ttcaacattt  4800
ccgtgtcgcc cttattccct tttttgcggc attttgcctt cctgtttttg ctcacccaga  4860
aacgctggtg aaagtaaaag atgctgaaga tcagttgggt gcacgagtgg gttacatcga  4920
```

```
actggatctc aacagcggta agatccttga gagttttcgc cccgaagaac gttttccaat  4980
gatgagcact tttaaagttc tgctatgtgg cgcggtatta tcccgtattg acgccgggca  5040
agagcaactc ggtcgccgca tacactattc tcagaatgac ttggttgagt actcaccagt  5100
cacagaaaag catcttacgg atggcatgac agtaagagaa ttatgcagtg ctgccataac  5160
catgagtgat aacactgcgg ccaacttact tctgacaacg atcggaggac cgaaggagct  5220
aaccgctttt ttgcacaaca tgggggatca tgtaactcgc cttgatcgtt gggaaccgga  5280
gctgaatgaa gccataccaa acgacgagcg tgacaccacg atgcctgtag caatggcaac  5340
aacgttgcgc aaactattaa ctggcgaact acttactcta gcttcccggc aacaattaat  5400
agactggatg gaggcggata aagttgcagg accacttctg cgctcggccc ttccggctgg  5460
ctggtttatt gctgataaat ctggagccgg tgagcgtggg tctcgcggta tcattgcagc  5520
actggggcca gatggtaagc cctcccgtat cgtagttatc tacacgacgg ggagtcaggc  5580
aactatggat gaacgaaata gacagatcgc tgagataggt gcctcactga ttaagcattg  5640
gtaactgtca gaccaagttt actcatatat actttagatt gatttaaaac ttcattttta  5700
atttaaaagg atctaggtga agatcctttt tgataatctc atgaccaaaa tcccttaacg  5760
tgagttttcg ttccactgag cgtcagaccc cgtagaaaag atcaaaggat cttcttgaga  5820
tcctttttt ctgcgcgtaa tctgctgctt gcaaacaaaa aaaccaccgc taccagcggt  5880
ggtttgtttg ccggatcaag agctaccaac tctttttccg aaggtaactg gcttcagcag  5940
agcgcagata ccaaatactg ttcttctagt gtagccgtag ttaggccacc acttcaagaa  6000
ctctgtagca ccgcctacat acctcgctct gctaatcctg ttaccagtgg ctgctgccag  6060
tggcgataag tcgtgtctta ccgggttgga ctcaagacga tagttaccgg ataaggcgca  6120
gcggtcgggc tgaacggggg gttcgtgcac acagcccagc ttggagcgaa cgacctacac  6180
cgaactgaga tacctacagc gtgagctatg agaaagcgcc acgcttcccg aagggagaaa  6240
ggcggacagg tatccggtaa gcggcagggt cggaacagga gagcgcacga gggagcttcc  6300
agggggaaac gcctggtatc tttatagtcc tgtcgggttt cgccacctct gacttgagcg  6360
tcgatttttg tgatgctcgt caggggggcg gagcctatgg aaaaacgcca gcaacgcggc  6420
ctttttacgg ttcctggcct tttgctggcc ttttgctcac atgttctttc ctgcgttatc  6480
ccctgattct gtggataacc gtattaccgc ctttgagtga gctgataccg ctcgccgcag  6540
ccgaacgacc gagcgcagcg agtcagtgag cgaggaagcg gaagagcgcc caatacgcaa  6600
accgcctctc cccgcgcgtt ggccgattca ttaatgcagc tggcacgaca ggtttcccga  6660
ctggaaagcg ggcagtgagc gcaacgcaat taatgtgagt tagctcactc attaggcacc  6720
ccaggcttta cactttatgc ttccggctcg tatgttgtgt ggaattgtga gcggataaca  6780
atttcacaca ggaaacagct atgaccatga ttacgccaga tttaattaag g           6831
```

```
SEQ ID NO: 35           moltype = DNA  length = 7437
FEATURE                 Location/Qualifiers
misc_feature            1..7437
                        note = constructed sequence
source                  1..7437
                        mol_type = other DNA
                        organism = synthetic construct
SEQUENCE: 35
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctactta agtgtttgct  180
gcttgcaatg tttgcccatt ttagggggaat tcactcaaag ttcaaacctt atcatttttt  240
gctttgttcc tcttggcctt ggttttgtac atcagctttg aaaataccat cccagggtta  300
atgctggggt taatttataa ctaagagtgc tctagttttg caatacagga catgctataa  360
aaatggaaag atgttgcttt ctgagagaca gcggccgcca ccatgcccga gcaggaaaga  420
cagatcaccg ccagagaggg cgccagccgg aagatcctga gcaagctgag cctgcccacc  480
agagcctggg agcccgccat gaagaagtcc ttcgccttcg acaacgtggg ctacgagggc  540
ggcctggacg gactgggacc atcttctcag gtggccacaa gcaccgtgcg cgaggccgcc  600
atcaagagca aggtggcccc tctgtctctg ggccccatcg acatcgagag actgcagagc  660
accaacccca agcggcctct gagcagcgcc aaccagaact tcaacaacag cgagacactg  720
ggccaccagg gcagccacgt cgtgacactg cagctgcgga tcgacggaat gcactgcaag  780
agctgtgtgc tgaacatcga ggaaaacatc ggccagctgc tgggagtgca gagcatccag  840
gtgtcactgg aaaacaagac cgcccaggtg aagtacgacc ccagctgcac aagccccgtg  900
gccctgcaga gagccattga agctctgccc cctggcaact tcaaagtgtc cctgcctgac  960
ggagccgagg gctccggaac agatcacaga agcagcagca gccacagccc tggcagcccc  1020
cctagaaatc aggtgcaggg cacctgtagc accaccctga tcgccattgc cggcatgaca  1080
tgcgccagct gcgtgcactc tattgagggc atgatctccc agctggaagg cgtgcagcag  1140
atcagtgtgt ctctggccga gggcaccgcc acagtgctgt acaaccctag cgtgatcagc  1200
cccgaagaac tgagagccgc cattgaggac atgggattcg aagccagcgt ggtgtccgag  1260
agctgctcca ccaaccctct gggcaatcac agcgccggca acagcatggt gcagaccacc  1320
gacggcaccc ccaccagcgt gcaggaagtg gccccacata caggcagact gcccgccaat  1380
cacgccccccg atatcctggc caagagcccc cagagtacaa gagccgtggc cccccagaag  1440
tgcttcctgc agatcaaggg catgacttgt gcctcttgtg tgtccaatat cgagcggaac  1500
ctgcagaaag aggccggcgt gctgtctgtg ctggtggctc tgatggccgg caaggccgag  1560
atcaaatacg accccgaagt gattcagccc ctggaaatcg cccagtttat ccaggacctg  1620
ggctttgaag ccgccgtgat ggaagattac gccggctccg acggcaacat cgagctgacc  1680
atcaccggaa tgacctgcgc ctcctgtgtg cacaacattg agtccaagct gacccggacc  1740
aacggcatca cctacgcctc tgtggctctg gccacctcca aggccctcgt gaagttcgat  1800
cccgagatca tcggccccag ggacatcatc aagatcatcg aagagatcgg cttccacgcc  1860
agcctggccc agaggaaccc taacgcccac cacctggacc acaagatgga aatcaagcag  1920
tggaagaaaa gcttcctgtg cagcctggtg ttcggcatcc ccgtgatggc cctgatgatc  1980
tacatgctga tccccagcaa cgagccccac cagtccatgg tgctggatca caacatcatc  2040
cccggcctgt ctatcctgaa cctgatcttc ttcatcctgt gcaccttcgt gcagctgctg  2100
ggcggctggt acttctacgt gcaggcctac aagtccctgc ggcacagatc cgccaacatg  2160
gacgtgctga tcgtgctggc cacatctatc gcctacgtgt actccctcgt gatcctggtg  2220
gtggccgtgg ccgagaaagc cgagagaagc cctgtgacct tcttcgacac ccccccctatg  2280
```

```
ctgttcgtgt ttatcgccct gggccggtgg ctggaacacc tggccaaaag caagaccagc  2340
gaggccctgg ctaagctgat gagtctgcag gccaccgagg ccacagtcgt gaccctgggc  2400
gaggacaacc tgatcatccg cgaggaacag gtgccaatgg aactggtgca gcggggcgac  2460
atcgtgaagg tggtgcctgg cggcaagttc cccgtggacg gaaaagtgct ggaagggaat  2520
accatggccg acgagagcct gatcacaggc gaggccatgc ccgtgaccaa gaaacctggc  2580
agcacagtga tcgccggcag catcaatgcc cacggcagcg tgctgattaa ggccacacac  2640
gtgggcaacg ataccaccct ggctcagatt gtgaagctgg tggaagaggc ccagatgagc  2700
aaggccccca ttcagcagct ggctgaccgg ttcagcggct acttcgtgcc ctttatcatc  2760
atcatgagca ccctgacact ggtcgtgtgg atcgtgatcg gctttatcga cttcggagtg  2820
gtgcagagat acttccccaa ccctaacaag cacatcagcc agacagaagt gatcatcaga  2880
ttcgcctttc agaccagcat caccgtgctg tgtatcgcct gcccctgtag cctgggactg  2940
gccacaccta ccgctgtgat ggtgggaaca ggcgtggccg ctcagaacgg catcctgatc  3000
aagggggggca agcctctgga aatggctcac aagatcaaga ccgtgatgtt cgacaagacc  3060
ggcaccatca cccacggcgt gcccagagtg atgagagtgc tgctgctggg ggatgtggcc  3120
accctgcctc tgagaaaggt gctggctgtc gtgggcacag ccgaggctag ctctgaacac  3180
ccactgggag tggccgtgac aaagtactgc aaagaggaac tgggcaccga aaccctgggc  3240
tactgcaccg actttcaggc cgtgcctggc tgtggcatcg gctgcaaggt gtccaacgtg  3300
gaaggcatcc tggcccacag cgagaggcca ctgtctgccc ctgccagcca cctgaacgag  3360
gccggatctc tgcccgccga aaaggacgct gtgccccaga ccttctctgt gctgattggc  3420
aacagagagt ggctgcggcg gaacggcctg accatctcct ccgatgtgtc cgacgccatg  3480
accgaccacg agatgaaggg ccagaccgcc attctggtgg ccattgacgg ggtgctgtgc  3540
ggcatgatcg caatcgccga tgccgtgaaa caggaagcag cactggccgt gcacaccctg  3600
cagtctatgg gagtggatgt ggtgctgatc accggcgaca acagaaagac cgccagggcc  3660
attgccaccc aggtgggcat caacaaggtg ttcgccgagg tgctgcccag ccacaaagtg  3720
gccaaggtgc aggaactgca gaacaaaggc aaaaaggtgg ccatggtggg agatggcgtg  3780
aacgactctc ctgctctggc ccaggcagat atgggcgtgg ccatcggcac aggcaccgac  3840
gtggcaattg aggctgctga cgtggtgctg attcggaacg acctgctgga cgtggtggcc  3900
tccatccacc tgtccaagag aaccgtgcgg cggatcagaa tcaacctggt gctggcactg  3960
atctataacc tcgtgggcat ccctatcgcc gctggcgtgt tcatgcctat cggaatcgtg  4020
ctgcagccct ggatgggctc tgccgccatg gctgcaagct ccgtgtctgt ggtgctgtcc  4080
agcctgcagc tgaagtgcta caagaagccc gacctggaaa gatacgaggc ccaggcccac  4140
ggacacatga agcctctgac agcctcccag gtgtccgtgc acatcggcat ggacgacaga  4200
tggcgggaca gccctagagc caccccttgg gatcaggtgt catacgtgtc acaggtgtcc  4260
ctgagcagcc tgaccagcga caagcccagc agacatagcg ccgctgccga cgacgatggg  4320
gacaagtggt ccctgctgct gaacggccgg gatgaggaac agtacatctg ataagcatgc  4380
aataaagtct gagtgggcgg cagcctgtgt gtgcctgggt tctctctgtc ccggaatgtg  4440
caaacaatgg aggtgctcga gtagataagt agcatggcgg gttaatcatt aactacaagg  4500
aacccctagt gatggagttg gccactccct ctctgcgcgc tcgctcgctc actgaggccg  4560
ggcgaccaaa ggtcgcccga cgcccgggct ttgcccgggc ggcctcagtg agcgagcgag  4620
cgcgcagcct taattaacct aattcactgg ccgtcgtttt acaacgtcgt gactgggaaa  4680
accctggcgt tacccaactt aatcgccttg cagcacatcc ccctttcgcc agctggcgta  4740
atagcgaaga ggcccgcacc gatcgccctt cccaacagtt gcgcagcctg aatggcgaat  4800
gggacgcgcc ctgtagcggc gcattaagcg cggcgggtgt ggtggttacg cgcagcgtga  4860
ccgctacact tgccagcgcc ctagcgcccg ctcctttcgc tttcttccct tcctttctcg  4920
ccacgttcgc cggctttccc cgtcaagctc taaatcgggg gctcccttta gggttccgat  4980
ttagtgcttt acggcacctc gaccccaaaa aacttgatta gggtgatggt tcacgtagtg  5040
ggccatcgcc ctgatagacg gtttttcgcc ctttgacgtt ggagtccacg ttctttaata  5100
gtggactctt gttccaaact ggaacaacac tcaaccctat ctcggtctat tcttttgatt  5160
tataagggat tttgccgatt tcggcctatt ggttaaaaaa tgagctgatt taacaaaaat  5220
ttaacgcgaa ttttaacaaa atattaacgc ttacaattta ggtggcactt ttcggggaaa  5280
tgtgcgcgga acccctattt gtttattttt ctaaatacat tcaaatatgt atccgctcat  5340
gagacaataa ccctgataaa tgcttcaata atattgaaaa aggaagagta tgagtattca  5400
acatttccgt gtcgccctta ttcccttttt tgcggcattt tgccttcctg tttttgctca  5460
cccagaaacg ctggtgaaag taaaagatgc tgaagatcag ttgggtgcac gagtgggtta  5520
catcgaactg gatctcaaca gcggtaagat ccttgagagt tttcgccccg aagaacgttt  5580
tccaatgatg agcactttta aagttctgct atgtggcgcg gtattatccc gtattgacgc  5640
cgggcaagag caactcggtc gccgcataca ctattctcag aatgacttgg ttgagtactc  5700
accagtcaca gaaaagcatc ttacggatgg catgacagta agagaattat gcagtgctgc  5760
cataaccatg agtgataaca ctgcggccaa cttacttctg acaacgatcg gaggaccgaa  5820
ggagctaacc gcttttttgc acaacatggg ggatcatgta actcgccttg atcgttggga  5880
accggagctg aatgaagcca taccaaacga cgagcgtgac accacgatgc ctgtagcaat  5940
ggcaacaacg ttgcgcaaac tattaactgg cgaactactt actctagctt cccggcaaca  6000
attaatagac tggatggagg cggataaagt tgcaggacca cttctgcgct cggcccttcc  6060
ggctggctgg tttattgctg ataaatctgg agccggtgag cgtgggtctc gcggtatcat  6120
tgcagcactg gggccagatg gtaagccctc ccgtatcgta gttatctaca cgacggggag  6180
tcaggcaact atggatgaac gaaatagaca gatcgctgag ataggtgcct cactgattaa  6240
gcattggtaa ctgtcagacc aagtttactc atatatactt tagattgatt taaaacttca  6300
tttttaattt aaaaggatct aggtgaagat cctttttgat aatctcatga ccaaaatccc  6360
ttaacgtgag ttttcgttcc actgagcgtc agaccccgta gaaaagatca aaggatcttc  6420
ttgagatcct ttttttctgc gcgtaatctg ctgcttgcaa acaaaaaaac caccgctacc  6480
agcggtggtt tgtttgccgg atcaagagct accaactctt tttccgaagg taactggctt  6540
cagcagagcg cagataccaa atactgttct tctagtgtag ccgtagttag gccaccactt  6600
caagaactct gtagcaccgc ctacatacct cgctctgcta atcctgttac cagtggctgc  6660
tgccagtggc gataagtcgt gtcttaccgg gttggactca agacgatagt taccggataa  6720
ggcgcagcgg tcgggctgaa cggggggttc gtgcacacag cccagcttgg agcgaacgac  6780
ctacaccgaa ctgagatacc tacagcgtga gctatgagaa agcgccacgc ttcccgaagg  6840
gagaaaggcg gacaggtatc cggtaagcgg cagggtcgga acaggagagc gcacgaggga  6900
gcttccaggg ggaaacgcct ggtatcttta tagtcctgtc gggtttcgcc acctctgact  6960
tgagcgtcga tttttgtgat gctcgtcagg ggggcggagc ctatggaaaa acgccagcaa  7020
```

-continued

```
cgcggccttt ttacggttcc tggccttttg ctggcctttt gctcacatgt tctttcctgc  7080
gttatcccct gattctgtgg ataaccgtat taccgccttt gagtgagctg ataccgctcg  7140
ccgcagccga acgaccgagc gcagcgagtc agtgagcgag gaagcggaag agcgcccaat  7200
acgcaaaccg cctctccccg cgcgttggcc gattcattaa tgcagctggc acgacaggtt  7260
tcccgactgg aaagcgggca gtgagcgcaa cgcaattaat gtgagttagc tcactcatta  7320
ggcaccccag gctttacact ttatgcttcc ggctcgtatg ttgtgtggaa ttgtgagcgg  7380
ataacaattt cacacaggaa acagctatga ccatgattac gccagattta attaagg     7437
```